(12) United States Patent
Tominari et al.

(10) Patent No.: US 11,639,354 B2
(45) Date of Patent: May 2, 2023

(54) HETEROCYCLIC COMPOUND

(71) Applicant: FIMECS, INC., Fujisawa (JP)

(72) Inventors: Yusuke Tominari, Sagamihara (JP); Yoshihide Tomata, Fujisawa (JP); Kanae Gamo, Yokohama (JP); Naomi Kitamoto, Amagasaki (JP)

(73) Assignee: FIMECS, INC., Fujisawa (JP)

( * ) Notice: Subject to any disclaimer, the term of this patent is extended or adjusted under 35 U.S.C. 154(b) by 22 days.

(21) Appl. No.: 17/263,580

(22) PCT Filed: Jul. 31, 2019

(86) PCT No.: PCT/JP2019/030083
§ 371 (c)(1),
(2) Date: Jan. 27, 2021

(87) PCT Pub. No.: WO2020/027225
PCT Pub. Date: Feb. 6, 2020

(65) Prior Publication Data
US 2021/0179614 A1 Jun. 17, 2021

(30) Foreign Application Priority Data

Jul. 31, 2018 (JP) .............................. JP2018-144308

(51) Int. Cl.
| | | |
|---|---|---|
| *C07D 209/08* | (2006.01) | |
| *C07D 209/42* | (2006.01) | |
| *C07D 403/06* | (2006.01) | |
| *C07D 471/04* | (2006.01) | |
| *C07D 231/14* | (2006.01) | |
| *C07D 231/56* | (2006.01) | |
| *C07D 235/08* | (2006.01) | |
| *C07D 403/12* | (2006.01) | |
| *C07D 413/14* | (2006.01) | |
| *C07D 417/14* | (2006.01) | |
| *C07D 487/04* | (2006.01) | |
| *C07D 487/08* | (2006.01) | |
| *C07D 495/14* | (2006.01) | |

(52) U.S. Cl.
CPC ........ *C07D 471/04* (2013.01); *C07D 209/08* (2013.01); *C07D 209/42* (2013.01); *C07D 231/14* (2013.01); *C07D 231/56* (2013.01); *C07D 235/08* (2013.01); *C07D 403/06* (2013.01); *C07D 403/12* (2013.01); *C07D 413/14* (2013.01); *C07D 417/14* (2013.01); *C07D 487/04* (2013.01); *C07D 487/08* (2013.01); *C07D 495/14* (2013.01)

(58) Field of Classification Search
CPC ... C07D 209/08; C07D 209/42; C07D 403/06
See application file for complete search history.

(56) References Cited

U.S. PATENT DOCUMENTS

| | | |
|---|---|---|
| 2002/0068063 A1 | 6/2002 | Deshaies |
| 2004/0038358 A1 | 2/2004 | Dashaies |
| 2007/0093428 A1 | 4/2007 | Laurent |
| 2009/0156508 A1 | 6/2009 | Schteingart |
| 2010/0075910 A1 | 3/2010 | Schteingart |
| 2011/0212882 A1 | 9/2011 | Schteingart |
| 2013/0172264 A1 | 7/2013 | Cohen |
| 2014/0135270 A1 | 5/2014 | Borzilleri |
| 2015/0291562 A1 | 10/2015 | Crew |
| 2016/0045607 A1 | 2/2016 | Crew |
| 2017/0008904 A1 | 1/2017 | Crew |
| 2017/0065719 A1 | 3/2017 | Qian |
| 2017/0121321 A1 | 5/2017 | Crews |
| 2018/0072711 A1 | 3/2018 | Crew |
| 2018/0099940 A1 | 4/2018 | Crew |

(Continued)

FOREIGN PATENT DOCUMENTS

| | | |
|---|---|---|
| CN | 106749513 A | 5/2017 |
| CN | 106977584 A | 7/2017 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Ashton C. Lai et al, "Induced protein degradation: an emerging drug discovery paradigm", HHS Public Access, Nat Rev Drug Discovery, 16 (2), Feb. 2017, 32 pages.

(Continued)

*Primary Examiner* — Shawquia Jackson
(74) *Attorney, Agent, or Firm* — Element IP, PLC

(57) ABSTRACT

One of the purposes of the present invention is to provide a heterocyclic derivative that has an IAP (particularly XIAP) binding (inhibiting) activity. Another of the purposes of the present invention is to provide a heterocyclic derivative that has an IAP (particularly XIAP) binding (inhibiting) activity and exhibits a protein degradation induction activity. The present invention provides a compound represented by formula (I) (the symbols in the formula are as defined in the present Description) and salts thereof.

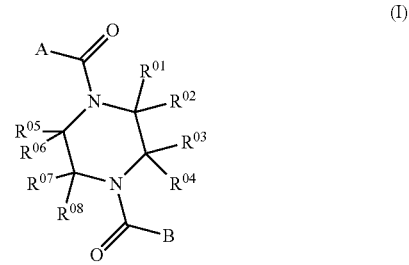

15 Claims, 1 Drawing Sheet
Specification includes a Sequence Listing.

(56) References Cited

U.S. PATENT DOCUMENTS

| | | |
|---|---|---|
| 2018/0118733 A1 | 5/2018 | Harling |
| 2018/0134684 A1 | 5/2018 | Bradner |
| 2018/0134688 A1 | 5/2018 | Casillas |
| 2018/0155322 A1 | 6/2018 | Crew |
| 2018/0169109 A1 | 6/2018 | Bradner |
| 2018/0179183 A1 | 6/2018 | Crew |
| 2018/0179522 A1 | 6/2018 | Buckley |
| 2018/0186785 A1 | 7/2018 | Crews |
| 2018/0193470 A1 | 7/2018 | Crew |
| 2018/0215731 A1 | 8/2018 | Crew |
| 2018/0228907 A1 | 8/2018 | Crew |
| 2018/0237418 A1 | 8/2018 | Crew |
| 2018/0256586 A1 | 9/2018 | Crew |
| 2018/0327419 A1 | 11/2018 | Bradner |
| 2019/0062281 A1 | 2/2019 | Schiltz |
| 2019/0119271 A1 | 4/2019 | Casillas |
| 2019/0119358 A1 | 4/2019 | Josephson |
| 2019/0127359 A1 | 5/2019 | Crews |
| 2019/0151457 A1 | 5/2019 | Bradner |
| 2019/0175612 A1 | 6/2019 | Pillow |
| 2019/0192514 A1 | 6/2019 | Crew |

FOREIGN PATENT DOCUMENTS

| | | |
|---|---|---|
| CN | 107382862 A | 11/2017 |
| CN | 107540608 A | 1/2018 |
| JP | 2008536861 A | 9/2008 |
| JP | 2012106958 A | 6/2012 |
| JP | 2012176934 A | 9/2012 |
| JP | 2013056837 A | 3/2013 |
| WO | 2006075023 A2 | 7/2006 |
| WO | 2006091737 A1 | 8/2006 |
| WO | 2006113376 A1 | 10/2006 |
| WO | 2007104162 A1 | 9/2007 |
| WO | 2007106192 A2 | 9/2007 |
| WO | 2007131366 A1 | 11/2007 |
| WO | 2008016893 A1 | 2/2008 |
| WO | 2008045905 A1 | 4/2008 |
| WO | 2008079735 A1 | 7/2008 |
| WO | 2008128171 A2 | 10/2008 |
| WO | 2009155709 A1 | 12/2009 |
| WO | 2010142994 A1 | 12/2010 |
| WO | 2011002684 A1 | 1/2011 |
| WO | 2011098904 A1 | 8/2011 |
| WO | 2011143657 A1 | 11/2011 |
| WO | WO-201208027 A1 | 6/2012 |
| WO | 2012143726 A1 | 10/2012 |
| WO | 2013106643 A2 | 7/2013 |
| WO | 2013106646 A2 | 7/2013 |
| WO | 2014023708 A1 | 2/2014 |
| WO | WO-2014031487 A1 | 2/2014 |
| WO | 2014060770 A1 | 4/2014 |
| WO | 2014108452 A1 | 7/2014 |
| WO | 2014180524 A1 | 11/2014 |
| WO | 2015000867 A1 | 1/2015 |
| WO | 2015000868 A1 | 1/2015 |
| WO | 2015160845 A2 | 10/2015 |
| WO | 2016105518 A1 | 6/2016 |
| WO | 2016118666 A1 | 7/2016 |
| WO | 2016146985 A1 | 9/2016 |
| WO | 2016169989 A1 | 10/2016 |
| WO | 2016172134 A2 | 10/2016 |
| WO | 2016197032 A1 | 12/2016 |
| WO | 2016197114 A1 | 12/2016 |
| WO | 2017007612 A1 | 1/2017 |
| WO | 2017011371 A1 | 1/2017 |
| WO | 2017011590 A1 | 1/2017 |
| WO | 2017024318 A1 | 2/2017 |
| WO | 2017030814 A1 | 2/2017 |
| WO | 2017117473 A1 | 7/2017 |
| WO | 2017117474 A1 | 7/2017 |
| WO | 2017181061 A1 | 10/2017 |
| WO | 2017182418 A1 | 10/2017 |
| WO | 2017185036 A1 | 10/2017 |
| WO | 2017197036 A1 | 11/2017 |
| WO | 2017197046 A1 | 11/2017 |
| WO | 2017197051 A1 | 11/2017 |
| WO | 2017197055 A1 | 11/2017 |
| WO | 2017197056 A1 | 11/2017 |
| WO | 2017201449 A1 | 11/2017 |
| WO | 2017204445 A2 | 11/2017 |
| WO | WO-2017194390 A1 | 11/2017 |
| WO | 2017211924 A1 | 12/2017 |
| WO | 2018051107 A1 | 3/2018 |
| WO | 2018053354 A1 | 3/2018 |
| WO | 2018066545 A1 | 4/2018 |
| WO | 2018102067 A2 | 6/2018 |
| WO | 2018102725 A1 | 6/2018 |
| WO | 2018119357 A1 | 6/2018 |
| WO | 2018119441 A1 | 6/2018 |
| WO | 2018119448 A1 | 6/2018 |
| WO | 2018140809 A1 | 8/2018 |
| WO | 2018144649 A1 | 8/2018 |
| WO | 2018148443 A1 | 8/2018 |
| WO | 2018189554 A1 | 10/2018 |
| WO | 2018237026 A1 | 12/2018 |
| WO | 2019014429 A1 | 1/2019 |
| WO | 2019060742 A1 | 3/2019 |
| WO | 2019078522 A1 | 4/2019 |
| WO | 2019079357 A1 | 4/2019 |
| WO | 2019079701 A1 | 4/2019 |
| WO | 2019084026 A1 | 5/2019 |
| WO | 2019084030 A1 | 5/2019 |
| WO | 2019094718 A1 | 5/2019 |
| WO | 2019094772 A1 | 5/2019 |
| WO | 2019099926 A1 | 5/2019 |
| WO | 2019109415 A1 | 6/2019 |
| WO | 2019113071 A1 | 6/2019 |
| WO | 2019114770 A1 | 6/2019 |
| WO | 2019118893 A1 | 6/2019 |
| WO | 2019123367 A1 | 6/2019 |
| WO | 2019133531 A1 | 7/2019 |
| WO | 2019140003 A1 | 7/2019 |

OTHER PUBLICATIONS

Craig B. Thompson, "Apoptosis in the Pathogenesis and Treatment of Disease", Science, vol. 267, Mar. 10, 1995, pp. 1456-1462.

Craig M. Crews, "Targeting the Undruggable Proteome: The Small Molecules of My Dreams", Chemistry & Biology, 17, Jun. 25, 2010, pp. 551-555.

Daniel P Bondeson et al., "Catalytic in vivo protein knockdown by small-molecule PROTACs", HHS Public Access, Nat Chem Biol., 11(8), Aug. 2015, 23 pages.

Daniel P. Bondeson et al, "Lessons in PROTAC Design from Selective Degradation with a Promiscuous Warhead", Cell Chemical Biology, 25, Jan. 18, 2018, pp. 78-87, e1-e5, supplemental pages.

George M. Burslem et al., "The Advantages of Targeted Protein Degradation Over Inhibition: An RTK Case Study", Cell Chemical Biology, 25, 2018, pp. 67-77, e1-e3.

International Search Report dated Oct. 21, 2019 in PCT/JP2019/030083 (with English translation), 10 pages.

Jemilat Salami, et al, "Waste disposal—An attractive strategy for cancer therapy", Science, 355, 2017, pp. 1163-1167.

John S. Schneekloth Jr. et al, "Chemical Approaches to Controlling Intracellular Protein Degradation", Chembiochem, 6(1), Jan. 2005, 16 pages.

John S. Tokarski et al, "The Structure of Dasatinib (BMS-354825) Bound to Activated ABL Kinase Domain Elucidates Its Inhibitory Activity against Imatinib-Resistant ABL Mutants", Cancer Res, 66: (11), Jun. 1, 2006, pp. 5790-5797.

Kentaro Hashimoto et al., "Design and Synthesis of Potent Inhibitor of Apoptosis (IAP) Proteins Antagonists Bearing an Octahydropyrrolo[1,2-a]pyrazine Scaffold as a Novel Proline Mimetic", Journal of Medicinal Chemistry, 56, 2013, pp. 1228-1246.

Mazen W Karaman et al, "A quantitative analysis of kinase inhibitor selectivity", Nature Biotechnology, vol. 26, No. 1, Jan. 2008, pp. 127-132.

(56) References Cited

OTHER PUBLICATIONS

Moriteru Asano et al, "Design, stereoselective synthesis, and biological evaluation of novel tri-cyclic compounds as inhibitor of apoptosis proteins (IAP) antagonists", Bioorganic & Medicinal Chemistry, 21, 2013, pp. 5725-5737.
Petra Obexer et al, "X-linked inhibitor of apoptosis protein—a critical death resistance regulator and therapeutic target for personalized cancer therapy", Frontiers in Oncology, vol. 4, Article 197, Jul. 28, 2014, pp. 1-9.
Philipp M. Cromm et al, "Targeted Protein Degradation: from Chemical Biology to Drug Discovery", Cell Chemical Biology, 24, Sep. 21, 2017, pp. 1181-1190.
Philipp Ottis et al, "Proteolysis-Targeting Chimeras: Induced Protein Degradation as a Therapeutic Strategy", ACS Chemical Biology, 12, 2017, 892-898.
Uwe Rix et al, "Chemical proteomic profiles of the BCR-ABL inhibitors imatinib, nilotinib, and dasatinib reveal novel kinase and nonkinase targets", Blood, vol. 110, No. 12, Dec. 1, 2007, pp. 4055-4063.
Extended European Search Report dated Mar. 21, 2022 in Application No. 19843599.2, 11 pages.
Norihito Shibata et al., "Development of protein degradation inducers of oncogenic BCR-ABL protein by conjugation of ABL kinase inhibitors and IAP ligands", Cancer Science, vol. 108, No. 8, Jun. 19, 2017, pp. 1657-1666.

\* cited by examiner

HETEROCYCLIC COMPOUND

TECHNICAL FIELD

The present invention relates to a novel heterocyclic compound and its use.

BACKGROUND ART

Development of compounds that induce ubiquitination of target proteins and proteasome degradation by E3 ligase (referred to as Proteolysis Targeting Chimeras (PROTAC (registered trademark) or Specific and Nongenetic IAP-dependent Protein Eraser (SNIPER) and the like in some cases) has been attempted for the purpose of treatment by reducing disease-related proteins (Non-Patent Documents 1 to 9). For example, SFC ligand, VHL ligand, CRBN ligand, IAP ligand, MDM2 ligand and the like are used in this application as a ligand that binds to E3 ligase, and compounds for which target protein is Met-AP2, ER, AR, BRD4, TKB1, ERRα, cMyc, BET, FKBP, RIPK2, BTK, PLK1, JNK, EZH2, HER3, EGFR, ABL, JAK2, IRAK3, GAK, TEC, AURKA, JNK2, AKT2, BCL2, MCl-1, Ras, ABL, PDE4, ALK, B-Raf, RTK, Tau, FLT3, VHL, TNIK, ASH1L, SALL4, IRAK4, HMGCR, GR, MDM2, TBK or the like are suggested (Patent Documents 1 to 98).

Apoptosis inhibitory factors (Inhibitor of Apoptosis Protein, IAP) are a group of proteins that suppress apoptosis by directly binding to caspase and suppressing its function. IAPs have been identified as proteins having the Baculovirus IAP repeat (BIR) domain(s) as the common structure, and there are reports on XIAP, cIAP1, cIAP2, ML-IAP, ILP-2 and the like. Most of these are known as ubiquitin E3 ligases with a RING finger motif (Non-Patent Documents 10). For example, Human X-linked IAP (XIAP) inhibits activation of caspase 3, 7 and caspase 9 via Apaf-1-cytochrome C. Caspases 3 and 7 are inhibited by the BIR2 domain of XIAP, and the BIR3 domain is involved in inhibiting caspase 9 activity.

Apoptosis or controlled and regulated cell suicide (programmed cell death) plays an important role in the development and homeostasis of living organisms, and disruption of apoptotic (cell death) signals is closely related to various diseases such as cancers, autoimmune diseases, neurodegenerative diseases, inflammatory diseases and the like (Non-Patent Documents 11). An important factor in apoptosis (cell death) is caspase, which is a serine protease, and is involved in various proteolytic degradations as an execution factor of apoptosis. In many cancers, apoptosis (cell death) resistance is acquired by suppressing caspase function via various signal molecules, and the cancers survive and proliferate.

Expression of IAP is upregulated in many kinds of cancers, and it has been reported to be positively correlated with cancer malignancy and poor prognosis. In contrast, it has been clarified that Smac (DIABLO) which is a protein released from mitochondria by various cell death signals and inducing apoptosis (cell death) binds to the BIR domain of the IAP protein to release caspase suppression and induces strong apoptosis (cell death), and various IAP inhibitors have been reported (Patent Documents 99 to 117).

In addition, based on the relationship between protein kinases and various diseases, GSK3 inhibitor (Patent Documents 118 and 119), GCN2 inhibitor (Patent Document 120), BRD inhibitors (Patent Document 121), and multikinase inhibitors for ABL, BCR-ABL, SRC, KIT, DDR, TEC, EPH-A2, PDGFR and the like (Non-patent Documents 12 to 14) have been reported.

Therefore, IAP inhibitors and, small molecules that bind to E3 ligase to induce the degradation of target proteins (GSK3, GCN2, BRD, ABL, BCR-ABL, SRC, KIT, DDR, TEC, EPH-A2, PDGFR, XIAP, etc.), can be promising therapeutic agents that reduce disease-related proteins.

Patent Documents 122 to 124 report heterocyclic compounds that are K opioid receptor agonists.

Patent Documents 48 to 59, 81 and 94 report compounds as targeted protein degraders using IAP ligands.

Patent Documents 29 to 48, 68, 73, 74, 77, 82, 83, 90, 96 and 98 report compounds that induce degradation of BRD4.

Patent Documents 21, 40, 41, 43, 48 and 61 report compounds that induce degradation of ABL.

Patent Documents 99 to 117 report compounds as IAP antagonists.

CITATION LIST

Patent Document

Patent Document 1: US2002/0068063 A1
Patent Document 2: US2004/0038358 A1
Patent Document 3: WO2013/106643
Patent Document 4: WO2013/106646
Patent Document 5: WO2014/108452
Patent Document 6: WO2015/000867
Patent Document 7: WO2015/000868
Patent Document 8: US2015/0291562 A1
Patent Document 9: US2016/0045607 A1
Patent Document 10: WO2016/118666
Patent Document 11: WO2016/197114
Patent Document 12: WO2016/172134
Patent Document 13: CN106749513 A
Patent Document 14: WO2017/117473
Patent Document 15: WO2017/117474
Patent Document 16: WO2017/185036
Patent Document 17: WO2017/181061
Patent Document 18: WO2017/204445
Patent Document 19: CN107382862 A
Patent Document 20: CN107540608 A
Patent Document 21: US2017/0121321 A1
Patent Document 22: WO2018/053354
Patent Document 23: WO2018/102725
Patent Document 24: WO2018/102067
Patent Document 25: US2018/0072711 A1
Patent Document 26: US2018/0099940 A1
Patent Document 27: US2018/0134684 A1
Patent Document 28: US2018/0155322 A1
Patent Document 29: WO2015/160845
Patent Document 30: WO2016/105518
Patent Document 31: WO2016/146985
Patent Document 32: WO2016/197032
Patent Document 33: CN106977584 A
Patent Document 34: US2017/0008904 A1
Patent Document 35: WO2017/024318
Patent Document 36: WO2017/007612
Patent Document 37: WO2017/011371
Patent Document 38: WO2017/030814
Patent Document 39: WO2017/197056
Patent Document 40: WO2017/197055
Patent Document 41: WO2017/197051
Patent Document 42: WO2017/197046
Patent Document 43: WO2017/197036
Patent Document 44: US2017/0065719 A1
Patent Document 45: WO2018/051107
Patent Document 46: US2018/0134684 A1
Patent Document 47: US2018/0169109 A1

Patent Document 48: WO2018/066545
Patent Document 49: Japanese Unexamined Patent Application Publication No. 2013-056837
Patent Document 50: WO2016/169989
Patent Document 51: WO2016/172134
Patent Document 52: WO2017/011590
Patent Document 53: WO2017/182418
Patent Document 54: WO2017/201449
Patent Document 55: WO2017/211924
Patent Document 56: US2018/0118733 A1
Patent Document 57: US2018/0134688 A1
Patent Document 58: WO2018/119448
Patent Document 59: WO2018/119357
Patent Document 60: WO2018/119441
Patent Document 61: US2018/0186785 A1
Patent Document 62: US2018/0179522 A1
Patent Document 63: US2018/0179183 A1
Patent Document 64: US2018/0193470 A1
Patent Document 65: US2018/0215731 A1
Patent Document 66: WO2018/140809
Patent Document 67: US2018/0228907 A1
Patent Document 68: WO2018/144649
Patent Document 69: WO2018/148443
Patent Document 70: US2018/0237418 A1
Patent Document 71: US2018/0256586 A1
Patent Document 72: WO2018/189554
Patent Document 73: US2018/0327419 A1
Patent Document 74: WO2018/237026
Patent Document 75: WO2019/014429
Patent Document 76: US2019/0062281 A1
Patent Document 77: WO2019/079701
Patent Document 78: WO2019/079357
Patent Document 79: WO2019/078522
Patent Document 80: US2019/0119358 A1
Patent Document 81: US2019/0119271 A1
Patent Document 82: WO2019/084030
Patent Document 83: WO2019/084026
Patent Document 84: US2019/0127359 A1
Patent Document 85: WO2019/094772
Patent Document 86: WO2019/094718
Patent Document 87: WO2019/099926
Patent Document 88: WO2019/113071
Patent Document 89: WO2019/109415
Patent Document 90: US2019/0151457 A1
Patent Document 91: WO2019/114770
Patent Document 92: WO2019/118893
Patent Document 93: WO2019/123367
Patent Document 94: US2019/0175612 A1
Patent Document 95: US2019/0192514 A1
Patent Document 96: WO2019/060742
Patent Document 97: WO2019/133531
Patent Document 98: WO2019/140003
Patent Document 99: WO2006/113376
Patent Document 100: WO2007/104162
Patent Document 101: WO2007/106192
Patent Document 102: WO2007/131366
Patent Document 103: US2007/0093428 A1
Patent Document 104: WO2008/016893
Patent Document 105: WO2008/045905
Patent Document 106: WO2008/079735
Patent Document 107: WO2008/128171
Patent Document 108: WO2010/142994
Patent Document 109: WO2011/002684
Patent Document 110: WO2011/098904
Patent Document 111: WO2012/143726
Patent Document 112: Japanese Unexamined Patent Application Publication No. 2012-106958
Patent Document 113: Japanese Unexamined Patent Application Publication No. 2012-176934
Patent Document 114: US2013/0172264 A1
Patent Document 115: US2014/0135270 A1
Patent Document 116: WO2014/023708
Patent Document 117: WO2014/060770
Patent Document 118: WO2006/075023
Patent Document 119: WO2006/091737
Patent Document 120: WO2014/180524
Patent Document 121: WO2011/143657
Patent Document 122: US2009/0156508 A1
Patent Document 123: US2010/0075910 A1
Patent Document 124: US2011/0212882 A1

Non-Patent Document

Non-Patent Document 1: Science. 2017 Mar. 17; 355(6330) 1163-1 167.
Non-Patent Document 2: Cell Chem Biol. 2018 Jan. 18; 25(1):67-7 7.e3.
Non-Patent Document 3: Cell Chem. Biol. 2017 Sep. 21; 24(9) 118 1-1190.
Non-Patent Document 4: ACS Chem Biol. 2017 Apr. 21; 12(4):892-8 98.
Non-Patent Document 5: Cell Chem Biol. 2018 Jan. 18; 25(1):78-8 7.e5.
Non-Patent Document 6: Nat Rev Drug Discov. 2017 February; 16(2):10 1-114.
Non-Patent Document 7: Nat Chem Biol. 2015 August; 11(8):611-7.
Non-Patent Document 8: Chemistry & Biology, 2010, 17(6): 551-555
Non-Patent Document 9: Chembiochem, 2005, 6(1):40-46
Non-Patent Document 10: Front Oncol. 2014 Jul. 28; 4:197.
Non-Patent Document 11: Science. 1995 Mar. 10; 267 (5203):1456-62.
Non-Patent Document 12: Cancer Res. 2006 Jun. 1; 66(11): 5790-7
Non-Patent Document 13: Blood. 2007 Dec. 1; 110(12): 4055-63.
Non-Patent Document 14: Nat Biotechnol. 2008 January; 26(1):127-32.

SUMMARY OF THE INVENTION

Technical Problem

The present invention has an object of providing a novel compound that binds to a target protein to provide a biologically useful activity.

Solution to Problem

Compounds which are excellent in drug efficacy onset, pharmacokinetics, solubilities, interactions with other drugs, safeties (toxicity), stabilities and the like and bind to a target protein to provide a biologically useful activity, for example, targeted protein degraders, can be expected to have excellent therapeutic effects. Hence, the present inventors have intensively studied to find a compound excellent in at least one of the above aspects, preferably, targeted protein degraders, and resultantly found that compounds represented by the following formula provides an excellent IAP binding (inhibiting) activity or bind to another target protein and IAP (including cases where another target protein is other IAPs) to provide a biologically useful activity, leading to completion of the present invention.

The present invention is below.

[1] A compound represented by the following formula (I):

[chemical formula 1]

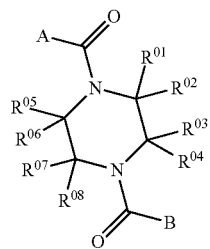

(I)

wherein A represents a fragment structure of a substance that binds to IAP(s), B represents a substituent, or a nitrogen-containing aromatic heterocyclic group to which a compound having function or an antibody may bind via a linker, and $R^{01}$, $R^{02}$, $R^{03}$, $R^{04}$, $R^{05}$, $R^{06}$, $R^{07}$ and $R^{08}$ each independently represent a hydrogen atom or a C1-6 alkyl group which may form a ring with each other or a salt thereof (in the present specification, referred to as "compound (I)" in some cases).

[2] A compound represented by the following formula (I):

[chemical formula 2]

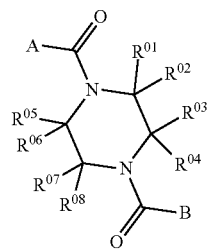

(I)

wherein $R^{01}$, $R^{02}$, $R^{03}$, $R^{04}$, $R^{05}$, $R^{06}$, $R^{07}$ and $R^{08}$ each independently represent a hydrogen atom or a C1-6 alkyl group which may form a ring with each other;

"A" represents a group represented by the formula (AI)

[chemical formula 3]

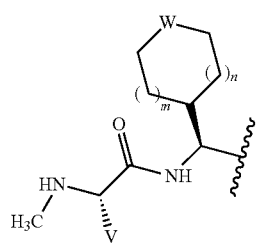

(AI)

wherein m represents 0 to 2; n represents 0 to 2; V represents an optionally halogenated C1-3 alkyl group; W represents a methylene group, a difluoromethylene group, O, S, SO, $SO_2$, NR (wherein R represents a hydrogen atom, a C1-6 alkyl group, a C1-6 alkyl-carbonyl group, a C6-14 aryl-carbonyl group or a C1-6 alkylsulfonyl group), an imino group, or the formula (L1): $N-L^{11}-L^{12}-L^{13}-L^{14}-L^{15}-L^{16}-L^{17}-R^1$ wherein $L^{11}$, $L^{12}$, $L^{13}$, $L^{14}$, $L^{15}$, $L^{16}$ and $L^{17}$ each independently represent a bond, an oxygen atom, a sulfur atom, a C1-6 alkylene group, a C3-10 cycloalkylene group, a carbonyl group, an imino group optionally substituted with a C1-6 alkyl group, an ethynylene group, a vinylene group optionally substituted with a C1-6 alkyl group, a C3-10 cycloalkenylene group, a phenylene group, a thiazolilene group, a pyrrolidinylene group optionally substituted with a fluorine atom, an azetidinylene group optionally substituted with a fluorine atom, the formula —$SO_2$—, the formula —$CH_2CH_2O$—, the formula —$OCH_2CH_2$—, the formula —$COCH_2$—, the formula —$CH_2CO$—, the formula —$CO_2$—, the formula —OCO—, the formula —$COCHR^{101}NR^{102}$—, the formula —$OCH_2CHR^{103}NR^{104}$—, the formula —$NR^{105}CHR^{106}CO$—, the formula —$NR^{107}CO$—, the formula —$CONR^{108}$—, the formula —$SO_2NR^{109}$—, the formula —$NR^{110}SO_2$— or the formula —$NR^{111}CHR^{112}CH_2O$— wherein $R^{101}$, $R^{103}$, $R^{106}$ and $R^{112}$ each independently represent a hydrogen atom, a C1-6 alkyl group, a 3-guanidinopropyl group, a carbamoylmethyl group, a carboxymethyl group, a mercaptomethyl group, a 2-carbamoylethyl group, a 2-carboxyethyl group, an imidazole-4-ylmethyl group, a 4-aminobutyl group, a 2-methylthioethyl group, a benzyl group, a hydroxymethyl group, a 1-hydroxyethyl group, an indol-3-ylmethyl group, a 4-hydroxyphenylmethyl group or a pyridylmethyl group; and, $R^{102}$, $R^{104}$, $R^{105}$, $R^{107}$, $R^{108}$, $R^{109}$, $R^{110}$ and $R^{111}$ each independently represent a hydrogen atom or a C1-6 alkyl group; and $R^1$ represents a hydrogen atom, a methyl group, a benzyl group, a t-butoxycarbonyl group, a benzyloxycarbonyl group, a 9-fluorenylmethyloxycarbonyl group, an azide group, a group represented by the formula (II) as a ligand of GSK3α/β and GCN2

[chemical formula 4]

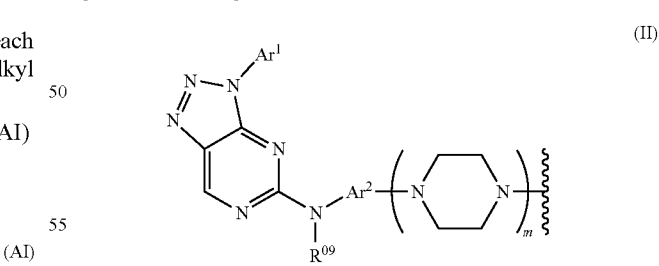

(II)

wherein $Ar^1$ represents an optionally substituted C6-14 aryl group or an optionally substituted aromatic heterocyclic group; $Ar^2$ represents a divalent group derived from an optionally substituted C6-14 aryl group or an optionally substituted aromatic heterocyclic group; m represents any integer of 0 to 1; $R^{09}$ represents a hydrogen atom or a C1-3 alkyl group, a group represented by the formula (III) as a ligand of BRD,

[chemical formula 5]

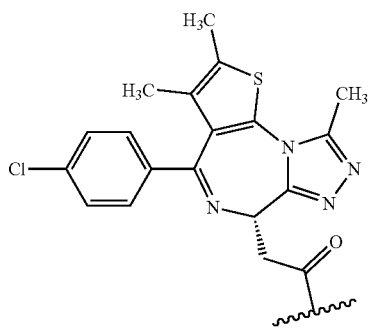

(III)

a group represented by the formula (IV) as a ligand of ABL, BCR-ABL, SRC, KIT, DDR, TEC, EPH-A2, PDGFR and the like,

[chemical formula 6]

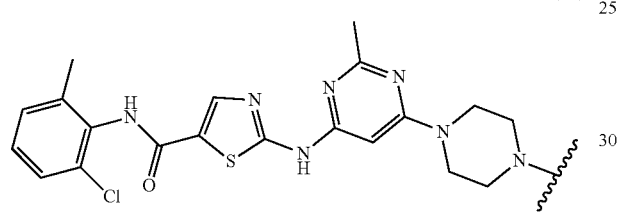

(IV)

or a compound of Smac peptide mimetics as a ligand of XIAP, or a group represented by the formula (AII)

[chemical formula 7]

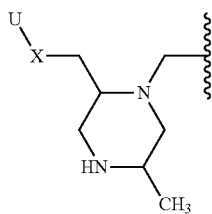

(AII)

wherein X represents an oxygen atom or the formula —$NR^{21}$— wherein $R^{21}$ represents a hydrogen atom or a C1-6 alkyl group; U represents a hydrogen atom, a C1-6 alkyl group, or the formula (L2): —$(CH_2)_n$—Y-$L^{21}$-$L^{22}$-$L^{23}$-$L^{24}$-$L^{25}$-$L^{26}$-$L^{27}$-$R^2$ wherein n represents any integer of 0 to 3; Y represents an oxygen atom or the formula —$NR^{22}$— wherein $R^{22}$ represents a hydrogen atom or a C1-6 alkyl group, and may form a ring together with $R^{21}$ described above; $L^{21}$, $L^{22}$, $L^{23}$, $L^{24}$, $L^{25}$, $L^{26}$ and $L^{27}$ each independently represent a bond, an oxygen atom, a sulfur atom, a C1-6 alkylene group which may form a ring together with $R^{21}$, a C3-10 cycloalkylene group, a carbonyl group, an imino group optionally substituted with a C1-6 alkyl group, an ethynylene group, a vinylene group optionally substituted with a C1-6 alkyl group, a C3-10 cycloalkenylene group, a phenylene group, a thiazolilene group, a pyrrolidinylene group optionally substituted with a fluorine atom, an azetidinylene group optionally substituted with a fluorine atom, the formula —$SO_2$—, the formula —$CH_2CH_2O$—, the formula —$OCH_2CH_2$—, the formula —$COCH_2$—, the formula —$CH_2CO$—, the formula —$CO_2$—, the formula —OCO—, the formula —$COCHR^{201}NR^{202}$—, the formula —$OCH_2CHR^{203}NR^{204}$—, the formula —$NR^{205}CHR^{206}CO$—, the formula —$NR^{207}CO$—, the formula —$CONR^{208}$—, the formula —$SO_2NR^{209}$—, the formula —$NR^{210}SO_2$— or the formula —$NR^{211}CHR^{212}CH_2O$— wherein $R^{201}$, $R^{203}$, $R^{206}$ and $R^{212}$ each independently represent a hydrogen atom, a C1-6 alkyl group, a 3-guanidinopropyl group, a carbamoylmethyl group, a carboxymethyl group, a mercaptomethyl group, a 2-carbamoylethyl group, a 2-carboxyethyl group, an imidazole-4-ylmethyl group, a 4-aminobutyl group, a 2-methylthioethyl group, a benzyl group, a hydroxymethyl group, a 1-hydroxyethyl group, an indol-3-ylmethyl group, a 4-hydroxyphenylmethyl group or a pyridylmethyl group, and $R^{202}$, $R^{204}$, $R^{205}$, $R^{207}$, $R^{208}$, $R^{209}$, $R^{210}$ and $R^{211}$ each independently represent a hydrogen atom or a C1-6 alkyl group; and $R^2$ represents a hydrogen atom, a methyl group, a benzyl group, a t-butoxycarbonyl group, a benzyloxycarbonyl group, a 9-fluorenylmethyloxycarbonyl group, an azide group, a group represented by the formula (II) as a ligand of GSK3α/β and GCN2

[chemical formula 8]

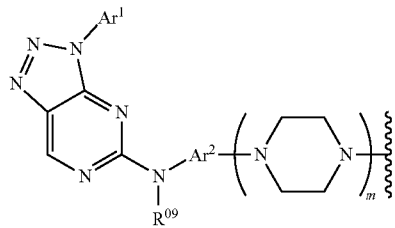

(II)

wherein $Ar^1$ represents an optionally substituted C6-14 aryl group or an optionally substituted aromatic heterocyclic group; $Ar^2$ represents a divalent group derived from an optionally substituted C6-14 aryl group or an optionally substituted aromatic heterocyclic group; m represents any integer of 0 to 1; $R^{09}$ represents a hydrogen atom or a C1-3 alkyl group, a group represented by the formula (III) as a ligand of BRD,

[chemical formula 9]

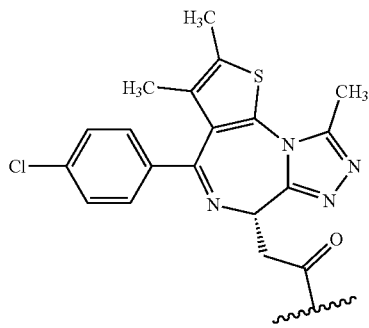

(III)

a group represented by the formula (IV) as a ligand of ABL, BCR-ABL, SRC, KIT, DDR, TEC, EPH-A2, PDGFR and the like,

[chemical formula 10]

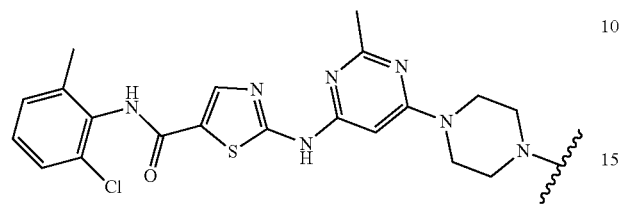

(IV)

or a compound of Smac peptide mimetics as a ligand of XIAP;

B represents "a pyrazolyl group, an indolyl group, an indazolyl group, a benzoimidazoyl group, a 7-azaindolyl group, an indolidinyl group, a 1-azaindolidinyl group, a 3-azaindolidinyl group or a 1,3-diazaindolidinyl group" optionally substituted with any of a halogen atom, a C3-10 cycloalkyl group, an optionally halogenated C1-6 alkyl group, a C1-6 alkoxy group, a C1-6 alkoxy group substituted with a C1-6 alkoxy group, or a vinyl group substituted with a C1-6 alkoxy-carbonyl group, or the following formula (B'):

[chemical formula 11]

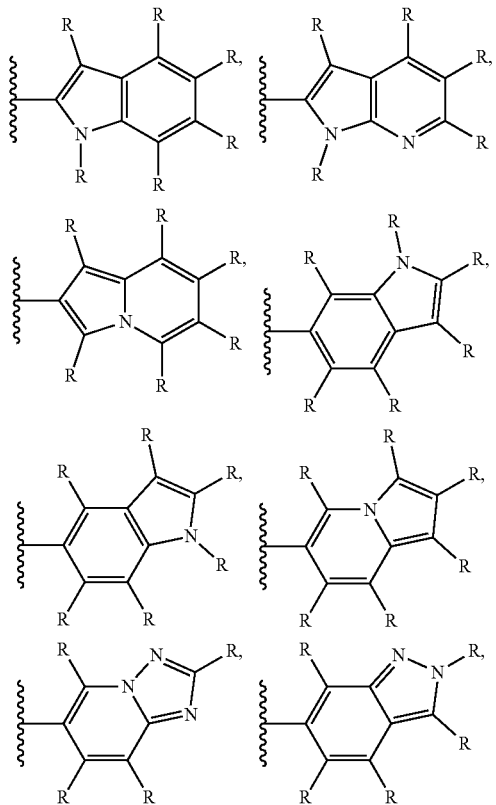

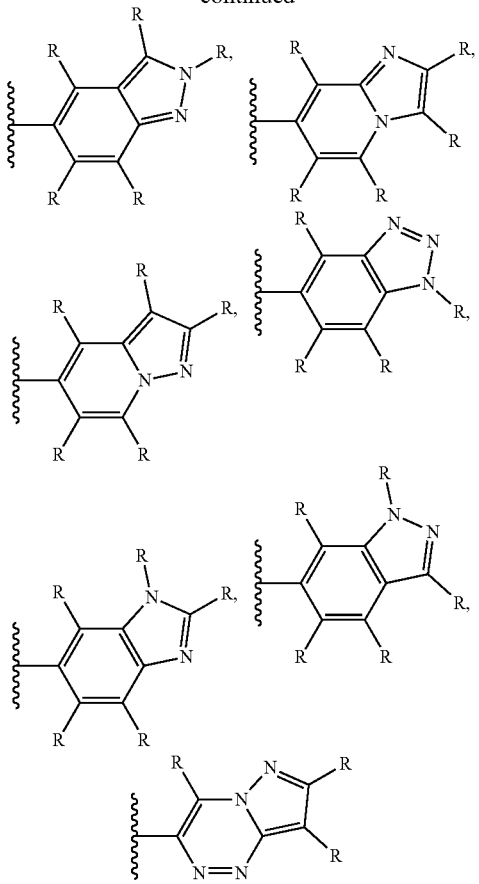

wherein R each independently represents a hydrogen atom, a halogen atom, a C1-6 alkyl group, a C1-6 alkoxy group, or the formula (L3): $-Z-L^{31}-L^{32}-L^{33}-L^{34}-L^{35}-L^{36}-L^{37}-R^3$ wherein Z represents an oxygen atom, a carbonyl group, a C1-6 alkylene group, a C3-10 cycloalkylene group, the formula $-NR^{31}-$, the formula $-CONR^{32}-$, the formula $-NR^{33}CO-$, the formula $-SO_2NR^{34}-$ or the formula $-NR^{35}SO_2-$ wherein $R^{31}$, $R^{32}$, $R^{33}$, $R^{34}$ and $R^{35}$ each independently represent a hydrogen atom or a C1-6 alkyl group; $L^{31}$, $L^{32}$, $L^{33}$, $L^{34}$, $L^{35}$, $L^{36}$ and $L^{37}$ each independently represent a bond, an oxygen atom, a sulfur atom, a C1-6 alkylene group, a C3-10 cycloalkylene group, a carbonyl group, an imino group optionally substituted with a C1-6 alkyl group, an ethynylene group, a vinylene group optionally substituted with a C1-6 alkyl group, a C3-10 cycloalkenylene group, a phenylene group, a thiazolilene group, a pyrrolidinylene group optionally substituted with a fluorine atom, an azetidinylene group optionally substituted with a fluorine atom, the formula $-SO_2-$, the formula $-CH_2CH_2O-$, the formula $-OCH_2CH_2-$, the formula $-COCH_2-$, the formula $-CH_2CO-$, the formula $-CO_2-$, the formula $-OCO-$, the formula $-COCHR^{301}NR^{302}-$, the formula $-OCH_2CHR^{303}NR^{304}-$, the formula $-NR^{305}CHR^{306}CO-$, the formula $-NR^{307}CO-$, the formula $-CONR^{308}-$, the formula $-SO_2NR^{309}-$, the formula $-NR^{310}SO_2-$ or the formula $-NR^{311}CHR^{312}CH_2O-$ wherein $R^{301}$, $R^{303}$, $R^{306}$ and $R^{312}$ each independently represent a hydrogen atom, a C1-6 alkyl group, a 3-guanidinopropyl group, a carbamoylmethyl group, a carboxymethyl group, a mercaptomethyl group, a 2-carbamoylethyl group, a 2-carboxyethyl group, an imidazole-4-ylmethyl group, a 4-aminobutyl group, a 2-methylthioethyl group, a benzyl group, a hydroxymethyl group, a 1-hydroxyethyl group, an indol-3-ylmethyl group, a 4-hydroxyphenylmethyl group or a pyridylmethyl group, and, $R^{302}$, $R^{304}$, $R^{305}$, $R^{307}$, $R^{308}$, $R^{309}$, $R^{310}$ and $R^{311}$ each independently represent a hydrogen atom or a C1-6 alkyl group; and $R^3$ represents a hydrogen atom, a methyl group, a benzyl group, a t-butoxycarbonyl group, a benzyloxycarbonyl group, a 9-fluorenylmethyloxycarbonyl group, an azide group, a group represented by the formula (II) as a ligand of GSK3α/β and GCN2,

[chemical formula 12]

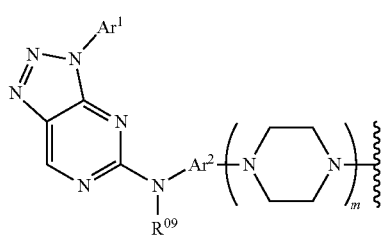

(II)

wherein $Ar^1$ represents an optionally substituted C6-14 aryl group or an optionally substituted aromatic heterocyclic group; $Ar^2$ represents a divalent group derived from an optionally substituted C6-14 aryl group or an optionally substituted aromatic heterocyclic group; m represents any integer of 0 to 1; and $R^{09}$ represents a hydrogen atom or a C1-3 alkyl group, a group represented by the formula (III) as a ligand of BRD,

[chemical formula 13]

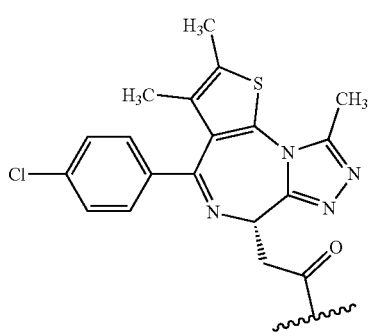

(III)

a group represented by the formula (IV) as a ligand of ABL, BCR-ABL, SRC, KIT, DDR, TEC, EPH-A2, PDGFR and the like,

[chemical formula 14]

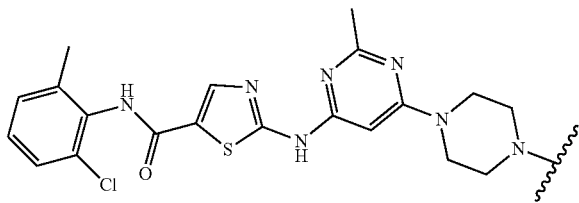

(IV)

or a compound of Smac peptide mimetics as a ligand of XIAP, wherein when R binds to N, R is not a halogen atom or a C1-6 alkoxy group, and two or more groups R are not simultaneously represented by the formula (L3), or a salt thereof.

[3] The compound or salt thereof according to the above [2], wherein A is represented by the formula (AI-1)

[chemical formula 15]

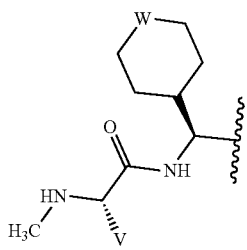

(AI-1)

wherein V represents an optionally halogenated C1-3 alkyl group; W represents a methylene group, a difluoromethylene group, O, S, SO, $SO_2$, NR (wherein R represents a hydrogen atom, a C1-6 alkyl group, a C1-6 alkyl-carbonyl group, a C6-14 aryl-carbonyl group or a C1-6 alkylsulfonyl group), an imino group, or the formula (L1): N-$L^{11}$-$L^{12}$-$L^{13}$-$L^{14}$-$L^{15}$-$L^{16}$-$L^{17}$-$R^1$ wherein $L^{11}$, $L^{12}$, $L^{13}$, $L^{14}$, $L^{15}$, $L^{16}$, $L^{17}$ and $R^1$ represent the same definition as described above.

[4] The compound or salt thereof according to the above [2] or [3], wherein B is represented by the formula (B-1)

[chemical formula 16]

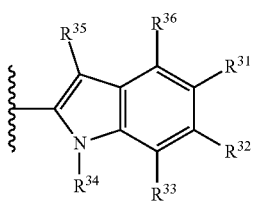

(B-1)

wherein $R^{31}$, $R^{32}$ and $R^{33}$ each independently represent a hydrogen atom, a halogen atom, a C1-6 alkyl group or a C1-6 alkoxy group; $R^{35}$ and $R^{36}$ each independently represent a hydrogen atom, a halogen atom, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above; $R^{34}$ represents a hydrogen atom, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above, wherein two or more of $R^{34}$, $R^{35}$ and $R^{36}$ are not simultaneously represented by the formula (L3).

[5] The compound or salt thereof according to the above [2] or [3], wherein B is represented by the formula (B-2)

[chemical formula 17]

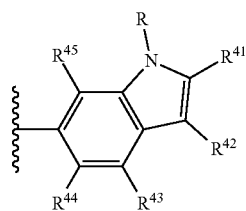

(B-2)

wherein $R^{41}$, $R^{42}$, $R^{43}$, $R^{44}$ and $R^{45}$ each independently represent a hydrogen atom, a halogen atom, a C1-6 alkyl group or a C1-6 alkoxy group; R represents a hydrogen atom or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above.

[6] The compound or salt thereof according to the above [2], wherein A is represented by the formula (AI)

[chemical formula 18]

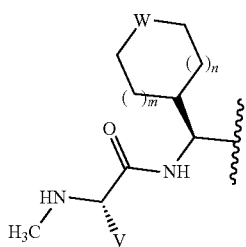

(AI)

wherein m represents 0 to 2; n represents 0 to 2; V represents an optionally halogenated C1-3 alkyl group; W represents a group represented by the formula (L1): N-$L^{11}$-$L^{12}$-$L^{13}$-$L^{14}$-$L^{15}$-$L^{16}$-$L^{17}$-$R^1$ wherein $L^{11}$, $L^{12}$, $L^{13}$, $L^{14}$, $L^{15}$, $L^{16}$ and $L^{17}$ have the same definition as above, and $R^1$ represents a group represented by the formula (II) as a ligand of GSK3α/β and GCN2,

[chemical formula 19]

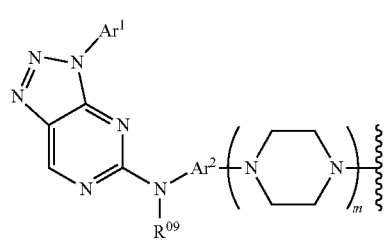

(II)

wherein the definition is the same as above, a group represented by the formula (III) as a ligand of BRD,

[chemical formula 20]

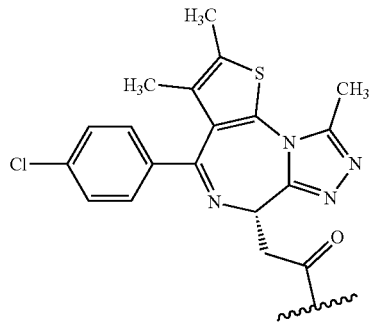

(III)

a group represented by the formula (IV) as a ligand of ABL, BCR-ABL, SRC, KIT, DDR, TEC, EPH-A2, PDGFR and the like,

[chemical formula 21]

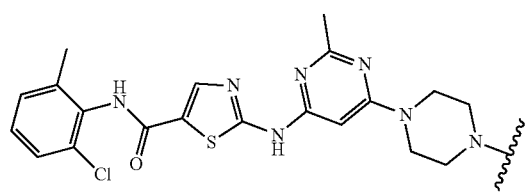

(IV)

wherein the definition is the same as above, or a compound of Smac peptide mimetics as a ligand of XIAP, or the formula (AII)

[chemical formula 22]

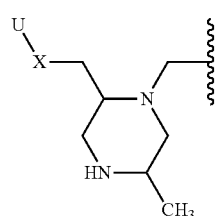

(AII)

wherein X represents an oxygen atom or the formula —$NR^{21}$— wherein $R^{21}$ represents a hydrogen atom or a C1-6 alkyl group; U represents a group represented by the formula ($L^2$): —$(CH_2)_n$—Y-$L^{21}$-$L^{22}$-$L^{23}$-$L^{24}$-$L^{25}$-$L^{26}$-$L^{27}$-$R^2$ wherein Y, $L^{21}$, $L^{22}$, $L^{23}$, $L^{24}$, $L^{25}$, $L^{26}$ and $L^{27}$ have the same definition as above, and $R^2$ represents a group represented by the formula (II) as a ligand of GSK3α/β and GCN2

[chemical formula 23]

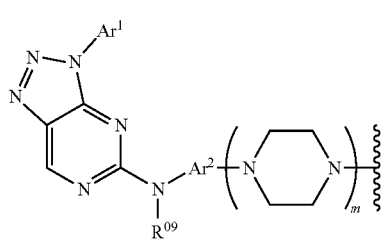
(II)

wherein the definition is the same as above, a group represented by the formula (III) as a ligand of BRD,

[chemical formula 24]

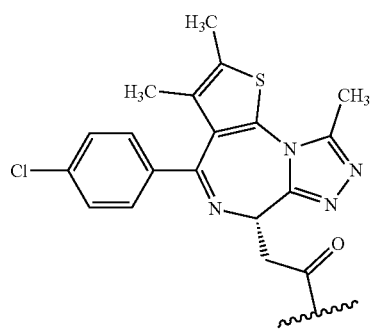
(III)

a group represented by the formula (IV) as a ligand of ABL, BCR-ABL, SRC, KIT, DDR, TEC, EPH-A2, PDGFR and the like,

[chemical formula 25]

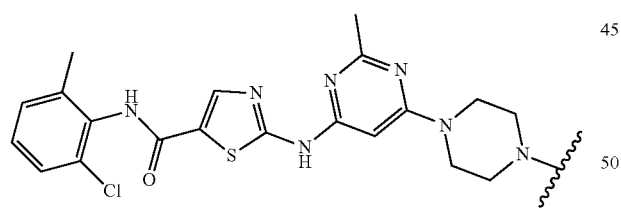
(IV)

wherein the definition is the same as above, or a compound of Smac peptide mimetics as a ligand of XIAP, B represents "a pyrazolyl group, an indolyl group, an indazolyl group, a benzoimidazoyl group, a 7-azaindolyl group, an indolidinyl group, a 1-azaindolizinyl group, a 3-azaindolizinyl group or a 1,3-diazaindolizinyl group" optionally substituted with any of a halogen atom, a C3-10 cycloalkyl group, an optionally halogenated C1-6 alkyl group, a C1-6 alkoxy group, a C1-6 alkoxy group substituted with a C1-6 alkoxy group, or a vinyl group substituted with a C1-6 alkoxy-carbonyl group, or represented by the formula (B')

[chemical formula 26]

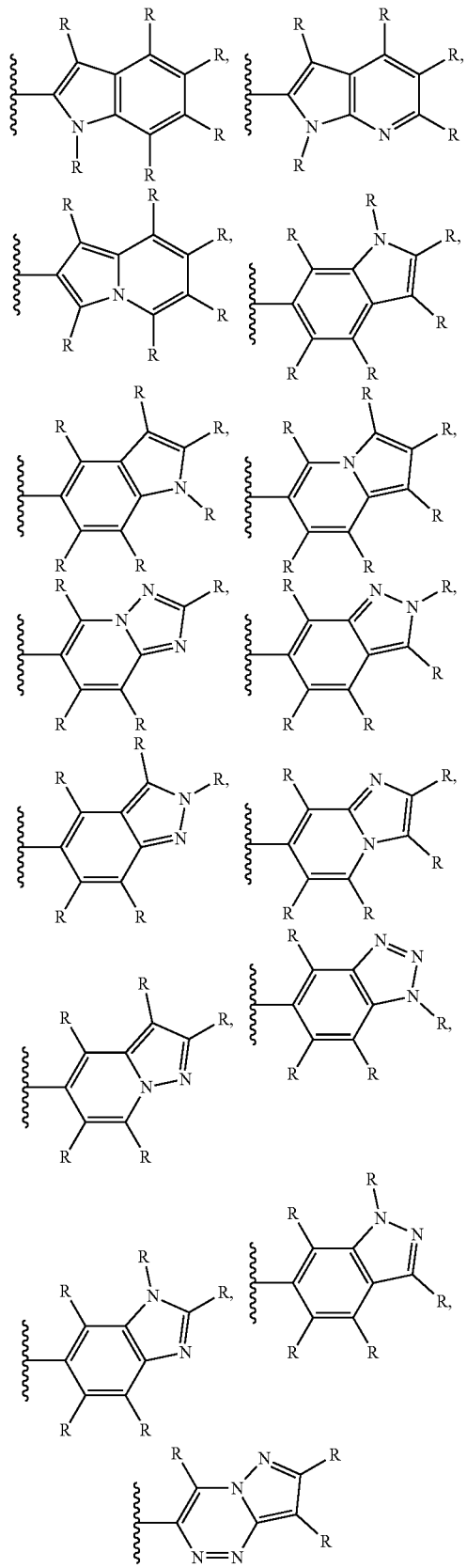

wherein groups R bonded to N each independently represent a hydrogen atom, a C1-6 alkyl group or an amide group; and other groups R each independently represent a hydrogen atom, a halogen atom, a C1-6 alkyl group, a C1-6 alkoxy group or an amide group.

[7] The compound or salt thereof according to the above [2], wherein A is a group represented by the formula (AI)

[chemical formula 27]

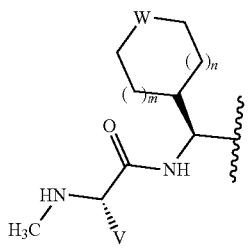

(AI)

wherein m represents 0 to 2; n represents 0 to 2; V represents an optionally halogenated C1-3 alkyl group; and W represents a methylene group, a difluoromethylene group, O, S, SO, $SO_2$, NR wherein R represents a hydrogen atom, a C1-6 alkyl group, a C1-6 alkyl-carbonyl group, a C6-14 aryl-carbonyl group or a C1-6 alkylsulfonyl group, or an imino group, or the formula (AII)

[chemical formula 28]

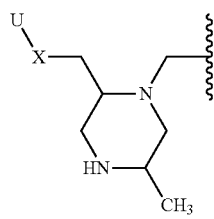

(AII)

wherein X represents an oxygen atom or the formula —$NR^{21}$— wherein $R^{21}$ represents a hydrogen atom or a C1-6 alkyl group; U represents a hydrogen atom or a C1-6 alkyl group, and
B represents a group represented by the following formula (B'):

[chemical formula 29]

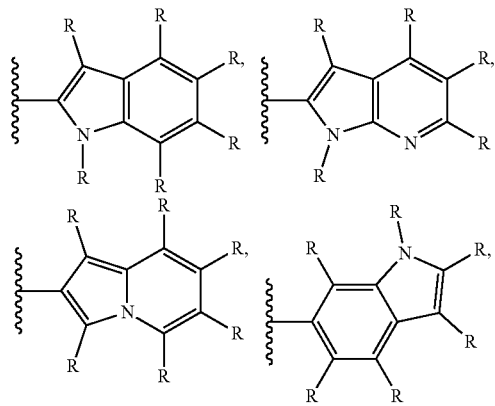

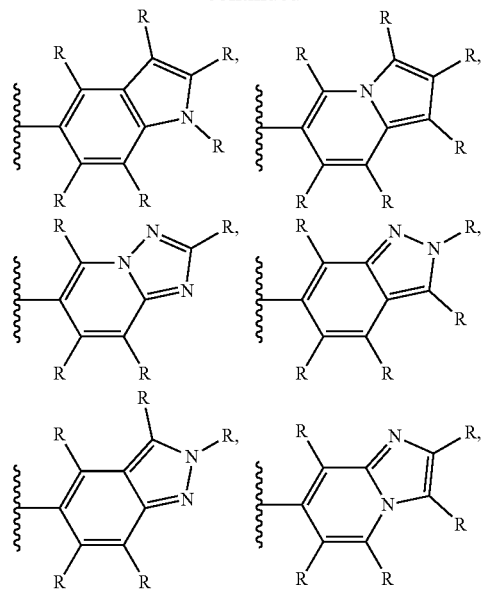

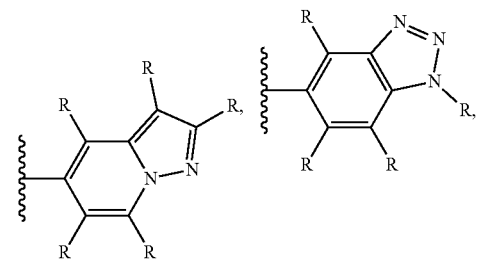

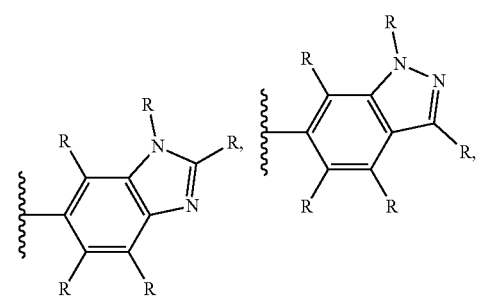

wherein one R is represented by the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$ and $L^{37}$ have the same definition as described above; and $R^3$ represents a group represented by the formula (II) as a ligand of GSK3α/β and GCN2,

[chemical formula 30]

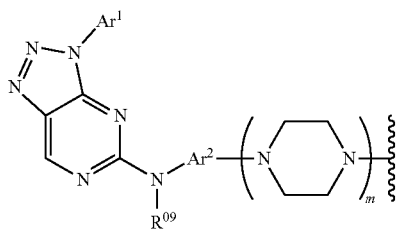
(II)

wherein the definition is the same as above, a group represented by the formula (III) as a ligand of BRD,

[chemical formula 31]

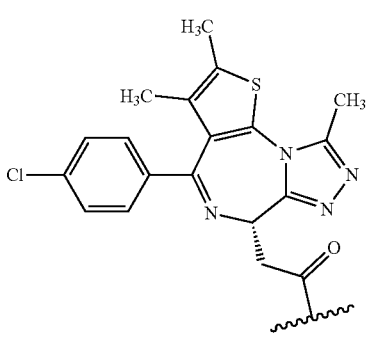
(III)

a group represented by the formula (IV) as a ligand of ABL, BCR-ABL, SRC, KIT, DDR, TEC, EPH-A2, PDGFR and the like,

[chemical formula 32]

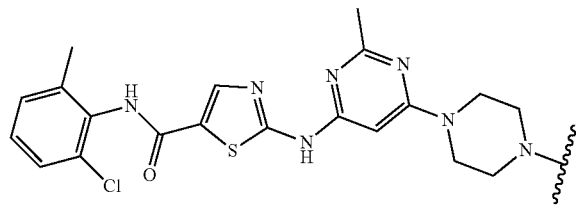
(IV)

wherein the definition is the same as above,
or a compound of Smac peptide mimetics as a ligand of XIAP; and other groups R each independently represent a hydrogen atom, a halogen atom, a C1-6 alkyl group or a C1-6 alkoxy group,
wherein when R binds to N, R is not a halogen atom or a C1-6 alkoxy group.

[8] The compound or salt thereof according to the above [7], wherein B is the formula (B-1)

[chemical formula 33]

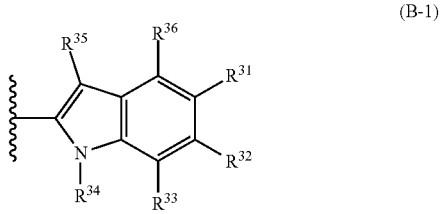
(B-1)

wherein $R^{31}$, $R^{32}$ and $R^{33}$ each independently represent a hydrogen atom, a halogen atom, a C1-6 alkyl group or a C1-6 alkoxy group; $R^{35}$ and $R^{36}$ each independently represent a hydrogen atom, a halogen atom, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above; and $R^{34}$ represents a hydrogen atom, or the formula (L3): —Z-$L^{31}$-$L^{32}$-$L^{33}$-$L^{34}$-$L^{35}$-$L^{36}$-$L^{37}$-$R^3$ (in the formula, Z, $L^{31}$, $L^{32}$, $L^{33}$, $L^{34}$, $L^{35}$, $L^{36}$, $L^{37}$ and $R^3$ represent the same definition as described above,
wherein one of $R^{34}$, $R^{35}$ or $R^{36}$ represents the formula (L3).

[9] The compound or salt thereof according to the above [7], wherein B is represented by the formula (B-2)

[chemical formula 34]

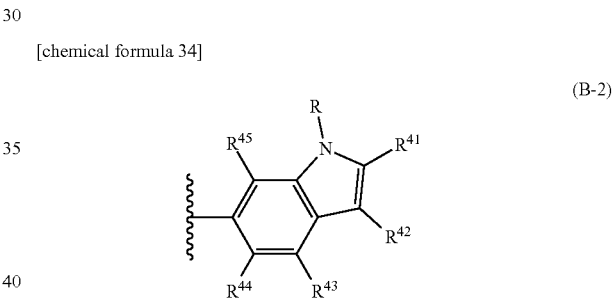
(B-2)

wherein $R^{41}$, $R^{42}$, $R^{43}$, $R^{44}$ and $R^{45}$ each independently represent a hydrogen atom, a halogen atom, a C1-6 alkyl group or a C1-6 alkoxy group; R represents the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above.

[10] The compound or salt thereof according to the above [2], wherein any two compounds selected from group consisting of the following (i) to (iii) are bonded: (i) a compound of the formula (I) in which A is the formula (AI)

[chemical formula 35]

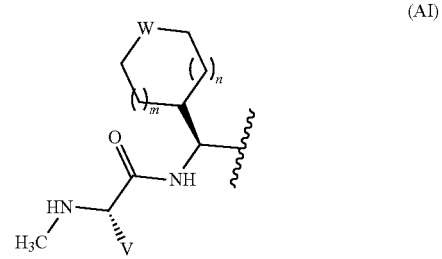
(AI)

wherein m represents 0 to 2; n represents 0 to 2; V is the formula (L1): N-$L^{11}$-$L^{12}$-$L^{13}$-$L^{14}$-$L^{15}$-$L^6$-$L^7$-$R^1$ wherein $L^{11}$, $L^{12}$, $L^{13}$, $L^{14}$, $L^{15}$, $L^{16}$ and $L^{17}$ have the same definition as described above, and $R^1$ represents a bond, (ii) a compound of the formula (I) in which A is the formula (AII)

[chemical formula 36]

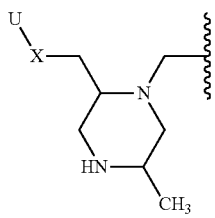

(AII)

wherein X represents an oxygen atom or the formula —$NR^{21}$— wherein $R^{21}$ represents a hydrogen atom or a C1-6 alkyl group; U represents the formula (L2): —$(CH_2)_n$—Y-$L^{21}$-$L^{22}$-$L^{23}$-$L^{24}$-$L^{25}$-$L^{26}$-$L^{27}$-$R^2$ wherein Y, $L^{21}$, $L^{22}$, $L^{23}$, $L^{24}$, $L^{25}$, $L^{26}$ and $L^{21}$ have the same definition as described above, and $R^2$ represents a bond, and (iii) a compound of the formula (I) in which B is the formula (B')

[chemical formula 37]

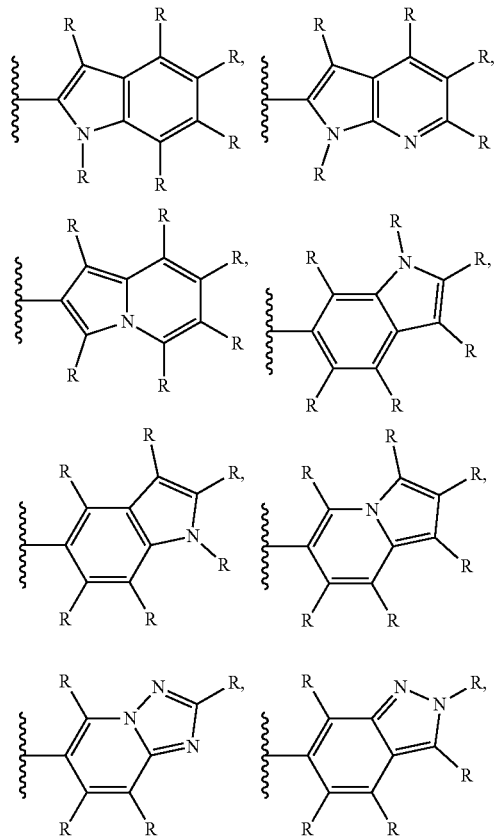

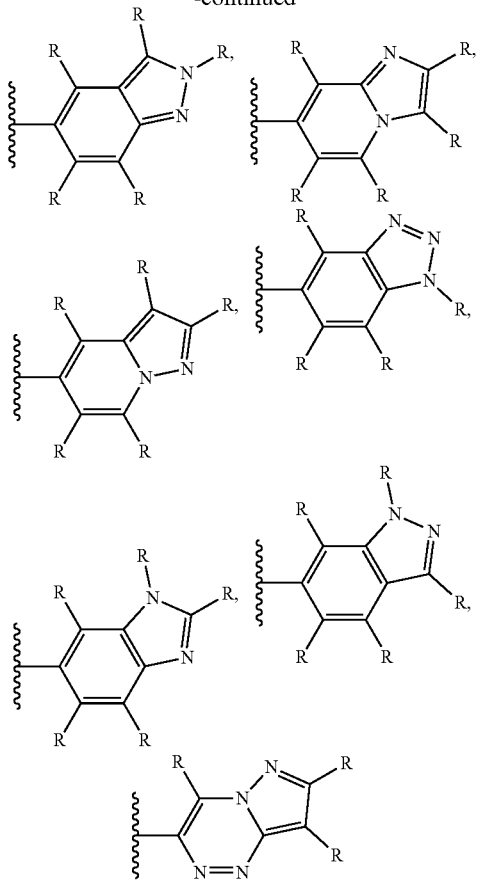

wherein groups R each independently represent a hydrogen atom, a halogen atom, a C1-6 alkyl group, a C1-6 alkoxy group, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$ and $L^{37}$ have the same definition as described above, and $R^3$ represents a bond, wherein when R binds to N, R is not a halogen atom or a C1-6 alkoxy group, and any one R represents the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$ and $L^{37}$ have the same definition as described above, and $R^3$ represents a bond, and A is the formula (AI) wherein V is not the formula (L1) or the formula (AII) wherein U is not the formula (L2).

[11] The compound or salt thereof according to the above [2], wherein any two compounds selected from the group consisting of the following (a) and (b) are bonded: (a) a compound of the formula (I) in which B is the formula (B'-1)

[chemical formula 38]

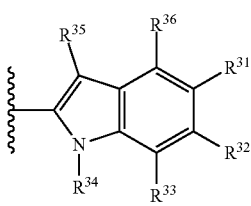

(B'-1)

wherein $R^{31}$, $R^{32}$ and $R^{33}$ each independently represent a hydrogen atom, a halogen atom, a C1-6 alkyl group or a C1-6 alkoxy group; $R^{35}$ and $R^{36}$ each independently represent a hydrogen atom, a halogen atom, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$ and $L^{37}$ have the same definition as described above, and $R^3$ represents a bond; and $R^{34}$ represents a hydrogen atom or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$ and $L^{37}$ have the same definition as described above, and $R^3$ represents a bond, wherein any one of $R^{34}$, $R^{35}$ and $R^{36}$ represents the formula (L3), and
A is the formula (AI) wherein V is not the formula (L1) or the formula (AII) wherein U is not the formula (L2), and (b) a compound of the formula (I) in which B is the formula (B'-2)

[chemical formula 39]

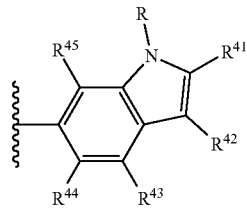

(B'-2)

wherein $R^{41}$, $R^{42}$, $R^{43}$, $R^{44}$ and $R^{46}$ each independently represent a hydrogen atom, a halogen atom, a C1-6 alkyl group or a C1-6 alkoxy group; R represents a hydrogen atom or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$ and $L^{37}$ have the same definition as described above; and $R^3$ represents a bond, wherein any one of $R^{41}$, $R^{42}$, $R^{43}$, $R^{44}$ and $R^{46}$ represents the formula (L3), and A is the formula (AI) wherein V is not the formula (L1) or the formula (AII) wherein U is not the formula (L2).

[12] A medicament comprising the compound or salt thereof according to any one of the above [1] to [11].

[13] The medicament according to the above [12], wherein it is an IAP inhibitor.

[14] The medicament according to the above [12], wherein it is a targeted protein degrader.

[15] The medicament according to the above [12], wherein it is a prophylactic or therapeutic agent for cancers.

[16] The medicament according to the above [12], wherein it is a prophylactic or therapeutic agent for pathogenic protein-related diseases.

[17] A method of inhibiting IAP(s) in mammals, comprising administering an effective amount of the compound or salt thereof according to any one of the above [1] to [11] to the mammals.

[18] A method of inducing targeted protein degradation in mammals, comprising administering an effective amount of the compound or salt thereof according to any one of the above [1] to [11] to the mammals.

[19] A method of prophylaxis or treatment of cancers in mammals, comprising administering an effective amount of the compound or salt thereof according to any one of the above [1] to [11] to the mammals.

[20] A method of prophylaxis or treatment of pathogenic protein-related diseases in mammals, comprising administering an effective amount of the compound or salt thereof according to any one of the above [1] to [11] to the mammals.

[21] Use of the compound or salt thereof according to any one of the above [1] to [11], for producing an IAP inhibitor.

[22] Use of the compound or salt thereof according to any one of the above [1] to [11], for producing a protein degrader.

[23] Use of the compound or salt thereof according to any one of the above [1] to [11], for producing a prophylactic or therapeutic agent for cancers.

[24] Use of the compound or salt thereof according to any one of the above [1] to [11], for producing a prophylactic or therapeutic agent for pathogenic protein-related diseases.

Advantageous Effect of the Invention

The compound of the present invention shows an excellent inhibitory activity on IAP(s), or binds to targeted intracellular proteins in addition to IAP(s) (including cases where targeted intracellular proteins are other IAP(s)) to show a biologically useful activity.

DESCRIPTION OF EMBODIMENTS

Figure 1:
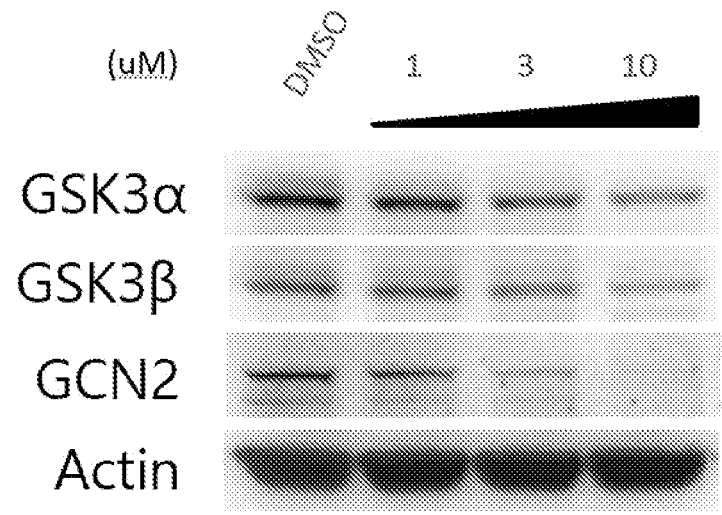
FIG. 1 shows the results obtained by detecting GSK3α/β and GCN2 proteins in a THP1 human monocyte-derived cell line by Western blotting, and confirming the protein degradation activity of the example compounds.

Hereinafter, the present invention as well as compounds of the present invention and the method of producing them and their use will be illustrated with reference to the exemplary embodiments along with the preferred methods and materials which can be used in practice of the present invention. Unless otherwise specified in the sentences, any technical terms and scientific terms used in the present specification have the same meaning as those generally understood by those of ordinary skill in the art to which the present invention belongs. Any materials and methods equivalent or similar to those described in the present specification can be used for practicing the present invention. All publications and patents cited herein in connection with the present invention described herein are incorporated by reference, for example, as indicating methodology, materials, etc. that can be used in the present invention.

Hereinafter, the definition of each substituent used in the present specification will be described in detail. Unless otherwise specified, each substituent has the following definition.

In the present specification, the "halogen atom" includes, e.g., fluorine, chlorine, bromine and iodine.

In the present specification, the "C1-3 alkyl group" includes methyl, ethyl, propyl, isopropyl and cyclopropyl.

In the present specification, the "optionally halogenated C1-3 alkyl group" includes, e.g., a C1-3 alkyl group optionally having 1 to 5 halogen atoms. Specific examples thereof include methyl, chloromethyl, fluoromethyl, dichloromethyl, difluoromethyl, trichloromethyl, trifluoromethyl, ethyl, 2-bromoethyl, 2,2,2-trifluoroethyl, tetrafluoroethyl, pentafluoroethyl, 2-fluoroethyl, 2,2-difluoroethyl, propyl, 2,2-difluoropropyl, 3,3,3-trifluoropropyl, isopropyl, cyclopropyl, 1-fluorocyclopropyl, 2-chlorocyclopropyl, 2-fluorocyclopropyl, 2,2-difluorocyclopropyl and 2,3-difluorocyclopropyl.

In the present specification, the "C1-6 alkyl group" includes, e.g., methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, the "optionally halogenated C1-6 alkyl group" includes, e.g., a C1-6 alkyl group optionally having 1 to 7 halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, the "C2-6 alkenyl group" includes, e.g., ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, the "C2-6 alkynyl group" includes, e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, the "C3-10 cycloalkyl group" includes, e.g., cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, the "C3-10 cycloalkenyl group" includes, e.g., cyclopropenyl, cyclobutenyl, cyclopentenyl, cyclohexenyl, cycloheptenyl and cyclooctenyl.

In the present specification, the "C6-14 aryl group" includes, e.g., phenyl, 1-naphthyl, 2-naphthyl, 1-anthryl, 2-anthryl and 9-anthryl.

In the present specification, the "C7-16 aralkyl group" includes, e.g., benzyl, phenethyl, naphthylmethyl and phenylpropyl.

In the present specification, the "C1-6 alkoxy group" includes, e.g., methoxy, ethoxy, propoxy, isopropoxy, butoxy, isobutoxy, sec-butoxy, tert-butoxy, pentyloxy and hexyloxy.

In the present specification, the "optionally halogenated C1-6 alkoxy group" includes, e.g., a C1-6 alkoxy group optionally having 1 to 7 halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, the "C1-6 alkylthio group" includes, e.g., methylthio, ethylthio, propylthio, isopropylthio, butylthio, sec-butylthio, tert-butylthio, pentylthio and hexylthio.

In the present specification, the "optionally halogenated C1-6 alkylthio group" includes, e.g., a C1-6 alkylthio group optionally having 1 to 7 halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, the "C1-6 alkyl-carbonyl group" includes, e.g., acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, the "optionally halogenated C1-6 alkyl-carbonyl group" includes, e.g., a C1-6 alkyl-carbonyl group optionally having 1 to 7 halogen atoms. Specific examples thereof include acetyl, chloroacetyl, trifluoroacetyl, trichloroacetyl, propanoyl, butanoyl, pentanoyl and hexanoyl.

In the present specification, the "C1-6 alkoxy-carbonyl group" includes, e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, the "C6-14 aryl-carbonyl group" includes, e.g., benzoyl, 1-naphthoyl and 2-naphthoyl.

In the present specification, the "C7-16 aralkyl-carbonyl group" includes, e.g., phenylacetyl and phenylpropionyl.

In the present specification, the "5 to 14-membered aromatic heterocyclylcarbonyl group" includes, e.g., nicotinoyl, isonicotinoyl, tenoyl and furoyl.

In the present specification, the "3 to 14-membered non-aromatic heterocyclylcarbonyl group" includes, e.g., morpholinylcarbonyl, piperidinylcarbonyl and pyrrolidinylcarbonyl.

In the present specification, the "mono- or di-C1-6 alkyl-carbamoyl group" includes, e.g., methylcarbamoyl, ethylcarbamoyl, dimethylcarbamoyl, diethylcarbamoyl and N-ethyl-N-methylcarbamoyl.

In the present specification, the "mono- or di-C7-16 aralkyl-carbamoyl group" includes, e.g., benzylcarbamoyl and phenethylcarbamoyl.

In the present specification, the "C1-6 alkylsulfonyl group" includes, e.g., methylsulfonyl, ethylsulfonyl, propylsulfonyl, isopropylsulfonyl, butylsulfonyl, sec-butylsulfonyl and tert-butylsulfonyl.

In the present specification, the "optionally halogenated C1-6 alkylsulfonyl group" includes, e.g., a C1-6 alkylsulfonyl group optionally having 1 to 7 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, the "C6-14 arylsulfonyl group" includes, e.g., phenylsulfonyl, 1-naphthylsulfonyl and 2-naphthylsulfonyl.

In the present specification, the "substituent" includes, e.g., a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, the "hydrocarbon group" (including the "hydrocarbon group" in the "optionally substituted hydrocarbon group") includes, e.g., a C1-6 alkyl group, a C2-6 alkenyl group, a C2-6 alkynyl group, a C3-10 cycloalkyl group, a C3-10 cycloalkenyl group, a C6-14 aryl group and a C7-16 aralkyl group.

In the present specification, the "optionally substituted hydrocarbon group" includes, e.g., a hydrocarbon group optionally having a substituent selected from Group A of substituent described below.

[Group A of Substituent]
(1) a halogen atom,
(2) a nitro group,
(3) a cyano group, (4) an oxo group,
(5) a hydroxy group,
(6) an optionally halogenated C1-6 alkoxy group,
(7) a C6-14 aryloxy group (e.g., phenoxy, naphthoxy),
(8) a C7-16 aralkyloxy group (e.g., benzyloxy),
(9) a 5 to 14-membered aromatic heterocyclyloxy group (e.g., pyridyloxy),
(10) a 3 to 14-membered non-aromatic heterocyclyloxy group (e.g., morpholinyloxy, piperidinyloxy),
(11) a C1-6 alkyl-carbonyloxy group (e.g., acetoxy, propanoyloxy),
(12) a C6-14 aryl-carbonyloxy group (e.g., benzoyloxy, 1-naphthoyloxy, 2-naphthoyloxy),
(13) a C1-6 alkoxy-carbonyloxy group (e.g., methoxycarbonyloxy, ethoxycarbonyloxy, propoxycarbonyloxy, butoxycarbonyloxy),
(14) a mono- or di-C1-6 alkyl-carbamoyloxy group (e.g., methylcarbamoyloxy, ethylcarbamoyloxy, dimethylcarbamoyloxy, diethylcarbamoyloxy),
(15) a C6-14 aryl-carbamoyloxy group (e.g., phenylcarbamoyloxy, naphthylcarbamoyloxy),
(16) a 5 to 14-membered aromatic heterocyclylcarbonyloxy group (e.g., nicotinoyloxy),
(17) a 3 to 14-membered non-aromatic heterocyclylcarbonyloxy group (e.g., morpholinylcarbonyloxy, piperidinylcarbonyloxy),
(18) an optionally halogenated C1-6 alkylsulfonyloxy group (e.g., methylsulfonyloxy, trifluoromethylsulfonyloxy),
(19) a C6-14 arylsulfonyloxy group optionally substituted with a C1-6 alkyl group (e.g., phenylsulfonyloxy, toluenesulfonyloxy),
(20) an optionally halogenated C1-6 alkylthio group,
(21) a 5 to 14-membered aromatic heterocyclic group,
(22) a 3 to 14-membered non-aromatic heterocyclic group,
(23) a formyl group,
(24) a carboxy group,
(25) an optionally halogenated C1-6 alkyl-carbonyl group,
(26) a C6-14 aryl-carbonyl group,
(27) a 5 to 14-membered aromatic heterocyclylcarbonyl group,
(28) a 3 to 14-membered non-aromatic heterocyclylcarbonyl group,
(29) a C1-6 alkoxy-carbonyl group,
(30) a C6-14 aryloxy-carbonyl group (e.g., phenyloxycarbonyl, 1-naphthyloxycarbonyl, 2-naphthyloxycarbonyl),
(31) a C7-16 aralkyloxy-carbonyl group (e.g., benzyloxycarbonyl, phenethyloxycarbonyl),
(32) a carbamoyl group,
(33) a thiocarbamoyl group,
(34) a mono- or di-C1-6 alkyl-carbamoyl group,
(35) a C6-14 aryl-carbamoyl group (e.g., phenylcarbamoyl),
(36) a 5 to 14-membered aromatic heterocyclylcarbamoyl group (e.g., pyridylcarbamoyl, thienylcarbamoyl),
(37) a 3 to 14-membered non-aromatic heterocyclylcarbamoyl group (e.g., morpholinylcarbamoyl, piperidinylcarbamoyl),
(38) an optionally halogenated C1-6 alkylsulfonyl group,
(39) a C6-14 arylsulfonyl group,
(40) a 5 to 14-membered aromatic heterocyclylsulfonyl group (e.g., pyridylsulfonyl, thienylsulfonyl),
(41) an optionally halogenated C1-6 alkylsulfinyl group,
(42) a C6-14 arylsulfinyl group (e.g., phenylsulfinyl, 1-naphthylsulfinyl, 2-naphthylsulfinyl),
(43) a 5 to 14-membered aromatic heterocyclylsulfinyl group (e.g., pyridylsulfinyl, thienylsulfinyl),
(44) an amino group,
(45) a mono- or di-C1-6 alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-C6-14 arylamino group (e.g., phenylamino),
(47) a 5 to 14-membered aromatic heterocyclylamino group (e.g., pyridylamino),
(48) a C7-16 aralkylamino group (e.g., benzylamino),
(49) a formylamino group,
(50) a C1-6 alkyl-carbonylamino group (e.g., acetylamino, propanoylamino, butanoylamino),
(51) a (C1-6 alkyl)(C1-6 alkylcarbonyl)amino group (e.g., N-acetyl-N-methylamino),
(52) a C6-14 aryl-carbonylamino group (e.g., phenylcarbonylamino, naphthylcarbonylamino),
(53) a C1-6 alkoxy-carbonylamino group (e.g., methoxycarbonylamino, ethoxycarbonylamino, propoxycarbonylamino, butoxycarbonylamino, tert-butoxycarbonylamino),
(54) a C7-16 aralkyloxy-carbonylamino group (e.g., benzyloxycarbonylamino),
(55) a C1-6 alkylsulfonylamino group (e.g., methylsulfonylamino, ethylsulfonylamino),
(56) a C6-14 arylsulfonylamino group optionally substituted with a C1-6 alkyl group (e.g., phenylsulfonylamino, toluenesulfonylamino),
(57) an optionally halogenated C1-6 alkyl group,
(58) a C2-6 alkenyl group,
(59) a C2-6 alkynyl group,
(60) a C3-10 cycloalkyl group,
(61) a C3-10 cycloalkenyl group, and
(62) a C6-14 aryl group.

The number of the above-described substituent in the "optionally substituted hydrocarbon group" is, e.g., 1 to 5. When the number of the substituent is two or more, each substituent may be the same or different.

In the present specification, the "heterocyclic group" (including the "heterocyclic group" in the "optionally substituted heterocyclic group") includes, e.g., (i) an aromatic heterocyclic group, (ii) a non-aromatic heterocyclic group and (iii) a 7 to 10-membered bridged heterocyclic group each containing 1 to 4 heteroatoms selected from a nitrogen atom, a sulfur atom and an oxygen atom as a ring-constituting atom besides carbon atom.

In the present specification, the "optionally substituted C6-14 aryl group" includes, e.g., a C6-14 aryl group optionally having a substituent selected from Group A of substituent described above. The number of the substituent in the "optionally substituted C6-14 aryl group" is, e.g., 1 to 3. When the number of the substituent is two or more, each substituent may be the same or different.

In the present specification, the "aromatic heterocyclic group" (including the "5 to 14-membered aromatic heterocyclic group") includes, e.g., a 5 to 14-membered aromatic heterocyclic group containing 1 to 4 hetero atoms selected from a nitrogen atom, a sulfur atom and an oxygen atom as a ring-constituting atom besides carbon atom.

In the present specification, the "optionally substituted aromatic heterocyclic group" includes, e.g., an aromatic heterocyclic group optionally having a substituent selected from Group A of substituent described above. The number of the substituent in the "optionally substituted aromatic heterocyclic group" is, e.g., 1 to 3. When the number of the substituent is two or more, each substituent may be the same or different.

In the present specification, the "nitrogen-containing aromatic heterocyclic group" includes those containing at least one or more nitrogen atoms as a ring-constituting atom among the "aromatic heterocyclic group".

In the present specification, the "optionally substituted heterocyclic group" includes, e.g., a heterocyclic group optionally having a substituent selected from Group A of substituent described above. The number of the substituent in the "optionally substituted heterocyclic group" is, e.g., 1 to 3. When the number of the substituent is two or more, each substituent may be the same or different.

In the present specification, the "acyl group" includes, e.g., a formyl group, a carboxy group, a carbamoyl group, a thiocarbamoyl group, a sulfino group, a sulfo group, a sulfamoyl group and a phosphono group, each optionally having "one or two substituents selected from a C1-6 alkyl group, a C2-6 alkenyl group, a C3-10 cycloalkyl group, a C3-10 cycloalkenyl group, a C6-14 aryl group, a C7-16 aralkyl group, a 5 to 14-membered aromatic heterocyclic group and a 3 to 14-membered non-aromatic heterocyclic group, each of which optionally having 1 to 3 substituents selected from a halogen atom, an optionally halogenated C1-6 alkoxy group, a hydroxy group, a nitro group, a cyano group, an amino group and a carbamoyl group.

Further, the "acyl group" also includes a hydrocarbon-sulfonyl group, a heterocyclic-sulfonyl group, a hydrocarbon-sulfinyl group and a heterocyclic-sulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group, and the heterocyclylsulfinyl group means a heterocyclic group-bonded sulfinyl group, respectively.

In the present specification, the "optionally substituted amino group" includes, e.g., an amino group optionally having "one or two substituents selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5 to 14-membered aromatic heterocyclylcarbonyl group, a 3 to 14-membered non-aromatic heterocyclylcarbonyl group, a C1-6 alkoxy-carbonyl group, a 5 to 14-membered aromatic heterocyclic group, a carbamoyl group, a mono- or di-C1-6 alkyl-carbamoyl group, a mono- or di-C7-16 aralkyl-carbamoyl group, a C1-6 alkylsulfonyl group and a C6-14 arylsulfonyl group, each of which optionally having 1 to 3 substituents selected from Group A of substituent".

In the present specification, the "optionally substituted carbamoyl group" includes, e.g., a carbamoyl group optionally having "one or two substituents selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5 to 14-membered aromatic heterocyclylcarbonyl group, a 3 to 14-membered non-aromatic heterocyclylcarbonyl group, a C1-6 alkoxy-carbonyl group, a 5 to 14-membered aromatic heterocyclic group, a carbamoyl group, a mono- or di-C1-6 alkyl-carbamoyl group and a mono- or di-C7-16 aralkyl-carbamoyl group, each of which optionally having 1 to 3 substituents selected from Group A of substituent".

In the present specification, the "optionally substituted thiocarbamoyl group" includes, e.g., a thiocarbamoyl group optionally having "one or two substituents selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5 to 14-membered aromatic heterocyclylcarbonyl group, a 3 to 14-membered non-aromatic heterocyclylcarbonyl group, a C1-6 alkoxy-carbonyl group, a 5 to 14-membered aromatic heterocyclic group, a carbamoyl group, a mono- or di-C1-6 alkyl-carbamoyl group and a mono- or di-C7-16 aralkyl-carbamoyl group, each of which optionally having 1 to 3 substituents selected from Group A of substituent".

In the present specification, the "optionally substituted sulfamoyl group" includes, e.g., a sulfamoyl group optionally having "one or two substituents selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5 to 14-membered aromatic heterocyclylcarbonyl group, a 3 to 14-membered non-aromatic heterocyclylcarbonyl group, a C1-6 alkoxy-carbonyl group, a 5 to 14-membered aromatic heterocyclic group, a carbamoyl group, a mono- or di-C1-6 alkyl-carbamoyl group and a mono- or di-C7-16 aralkyl-carbamoyl group, each of which optionally having 1 to 3 substituents selected from Group A of substituent".

In the present specification, the "optionally substituted hydroxy group" includes, e.g., a hydroxy group optionally having "a substituent selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group, a C7-16 aralkyl-carbonyl group, a 5 to 14-membered aromatic heterocyclylcarbonyl group, a 3 to 14-membered non-aromatic heterocyclylcarbonyl group, a C1-6 alkoxy-carbonyl group, a 5 to 14-membered aromatic heterocyclic group, a carbamoyl group, a mono- or di-C1-6 alkyl-carbamoyl group, a mono- or di-C7-16 aralkyl-carbamoyl group, a C1-6 alkylsulfonyl group and a C6-14 arylsulfonyl group, each of which optionally having 1 to 3 substituents selected from Group A of substituent".

In the present specification, the "optionally substituted sulfanyl group" includes, e.g., a sulfanyl group and a halogenated sulfanyl group optionally having "a substituent selected from a C1-6 alkyl group, a C2-6 alkenyl group, a C3-10 cycloalkyl group, a C6-14 aryl group, a C7-16 aralkyl group, a C1-6 alkyl-carbonyl group, a C6-14 aryl-carbonyl group and a 5 to 14-membered aromatic heterocyclic group, each of which optionally having 1 to 3 substituents selected from Group A of substituent".

In the present specification, the "optionally substituted silyl group" includes, e.g., a silyl group optionally having "1 to 3 substituents selected from a C1-6 alkyl group, a C2-6 alkenyl group, a C3-10 cycloalkyl group, a C6-14 aryl group and a C7-16 aralkyl group, each of which optionally having 1 to 3 substituents selected from Group A of substituent".

In the present specification, the "non-aromatic heterocyclic group" (including the "3 to 14-membered non-aromatic heterocyclic group") includes, e.g., non-aromatic heterocyclic groups containing 1 to 4 hetero atoms selected from a nitrogen atom, a sulfur atom and an oxygen atom as a ring-constituting atom besides carbon atom.

Specific examples thereof include aziridinyl, azetidinyl, pyrrolidinyl, piperidinyl, piperazinyl, imidazolidinyl, pyrazolidinyl, morpholinyl, oxiranyl, oxetanyl, oxolanyl, oxanyl, dioxanyl, oxepanyl, thiolanyl, oxathianyl, triazaspirononyl (e.g., 1,3,7-triazaspiro[4.4]nonyl), thiadiazaspirononyl (e.g., 7-thia-1,3-diazaspiro[4.4]nonyl), dioxidethiadiazaspirononyl (e.g., 7,7-dioxide-7-thia-1,3-diazaspiro[4.4]nonyl), etc.

In the present specification, the "linker" refers to a chemical moiety (structure) used to conjugate a part of a subject compound to another compound. Exemplary linkers are described in the present specification. For example, in any compounds described in the present specification, a chemical structure used to conjugate a partial structure of a compound and a partial structure of another compound can be used as a linker, and corresponds to the "linker" referred to in the present specification. The linker preferably used in the present invention includes, but not limited to, a structure represented by "L$^x$" (x is any numerical value) in the present specification and a structure obtained by binding one or more atomic groups to the structure.

In the present specification, the "C1-6 alkylene group" includes, e.g., methylene, 1,2-ethylene, 1,1-ethylene, 1,2-propylene, 1,3-propylene, 2,2-propylene, 1,4-butylene, 1,2-butylene, 1,3-butylene, 2,2-butylene, 1,5-pentylene, 3,3-pentylene and 1,6-hexylene.

In the present specification, the "C3-10 cycloalkylene group" includes, e.g., 1,1-cyclopropylene, cis-1,2-cyclopropylene, trans-1,2-cyclopropylene, 1,1-cyclobutylene, cis-1,2-cyclobutylene, trans-1,2-cyclobutylene, cis-1,3-cyclobutylene, trans-1,3-cyclobutylene, 1,1-cyclopentylene, cis-1,2-cyclopentylene, trans-1,2-cyclopentylene, cis-1,3-cyclopentylene, trans-1,3-cyclopentylene, 1,1-cyclohexylene, cis-1,2-cyclohexylene, trans-1,2-cyclohexylene, cis-1,3-cyclohexylene, trans-1,3-cyclohexylene, cis-1,4-cyclohexylene, trans-1,4-cyclohexylene, 1,1-cycloheptynylene, 1,1-cyclooctynylene, 2,2-dimethyl-1,1-cyclopropylene, 2,3-dimethyl-1,1-cyclopropylene, 2,2,3,3,4,4-tetramethyl-1,1-cyclobutylene, 7,7-norcaranylene, 7,7-norpinanylene and 7,7-norbornanylene.

In the present specification, the "C3-10 cycloalkenylene group" includes, e.g., 1,2-cyclopropenylene, 1,2-cyclobutenylene, 1,2-cyclopentenylene, 1,2-cyclohexenylene and 2-bornen-2,3-yl.

In the present specification, the "bond" indicates a state in which two substituents adjacent via the single bond are bonded by a single bond. Further, when a plurality of the "single bonds" are connected, it indicates a state in which all of them are connected together by a single bond.

In the present specification, the "fragment structure of a substance that binds to IAPs" is a fragment structure having binding affinity to a specific site of IAPs to which an Ala-Val derivative binds, and includes, e.g., those having a three-dimensional structure similar to Ala-Val, Ala-Val derivative and at least a part thereof.

Further, the "fragment structure of a substance that binds to IAP(s)" includes a structure that form a structure represented by the formula (I) together with a piperadine-1-carbonyl structure or together with a piperazine-1,4-dicarbonyl structure having the group B, and bind to BIR domain(s) of IAP proteins.

In the present specification, the "structure binding to BIR domain(s) of IAP proteins" denotes a structure that binds to BIR domain(s) that the IAP family (e.g., XIAP, cIAP1, cIAP2) contains in common, and is a structure having a molecular weight of preferably 2000 or less, more preferably 1500 or less. It includes, e.g., but not limited to, those having a three-dimensional structure similar to at least a part of Ala-Val-Pro.

In the present specification, the "compound that adds a function" means a ligand of any protein present in a living body, a cell penetrating peptide (CPP), or a kinetophore that keeps a compound in the intestinal tract (e.g., polyethylene oxides capped with a short-chain peptide, sugar and quaternary ammonium; etc.).

In the present specification, the "Smac peptide mimetics" means compounds binding to the same space as the space occupied by the Smac N-terminal peptide AVPIAQK (SEQ ID No. 1)(particularly AVPI (SEQ ID No. 2)) when these bind to XIAP and exhibiting an inhibitory activity on the binding of the Smac peptide.

In the present specification, the "pathogenic protein-related diseases" is diseases in which the disease or disorder is explained or inferred in the context of pathogenic protein abnormalities. Protein abnormalities include, e.g., but not limited to, abnormal expression and enhancement of proteins in a living body, and the presence of mutant proteins. The pathogenic protein-related diseases include, but not limited to, cancers, inflammatory diseases, autoimmune diseases, osteoarticular degenerative diseases, central nervous system diseases, cardiovascular diseases, metabolic diseases, and infectious diseases.

In the present specification, the "ligand of any protein present in a living body" means a structural unit that forms a part of the compound (I) and has an activity to bind to any protein present in a living body. A substance constituting the structural unit may be a substance that binds to a protein, and examples thereof include DNA, RNA, nucleosides, nucleotides, proteins, peptides, amino acids, lipids, alkaloids, terpenes and their derivatives thereof, coenzymes and small molecules (particularly, small molecules).

The above-described substance binding to proteins present in a living body includes compounds binding to enzymes (e.g., kinase, pseudokinase, phosphatase, pseudophosphatase, histone-modifying enzyme, DNA modifying enzyme, DNA repair enzyme, oxidoreductase, deoxidase, synthase, transferase, protease, phosphodiesterase, carboxylase, decarboxylase, etc.), receptors (e.g., G-protein-coupled receptor, nuclear receptor, growth factor receptor, aryl hydrocarbon receptor, etc.), transcription factors, DNA replication factors, bromodomains, chaperones, telomere binding proteins, ion channels, transporters, integrins, etc.

The above-described substance binding to proteins present in a living body is preferably a ligand for a disease-related protein (pathogenic protein)

A compound included in the compound (I) can be used as a synthetic intermediate in producing another compound (I) of the present invention, and is also the compound of the present invention. Further, it can also be used as a synthetic intermediate in producing IAP inhibitors other than the compound (I), compounds binding to other target proteins together with IAP(s) to provide a biologically useful activity, or targeted protein degraders.

When the compound (I) is in a form of a salt, the salt includes, e.g., metal salts, ammonium salts, salts with organic base, salts with inorganic acid, salts with organic acid, salts with basic or acidic amino acid, and the like. Suitable examples of the metal salt include, e.g., alkali metal salts such as sodium salts, potassium salts and the like; alkaline-earth metal salts such as calcium salts, magnesium salts, barium salts and the like; aluminum salts, and the like. Suitable examples of the salt with organic base include, e.g., salts with trimethylamine, triethylamine, pyridine, picoline, 2,6-rutidine, ethanolamine, diethanolamine, triethanolamine, cyclohexylamine, dicyclohexylamine, N,N'-dibenzylethylenediamine and the like. Suitable examples of the salt with inorganic acid include, e.g., salts with hydrochloric acid, hydrobromic acid, nitric acid, sulfuric acid, phosphoric acid and the like. Suitable examples of the salt with organic acid include, e.g., salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Suitable examples of the salt with basic amino acid include, e.g., salts with arginine, lysine, ornithine and the like, and suitable examples of the salts with acidic amino acids include, e.g., salts with aspartic acid, glutamic acid and the like.

Among them, pharmaceutically acceptable salts are preferred. For example, when an acidic functional group is present in a compound, the salt includes inorganic salts such as alkali metal salts (e.g., sodium salts, potassium salts, etc.) and alkaline-earth metal salts (e.g., calcium salts, magnesium salts, etc.) and ammonium salts, while when a basic functional group is present in a compound, the salt includes salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

The production method of the compound of the present invention is explained in the followings. The raw material and reagent used and the compound obtained in each step in the following production method may be each in a form of a salt, and examples of such salt include those similar to the salts of the compound of the present disclosure.

When the compound obtained in each step is in a free form, it can be converted to the objective salt according to a method known per se. When the compound obtained in each step is in a salt form, it can be converted to the free form or the objective other salt form according to a method known per se.

The compound obtained in each step can be used directly as the resultant reaction mixture or as a resultant crude product for the next reaction. Alternatively, the compound obtained in each step can be isolated and/or purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min to 48 hr, preferably 10 min to 8 hr, unless otherwise specified.

In the reaction in each step, while the reaction temperature varies depending on the kind of the reagent and solvent to be used, it is generally −78° C. to 300° C., preferably −78° C. to 150° C., unless otherwise specified.

In the reaction in each step, while the pressure varies depending on the kind of the reagent and solvent to be used, it is generally 1 atm to 20 atm, preferably 1 atm to 3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature to 300° C., preferably 50° C. to 250° C., unless otherwise specified. While the reaction time varies depending on the kind of the reagent and solvent to be used, it is generally 1 min to 48 hr, preferably 1 min to 8 hr, unless otherwise specified.

In the reaction in each step, the reagent is used in an amount of 0.5 equivalent to 20 equivalents, preferably 0.8 equivalent to 5 equivalents, relative to the substrate, unless otherwise specified. When the reagent is used as a catalyst, the reagent is used in an amount of 0.001 equivalent to 1 equivalent, preferably 0.01 equivalent to 0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide and the like;
basic salts: sodium carbonate, calcium carbonate, sodium hydrogencarbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like; metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminium chloride, anhydrous zinc chloride, anhydrous iron chloride and the like.

Unless otherwise specified, the reaction in each step is carried out according to a method known per se, for example, the method described in Jikken Kagaku Kouza, $5^{th}$ Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like or a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; and carbonate ester type protecting groups such as tert-butylcarbonate and the like.

Examples of the protecting group for a carbonyl group of an aldehyde include acetal type protecting groups such as dimethylacetal and the like; and cyclic acetal-type protecting groups such as 1,3-dioxane and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; and hydrazone-type protecting groups such as N,N-dimethylhydrazone and the like.

Examples of the protecting group for a carboxyl group include ester-type protecting groups such as methyl ester and the like; and amide-type protecting groups such as N,N-dimethylamide and the like.

Examples of the protecting group for a thiol include ether-type protecting groups such as benzyl thioether and the like; and ester-type protecting groups such as thioacetate ester, thiocarbonate, thiocarbamate and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; and sulfonamide-type protecting groups such as methanesulfonamide and the like.

The protecting groups can be removed according to a method known per se, such as a method using acid, base, ultraviolet rays, hydrazine, phenylhydrazine, sodium N-methyldithiocarbamate, tetrabutylammonium fluoride, palladium acetate or trialkylsilyl halide (e.g., trimethylsilyl iodide, trimethylsilyl bromide), or a reduction method.

When reduction reaction is carried out in each step, examples of the reducing agent to be used include metal hydrides such as lithium aluminium hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N bromosuccinimide (NBS) and the like; oxygen; ozone; sulfur trioxido-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole) and a base (e.g., a basic salt, an organic base) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; alkylmagnesium halides such as methylmagnesium bromide and the like. The Grignard reagent can be prepared according to a method known per se, for example, by reacting an alkyl halide or an aryl halide with metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen and formic acid and the like.

When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy 1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; 2,4,6-tripropyl-1,3,5,2,4,6-trioxatriphosphorinane-2,4,6-trioxide (T3P); combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases, basic salts and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two-step reaction comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. When acid hydrolysis reaction of t-butyl ester is carried out, formic acid, triethylsilane and the like may be added to reductively trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When a nitration reaction is performed in each step, the nitrating agent to be used includes nitric acid, fuming nitric acid, copper nitrate and the like, and the reaction is performed by being activated with concentrated sulfuric acid, acetic anhydride and the like.

When the Sandmeyer reaction is performed in each step, the diazonium agent to be used includes sodium nitrite, isoamyl nitrite, and the like, and the reaction is performed by being activated with concentrated sulfuric acid, concentrated hydrobromic acid, concentrated hydrochloric acid, or the like. The halogenating agent for the diazonium salt includes potassium iodide, copper (I) bromide, copper (I) chloride and the like.

When the diazonium cyclization reaction is performed in each step, the diazonium agent to be used includes sodium nitrite, isoamyl nitrite, and the like, and the reaction is performed by being activated by concentrated sulfuric acid, concentrated hydrobromic acid, concentrated hydrochloric acid, and the like.

When the alkylation reaction of alcohols or amines or aromatic heterocyclics having an NH group in the ring (e.g., imidazole, pyrazole) is performed in each step, the alkylating agent includes optionally substituted alkyl halides (e.g., iodomethane), optionally substituted alkyls having an optionally substituted $C_{1-6}$ alkylsulfonyloxy group as a leaving group, optionally substituted alkyls having a $C_{6-14}$ arylsulfonyloxy group optionally substituted with a $C_{1-6}$ alkyl group, sodium 2-chloro-2,2-difluoroacetate, 2,2-difluoro-2-(fluorosulfonyl)acetate, and the like. Further, the base to be used includes organic lithiums, metal alkoxides, inorganic bases, organic bases, and the like.

When the fluorination reaction is performed in each step, the fluorinating agent to be used includes DAST (diethylaminosulfur trifluoride), bis(2-methoxyethyl) aminosulfur trifluoride, 1-chloromethyl-4-fluoro-1,4-diazoniabicyclo[2.2.2]octane bis (tetrafluoroborate) (Selectfluor), 4-tert-butyl-2,6-dimethylphenylsulfur trifluoride (FLUOLEAD) and the like.

When the coupling reaction is performed in each step, the coupling reaction includes Suzuki coupling, Stille coupling, Buchwald-Hartwig coupling, Negishi coupling, Mizoroki-Heck reaction, cyanation reaction using copper cyanide or zinc cyanide, and the like. Reagents such as metal catalysts, phosphine ligands, bases and the like used in the coupling reaction can be used in methods known per se [methods described in, e.g., J. F. Hartwig, S. Shekhar, Q. Shen, F. Barrios-Landeros, in The Chemistry of Anilines, Z. Rappoport, Ed., Wiley-Intersicence, New York (2007); L. Jiang, S. L. Buchwald, in Metal-Catalyzed Cross-Coupling Reactions, $2^{nd}$ Ed., A. de Meijere, F. Diederich, Eds., Wiley-VCH, Weinheim, Germany (2004); J. F. Hartwig, in Handbook of Organopalladium Chemistry for Organic Synthesis, A. de Meijere, F. Diederich, Eds., Wiley, New York (2002); J. F. Hartwig, in Modern Amination Methods, A. Ricci, Ed., Wiley-VCH, Weinheim, (2000)] or methods according to them, in addition to reagents described above.

Hereinafter, a method for producing the compound (I) will be described.

Each symbol in the following reaction schemes has the same meaning as described above unless otherwise specified. When a specific production method is not described, a commercially available raw material compound can be easily obtained, or a raw material compound can be produced by a method known per se or a method according to the method, and a method described in Examples.

When performing a reaction in each step, if there is a reactive site where a reaction other than the intended reaction occurs, a protecting group is introduced into the reactive site in advance by means known per se as necessary, and the desired reaction is performed, and thereafter, the protecting group may be removed also by means known per se.

For example, when the raw material compounds or the intermediates have an amino group, a carboxyl group or a hydroxyl group as a substituent, these groups may be protected with a protecting group generally used in peptide chemistry and the like. In this case, after the reaction, the target compound can be obtained by removing the protecting group(s) as necessary.

The production method of compound (Ia) in which A is represented by the following formula (AI) in compound (I) will be described below.

[chemical formula 40]

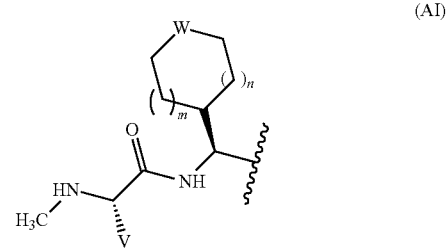

(AI)

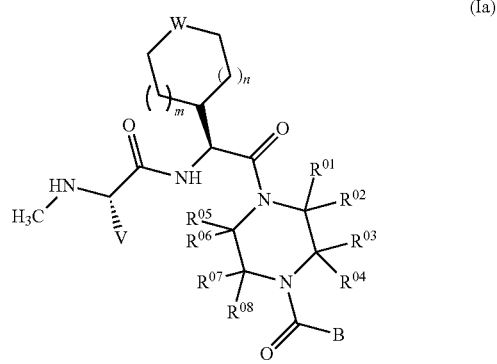

(Ia)

[chemical formula 41]

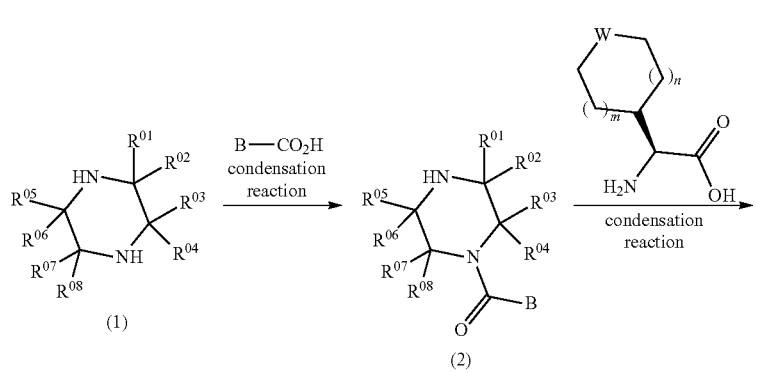

-continued
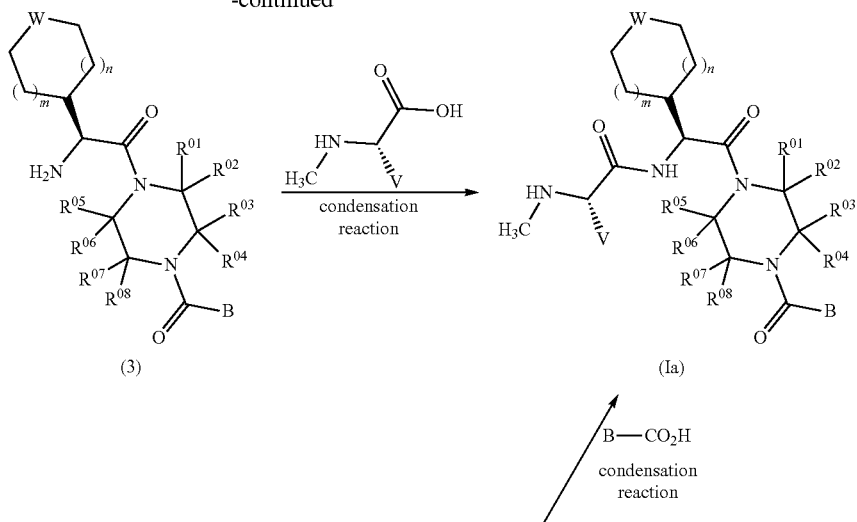
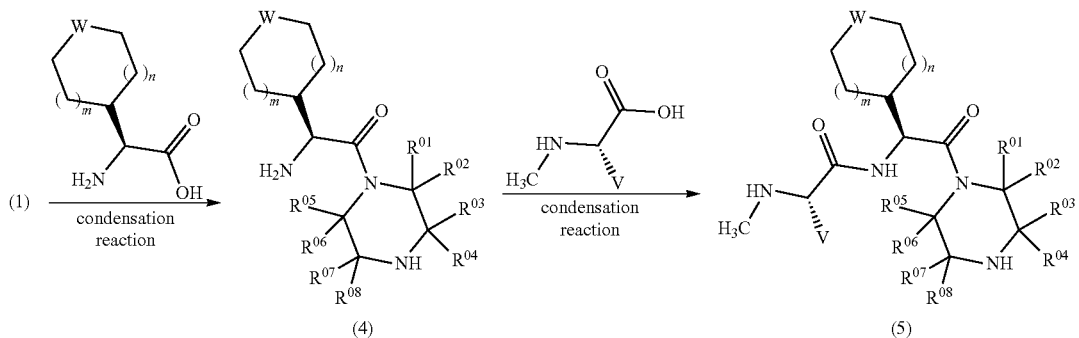
The production method of compound (Ib) in which A is represented by the following formula (AII) in compound (I) will be described below.
[chemical formula 42]
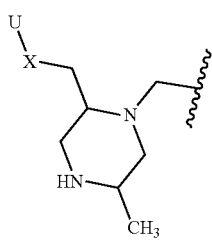
(AII)
-continued
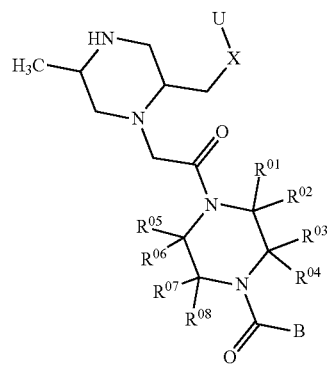
(Ib)

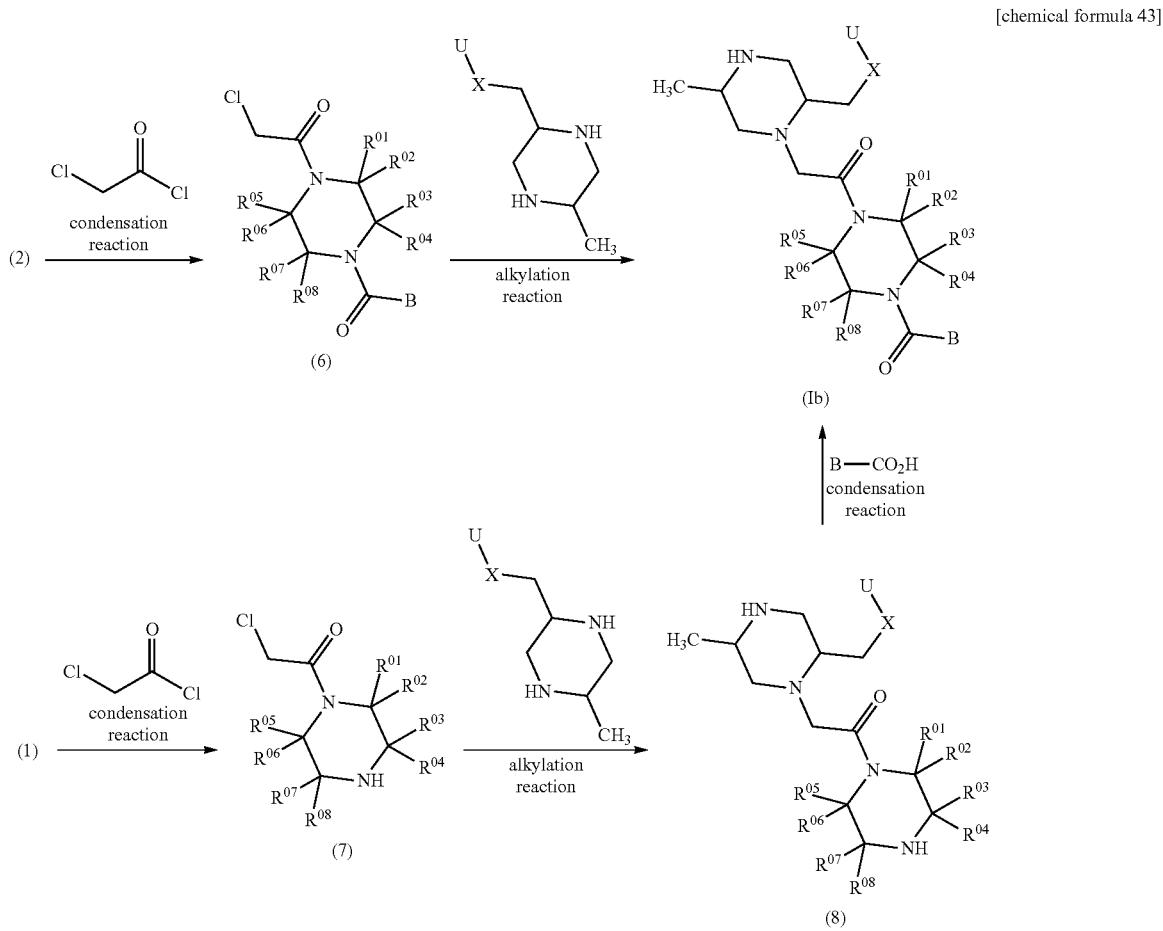
The production method of compound (II) represented by the following formula as a ligand of GSK3α/β and GCN2 will be described below.
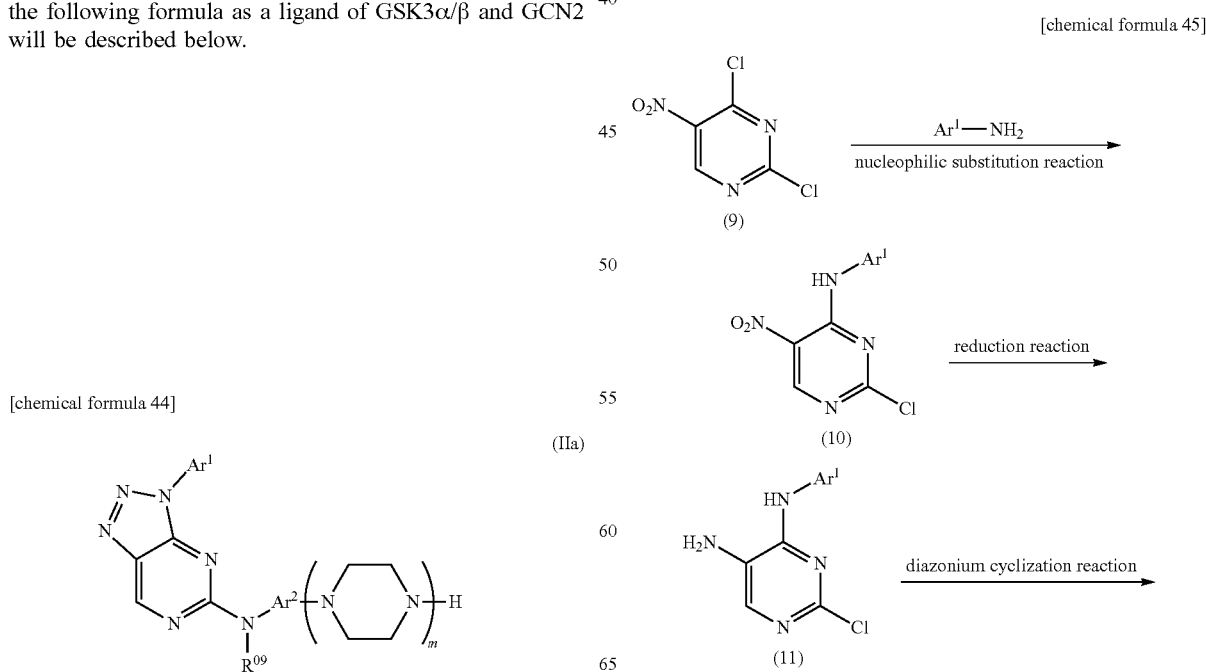

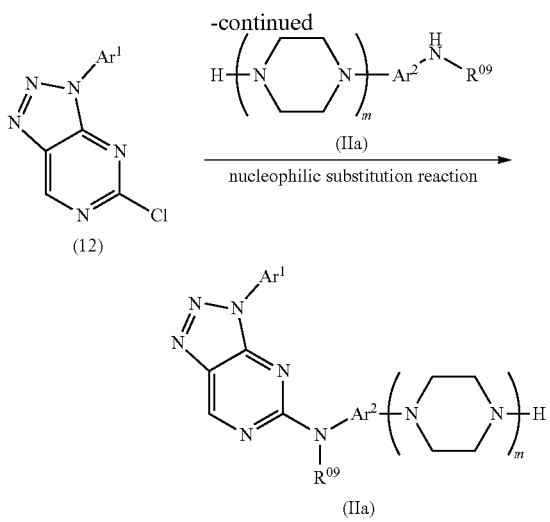

(12)

(IIa)

nucleophilic substitution reaction (IIa)

The compound (IIIa) as a ligand of BRD and the compound (IVa) as a ligand of ABL, BCR-ABL, SRC, KIT, DDR, TEC, EPH-A2, PDGFR and the like can be produced by methods known per se or methods according to them or methods described in Examples.

[chemical formula 46]

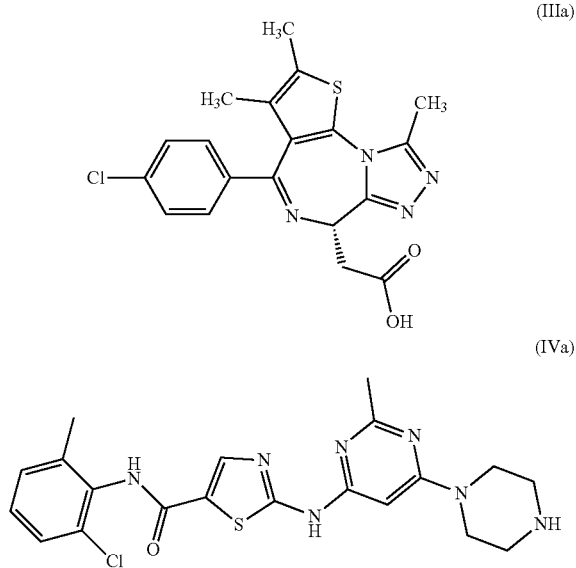

(IIIa)

(IVa)

By converting a substituent in compound (I) thus obtained by applying a means known per se (that is, introducing a substituent or converting a functional group or introducing a linker and a ligand of a protein), another compound included in compound (I) or a salt thereof can also be produced. As a method for introducing a substituent, converting a functional group, or introducing a linker and a ligand for a protein, a known general method is used, and the method includes, e.g., conversion of a halogen atom (e.g., fluorine, chlorine, bromine, iodine) or an optionally halogenated C1-6 alkylsulfonyl-oxy group [e.g., methanesulfonyloxy, ethanesulfonyloxy, trichloromethanesulfonyloxy, trifluoromethanesulfonyloxy (triflate)] to a methyl group, a cyclopropyl group, a vinyl group, a cyano group, a formyl group, a carbonyl group, a carboxyl group, a hydroxyl group, an amino group, a boryl group or the like; conversion of a formyl group to an ethynyl group by Seyferth-Gilbert homologation; conversion of an ester to a carboxy group by hydrolysis; conversion of a carboxy group to a carbamoyl group by amidation; conversion of a carboxy group to a hydroxymethyl group by reduction; conversion of a carbonyl group to an alcohol form by reduction or alkylation; reductive amination of a carbonyl group; oximation of a carbonyl group; acylation of an amino group; ureation of an amino group; sulfonylation of an amino group; alkylation of an amino group; substitution or amination of an active halogen with an amine; alkylation of a hydroxy group; substitution or amination of a hydroxy group; alkylation of a heterocyclic nitrogen atom; acylation of a heterocyclic nitrogen atom; sulfonylation of a heterocyclic nitrogen atom; and the like.

In performing these reactions, if there is a reactive site where a reaction other than the intended reaction occurs, a protecting group is previously introduced into the reactive site in advance by means known per se as necessary, and the desired reaction is performed, and thereafter, the protecting group may be removed also by a means known per se to produce a compound included in the scope of the present invention.

For example, when the raw material compound or the intermediate has an amino group, a carboxyl group or a hydroxyl group as a substituent, these groups may be protected with a protecting group generally used in peptide chemistry and the like. In this case, after the reaction, the target compound can be obtained by removing the protecting group(s) as necessary.

Compound (I) obtained by the above production method can be isolated and purified by known means, e.g., solvent extraction, solution pH conversion, phase transfer, crystallization, recrystallization or chromatography.

When compound (I) contains an optical isomer, a stereoisomer, a regioisomer, and a rotational isomer, these are also contained as the compound (I), and each compound can be obtained as a single item by a synthesis method and a separation method known per se. For example, when compound (I) has an optical isomer, the optical isomer resolved from the compound is also included in the compound (I).

Here, the optical isomer can be produced by a method known per se.

Compound (I) may be a crystal.

The crystal of compound (I) (hereinafter sometimes abbreviated as crystals of the present invention) can be produced by crystallization of compound (I) by applying a crystallization method known per se.

Compound (I) may be a pharmaceutically acceptable co-crystal or a salt thereof. Here, the co-crystal or the salt thereof mean a crystalline substance constituted of two or more special solids at room temperature, each having different physical properties (e.g., structure, melting point, heat of fusion, hygroscopicity, solubility, and stability). The co-crystal or the salt thereof can be produced according to a co-crystallization method known per se.

Compound (I) may be a hydrate, a non-hydrate, a non-solvate, or a solvate.

Furthermore, deuterium converted materials obtained by converting $^{1}H$ into $^{2}H(D)$ are also included in the compound (I).

Compound (I) may be labeled with an isotope (e.g., $^{3}H$, $^{13}C$, $^{14}C$, $^{18}F$, $^{35}S$, $^{125}I$) and the like. The compound (I) labeled or substituted with an isotope can be used, e.g., as a tracer (PET tracer) for use in positron emission tomography (PET) and is expected to be useful in fields such as medical diagnosis and the like.

Compound (I) may be used as a prodrug.

A prodrug of compound (I) means a compound which is converted into the compound (I) with a reaction due to an enzyme, a gastric acid, etc. under the physiological condition in a living body, that is, a compound which is enzymatically oxidized, reduced, hydrolyzed, etc. to be converted into the compound (I), or a compound which is hydrolyzed with gastric acid, etc., to be converted into the compound (I).

A prodrug of compound (I) includes, a compound in which an amino group of the compound (I) is acylated, alkylated or phosphorylated (e.g., compounds in which an amino group of the compound (I) is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated or tert-butylated);

a compound in which a hydroxy group of the compound (I) is acylated, alkylated, phosphorylated or borated (e.g., compounds in which a hydroxy group of the compound (I) is acetylated, palmitoylated, propanoylated, pivaloylated, succinylated, fumarylated, alanylated or dimethylaminomethylcarbonylated);

a compound in which a carboxy group of the compound (I) is esterified or amidated (e.g., compounds in which a carboxy group of the compound (I) is ethylesterified, phenylesterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated), and the like. These compounds can be produced from compound (I) by a method known per se.

Further, a prodrug of compound (I) may be a compound which is converted to compound (I) under physiological conditions as described in ""IYAKUHIN no KAIHATSU (Development of Pharmaceuticals)", Vol. 7, Design of Molecules, p. 163-198, published by HIROKAWA SHOTEN (1990).

In the present specification, the prodrug may be in a form of a salt, and examples of such salt include those exemplified as the salt of the compound represented by the formula (I) described above.

Compound (I) can also be used as a targeted protein degrader or a ligand that binds to E3 ligase of the targeted protein degrader. When the compound (I) is used as a ligand that binds to E3 ligase of the targeted protein degrader, the compound (I) may conjugate with a ligand of the target protein directly or via a linker.

Compound (I) may be conjugated with a compound that adds a function, e.g., a cell penetrating peptide (CPP), or a kinetophore which keeps a compound in the intestinal tract (e.g., polyethylene oxides capped with a short-chain peptide, sugar and quaternary ammonium; etc.), and the compound (I) may bind directly or via a linker to a compound that adds a function.

Compound (I) can also be used as a payload (the moiety corresponding to the drug described above) in an antibody (or peptidic antigen recognition sequence)-drug conjugate. When the compound (I) is used as a payload, the compound (I) may bind to an antibody (or a peptidic antigen recognition sequence) directly or via a linker. When the compound (I) is used as a payload, the linker as described in Chem. Rev., 114, 9154-9218 (2014), Pharma. Res. 32, 3526-3540 (2015), Bioconjugate Chem. 21, 5-13 (2010), The AAPS journal, 17, 339-351 (2015), WO2011/005761, and the like, may be used in addition to the linkers exemplified in the present specification.

Compound (I) or a prodrug thereof (which may be abbreviated as the "compound of the present invention" in the present specification) has IAP binding (inhibiting) activity, and is useful as cancer prophylactic or therapeutic agent, a cancer growth inhibitor, a cancer metastasis suppressor, an apoptosis promoter, and the like for mammals (e.g., mouse, rat, hamster, rabbit, cat, dog, cow, sheep, monkey, and human).

The compound of the present invention also has activity which induces degradation of a target protein (particularly, a protein associated with a disease state) for mammals (e.g., mouse, rat, hamster, rabbit, cat, dog, cow, sheep, monkey, and human), and is useful as a prophylactic or therapeutic agent for diseases correlated with a target protein. The compounds of the present invention may be effective in prophylaxis or treatment of any diseases correlated with a target protein (e.g., cancers, inflammatory diseases, autoimmune diseases, osteoarticular degenerative diseases, central nervous system diseases, cardiovascular diseases, metabolic diseases, infectious diseases, etc.) in view of the mechanism of action. Of them, it is expected to be effective in treating or preventing cancers, but is not limited thereto.

In addition, the compound of the present invention is useful as a medicament, since it is superior in at least one of the points in terms of drug efficacy, pharmacokinetics (absorption, distribution, metabolism, excretion, etc.), solubility (water solubility, etc.), interaction with other medicaments, safety (lower toxicity such as acute toxicity, chronic toxicity, genetic toxicity, reproductive toxicity, cardiotoxicity, carcinogenicity, etc.), and stability (chemical stability, stability to an enzyme, etc.).

It is exemplified that prophylaxis or treatment of cancer which includes, e.g., colon cancers (e.g., colon cancer, rectal cancer, anus cancer, familial colorectal cancer, hereditary nonpolyposis colorectal cancer, gastrointestinal stromal tumor), lung cancers (e.g., non-small-cell lung cancer, small-cell lung cancer, malignant mesothelioma), mesothelioma, pancreatic cancers (e.g., pancreatic ductal adenocarcinoma, pancreatic endocrine tumor), pharyngeal cancer, laryngeal cancer, esophageal cancer, stomach cancers (e.g., papillary adenocarcinoma, mucinous adenocarcinoma, adenosquamous carcinoma), duodenal cancer, small intestinal cancer, breast cancers (e.g., invasive ductal carcinoma, non-invasive ductal carcinoma, inflammatory breast cancer), ovarian cancers (e.g., ovarian epithelial cancer, extragonadal germ cell tumor, ovarian germ cell tumor, ovarian low-malignant potential tumors), testis tumors, prostate cancers (e.g., hormone-dependent prostate cancer, non-hormone dependent prostate cancer, castration-resistant prostate cancer), liver cancers (e.g., hepatocellular cancer, primary liver cancer, extrahepatic bile duct cancer), thyroid cancers (e.g., medullary thyroid carcinoma), renal cancers (e.g., renal cell carcinomas (e.g., clear cell renal cell carcinoma), transitional cell cancer of the renal pelvis and ureter), uterine cancers (e.g., cervical cancer, uterine body cancer, uterus sarcoma), gestational choriocarcinoma, brain tumors (e.g., medulloblastoma, glioma, pineal astrocytic tumor, pilocytic astrocytoma, diffuse astrocytoma, anaplastic astrocytoma, pituitary adenoma), retinoblastoma, skin cancers (e.g., basalioma, malignant melanoma), sarcomas (e.g., rhabdomyosarcoma, leiomyosarcoma, soft tissue sarcoma, spindle cell sarcoma, osteosarcoma), malignant bone tumor, bladder cancer, blood cancers (e.g., multiple myeloma, leukaemias (e.g., acute myeloid leukaemia, acute lymphocytic leukaemia), malignant lymphoma, Hodgkin's disease, chronic myeloproliferative disease), cancer of unknown primary; inhibition of a cancer growth, suppression of metastasis; promotion of an apoptosis; and treatment of precancerous lesions (e.g., myelodysplastic syndrome).

Further, the inflammatory diseases include, e.g., acute pancreatitis, chronic pancreatitis, asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, idiopathic pulmonary fibrosis, nephritis, acute kidney injury, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis, diabetic nephropathy, uveitis, hidradenitis suppurativa and the like.

Further, the autoimmune disease includes, e.g., rheumatoid arthritis, psoriasis, inflammatory bowel disease (e.g., Crohn's disease, ulcerative colitis, etc.), Sjogren's syndrome, Behcet's disease, multiple sclerosis, systemic lupus erythematosus, lupus nephritis, discoid lupus erythematosus, Castleman's disease, ankylosing spondylitis, polymyositis, dermatomyositis, polyarteritis nodosa, mixed connective tissue disease, scleroderma, profundus lupus erythematosus, chronic thyroiditis, Graves' disease, autoimmune gastritis, type I diabetes, autoimmune hemolytic anemia, autoimmune neutropenia, thrombocytopenia, atopic dermatitis, chronic active hepatitis, myasthenia gravis, graft versus host disease, Addison's disease, abnormal immunoresponse, arthritis, dermatitis, radiodermatitis, primary biliary cirrhosis and the like.

The osteoarticular degenerative diseases include, e.g., rheumatoid arthritis, osteoporosis, osteoarthritis, osteopenia, bone Behcet's disease, osteomalacia and the like.

The central nervous system diseases include, e.g., schizophrenia, Alzheimer's disease (e.g., Alzheimer-type dementia), Parkinson's disease, Huntington's disease, Rubenstein-Taybis syndrome, muscular dystrophy, Rett syndrome, Charcot-Marie-Tooth disease, depression and the like.

The cardiovascular diseases include, e.g., chronic heart failure, acute heart failure, acute decompensated heart failure, ischemic heart disease, cardiomyopathy, myocarditis, valvular disease and the like.

The metabolic diseases include, e.g., symptomatic obesity, obesity based on simple obesity, obesity-related pathologies or diseases, eating disorder, diabetes (e.g., type 1 diabetes, type 2 diabetes, gestational diabetes, obesity type diabetes), hyperlipidemia (e.g., hypertriglyceridemia, hypercholesterolemia, hyper LDL cholesterolemia, hypo HDL cholesterolemia, postprandial hyperlipemia), metabolic syndrome, non-alcoholic steatohepatitis and the like.

The infectious disease includes, e.g., influenza infection, malaria, human immunodeficiency virus (HIV) infection, acute bacterial meningitis, *Helicobacter pylori* infection, invasive *Staphylococcus aureus* infection, tuberculosis, systemic fungal infection, herpes simplex virus infection, varicella zoster virus infection, human papillomavirus infection, acute viral encephalitis, encephalitis, meningitis, decreased immune function associated with infection and the like.

The compound of the present invention may be administered orally or parenterally as it is or in a mixture with a pharmacologically acceptable carrier as a medicament to a mammal (preferably, humans).

Hereinafter, the medicament containing the compound of the present invention (sometimes to be abbreviated as "the medicament of the present invention") is described in detail. Examples of the dosage form of the medicament of the present invention include oral preparations such as tablets (e.g., sugar-coated tablets, film-coated tablets, sublingual tablets, buccal tablets, orally disintegrating tablets), pills, granules, powders, capsules (e.g., soft capsules, microcapsules), syrups, emulsions, suspensions, films (e.g., orally disintegrating films, oral mucosa-sticking films) and the like. Further, examples of the dosage form of the medicament of the present invention include also parenteral preparations such as injections, drip infusions, transdermal absorption type preparations (e.g., iontophoretic transdermal absorption type preparations), suppositories, ointments, nasal preparations, pulmonary preparations, and eye drops and the like. Also, the medicament of the present invention may be a release control preparation such as an immediate-release preparation or a sustained-release preparation (e.g., a sustained-release microcapsule) and the like.

The medicament of the present invention may be prepared by a known preparation method generally used in the field of preparation technology (e.g., the method described in the Japanese Pharmacopoeia). The medicament of the present invention may contain a suitable amount of an additive such as an excipient, a binder, a disintegrant, a lubricant, a sweeting agent, a surfactant, a suspending agent, an emulsifier, a colorant, a preservative, an aromatic, a corrigent, a stabilizer, a thickening agent and the like generally used in the field of preparation as necessary.

Examples of the above-mentioned pharmacologically acceptable carriers include these additives.

For example, tablet may be prepared using an excipient, a binder, a disintegrant, a lubricant and the like, and pill and granule may be prepared using an excipient, a binder and a disintegrant. Also, powder and capsule may be prepared using an excipient and the like, syrup may be prepared using a sweeting agent and the like, and emulsion or suspension may be prepared using a suspending agent, a surfactant, an emulsifier and the like.

Examples of the excipient include lactose, white sugar, glucose, starch, sucrose, crystalline cellulose, powdered glycyrrhiza, mannitol, sodium hydrogencarbonate, calcium phosphate and calcium sulfate.

Examples of the binder include 5 to 10 wt % starch liquid paste, 10 to 20 wt % gum arabic solution or gelatin solution, 1 to 5 wt % tragacanth solution, carboxymethyl cellulose solution, sodium alginate solution and glycerin.

Examples of the disintegrant include starch and calcium carbonate.

Examples of the lubricant include magnesium stearate, stearic acid, calcium stearate and purified talc.

Examples of the sweeting agent include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethyl cellulose, methyl cellulose and bentonite.

Examples of the emulsifier include gum arabic, tragacanth, gelatin and polysorbate 80.

For example, when the medicament of the present invention is a tablet, the tablet may be prepared, e.g., by adding an excipient (e.g., lactose, sucrose, starch), a disintegrant (e.g., starch, calcium carbonate), a binder (e.g., starch, gum arabic, carboxymethyl cellulose, polyvinyl pyrrolidone, hydroxypropyl cellulose) or a lubricant (e.g., talc, magnesium stearate, polyethylene glycol 6000) to the compound of the present invention, compression-molding according to a method known per se, and then, if necessary, coating it for the purpose of taste masking, enteric property or durability to give a tablet according to a method known per se. As the coating agent used for coating, e.g., hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (methacrylic acid/acrylic acid copolymer, Rohm, Germany) and pigments (e.g., iron oxide red, titanium dioxide) may be used.

Examples of the above-described injection include intravenous injection as well as subcutaneous injection, intradermal injection, intramuscular injection, intraperitoneal injection, drip injection and the like.

Such injections are prepared according to a method known per se, that is, by dissolving, suspending or emulsifying the compound of the present invention in a sterilized aqueous liquid or oily liquid. Examples of the aqueous liquid include physiological saline, isotonic solutions containing glucose or other auxiliary drugs (e.g., D-sorbitol, D-mannitol, sodium chloride) and the like. The aqueous liquid may contain a suitable solubilizer, e.g., an alcohol (e.g., ethanol), a polyalcohol (e.g., propylene glycol, polyethylene glycol), a nonionic surfactant (e.g., polysorbate 80, HCO-50). Examples of the oily liquid include sesame oil and soybean oil and the like. The oily liquid may contain a suitable solubilizing agent. Examples of the solubilizing agent include benzyl benzoate, benzyl alcohol and the like. In addition, the injection may be blended with a buffer (e.g., phosphate buffer, sodium acetate buffer), a soothing agent (e.g., benzalkonium chloride, procaine hydrochloride), a stabilizer (e.g., human serum albumin, polyethylene glycol), a preservative (e.g., benzyl alcohol, phenol) and the like. A prepared injection solution may be usually filled into an ampoule.

The content of the compound of the present invention in the medicament of the present invention varies depending on the form of the pharmaceutical preparation, and is usually about 0.01 to about 100 wt %, preferably about 2 to about 85 wt %, more preferably about 5 to about 70 wt %, based on the whole preparation.

The content of the additive in the medicament of the present invention varies depending on the form of the pharmaceutical preparation, and is usually about 1 to about 99.9 wt %, preferably about 10 to about 90 wt %, based on the whole preparation.

The compound of the present invention is stable and has low toxicity and may be used safely. The daily dose of the compound of the present invention varies depending on the condition and body weight of a patient, the kind of compound, administration route and the like, in the case of, for example, oral administration to patients for the purpose of treating cancer, the daily dose for an adult (body weight about 60 kg) is about 1 to about 1000 mg, preferably about 3 to about 300 mg, and more preferably about 10 to about 200 mg, as the compound of the present invention, which may be administered once or in two or three divided doses.

When the compound of the present invention is administered parenterally, it is usually administered in the form of a liquid (e.g., injection). The dose of the compound of the present invention varies depending on the subject of administration, target organ, symptoms, administration method and the like, and for example, it is usually about 0.01 to about 100 mg, preferably about 0.01 to about 50 mg, more preferably about 0.01 to about 20 mg, as the compound of the present invention, relative to 1 kg of body weight, which is preferably given by intravenous injection.

When used for prophylaxis or treatment of cancer, the compound of the present invention may be used concurrently with other drugs. Specifically, the compound of the present invention may be used together with a medicament such as hormonal therapeutic agents, chemotherapeutic agents, immunotherapeutic agents, or medicaments inhibiting the action of cell growth factors or their receptors and the like. Hereinafter, drugs that can be used in combination or concurrently with the compound of the present invention are abbreviated as concomitant drugs.

As the "hormonal therapeutic agents" include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testololactone, aminoglutethimide, LH-RH agonists (e.g. goserelin acetate, buserelin, leuprorelin acetate), droloxifene, epitiostanol, ethinyl estradiol sulfonate, aromatase inhibitors (e.g., fadrozole hydrochloride, anastrozole, letrozole, exemestane, vorozole, formestane), anti-androgens (e.g., flutamide, bicalutamide, nilutamide, enzalutamide), 5α-reductase inhibitors (e.g., finasteride, episteride, dutasteride), adrenal cortex hormone drugs (e.g., dexamethasone, prednisolone, betamethasone, triamcinolone), androgen synthesis inhibitors (e.g., abiraterone), retinoids and drugs that retard the metabolism of retinoids (e.g., liarozole), thyroid hormone, and their DDS (Drug Delivery System) preparations may be used.

As the "chemotherapeutic agents", e.g., alkylating agents, antimetabolites, anticancer antibiotics and plant-derived anticancer agents may be used.

As the "alkylating agents", e.g., nitrogen mustard, nitrogen mustard N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucide, carboplatin, cisplatin, miboplatin, nedaplatin, oxaliplatin, altretamine, ambamustine, dibrospidium hydrochloride, fotemustine, prednimustine, pumitepa, ribomustine, temozolomide, treosulfan, trofosfamide, zinostatin stimalamer, adozelesin, cystemustine, bizelesin and DDS preparations thereof may be used.

As the "antimetabolits", e.g., mercaptopurine, 6-mercaptopurine riboside, thioinosine, methotrexate, pemetrexed, enocitabine, cytarabine, cytarabine ocfosphate, ancitabine hydrochloride, 5-FU drugs (e.g., fluorouracil, tegafur, UFT, doxifluridine, carmofur, galocitabine, emitefur, capecitabine), aminopterin, nelzarabine, leucovorin calcium, tabloid, butocine, calcium folinate, levofolinate calcium, cladribine, emitefur, fludarabine, gemcitabine, hydroxycarbamide, pentostatine, piritrexim, idoxuridine, mitoguazone, thiazofurin, ambamustine, bendamustine and their DDS preparations may be used.

As the "anticancer antibiotics", e.g., actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride and their DDS preparations (e.g., doxorubicin-encapsulated PEG liposomes) may be used.

As the "plant-derived anticancer agents", e.g., etoposide, etoposide phosphate, vinblastine sulfate, vincristine sulfate, vindesine sulfate, teniposide, paclitaxel, docetaxel, cabazitaxel, vinorelbine and DDS preparations thereof may be used.

As the "immunotherapeutic agents", e.g., picibanil, krestin, schizophyllan, lentinan, ubenimex, interferons, interleukins, macrophage colony stimulating factor, granulocyte colony stimulating factor, erythropoietin, lymphotoxin, BCG vaccine, Corynebacterium parvum, levamisole, polysaccharide K, procodazole, anti-CTLA4 antibodies (e.g., ipilimumab, tremelimumab), anti-PD-1 antibodies (e.g., nivolumab, pembrolizumab), and anti-PD-L1 antibody may be used.

The "cell growth factors" in the "medicaments inhibiting the action of cell growth factors or their receptors" may be any substance that promote cell growth, and usually include peptides having a molecular weight of 20,000 or less and exhibiting the action at low concentrations by binding to a receptor, and specifically, (1) EGF (epidermal growth factor) or substances having substantially the same activity as EGF (e.g., TGFα); (2) insulin or substances having substantially the same activity as insulin (e.g., insulin, IGF (insulin-like growth factor)-1, IGF-2), (3) FGF (fibroblast growth factor) or substances having substantially the same activity as FGF (e.g., acidic FGF, basic FGF, KGF (keratinocyte growth factor), FGF-10), and (4) other cell growth factors [e.g., CSF (colony stimulating factor), EPO (erythropoietin), IL-2 (interleukin-2), NGF (nerve growth factor), PDGF (platelet-derived growth factor) TGF-β (transforming growth factor β), HGF (hepatocyte growth factor), VEGF (vascular endothelial growth factor), heregulin, angiopoietin may be used.

The "cell growth factor receptors" may be any receptor as long as it has the ability to bind to the above-mentioned cell growth factors, and specifically, EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor and the like may be used.

As the "medicament inhibiting the action of cell growth factors or their receptors", EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGF(inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Smo inhibitor, ALK inhibitor, ROR1 inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor, PI3K inhibitor and the like may be used. More specifically, anti-VEGF antibody (e.g., Bevacizumab, Ramucirumab), anti-HER2 antibody (e.g., Trastuzumab, Pertuzumab), anti-EGFR antibody (e.g., Cetuximab, Panitumumab, Matuzumab, Nimotuzumab), anti-HGF antibody, Imatinib, Erlotinib, Gefitinib, Sorafenib, Sunitinib, Dasatinib, Lapatinib, Vatalanib, Ibrutinib, Bosutinib, Cabozantinib, Crizotinib, Alectinib, Vismodegib, Axitinib, Motesanib, Nilotinib, 6-[4-(4-ethylpiperazin-1-ylmethyl)phenyl]-N-[1(R)-phenylethyl]-7H-pyrrolo[2,3-d] pirimidine-4-amine (AEE-788), Vandetanib, Temsirolimus, Everolimus, Enzastaurin, Tozasertib, 2-[N-[3-[4-[5-[N-(3-fluorophenyl)carbamoylmethyl]-1H-pyrazol-3-ylamino] quinazolin-7-yloxy]propyl]-N-ethylamino]ethyl phosphate ester (AZD-1152), 4-[9-chloro-7-(2,6-difluorophenyl)-5H-pyrimido[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), Volasertib, Selumetinib, Trametinib, N-[2(R),3-dihydroxypropoxy]-3,4-difluoro-2-(2-fluoro4-iodophenylamino)benzamide (PD-0325901), Bosutinib, Regorafenib, Afatinib, Idelalisib, Ceritinib, Dabrafenib and the like may be used.

In addition to the above-mentioned drugs, asparaginase, aceglaton, procarbazine hydrochloride, protoporphyrin-cobalt complex salt, mercury hematoporphyrin-sodium, topoisomerase I inhibitors (e.g., irinotecan, topotecan, indotecan, indimitecan), topoisomerase II inhibitors (e.g., sobuzoxane)), differentiation-inducing agents (e.g., retinoid, vitamin D), other angiogenesis inhibitors (e.g., fumagillin, shark extract, COX-2 inhibitor), α-blockers (e.g., tamsulosin hydrochloride), bisphosphonic acids (e.g., pamidronate, zoledronate), thalidomide, lenalidomide, pomalidomide, 5-azacitidine, decitabine, proteasome inhibitors (e.g., bortezomib, carfilzomib, ixazomib), NEDD8 inhibitors (e.g., Pevonedistat), UAE inhibitors, PARP inhibitors (e.g., Olaparib, Niraparib, Veliparib), anti-tumor antibodies such as anti-CD20 antibodies (e.g., Rituximab, Obinutuzumab), anti-CCR4 antibodies (e.g., Mogamulizumab) and the like, antibody drug conjugates (e.g., Trastuzumab emtansine, Brenximab vedotin) and the like may also be used as a concomitant drug.

When the compound of the present invention is used for purposes other than cancer, besides the above-mentioned concomitants, e.g., antibacterial drugs, antifungal drugs, nonsteroidal anti-inflammatory drugs, steroid drugs, anticoagulants, antiplatelet drugs, thrombolytic drugs, immunomodulators, antiprotozoal drugs, antitussives/expectorants, sedatives, anesthetics, narcotic antagonists, anti-ulcer drugs, therapeutic drugs for hyperlipidemia, therapeutic drugs for arteriosclerosis, HDL-increasing drugs, unstable plaque stabilization drugs, cardioprotective drugs, therapeutic drugs for hypothyroidism, therapeutic drugs for nephrotic syndrome, chronic renal failure drugs, diuretics, therapeutic drugs for hypertension, therapeutic drugs for cardiac failure, muscle relaxants, antiepileptic drugs, inotropic drugs, vasodilators, vasoconstrictors, therapeutic drugs for arrhythmia, therapeutic drugs for diabetes, vasopressor, tranquilizer drugs, antipsychotic drugs, Alzheimer's disease drugs, anti-Parkinson drugs, therapeutic drugs for amyotrophic lateral sclerosis remedies, neurotrophic factors, antidepressants, therapeutic drugs for schizophrenia, vitamins, vitamins derivatives, therapeutic drugs for arthritis, antirheumatic drugs, antiallergic drugs, anti-asthmatic drugs, therapeutic drugs for dermatitis atopic, therapeutic drugs for rhinitis allergic, therapeutic drugs for pollakiuria/urinary incontinence, proteolytic drugs, proteolytic enzyme inhibitors, anti-SIDS drugs, anti-sepsis drugs, anti-septic shock drugs, endotoxin antagonists or antibodies, signal transduction inhibitors, inflammatory mediator action suppressants, inflammatory mediator action suppression antibodies, inflammatory mediator production suppressants, anti-inflammatory mediator action suppressants, anti-inflammatory mediator action suppression antibodies, anti-inflammatory mediator production suppressants, α1-adrenergic agonist, antiemetic, methemoglobin elevation inhibitors, and the like may be used as a concomitant drugs.

(1) Antibacterial Drugs (i) Sulfa drugs

Sulfamethizole, sulfisoxazole, sulfamonomethoxine, sulfamethizole, salazosulfapyridine, silver sulfadiazine, etc.

(ii) Quinoline antibacterial drugs nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin, etc.

(iii) Antiphthisics isoniazid, ethambutol (ethambutol hydrochloride), para-aminosalicylic acid (calcium para-aminosalicylate), pyrazinamide, ethionamide, prothionamide, rifampicin, streptomycin sulfate, kanamycin sulfate, cycloserine, etc.

(iv) Antiacidfast bacterium drug diaminodiphenyl sulfone, rifampicillin, etc.

(v) Antiviral drugs idoxuridine, aciclovir, vidarabine, ganciclovir, etc.

(vi) Anti-HIV drugs zidovudine, didanosine, zalcitabine, indinavir sulfate ethanolate, ritonavir, etc.

(vii) Anti-spirochete drugs (viii) Antibiotics tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cefalotin, cephapirin, cefaloridine, cefaclor, cefalexin, cefroxadine, cefadroxil, cefamandole, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or salts thereof, griseofulvin, lankacidin, etc.

(2) Antifungal Drugs (i) Polyene antibiotics (e.g., amphotericin B, nystatin, trichomycin)

(ii) Griseofulvin, pyrrolnitrin, etc.

(iii) Cytosine antimetabolites (e.g., flucytosine)

(iv) Imidazole derivatives (e.g., econazole, clotrimazole, miconazole nitrate, bifonazole, croconazole)

(v) Triazole derivatives (e.g., fluconazole, itraconazole, azole compounds [2-[(1R, 2R)-2-(2,4-difluorophenyl)-2-hydroxy-1-methyl-3-(1H-1,2,4-triazol-1-yl) propyl]-4-[4-(2,2,3,3-tetrafluoropropoxy) phenyl]-3-(2H,4H)-1,2,4-triazolone]

(vi) Thiocarbamic acid derivatives (e.g., tolnaftate)

(vii) Echinocandin derivatives (e.g., caspofungin, micafungin, anidulafungin), etc.

(3) Non-Steroidal Anti-Inflammatory Drugs acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesylate, ulinastatin, colchicine, probenecid, sulfinpyrazone, benzbromarone, allopurinol, gold sodium thiomalate, sodium hyaluronate, sodium salicylate, morphine hydrochloride, salicylic acid, atropine, scopolamine, morphine, pethidine, levorphanol, ketoprofen, naproxen, oxymorphone, meloxicam, celecoxib, rofecoxib, or salts thereof.

(4) Steroid Drugs dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclometasone propionate, estriol, etc.

(5) Anticoagulants heparin sodium, sodium citrate, activated protein C, tissue factor pathway inhibitor, antithrombin III, dalteparin sodium, warfarin potassium, argatroban, gabexate, sodium citrate, etc.

(6) Antiplatelet Drugs ozagrel sodium, ethyl icosapentate, beraprost sodium, alprostadil, ticlopidine hydrochloride, pentoxifylline, dipyridamole, etc.

(7) Thrombolytic Drugs tisokinase, urokinase, streptokinase, etc.

(8) Immunomodulators cyclosporin, tacrolimus, gusperimus, azathioprine, anti-lymphocyte serum, freeze-dried sulfonated normal immunoglobulin, erythropoietin, colony stimulating factor, interleukin, interferon, etc.

(9) Antiprotozoal Drugs metronidazole, tinidazole, diethylcarbamazine citrate, quinine hydrochloride, quinine sulfate, etc.

(10) Antitussive and Expectorant Drugs ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline, oxymetebanol, morphine hydrochloride, dextropetorphan hydrobromide, oxycodone hydrochloride, dimorphane phosphate, tipepidine hibenzate, pentoxyverine citrate, clofedanol hydrochloride, benzonatate, guaifenesin, bromhexine hydrochloride, ambroxol hydrochloride, acetylcysteine, ethylcysteine hydrochloride, carbocysteine, etc.

(11) Sedatives chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromvalerylurea, chloral hydrate, triclofos sodium, etc.

(12) Anesthetics (12-1) Local Anesthetics cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine, etc.

(12-2) General Anesthetics (i) Inhalation anesthetics (e.g., ether, halothane, nitrous oxide, isoflurane, enflurane), (ii) Intravenous anesthetics (e.g., ketamine hydrochloride, droperidol, thiopental sodium, thiamylal sodium, pentobarbital), etc.

(13) Narcotic Antagonists levallorphan, nalorphine, naloxone or a salt thereof, etc.

(14) Anti-Ulcer Drugs metoclopramide, histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin, etc.

(15) Therapeutic Drugs for Hyperlipidemia

HMG-CoA reductase inhibitors (e.g., fluvastatin, cerivastatin, atorvastatin, etc.), fibrate drugs (e.g., simfibrate, clofibrate aluminum, clinofibrate, fenofibrate, etc.), bile acid adsorbents (e.g., colestyramine, etc.), nicotinic acid preparations (e.g., nicomol, niceritrol, tocopherol nicotinate, etc.), probucol and its derivatives, polyunsaturated fatty acid derivatives (e.g., ethyl icosapentate, polyenephosphatidylcholine, melinamide, etc.), plant sterols (e.g., gamma-oryzanol, soysterol, etc.), elastase, dextran sulfate sodium, squalene synthase inhibitor, squalene epoxidase inhibitor, CETP inhibitor, ethyl 2-chloro-3-[4-(2-methyl-2-phenyl-propoxy)phenyl]propionate, LDL receptor increasing drugs, cholesterol absorption inhibitors (Ezetimibe, etc.), MTP inhibitors, ileal bile acid transporter inhibitors, SCAP ligands, FXR ligands, etc.

(16) Therapeutic Drugs for Arteriosclerosis

MMP inhibitors, chymase inhibitors, ACAT inhibitors (Avasimibe, Eflucimibe, etc.), apoAI Milano and its analogs, scavenger receptor inhibitors, 15-lipoxygenase inhibitors, phospholipase A2 inhibitors, ABCA1 activators, LXR ligands, sphingomyelinase inhibitors, paraoxonase activators, estrogen receptor agonists, etc.

(17) HDL Increasing Drug

Squalene synthase inhibitors, CETP inhibitors, LPL activators, etc.

(18) Unstable Plaque Stabilizers

MMP inhibitors, chymase inhibitors, ACAT inhibitors, lipid-rich plaque regressing agents, etc.

(19) Cardioprotective Drugs oral drugs for cardiac ATP-K, endothelin antagonists, urotensin antagonists, etc.

(20) Therapeutic Drugs for Hypothyroidism

Freeze-dried thyroid (Thyroid), levothyroxine sodium (Thyradin S), liothyronine sodium (thyronine, thyronine), etc.

(21) Therapeutic Drugs for Nephrotic Syndrome prednisolone (predonine), prednisolone sodium succinate (predonine), methylprednisolone sodium succinate (solu-medrol), betamethasone (rinderone), etc.

(22) Therapeutic Drugs for Chronic Renal Failure diuretics (e.g., furosemide (Lasix), bumetanide (Lunetron), azosemide (Diart)), antihypertensives (e.g., ACE inhibitors, enalapril maleate (Lenivase), calcium antagonists (Manidipine), α receptor blockers, AII antagonist (candesartan)], etc.

(23) Diuretic Drug thiazide diuretics (bentyl hydrochlorothiazide, cyclopentiazide, ethiazide, hydrochlorothiazide, hydroflumethiazide, methyclothiazide, penfluthiazide, polythiazide, trichlormethiazide, etc.), loop diuretics (chlorthalidone, clofenamide, indapamide, mefruside, meticrane, sotrazone, tripamide, quinethazone, metolazone, furosemide, etc.), potassium-sparing diuretics (spironolactone, triamterene, etc.)

(24) Therapeutic Drugs for Antihypertensive (i) Sympathetic suppressors

α2 stimulants (e.g., clonidine, guanabenz, guanfacine, methyldopa, etc.), ganglion blockers (e.g., hexamethonium, trimetaphan, etc.), presynaptic blockers (e.g., alseroxylon, dimethylaminoreserpinate, recinnamine, reserpine, syrosingopine, etc.), neuron blockers (e.g., betanidine, guanethidine, etc.), α1 blockers (e.g., bunazosin, doxazosin, prazosin, terazosin, urapidil, etc.), p blockers (e.g., propranolol, timolol, nipradilol, bunitrolol, indenolol, penbutolol, carteolol, carvedilol, pindolol, acebutolol, atenolol, bisoprolol, metoprolol, labetalol, amosulalol, arotinolol, etc.), et.

(ii) Vasodilators calcium channel antagonists (e.g., manidipine, nicardipine, nilvadipine, nisoldipine, nitrendipine, benidipine, amlodipine, aranidipine, etc.), phthalazine derivatives (e.g., budralazine, cadralazine, ecarazine, hydralazine, todralazine, etc.), etc.

(iii) ACE inhibitors alacepril, captopril, cilazapril, delapril, enalapril, lisinopril, temocapril, trandolapril, quinapril, imidapril, benazepril, perindopril, etc.

(iv) AII antagonists losartan, candesartan, valsartan, telmisartan, irbesartan, forasartan, etc.

(v) Diuretics (such as the diuretics mentioned above)

(25) Therapeutic Drugs for Cardiac Failure cardiotonics (e.g., digitoxin, digoxin, methyldigoxin, lanatoside C, proscillaridin, etc.), α,β stimulants (e.g., epinephrine, norepinephrine, isoproterenol, dopamine, docarpamine, dobutamine, denopamine, etc.), phosphodiesterase inhibitors (e.g., amrinone, milrinone, olprinone hydrochloride, etc.), calcium channel sensitivity enhancers (e.g., pimobendan, etc.), nitrates (e.g., nitroglycerin, isosorbide dinitrate, etc.), ACE inhibitors (e.g., ACE inhibitors described above), diuresis drugs (e.g., the aforementioned diuretics), carperitide, ubidecarenone, vesnarinone, aminophylline, etc.

(26) Muscle Relaxants pridinol, tubocurarine, pancuronium, tolperisone hydrochloride, chlorphenesin carbamate, baclofen, chlormezanone, mephenesin, chlorzoxazone, eperisone, tizanidine, etc.

(27) Antiepileptic Drugs phenytoin, ethosuximide, acetazolamide, chlordiazepoxide, trimethadione, carbamazepine, phenobarbital, primidone, sultiam, sodium valproate, clonazepam, diazepam, nitrazepam, etc.

(28) Cardiotonics aminophylline, etilefrine, dopamine, dobutamine, denopamine, aminophylline, amrinone, pimobendan, ubidecarenone, digitoxin, digoxin, methyldigoxin, lanatoside C, G-strophanthin, etc.

(29) Vasodilators oxyfedrine, diltiazem, tolazoline, hexobendine, bamethane, clonidine, methyldopa, guanabenz, etc.

(30) Vasoconstrictors dopamine, dobutamine, denopamin, etc.

(31) Therapeutic Drugs for Arrhythmic (i) Sodium channel blockers (e.g., quinidine, procainamide, disopyramide, ajmaline, cibenzoline, lidocaine, diphenylhydantoin, mexiletine, propafenone, flecainide, pilsicainide, phenytoin, etc.), (ii) β-Blockers (e.g., propranolol, alprenolol, bufetrol, oxprenolol, atenolol, acebutolol, metoprolol, bisoprolol, pindolol, carteolol, arotinolol, etc.), (iii) Potassium channel blockers (e.g., amiodarone, etc.), (iv) Calcium channel blockers (e.g., verapamil, diltiazem, etc.), etc.

(32) Vasopressors dopamine, dobutamine, denopamine, digitoxin, digoxin, methyldigoxin, lanatoside C, G-strophanthin, etc.

(33) Antidiabetics sulfonylurea agents (e.g., tolbutamide, chlorpropamide, glyclopyramide, acetohexamide, tolazamide, glibenclamide, glybuzole, etc.), biguanides (e.g., metformin hydrochloride, buformin hydrochloride, etc.), α-glucosidase inhibitors (e.g., voglibose, acarbose, etc.), insulin sensitizers (e.g., pioglitazone, rosiglitazone, troglitazone, etc.), insulin, glucagon, agents for treating diabetic complications (e.g., epalrestat, etc.), DPP4 inhibitors (e.g., sitagliptin, vildagliptin, alogliptin, linagliptin, etc.), etc.

(34) Tranquilizers diazepam, lorazepam, oxazepam, chlordiazepoxide, medazepam, oxazolam, cloxazolam, clotiazepam, bromazepam, etizolam, fludiazepam, hydroxyzine, etc.

(35) Antipsychotics chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine, etc.

(36) Alzheimer's Disease Therapeutic Agents (i) Cholinesterase inhibitors such as donepezil, rivastigmine, and galanthamine, (ii) Brain function activators such as idebenone, memantine, vinpocetine, etc.

(37) Anti-Parkinson Drugs

L-dopa, deprenyl, carbidopa+levodopa, pergolide, ropinirole, cabergoline, pramipexole, entacapone, lazabemide, etc.

(38) Amyotrophic Lateral Sclerosis Therapeutic Agent

Riluzole, Mecasermin, Gabapentin, Etc.

(39) Antidepressants imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride, etc.

(40) Therapeutic Drugs for Schizophrenia olanzapine, risperidone, quetiapine, iloperidone, etc.

(41) Vitamin Drugs (i) Vitamin A: vitamin A1, vitamin A2 and retinol palmitate (ii) Vitamin D: Vitamin D1, D2, D3, D4 and D5

(iii) Vitamin E: α-tocopherol, β-tocopherol, γ-tocopherol, δ-tocopherol, d1-α-tocopherol nicotinate (iv) Vitamin K: vitamin K1, K2, K3 and K4

(v) Folic acid (vitamin M)

(vi) Vitamin B: vitamin B1, vitamin B2, vitamin B3, vitamin B5, vitamin B6 and vitamin B12

(vii) Biotin (vitamin H), etc.

(42) Vitamin Derivatives various derivatives of vitamins, e.g., ascorbic acid, vitamin D3 derivatives such as 5,6-trans-cholecalciferol, 2,5-hydroxycholecalciferol, 1-α-hydroxycholecalciferol, etc., vitamin D2 derivatives such as 5,6-trans-ergocalciferol, etc., etc.

(43) Antiallergic Drugs diphenhydramine, chlorpheniramine, tripelennamine, clemizole, diphenylpyraline, methoxyphenamine, sodium cromoglicate, tranilast, repirinast, amlexanox, ibudilast, ketotifen, terfenadine, mequitazine, azelastine, epinastine, ozagrel hydrochloride, pranlukast hydrate, seratrodast, etc.

(44) Anti-Asthmatic Drugs isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, ibudilast, ketotifen, terfenadine, mequitazine, azelastine, epinastine, ozagrel hydrochloride, pranlukast hydrate, seratrodast, dexamethasone, prednisolone, hydrocortisone, beclomethasone propionate, etc.

(45) Therapeutic Drugs for Dermatitis Atopic sodium cromoglicate, etc.

(46) Therapeutic Drugs for Rhinitis Allergic sodium cromoglicate, chlorpheniramine maleate, alimemazine tartrate, clemastine fumarate, homochlorcyclizine hydrochloride, terfenadine, mequitazine, etc.

(47) Therapeutic drug for urinary frequency/urinary incontinence flavoxate hydrochloride, etc.

(48) Anti-Sepsis Drugs peptidic compounds such as rBPI-21 (bactericidal permeability increasing protein), BI-51017 (antithrombin III), SC-59735 (rTFPI), r-PAF acetylhydrolase, LY-203638 (r-activated protein C), anti-TNF-α antibody, anti-CD14 antibody, CytoFab, alkaline phosphatase (LPS inactivator), etc., non-peptidic compounds such as JTE-607, eritoran, S-5920, FR-167653, ONO-1714, ONO-5046 (sivelestat), GW-273629, RWJ-67657, GR-270773, NOX-100, GR-270773, NOX-100, INO-1001, etc.

(49) Prognosis Improving Drugs after Coronary Artery Bypass Graft Surgery eritoran, etc.

(50) Antiemetics phenothiazine derivatives, 5-HT3 receptor antagonists, etc.

(51) Methemoglobin Elevation Inhibitors methylene blue, ascorbic acid, etc.

(52) Anti-Cytokine Drugs (I) Protein Drugs (I) TNF inhibitors etanercept, infliximab, adalimumab, certolizumab pegol, golimumab, PASSTNF-α, soluble TNF-α receptor, TNF-α binding protein, anti-TNF-α antibody, etc.

(ii) Interleukin-1 inhibitors anakinra (interleukin-1 receptor antagonist), soluble interleukin-1 receptor, etc.

(iii) Interleukin-6 inhibitors tocilizumab (anti-interleukin-6 receptor antibody), anti-interleukin-6 antibody, etc.

(iv) Interleukin-10 drugs interleukin-10, etc.

(v) Interleukin-12/23 inhibitors ustekinumab, briakinumab (anti-interleukin-12/23 antibody), etc.

(Vi) Interleukin-17 inhibitors secukinumab, ixekizumab, brodalumab, etc.

(II) Non-Protein Drugs (i) MAPK inhibitors

BMS-582949, etc.

(ii) Gene modulators

Inhibitors for molecules involved in signal transduction such as NF-κ, NF-κB, IKK-1, IKK-2, AP-1, etc.

(iii) Cytokine production suppressors iguratimod, tetomilast, etc.

(iv) TNF-α converting enzyme inhibitors (v) Interleukin-1β converting enzyme inhibitors VX-765, etc.

(vi) Interleukin-6 antagonists

HMPL-004, etc.

(vii) Interleukin-8 inhibitors

IL-8 antagonists, CXCR1 & CXCR2 antagonists, cefalexin, etc.

(viii) Chemokine antagonists

CCR9 antagonists (CCX-282, CCX-025), MCP-1 antagonists, etc.

(ix) Interleukin-2 receptor antagonists denileukin diftitox, etc.

(x) Therapeutics vaccines
  TNF-α vaccine, etc.
(xi) Gene therapy agents
  gene therapy drugs aiming at promoting the expression of a gene having an anti-inflammatory action such as interleukin-4, interleukin-10, soluble interleukin-1 receptor, soluble TNF-α receptor, etc.
(Xii) Antisense compounds
  ISIS-104838, etc.
(53) Integrin Inhibitors
  natalizumab, vedolizumab, AJM300, TRK-170, E-6007, etc.
  Antidepressants (e.g., amitriptyline, imipramine, clomipramine, desipramine, doxepin, nortriptyline, duloxetine, milnacipran, fluoxetine, paroxetine, sertraline, citalopram, etc.)
  Anticonvulsants (e.g., carbamazepine, pregabalin, gabapentine, lamotrigine, phenytoin, valproic acid, etc.) Narcotics (e.g., morphine, oxycodone, fentanyl, methadone, codeine, tramadol, etc.)
(54) Others
  hydroxycam, diacerein, megestrol acetate, nicergoline, prostaglandins, etc.

By combining the compound of the present invention and a concomitant drug, a superior effect may be obtained such as (1) the dose of the compound of the present invention or the concomitant drug may be reduced as compared with a case where the compound is administered alone, (2) the drug to be used in combination with the compound of the present invention may be selected depending on the patient's condition (mild case, severe case, etc.), (3) the treatment period may be set longer, (4) a therapeutic effect maintaining longer is designed, and (5) by using the compound of the present invention in combination with a concomitant drug, a synergistic effect may be obtained.

Hereinafter, when the compound of the present invention is used in combination with a concomitant drug, it is referred to as the "combination drug of the present invention".

When using the combination drug of the present invention, the administration time of the compound of the present invention and the concomitant drug is not limited, and the compound of the present invention and the concomitant drug may be administered simultaneously to a subject to be administered, or with a time interval. When the administration is carried out with a time interval, the time interval varies depending on the effective ingredient to be administered, dosage form and administration method, and for example, when the concomitant drug is administered first, the compound of the present invention may be administered within 1 minute to 3 days, preferably within 10 minutes to 1 day, more preferably within 15 minutes to 1 hour after administration of the concomitant drug. When the compound of the present invention is administered first, the concomitant drug may be administered within 1 minute to 1 day, preferably within 10 minutes to 6 hours, more preferably within 15 minutes to 1 hour after administering the compound of the present invention. The dosage of the concomitant drug may be in accordance with the dose clinically used, and may be appropriately selected depending on the administration subject, administration route, disease, combination, and the like.

Examples of the administration mode when the compound of the present invention and the concomitant drug are used concurrently include (1) administration of a single preparation obtained by simultaneously preparing the compound of the present invention and the concomitant drug, (2) simultaneous administration by the same administration route of two preparations obtained by separately preparing the compound of the present invention and a concomitant drug, (3) administration with an time interval by the same administration route of two preparations obtained by separately preparing the compound of the present invention and a concomitant drug, (4) simultaneous administration by the different administration routes of two preparations obtained by separately preparing the compound of the present invention and a concomitant drug, and (5) administration with a time interval by the different administration routes of two preparations obtained by separately preparing the compound of the present invention and a concomitant drug (e.g., administration in the order of the compound of the present invention and the concomitant drug, or administration in the reverse order).

The dose of the concomitant drug may be appropriately determined based on the clinically used dose. The ratio of the compound of the present invention and the concomitant drug may be appropriately determined depending on the administration subject, administration route, target disease, symptom, combination and the like. For example, when the administration subject is a human, the concomitant drug may be used in an amount of 0.01 to 100 parts by weight relative to 1 part by weight of the compound of the present invention.

Further, the compound of the present invention or the combination drug of the present invention may be used in combination with non-drug therapy. Specifically, the compound of the present invention or the combination drug of the present invention may be combined with non-drug therapy such as (1) surgery, (2) hypertensive chemotherapy using angiotensin II or the like, (3) gene therapy, (4) thermotherapy, (5) cryotherapy, (6) laser cauterization and (7) radiotherapy.

For example, by using the compound of the present invention or the combination drug of the present invention before or after the above-mentioned surgery or the like, or using the compound or the drug before or after a combined treatment of two or three kinds thereof, effects may be obtained such as prevention of the onset of resistance, prolongation of disease-free survival, suppression of metastasis or recurrence of cancer, prolongation of life, and the like.

Further, it is possible to combine a treatment with the compound of the present invention or the combination drug of the present invention with a supportive therapy [(i) administration of antibiotics (e.g., β-lactam type such as pansporin and the like, macrolide type such as clarithromycin and the like) for the complication with various infectious diseases, (ii) administration of high-calorie transfusion, amino acid preparation or multivitamin preparation for improving malnutrition, (iii) morphine administration for pain relief, (iv) administration of a drug for ameliorating side effects such as nausea, vomiting, anorexia, diarrhea, leukopenia, thrombocytopenia, decreased hemoglobin concentration, hair loss, liver damage, renal damage, DIC, fever and the like, and (v) administration of a drug for suppressing multiple drug resistance of cancer, etc.

The present invention is explained in detail by referring to the following Examples, Experimental Examples and Formulation Examples, which are not to be construed as limitative, and the disclosure may be changed within the scope of the present invention.

In the following Examples, the "room temperature" generally means about 10° C. to about 35° C. The ratios indicated for mixed solvents are volume mixing ratios, unless otherwise specified. "%" means "wt %," unless otherwise specified.

In silica gel column chromatography, "NH" means use of aminopropyl silane-bound silica gel and "C18" means use of octadecyl-bound silica gel. In HPLC (high-performance liquid chromatography), "C18" means use of octadecyl-bonded silica gel. The ratios of elution solvents are volume mixing ratios, unless otherwise specified.

In Examples, the following abbreviations are used.
MS: mass spectrum
M: mol concentration
DMSO-$d_6$: deuterated dimethyl sulfoxide
$^1$H NMR: proton nuclear magnetic resonance
LC/MS: liquid chromatograph mass spectrometer
ESI: ElectroSpray Ionization
APCI: Atmospheric Pressure Chemical Ionization
DCM: dichloromethane
DIEA: diisopropylethylamine
DMAP: 4-dimethylaminopyridine
DMF: N,N-dimethylformamide
HATU: 2-(7-azabenzotriazol-1-yl)-1,1,3,3-tetrametyluroniumhexafluorophosphate
TBTU: 1-[bis(dimethylamino)methylene]-1H-benzotriazorium-3-oxidetetrafluoroborate
TEA: triethylamine
THF: tetrahydrofuran
TFA: trifluoroacetate $^1$H NMR was measured by Fourier-transform type NMR. For the analysis, ACD/SpecManager (trade name) or Mnova (trade name) and the like were used. Peaks with very mild protons such as a hydroxy group, an amino group and the like are not described.

MS was measured by LC/MS. As an ionization method, ESI method or APCI method was used. The data indicates actual measured value (found). Generally, a molecular ion peak ([M+H]$^+$, [M−H]$^-$, etc.) was observed. In the case of a compound having a tert-butoxycarbonyl group, a peak after elimination of a tert-butoxycarbonyl group or a tert-butyl group may be observed as a fragment ion. In the case of a compound having a carboxyl group, a peak of sodium adduct thereof may be observed. In the case of a compound having a hydroxy group, a peak after elimination of H$_2$O may be observed as a fragment ion. In the case of a salt, a molecular ion peak or fragment ion peak of free form is generally observed.

Sample concentration (c) used in the optical rotation ([α]$_D$) is g/100 mL.

Elemental analysis value (Anal.) indicates both calculated value (Calcd) and measured value (Found).

Example 1

(S)—N—((S)-1-Cyclohexyl-2-(4-(6-methoxy-1-methyl-1H-indole-2-carbonyl)piperazin-1-yl)-2-oxoethyl)-2-(methylamino)propanamide Hydrochloride A) Methyl 6-methoxy-1-methyl-1H-indole-2-carboxylate To a mixture of methyl 6-methoxy-1H-indole-2-carboxylate (11.6 g) and DMF (100 mL) was added sodium hydride (60%, dispersion in paraffin liquid, 2.93 g) at 0° C. After the reaction mixture was stirred at the same temperature for 15 min, iodomethane (3.88 mL) was added to the reaction mixture and the reaction mixture was stirred at the same temperature for 1 h. To the reaction mixture was added water (150 mL) and 1 M hydrochloric acid (250 mL) at 0° C. and the aqueous layer was extracted with diethyl ether. The organic layer was washed with brine and then dried over anhydrous magnesium sulfate, and the solvent was removed under reduced pressure to give the title compound (11.4 g).

MS: [M+H]$^+$ 220.0.

B) 6-Methoxy-1-methyl-1H-indole-2-carboxylic Acid

To a mixture of methyl 6-methoxy-1-methyl-1H-indole-2-carboxylate (11.4 g) and methanol (100 mL) was added 2 M aqueous sodium hydroxide (52.0 mL) at room temperature and the reaction mixture was stirred at 60° C. for 1 h. The reaction mixture was cooled to 0° C. and neutralized with 1 M hydrochloric acid (110 mL), and the precipitates were collected by filtration to give the title compound (9.87 g).

MS: [M+H]$^+$ 206.0.

C) (S)-Benzyl 4-(2-((tert-butoxycarbonyl)amino)-2-cyclohexylacetyl)piperazine-1-carboxylate To a mixture of (S)-2-((tert-butoxycarbonyl)amino)-2-cyclohexylacetic acid (2.5 g,), benzyl piperazine-1-carboxylate (2.14 g), DIEA (5.09 mL) and DMF (48.6 mL) was added HATU (5.54 g) at room temperature. The reaction mixture was stirred at the same temperature for 6 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (4.34 g).

MS: [M+H]$^+$ 460.2.

D) (S)-Benzyl 4-(2-amino-2-cyclohexylacetyl)piperazine-1-carboxylate Hydrochloride To a mixture of (S)-benzyl 4-(2-((tert-butoxycarbonyl)amino)-2-cyclohexylacetyl)piperazine-1-carboxylate (4.34 g) and ethyl acetate (18.9 mL) was added 4 M hydrogen chloride ethyl acetate solution (18.9 mL) at room temperature, and the reaction mixture was stirred at 45° C. for 1 h. The reaction mixture was concentrated under reduced pressure and the crude product was recrystallized from ethyl acetate/hexane to give the title compound (2.96 g).

MS: [M+H]$^+$ 360.2.

E) Benzyl 4-((S)-2-((S)-2-((tert-butoxycarbonyl)(methyl)amino)propanamido)-2-cyclohexylacetyl)piperazine-1-carboxylate To a mixture of (S)-2-((tert-butoxycarbonyl)(methyl)amino)propanoic acid (1.63 g), (S)-benzyl 4-(2-amino-2-cyclohexylacetyl)piperazine-1-carboxylate hydrochloride (2.96 g), DIEA (5.22 mL) and DMF (37.4 mL) was added HATU (4.26 g) at room temperature. The reaction mixture was stirred at the same temperature for 6 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (3.62 g).
MS: [M+H]⁺ 545.4.

F) tert-Butyl ((S)-1-(((S)-1-cyclohexyl-2-oxo-2-(piperazin-1-yl)ethyl)amino)-1-oxopropan-2-yl)(methyl)carbamate To a mixture of benzyl 4-((S)-2-((S)-2-((tert-butoxycarbonyl)(methyl)amino)propanamido)-2-cyclohexylacetyl)piperazine-1-carboxylate (3.62 g), 10% palladium on carbon (362 mg) and ethyl acetate (67 mL) was stirred under the normal pressure hydrogen atmosphere at room temperature for 1 h. The catalysts were filtered off and the filtrate was concentrated under reduced pressure to give the title compound (2.46 g).
MS: [M+H]⁺ 411.3.

G) (S)—N—((S)-1-Cyclohexyl-2-(4-(6-methoxy-1-methyl-1H-indole-2-carbonyl)piperazin-1-yl)-2-oxoethyl)-2-(methylamino)propenamide Hydrochloride To a mixture of 6-methoxy-1-methyl-1H-indole-2-carboxylic acid (16.4 mg, 0.08 mmol), HATU (61 mg), DIEA (56 μL), and dimethylacetamide (500 μL) was added a mixture of tert-butyl ((S)-1-(((S)-1-cyclohexyl-2-oxo-2-(piperazin-1-yl)ethyl)amino)-1-oxopropan-2-yl)(methyl)carbamate (33 mg) and dimethylacetamide (500 μL) at room temperature. The reaction mixture was stirred at the same temperature for 21 h. The reaction mixture was diluted with ethyl acetate and water, the aqueous layer was extracted with ethyl acetate, and the solvent was removed under reduced pressure. The residue was purified by preparative HPLC (C18, mobile phase: water/acetonitrile (containing 0.1% TFA)). To the product thus obtained was added 5-10% hydrogen chloride methanol solution (1 mL) at room temperature and the reaction mixture was stirred at the same temperature for 5 h. The reaction mixture was concentrated under reduced pressure to give the title compound (26.5 mg).
MS: [M+H]⁺ 498.4.
¹H NMR (400 MHz, DMSO-d₆) δ 0.97-1.24 (5H, m), 1.34 (3H, d, J=6.85 Hz), 1.55-1.76 (6H, m) 2.47-2.53 (7H, m), 3.57-3.87 (11H, m), 4.67 (1H, t, J=7.83 Hz), 6.65 (1H, s), 6.75 (1H, dd, J=8.56, 2.20 Hz), 7.03 (1H, d, J=1.96 Hz), 7.48 (1H, d, J=8.56 Hz), 8.75 (1H, d, J=8.31 Hz), 8.75-8.90 (2H, brs).

Example 2-23

The title compounds of Examples 2 to 23 were synthesized in the same manner as step G of Example 1 using corresponding carboxylic acids (0.08 mmol).

TABLE 1

| Example No. | Compound Name | Carboxylic acid | Amount |
|---|---|---|---|
| Example 2 | (S)-N-((S)-1-cyclohexyl-2-oxo-2-(4-(pyrazolo[1,5-a]pyridine-5-carbonyl)piperazin-1-yl)-2-(methylamino)propanamide | pyrazolo[1,5-a]pyridine-5-carboxylic acid | 53.8 mg |
| Example 3 | (S)-N-((S)-1-cyclohexyl-2-(4-(6-methyl pyrazolo[1,5-a]pyridine-5-carbonyl)piperazin-1-yl)-2-oxoethyl)-2-(methylamino)propanamide | 6-methylpyrazolo[1,5-a]pyridine-5-carboxylic acid | 50.6 mg |
| Example 4 | (S)-N-((S)-1-cyclohexyl-2-(4-(4-methylpyrazolo[1,5-a]pyridine-5-carbonyl)piperazin-1-yl)-2-oxoethyl)-2-(methylamino)propanamide | 4-methylpyrazol[1,5-a]pyridine-5-carboxylic acid | 51.2 mg |
| Example 5 | (S)-N-((S)-1-cyclohexyl-2-(4-(4-fluoropyrazolo[1,5-a]pyridine-5-carbonyl)piperazin-1-yl)-2-oxoethyl)-2-(methylamino)propanamide | 4-fluoropyrazolo[1,5-a]pyridine-5-carboxylic acid | 44.5 mg |
| Example 6 | (S)-N-((S)-1-cyclohexyl-2-(4-(6-fluoro pyrazolo[1,5-a]pyridine-5-carbonyl)piperazin-1-yl)-2-oxoethyl)-2-(methylamino)propanamide | 6-fluoropyrazolo[1,5-a]pyridine-5-carboxylic acid | 48.8 mg |
| Example 7 | (S)-N-((S)-1-cyclohexyl-2-(4-(indolizine-2-carbonyl)piperazin-1-yl)-2-oxoethyl)-2-(methylamino)propanamide | indolizine-2-carboxylic acid | 52.2 mg |
| Example 8 | (S)-N-((S)-1-cyclohexyl-2-(4-(3-(2-methoxyethoxy)-1-methyl-1H-pyrazole-5-carbonyl)piperazin-1-yl)-2-oxoethyl)-2-(methylamino)propanamide | 3-(2-methoxyethoxy)-1-methyl-1H-pyrazole-5-carboxylic acid | 48.4 mg |

TABLE 2

| Example No. | Compound Name | Carboxylic acid | Amount |
|---|---|---|---|
| Example 9 | (S)-N-((S)-1-cyclohexyl-2-(4-(3-cyclopropyl-1-methyl-1H-pyrazole-5-carbonyl)piperazin-1-yl)-2-oxoethyl)-2-(methylamino)propanamide | 3-cyclopropyl-1-methyl-1H-pyrazole-5-carboxylic acid | 53.2 mg |
| Example 10 | (S)-N-((S)-1-cyclohexyl-2-(4-(1-methyl-3-propyl-1H-pyrazole-5-carbonyl)piperazin-1-yl)-2-oxoethyl)-2-(methylamino)propanamide | 1-methyl-3-propyl-1H-pyrazole-5-carboxylic acid | 49.1 mg |
| Example 11 | (S)-N-((S)-1-cyclohexyl-2-(4-(1-methyl-3-(trifluoromethyl)-1H-pyrazole-5-carbonyl)piperazin-1-yl)-2-oxoethyl)-2-(methylamino)propanamide | 1-methyl-3-(trifluoromethyl)-1H-pyrazole-5-carboxylic acid | 51.3 mg |
| Example 12 | (S)-N-((S)-1-cyclohexyl-2-(4-(3-ethoxy-1-methyl-1H-pyrazole-5-carbonyl)piperazin-1-yl)-2-oxoethyl)-2-(methylamino)propanamide | 3-ethoxy-1-methyl-1H-pyrazole-5-carboxylic acid | 45.8 mg |

TABLE 2-continued

| Example No. | Compound Name | Carboxylic acid | Amount |
|---|---|---|---|
| Example 13 | (S)-N-((S)-1-cyclohexyl-2-(4-(1-methyl-1H-pyrrolo[2,3-b]pyridine-2-carbonyl)piperazin-1-yl)-2-oxoethyl)-2-(methylamino)propanamide | 1-methyl-1H-pyrrolo[2,3-b]pyridine-2-carboxylic acid | 57.2 mg |
| Example 14 | (S)-N-((S)-1-cyclohexyl-2-(4-(6-fluoro-1-methyl-1H-indole-2-carbonyl)piperazin-1-yl)-2-oxoethyl)-2-(methylamino)propanamide | 6-fluoro-1-methyl-1H-indole-2-carboxylic acid | 54.6 mg |
| Example 15 | (S)-N-((S)-1-cyclohexyl-2-(4-(5-fluoro-1-methyl-1H-indole-2-carbonyl)piperazin-1-yl)-2-oxoethyl)-2-(methylamino)propanamide | 5-fluoro-1-methyl-1H-indole-2-carboxylic acid | 50.0 mg |

TABLE 3

| Example No. | Compound Name | Carboxylic acid | Amount |
|---|---|---|---|
| Example 16 | (S)-N-((S)-1-cyclohexyl-2-(4-(1,7-dimethyl-1H-indole-2-carbonyl)piperazin-1-yl)-2-oxoethyl)-2-(methylamino)propanamide | 1,7-dimethyl-1H-indole-2-carboxylic acid | 47.5 mg |
| Example 17 | (S)-N-((S)-1-cyclohexyl-2-(4-(1-methyl-1H-indazole-6-carbonyl)piperazin-1-yl)-2-oxoethyl)-2-(methylamino)propanamide | 1-methyl-1H-indazole-6-carboxylic acid | 48.4 mg |
| Example 18 | (S)-N-((S)-1-cyclohexyl-2-(4-(1,2-dimethyl-1H-benzo[d]imidazole-6-carbonyl)piperazin-1-yl)-2-oxoethyl)-2-(methylamino)propanamide | 1,2-dimethyl-1H-benzo[d]imidazole-6-carboxylic acid | 44.8 mg |
| Example 19 | (S)-N-((S)-1-cyclohexyl-2-(4-(2-methyl-[1,2,4]triazolo[1,5-a]pyridine-6-carbonyl)piperazin-1-yl)-2-oxoethyl)-2-(methylamino)propanamide | 2-methyl-[1,2,4]triazolo[1,5-a]pyridine-6-carboxylic acid | 46.1 mg |
| Example 20 | (S)-N-((S)-1-cyclohexyl-2-(4-(2-methylindolizine-6-carbonyl)piperazin-1-yl)-2-oxoethyl)-2-(methylamino)propanamide | 2-methylindolizine-6-carboxylic acid | 30.6 mg |
| Example 21 | (S)-N-((S)-1-cyclohexyl-2-(4-(2-methylimidazo[1,2-a]pyridine-7-carbonyl)piperazin-1-yl)-2-oxoethyl)-2-(methylamino)propanamide | 2-methylimidazo[1,2-a]pyridine-7-carboxylic acid" | 50.0 mg |

Example 24

(S)—N—((S)-1-cyclohexyl-2-((R)-4-(6-methoxy-1-methyl-1H-indole-2-carbonyl)-2-methylpiperazin-1-yl)-2-oxoethyl)-2-(methylamino)propanamide Hydrochloride A) (R)-(6-Methoxy-1-methyl-1H-indol-2-yl)(3-methylpiperazin-1-yl)methanone To a mixture of 6-methoxy-1-methyl-1H-indole-2-carboxylic acid (130 mg), (R)-2-methylpiperazine (317 mg), DIEA (443 μL) and DMF (3167 μL) was added HATU (361 mg) at room temperature. The reaction mixture was stirred at the same temperature for 6 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (134 mg).
MS: [M+H]$^+$ 288.1.

B) tert-Butyl ((S)-1-cyclohexyl-2-((R)-4-(6-methoxy-1-methyl-1H-indole-2-carbonyl)-2-methylpiperazin-1-yl)-2-oxoethyl)carbamate To a mixture of (S)-2-((tert-butoxycarbonyl)amino)-2-cyclohexylacetic acid (27.9 mg), (R)-(6-methoxy-1-methyl-1H-indol-2-yl)(3-methylpiperazin-1-yl)methanone (31.2 mg), DIEA (37.9 μL) and DMF (543 μL) was added HATU (49.5 mg) at room temperature. The reaction mixture was stirred at the same temperature for 2 h and the reaction mixture was diluted with water. The precipitates were collected by filtration to give the title compound (53.7 mg).
MS: [M+H]$^+$ 549.2.

C) (S)—N—((S)-1-Cyclohexyl-2-((R)-4-(6-methoxy-1-methyl-1H-indole-2-carbonyl)-2-methylpiperazin-1-yl)-2-oxoethyl)-2-(methylamino)propanamide To a mixture of tert-butyl ((S)-1-cyclohexyl-2-((R)-4-(6-methoxy-1-methyl-1H-indole-2-carbonyl)-2-methylpiperazin-1-yl)-2-oxoethyl)carbamate (53.7 mg) and ethyl acetate (510 μL) was added 4 N hydrogen chloride ethyl acetate solution (510 μL) at room temperature, and the reaction mixture was stirred at the same temperature for 1 h and the reaction mixture was concentrated under reduced pressure. To a mixture of (S)-2-amino-2-cyclohexyl-1-((R)-4-(6-methoxy-1-methyl-1H-indole-2-carbonyl)-2-methylpiperazin-1-yl)ethanone thus obtained, (S)-2-((tert-butoxycarbonyl)(methyl)amino)propanoic acid (20.3 mg), DIEA (87 μL) and DMF (500 μL) was added HATU (57.0 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane). To a mixture of the product thus obtained and ethyl acetate (500 μL) was added 4 N hydrogen chloride ethyl acetate solution (500 μL) at room temperature and the reaction mixture was stirred at the same temperature for 1 h. The reaction mixture was concentrated under reduced pressure to give the title compound (24.3 mg).

MS: [M+H]$^+$ 512.2.

Example 25

2-(4-((S)-2-Cyclohexyl-2-((S)-2-(methylamino)propanamido)acetyl)piperazine-1-carbonyl)-6-methoxy-N-(2-methoxyethyl)-1-methyl-1H-indole-3-carboxamide Hydrochloride A) tert-Butyl 4-(6-methoxy-1-methyl-1H-indole-2-carbonyl)piperazine-1-carboxylate To a mixture of 6-methoxy-1-methyl-1H-indole-2-carboxylic acid (9.87 g), tert-butyl piperazine-1-carboxylate (9.41 g), 1-hydroxy-1H-benzotriazole monohydrate (8.10 g) and DMF (150 mL) was added 1-ethyl-3-(3-dimethylaminopropyl)carbodiimide hydrochloride (10.14 g) at room temperature. The reaction mixture was stirred at the same temperature for 2 h. After the reaction mixture was cooled to 0° C., water was added thereto, and the precipitates were collected by filtration to give the title compound (16.8 g).

MS: [M+H]$^+$ 374.1.

B) tert-Butyl 4-(3-formyl-6-methoxy-1-methyl-1H-indole-2-carbonyl)piperazine-1-carboxylate To a mixture of tert-butyl 4-(6-methoxy-1-methyl-1H-indole-2-carbonyl)piperazine-1-carboxylate (10.4 g) and DMF (100 mL) was added (chloromethylene)dimethylammonium chloride (7.13 g) at room temperature. The reaction mixture was stirred at the same temperature for 2 h. To the reaction mixture was added water and the resultant mixture was stirred for 30 min, and then the aqueous layer was extracted with ethyl acetate. The organic layer was washed with water and brine, and then dried over anhydrous magnesium sulfate, and the solvent was removed under reduced pressure to give the title compound (10.6 g).

MS: [M+H]$^+$ 402.1.

C) 6-Methoxy-1-methyl-2-(piperazine-1-carbonyl)-1H-indole-3-carbaldehyde hydrochloride To a mixture of tert-butyl 4-(3-formyl-6-methoxy-1-methyl-1H-indole-2-carbonyl)piperazine-1-carboxylate (10.6 g), dimethyl sulfide (25 mL) and ethyl acetate (100 mL) was added 4 N hydrogen chloride ethyl acetate solution (198 mL) at room temperature, and the reaction mixture was stirred at the same temperature for 1 h. To the reaction mixture was added diisopropyl ether, and the precipitates were collected by filtration and washed with diisopropyl ether to give the title compound (8.1 mg).

MS: [M+H]$^+$ 302.0.

D) tert-Butyl ((S)-1-(((S)-1-cyclohexyl-2-(4-(3-formyl-6-methoxy-1-methyl-1H-indole-2-carbonyl)piperazin-1-yl)-2-oxoethyl)amino)-1-oxopropan-2-yl)(methyl)carbamate To a mixture of (S)-2-((tert-butoxycarbonyl)amino)-2-cyclohexylacetic acid (1.958 g), 6-methoxy-1-methyl-2-(piperazine-1-carbonyl)-1H-indole-3-carbaldehyde hydrochloride (2.57 g), DIEA (2.66 mL) and DMF (38 mL) was added HATU (3.47 g) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane). To a mixture of the product thus obtained and ethyl acetate (38 mL) was added 4 N hydrogen chloride ethyl acetate solution (38 mL) at room temperature, the reaction mixture was stirred at the same temperature for 1 h and the reaction mixture was concentrated under reduced pressure. To a mixture of (S)-2-(4-(2-amino-2-cyclohexylacetyl)piperazine-1-carbonyl)-6-methoxy-1-methyl-1H-indole-3-carbaldehyde (3.35 g) thus obtained, (S)-2-((tert-butoxycarbonyl)(methyl)amino)propanoic acid (1.55 g), DIEA (6.65 mL) and DMF (38.1 mL) was added HATU (4.34 g) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (2.12 g).

MS: [M+H]$^+$ 626.3.

E) 2-(4-((S)-2-((S)-2-((tert-Butoxycarbonyl)(methyl)amino)propanamido)-2-cyclohexylacetyl)piperazine-1-carbonyl)-6-methoxy-1-methyl-1H-indole-3-carboxylic Acid To a mixture of tert-butyl ((S)-1-(((S)-1-cyclohexyl-2-(4-(3-formyl-6-methoxy-1-methyl-1H-indole-2-carbonyl)piperazin-1-yl)-2-oxoethyl)amino)-1-oxopropan-2-yl)(methyl)carbamate (2.30 g), sodium dihydrogen phosphate (1.76 g), 2-methylbut-2-ene (1.95 mL), tert-butyl alcohol (29.4 mL) and water (7.4 mL) was added sodium chlorite (665 mg) at room temperature. The reaction mixture was stirred at the same temperature for 4 h. The reaction mixture was diluted with ethyl acetate and saturated aqueous sodium thiosulfate, and the aqueous layer was extracted with ethyl acetate. The organic layer was dried over anhydrous magnesium sulfate and the solvent was removed under reduced pressure. The residue was purified by silica gel column chromatography (methanol/ethyl acetate) to give the title compound (770 mg).

G) 2-(4-((S)-2-Cyclohexyl-2-((S)-2-(methylamino)propanamido)acetyl)piperazine-1-carbonyl)-6-methoxy-N-(2-methoxyethyl)-1-methyl-1H-indole-3-carboxamide Hydrochloride To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (20 mg), 2-methoxyethylamine (5.4 μL), DIEA (16.3 μL) and DMF (156 μL) was added HATU (17.8 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (C18, acetonitrile/5 mM ammonium acetate). To a mixture of the product thus obtained and ethyl acetate (0.2 mL) was added 4 N hydrogen chloride ethyl acetate solution (234 µL) at room temperature, and the reaction mixture was stirred at the same temperature for 1 h. The reaction mixture was concentrated under reduced pressure to give the title compound.

MS: [M+H]+ 599.4.

Example 26

2-(4-((S)-2-Cyclohexyl-2-((S)-2-(methylamino)propanamido)acetyl)piperazine-1-carbonyl)-6-methoxy-N-(2-methoxyethyl)-N,1-dimethyl-1H-indole-3-carboxamide Hydrochloride To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (20 mg), 2-methoxy-N-methylethanamine (6.4 µL), DIEA (16.3 µL) and DMF (156 µL) was added HATU (17.8 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (C18, acetonitrile/5 mM ammonium acetate). To a mixture of the product thus obtained and ethyl acetate (0.2 mL) was added 4 N hydrogen chloride ethyl acetate solution (234 µL) at room temperature, and the reaction mixture was stirred at the same temperature for 1 h. The reaction mixture was concentrated under reduced pressure to give the title compound.

MS: [M+H]+ 613.4.

Example 27

Methyl (2-(4-((S)-2-cyclohexyl-2-((S)-2-(methylamino)propanamido)acetyl)piperazine-1-carbonyl)-6-methoxy-1-methyl-1H-indole-3-carbonyl)glycinate Hydrochloride To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (20 mg), methyl 2-aminoacetate hydrochloride (9.1 µL), DIEA (16.3 µL) and DMF (156 µL) was added HATU (17.8 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (C18, acetonitrile/5 mM ammonium acetate). To a mixture of the product thus obtained and ethyl acetate (0.2 mL) was added 4 N hydrogen chloride ethyl acetate solution (234 µL) at room temperature and the reaction mixture was stirred at the same temperature for 1 h. The reaction mixture was concentrated under reduced pressure to give the title compound.

MS: [M+H]+ 613.4.

Example 28

Methyl N-(2-(4-((S)-2-cyclohexyl-2-((S)-2-(methylamino)propanamido)acetyl)piperazine-1-carbonyl)-6-methoxy-1-methyl-1H-indole-3-carbonyl)-N-methylglycinate Hydrochloride To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (20 mg), methyl 2-(methylamino)acetate hydrochloride (10.1 µL), DIEA (16.3 µL) and DMF (156 µL) was added HATU (17.8 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (C18, acetonitrile/5 mM ammonium acetate). To a mixture of the product thus obtained in ethyl acetate (0.2 mL) was added 4 N hydrogen chloride solution in ethyl acetate (234 µL) at room temperature and the reaction mixture was stirred at the same temperature for 1 h. The reaction mixture was concentrated under reduced pressure to give the title compound.

MS: [M+H]+ 627.4.

Example 29

(S)—N—((S)-1-Cyclohexyl-2-(4-(6-methoxy-3-((S)-2-(methoxymethyl)pyrrolidine-1-carbonyl)-1-methyl-1H-indole-2-carbonyl)piperazin-1-yl)-2-oxoethyl)-2-(methylamino)propanamide Hydrochloride To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (20 mg), (S)-(+)-2-(methoxymethyl)pyrrolidine (7.7 µL), DIEA (16.3 µL) and DMF (156 µL) was added HATU (17.8 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (C18, acetonitrile/5 mM ammonium acetate). To a mixture of the product thus obtained and ethyl acetate (0.2 mL) was added 4 N hydrogen chloride ethyl acetate solution (234 µL) at room temperature and the reaction mixture was stirred at the same temperature for 1 h. The reaction mixture was concentrated under reduced pressure to give the title compound.

MS: [M+H]+ 639.5.

Example 30

(S)—N—((S)-1-Cyclohexyl-2-(4-(6-methoxy-3-((R)-2-(methoxymethyl)pyrrolidine-1-carbonyl)-1-methyl-1H-indole-2-carbonyl)piperazin-1-yl)-2-oxoethyl)-2-(methylamino)propanamide Hydrochloride To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (20 mg), (R)-(−)-2-(methoxymethyl)pyrrolidine (7.7 µL), DIEA (16.3 µL) and DMF (156 µL) was added HATU (17.8 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (C18, acetonitrile/5 mM ammonium acetate). To a mixture of the product thus obtained and ethyl acetate (0.2 mL) was added 4 N hydrogen chloride in ethyl acetate solution (234 μL) at room temperature and the reaction mixture was stirred at the same temperature for 1 h. The reaction mixture was concentrated under reduced pressure to give the title compound.
MS: [M+H]$^+$ 639.5.

Example 31

(S)—N—((S)-1-Cyclohexyl-2-(4-(6-methoxy-3-(3-methoxyazetidine-1-carbonyl)-1-methyl-1H-indole-2-carbonyl)piperazin-1-yl)-2-oxoethyl)-2-(methylamino)propanamide Hydrochloride To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (20 mg), 3-methoxyazetidine hydrochloride (7.7 mg), DIEA (16.3 μL) and DMF (156 μL) was added HATU (17.8 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (C18, acetonitrile/5 mM ammonium acetate). To a mixture of the product thus obtained and ethyl acetate (0.2 mL) was added 4 N hydrogen chloride ethyl acetate solution (234 μL) at room temperature and the reaction mixture was stirred at the same temperature for 1 h. The reaction mixture was concentrated under reduced pressure to give the title compound.
MS: [M+H]$^+$ 611.4.

Example 32

(S)—N—((S)-1-Cyclohexyl-2-((S)-4-(6-methoxy-1-methyl-1H-indole-2-carbonyl)-2-methylpiperazin-1-yl)-2-oxoethyl)-2-(methylamino)propanamide Hydrochloride A) (S)-(6-Methoxy-1-methyl-1H-indol-2-yl)(3-methylpiperazin-1-yl)methanone To a mixture of 6-methoxy-1-methyl-1H-indole-2-carboxylic acid (130 mg), (S)-2-methylpiperazine (317 mg), DIEA (443 μL) and DMF (3167 μL) was added HATU (361 mg) at room temperature. The reaction mixture was stirred at the same temperature for 6 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (134 mg).
MS: [M+H]$^+$ 288.1.

B) tert-Butyl ((S)-1-cyclohexyl-2-((S)-4-(6-methoxy-1-methyl-1H-indole-2-carbonyl)-2-methylpiperazin-1-yl)-2-oxoethyl)carbamate To a mixture of (S)-2-((tert-butoxycarbonyl)amino)-2-cyclohexylacetic acid (29.6 mg), (S)-(6-methoxy-1-methyl-1H-indol-2-yl)(3-methylpiperazin-1-yl)methanone (33.0 mg), DIEA (40.1 μL) and DMF (574 μL) was added HATU (52.4 mg) at room temperature. The reaction mixture was stirred at the same temperature for 2 h and the reaction mixture was diluted with water. The precipitates were collected by filtration to give the title compound (58.8 mg).
MS: [M+Na]$^+$ 549.2.

C) (S)—N—((S)-1-Cyclohexyl-2-((S)-4-(6-methoxy-1-methyl-1H-indole-2-carbonyl)-2-methylpiperazin-1-yl)-2-oxoethyl)-2-(methylamino)propanamide Hydrochloride To a mixture of tert-butyl ((S)-1-cyclohexyl-2-((S)-4-(6-methoxy-1-methyl-1H-indole-2-carbonyl)-2-methylpiperazin-1-yl)-2-oxoethyl)carbamate (58.8 mg) and ethyl acetate (558 μL) was added 4 N hydrogen chloride ethyl acetate solution (558 μL) at room temperature, and the reaction mixture was stirred at the same temperature for 1 h and the reaction mixture was concentrated under reduced pressure. To a mixture of (S)-2-amino-2-cyclohexyl-1-((S)-4-(6-methoxy-1-methyl-1H-indole-2-carbonyl)-2-methylpiperazin-1-yl)ethanone thus obtained, (S)-2-((tert-butoxycarbonyl)(methyl)amino)propanoic acid (24.4 mg), DIEA (87 μL) and DMF (500 μL) was added HATU (64.6 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane). To a mixture of the product thus obtained and ethyl acetate (500 μL) was added 4 N hydrogen chloride ethyl acetate solution (500 μL) at room temperature and the reaction mixture was stirred at the same temperature for 1 h. The reaction mixture was concentrated under reduced pressure to give the title compound (34.5 mg).
MS: [M+H]$^+$ 512.4.

Example 33

(S)—N—((S)-1-Cyclohexyl-2-((S)-4-(6-methoxy-1-methyl-1H-indole-2-carbonyl)-3-methylpiperazin-1-yl)-2-oxoethyl)-2-(methylamino)propanamide Hydrochloride A) (S)-tert-Butyl 4-(6-methoxy-1-methyl-1H-indole-2-carbonyl)-3-methylpiperazine-1-carboxylate To a mixture of 6-methoxy-1-methyl-1H-indole-2-carboxylic acid (130 mg), (S)-tert-butyl 3-methylpiperazine-1-carboxylate (127 mg), DIEA (443 μL) and DMF (3167 μL) was added HATU (361 mg) at room temperature. The reaction mixture was stirred at the same temperature for 6 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (214 mg). MS: [M+H]$^+$ 388.1.

B) (S)-(6-Methoxy-1-methyl-1H-indol-2-yl)(2-methylpiperazin-1-yl)methanone Hydrochloride To a mixture of (S)-tert-butyl 4-(6-methoxy-1-methyl-1H-indole-2-carbonyl)-3-methylpiperazine-1-carboxylate (214 mg) and ethyl acetate (2761 μL) was added 4 N hydrogen chloride ethyl acetate solution (1381 μL) at room temperature and the reaction mixture was stirred at 50° C.

for 1 h. The precipitates were collected by filtration to give the title compound (163 mg).

MS: [M+H]$^+$ 288.1.

C) tert-Butyl ((S)-1-cyclohexyl-2-((S)-4-(6-methoxy-1-methyl-1H-indole-2-carbonyl)-3-methylpiperazin-1-yl)-2-oxoethyl)carbamate To a mixture of (S)-2-((tert-butoxycarbonyl)amino)-2-cyclohexylacetic acid (29.8 mg), (S)-(6-methoxy-1-methyl-1H-indol-2-yl)(2-methylpiperazin-1-yl)methanone hydrochloride (37.5 mg), DIEA (60.7 μL) and DMF (579 μL) was added HATU (52.8 mg) at room temperature. The reaction mixture was stirred at the same temperature for 2 h and the reaction mixture was diluted with water. The precipitates were collected by filtration to give the title compound (61.3 mg).

MS: [M+Na]$^+$ 549.2.

D) (S)—N—((S)-1-Cyclohexyl-2-((S)-4-(6-methoxy-1-methyl-1H-indole-2-carbonyl)-3-methylpiperazin-1-yl)-2-oxoethyl)-2-(methylamino)propanamide Hydrochloride To a mixture of tert-butyl ((S)-1-cyclohexyl-2-((S)-4-(6-methoxy-1-methyl-1H-indole-2-carbonyl)-3-methylpiperazin-1-yl)-2-oxoethyl)carbamate (61.3 mg) and ethyl acetate (582 μL) was added 4 N hydrogen chloride ethyl acetate solution (582 μL) at room temperature, and the reaction mixture was stirred at the same temperature for 30 min and the reaction mixture was concentrated under reduced pressure. To a mixture of (S)-2-amino-2-cyclohexyl-1-((S)-4-(6-methoxy-1-methyl-1H-indole-2-carbonyl)-3-methylpiperazin-1-yl)ethanone thus obtained, (S)-2-((tert-butoxycarbonyl)(methyl)amino)propanoic acid (24.4 mg), DIEA (87 μL) and DMF (500 μL) was added HATU (64.6 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and concentrated under reduced pressure. The residue was purified by silica gel column chromatography (ethyl acetate/hexane). To a mixture of the product thus obtained and ethyl acetate (500 μL) was added 4 N hydrogen chloride ethyl acetate solution (500 μL) at room temperature and the reaction mixture was stirred at the same temperature for 1 h. The reaction mixture was concentrated under reduced pressure to give the title compound (29.4 mg).

MS: [M+H]$^+$ 512.4.

Example 34

(S)—N—((S)-1-Cyclohexyl-2-((R)-4-(6-methoxy-1-methyl-1H-indole-2-carbonyl)-3-methylpiperazin-1-yl)-2-oxoethyl)-2-(methylamino)propanamide Hydrochloride

A) (R)-tert-Butyl 4-(6-methoxy-1-methyl-1H-indole-2-carbonyl)-3-methylpiperazine-1-carboxylate To a mixture of 6-methoxy-1-methyl-1H-indole-2-carboxylic acid (130 mg), (R)-tert-butyl 3-methylpiperazine-1-carboxylate (127 mg), DIEA (443 μL) and DMF (3167 μL) was added HATU (361 mg) at room temperature. The reaction mixture was stirred at the same temperature for 6 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (214 mg). MS: [M+H]$^+$ 388.1.

B) (R)-(6-Methoxy-1-methyl-1H-indol-2-yl)(2-methylpiperazin-1-yl)methanone Hydrochloride To a mixture of (R)-tert-butyl 4-(6-methoxy-1-methyl-1H-indole-2-carbonyl)-3-methylpiperazine-1-carboxylate (214 mg) and ethyl acetate (2761 μL) was added 4 N hydrogen chloride ethyl acetate solution (1381 μL) at room temperature and the reaction mixture was stirred at 50° C. for 1 h. The precipitates were collected by filtration to give the title compound (166 mg).

MS: [M+H]$^+$ 288.1.

C) tert-Butyl ((S)-1-cyclohexyl-2-((R)-4-(6-methoxy-1-methyl-1H-indole-2-carbonyl)-3-methylpiperazin-1-yl)-2-oxoethyl)carbamate To a mixture of (S)-2-((tert-butoxycarbonyl)amino)-2-cyclohexylacetic acid (27.3 mg), (R)-(6-methoxy-1-methyl-1H-indol-2-yl)(2-methylpiperazin-1-yl)methanone hydrochloride (34.3 mg), DIEA (55.5 μL) and DMF (530 μL) was added HATU (48.3 mg) at room temperature. The reaction mixture was stirred at the same temperature for 2 h and the reaction mixture was diluted with water. The precipitates were collected by filtration to give the title compound (54.9 mg).

MS: [M+Na]$^+$ 549.2.

D) (S)—N—((S)-1-Cyclohexyl-2-((R)-4-(6-methoxy-1-methyl-1H-indole-2-carbonyl)-3-methylpiperazin-1-yl)-2-oxoethyl)-2-(methylamino)propanamide Hydrochloride To a mixture of tert-butyl ((S)-1-cyclohexyl-2-((R)-4-(6-methoxy-1-methyl-1H-indole-2-carbonyl)-3-methylpiperazin-1-yl)-2-oxoethyl) carbamate (54.9 mg) and ethyl acetate (521 μL) was added 4 N hydrogen chloride ethyl acetate solution (521 μL) at room temperature, and the reaction mixture was stirred at the same temperature for 30 min and the reaction mixture was concentrated under reduced pressure. To a mixture of (S)-2-amino-2-cyclohexyl-1-((R)-4-(6-methoxy-1-methyl-1H-indole-2-carbonyl)-3-methylpiperazin-1-yl)ethanone thus obtained, (S)-2-((tert-butoxycarbonyl)(methyl)amino)propanoic acid (24.4 mg), DIEA (87 μL) and DMF (500 μL) was added HATU (64.6 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane). To a mixture of the product thus obtained and ethyl acetate (500 μL) was added 4 N hydrogen chloride ethyl acetate solution (500 μL) at room temperature, and the reaction mixture was stirred at the same temperature for 1 h. The reaction mixture was concentrated under reduced pressure to give the title compound (27.4 mg).

MS: [M+H]$^+$ 512.4.

Example 35

(S)—N—((S)-1-Cyclohexyl-2-(4-(5-fluoro-3-formyl-1-methyl-1H-indole-2-carbonyl)piperazin-1-yl)-2-oxoethyl)-2-(methylamino)propanamide Hydrochloride A) Methyl 5-fluoro-1-methyl-1H-indole-2-carboxylate A mixture of 5-fluoro-1H-indole-2-carboxylic acid (1.03 g), iodomethane (1.44 mL), potassium carbonate (2.38 g) and DMF (5.75 mL) was stirred at room temperature for 16 h, to the reaction mixture was added saturated aqueous ammonium chloride, and the precipitates were collected by filtration to give the title compound (1.15 g).

$^1$H NMR (300 MHz, DMSO-$d_6$) δ 3.86 (3H, s), 4.03 (3H, s), 7.14-7.29 (2H, m), 7.46 (1H, dd, J=9.44, 2.27 Hz), 7.64 (1H, dd, J=9.25, 4.34 Hz).

B) Methyl 5-fluoro-3-formyl-1-methyl-1H-indole-2-carboxylate

To a mixture of methyl 5-fluoro-1-methyl-1H-indole-2-carboxylate (529 mg) and DMF (1.28 mL) was added (chloromethylene)dimethylammonium chloride (654 mg) at room temperature. After the reaction mixture was stirred at 60° C. for 2 h, (chloromethylene)dimethylammonium chloride (654 mg) was added at room temperature and the reaction mixture was stirred at the same temperature for 1 h. To the reaction mixture was added water and the reaction mixture was stirred overnight. The precipitates were collected by filtration to give the title compound (488 mg).

MS: [M+H]$^+$ 236.1.

C) 5-Fluoro-3-formyl-1-methyl-1H-indole-2-carboxylic Acid

To a mixture of methyl 5-fluoro-3-formyl-1-methyl-1H-indole-2-carboxylate (484 mg) and methanol (10.3 mL) was added aqueous 2 N sodium hydroxide (5.14 mL) at room temperature, and the reaction mixture was stirred at room temperature for 16 h. The reaction mixture was neutralized with 1 N hydrochloric acid and the precipitates were collected by filtration to give the title compound (397 mg).

$^1$H NMR (300 MHz, DMSO-$d_6$) δ 4.06 (3H, s), 7.26-7.40 (1H, m), 7.71-7.83 (1H, m), 7.88-8.01 (1H, m), 10.45 (1H, s), 13.13-15.52 (1H, m).

D) tert-Butyl ((S)-1-(((S)-1-cyclohexyl-2-(4-(5-fluoro-3-formyl-1-methyl-1H-indole-2-carbonyl)piperazin-1-yl)-2-oxoethyl)amino)-1-oxopropan-2-yl)(methyl)carbamate To a mixture of 5-fluoro-3-formyl-1-methyl-1H-indole-2-carboxylic acid (242 mg), tert-butyl ((S)-1-(((S)-1-cyclohexyl-2-oxo-2-(piperazin-1-yl)ethyl)amino)-1-oxopropan-2-yl)(methyl)carbamate (449 mg), DIEA (611 μL) and DMF (3647 μL) was added HATU (707 mg) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (300 mg).

MS: [M+H]$^+$ 614.4.

E) (S)—N—((S)-1-Cyclohexyl-2-(4-(5-fluoro-3-formyl-1-methyl-1H-indole-2-carbonyl)piperazin-1-yl)-2-oxoethyl)-2-(methylamino)propanamide Hydrochloride To a mixture of tert-butyl ((S)-1-(((S)-1-cyclohexyl-2-(4-(5-fluoro-3-formyl-1-methyl-1H-indole-2-carbonyl)piperazin-1-yl)-2-oxoethyl)amino)-1-oxopropan-2-yl)(methyl)carbamate (28.4 mg) and ethyl acetate (463 μL) was added 4 N hydrogen chloride ethyl acetate solution (578 μL) at room temperature, and the reaction mixture was stirred at the same temperature for 1 h. The reaction mixture was concentrated under reduced pressure to give the title compound (22.4 mg).

MS: [M+H]$^+$ 514.4.

Example 36

1-(4-(6-Methoxy-1-methyl-1H-indole-2-carbonyl)piperazin-1-yl)-2-((2R,5R)-5-methyl-2-(((R)-3-methylmorpholino)methyl)piperazin-1-yl)ethan-1-one A) (6-Methoxy-1-methyl-1H-indol-2-yl)(piperazin-1-yl)methanone Hydrochloride To a mixture of tert-butyl 4-(6-methoxy-1-methyl-1H-indole-2-carbonyl)piperazine-1-carboxylate (1.17 g) and ethyl acetate (10 mL) was added 4 N hydrogen chloride ethyl acetate solution (23.5 mL) at room temperature and the reaction mixture was stirred at the same temperature for 1 h. The reaction mixture was added diisopropyl ether, the precipitates were collected by filtration and washed with diisopropyl ether to give the title compound (897 mg).

MS: [M+H]$^+$ 274.0.

B) (2R,5S)-tert-Butyl 4-(2-(4-(6-methoxy-1-methyl-1H-indole-2-carbonyl)piperazin-1-yl)-2-oxoethyl)-2-methyl-5-(((R)-3-methylmorpholino)methyl)piperazine-1-carboxylate To a mixture of (6-methoxy-1-methyl-1H-indol-2-yl)(piperazin-1-yl)methanone hydrochloride (16.0 mg), 2-((2S,5R)-4-(tert-butoxycarbonyl)-5-methyl-2-(((R)-3-methylmorpholino)methyl)piperazin-1-yl)acetic acid (19.2 mg), DIEA (18.0 μL) and DMF (0.2 mL) was added HATU (23.6 mg) at room temperature. The reaction mixture was stirred at the same temperature overnight and the reaction mixture was diluted with water. The precipitates were collected by filtration to give the title compound (10.3 mg).

MS: [M+Na]$^+$ 627.3.

C) 1-(4-(6-Methoxy-1-methyl-1H-indole-2-carbonyl)piperazin-1-yl)-2-((2R,5R)-5-methyl-2-(((R)-3-methylmorpholino)methyl)piperazin-1-yl)ethan-1-one A mixture of (2R,5S)-tert-butyl 4-(2-(4-(6-methoxy-1-methyl-1H-indole-2-carbonyl)piperazin-1-yl)-2-oxoethyl)-2-methyl-5-(((R)-3-methylmorpholino)methyl)piperazine-1-carboxylate (10.3 mg) and TFA (0.2 mL) was stirred at room temperature for 1 h. The reaction mixture was concentrated under reduced pressure and the residue was purified by silica gel column chromatography (NH, methanol/ethyl acetate) to give the title compound (2.3 mg).

$^1$H NMR (300 MHz, CDCl$_3$) δ 0.98 (3H, d, J=6.4 Hz), 1.34-1.47 (3H, m), 1.86-2.09 (2H, m), 2.09-2.27 (2H, m), 2.35 (2H, brs), 2.73 (2H, t, J=11.9 Hz), 2.84-3.03 (3H, m), 3.10-3.34 (4H, m), 3.44 (1H, d, J=15.5 Hz), 3.60-3.67 (5H, m), 3.75-3.80 (4H, m), 3.83 (3H, s), 3.90 (3H, s), 4.12 (1H, d, J=15.1 Hz), 6.58 (1H, s), 6.78 (1H, d, J=1.9 Hz), 6.83 (1H, dd, J=8.7, 1.9 Hz), 7.50 (1H, d, J=8.7 Hz).

Example 37

2-(2-(2-(2-(4-((S)-2-Cyclohexyl-2-((S)-2-(methylamino)propanamido)acetyl)piperazine-1-carbonyl)-6-methoxy-1-methyl-1H-indole-3-carboxamido)ethoxy)ethoxy)acetic Acid Hydrochloride A) 2-(2-(2-(2-(4-((S)-2-((S)-2-((tert-Butoxycarbonyl)(methyl)amino)propanamido)-2-cyclohexylacetyl)piperazine-1-carbonyl)-6-methoxy-1-methyl-1H-indole-3-carboxamido)ethoxy)ethoxy)acetic Acid To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (100 mg), DIEA (54 μL) and DMF (0.3 mL) was added HATU (89 mg) at room temperature. After the reaction mixture was stirred at the same temperature for 30 min, 2-(2-(2-aminoethoxy)ethoxy)acetic acid (254 mg) was added thereto and the resultant mixture was concentrated under reduced pressure. The residue was purified by silica gel column chromatography (C18, acetonitrile/5 mM ammonium acetate) to give the title compound (28.7 mg).

MS: [M+H]$^+$ 787.4.

B) 2-(2-(2-(2-(4-((S)-2-Cyclohexyl-2-((S)-2-(methylamino)propanamido)acetyl)piperazine-1-carbonyl)-6-methoxy-1-methyl-1H-indole3-carboxamido)ethoxy)ethoxy)acetic Acid Hydrochloride To 2-(2-(2-(2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxamido)ethoxy)ethoxy)acetic acid (4.2 mg) was added 4 N hydrogen chloride ethyl acetate solution (0.5 mL) at room temperature and the reaction mixture was stirred at the same temperature for 1 h. The reaction mixture was concentrated under reduced pressure to give the title compound (3.5 mg).

1H NMR (300 MHz, CD$_3$OD) δ 0.74-1.29 (7H, m), 1.34-1.45 (3H, m), 1.48-1.79 (6H, m), 2.57 (3H, brs), 3.45-3.68 (14H, m), 3.79 (7H, s), 3.95-4.05 (3H, m), 6.84 (1H, dd, J=8.7, 1.5 Hz), 6.92 (1H, d, J=1.5 Hz), 7.69 (1H, d, J=9.1 Hz).

Example 38

(9H-Fluoren-9-yl)methyl (2-(2-(2-(2-(4-((S)-2-cyclohexyl-2-((S)-2-(methylamino)propanamido)acetyl)piperazine-1-carbonyl)-6-methoxy-1-methyl-1H-indole-3-carboxamido)ethoxy)ethoxy)ethyl)carbamate Hydrochloride A) tert-Butyl ((S)-1-(((S)-2-(4-(3-((1-(9H-fluoren-9-yl)-3-oxo-2,7,10-trioxa-4-azadodecan-12-yl)carbamoyl)-6-methoxy-1-methyl-1H-indole-2-carbonyl)piperazin-1-yl)-1-cyclohexyl-2-oxoethyl)amino)-1-oxopropan-2-yl)(methyl)carbamate To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (167.5 mg), (9H-fluoren-9-yl)methyl (2-(2-(2-aminoethoxy)ethoxy)ethyl)carbamate hydrochloride (117 mg), DIEA (91 μL) and DMF (522 μL) was added HATU (149 mg) at room temperature. After the reaction mixture was stirred at the same temperature overnight, the reaction mixture was purified by silica gel column chromatography (C18, acetonitrile/5 mM ammonium acetate) to give the title compound (136 mg).

MS: [M+H]$^+$ 994.6.

B) (9H-Fluoren-9-yl)methyl (2-(2-(2-(2-(4-((S)-2-cyclohexyl-2-((S)-2-(methylamino)propanamido)acetyl)piperazine-1-carbonyl)-6-methoxy-1-methyl-1H-indole-3-carboxamido)ethoxy)ethoxy)ethyl)carbamate Hydrochloride To a mixture of tert-butyl ((S)-1-(((S)-2-(4-(3-((1-(9H-fluoren-9-yl)-3-oxo-2,7,10-trioxa-4-azadodecan-12-yl)carbamoyl)-6-methoxy-1-methyl-1H-indole-2-carbonyl)piperazin-1-yl)-1-cyclohexyl-2-oxoethyl)amino)-1-oxopropan-2-yl)(methyl)carbamate (2.6 mg) and ethyl acetate (0.3 mL) was added 4 N hydrogen chloride ethyl acetate solution (0.3 mL) at room temperature. The reaction mixture was concentrated under reduced pressure to give the title compound (2.3 mg).

MS: [M+H]$^+$ 894.6.

Example 39

2-((2R,5R)-2-(Hydroxymethyl)-5-methylpiperazin-1-yl)-1-(4-(6-methoxy-1-methyl-1H-indole-2-carbonyl)piperazin-1-yl)ethan-1-one Hydrochloride A) 2-Chloro-1-(4-(6-methoxy-1-methyl-1H-indole-2-carbonyl)piperazin-1-yl)ethanone To a mixture of (6-methoxy-1-methyl-1H-indol-2-yl)(piperazin-1-yl)methanone hydrochloride (302 mg), TEA (680 μL) and THF (4.9 mL) was added chloroacetyl chloride (233 μL) at room temperature. The reaction mixture was stirred at the same temperature for 1 h. To the reaction mixture was added water and the aqueous layer was extracted with ethyl acetate. The organic layer was washed with brine and then dried over anhydrous magnesium sulfate, and the solvent was removed under reduced pressure. The residue was purified by silica gel column chromatography (ethyl acetate/hexane) to give the title compound (265 mg).

MS: [M+H]$^+$ 350.1.

B) (2R,5R)-tert-Butyl 5-(hydroxymethyl)-4-(2-(4-(6-methoxy-1-methyl-1H-indole-2-carbonyl)piperazin-1-yl)-2-oxoethyl)-2-methylpiperazine-1-carboxylate To a mixture of 2-chloro-1-(4-(6-methoxy-1-methyl-1H-indole-2-carbonyl)piperazin-1-yl)ethanone (137 mg), TEA (109 μL) and THF (782 μL) was added (2R,5R)-tert-butyl 5-(hydroxymethyl)-2-methylpiperazine-1-carboxylate (117 mg) at room temperature. The reaction mixture was stirred at 60° C. for 7 h. To the reaction mixture was added water and the aqueous layer was extracted with ethyl acetate. The organic layer was washed with brine, and dried over anhydrous magnesium sulfate, and the solvent was removed under reduced pressure. The residue was purified by silica gel column chromatography (ethyl acetate/hexane) to give the title compound (185 mg).

MS: [M+H]⁺ 544.4.

C) 2-((2R,5R)-2-(Hydroxymethyl)-5-methylpiperazin-1-yl)-1-(4-(6-methoxy-1-methyl-1H-indole-2-carbonyl)piperazin-1-yl)ethan-1-one Hydrochloride To (2R,5R)-tert-butyl 5-(hydroxymethyl)-4-(2-(4-(6-methoxy-1-methyl-1H-indole-2-carbonyl)piperazin-1-yl)-2-oxoethyl)-2-methylpiperazine-1-carboxylate (6.3 mg) was added 4 N hydrogen chloride ethyl acetate solution (0.3 mL) at room temperature and the reaction mixture was stirred at the same temperature for 2 h. The reaction mixture was concentrated under reduced pressure to give the title compound (5.5 mg).

MS: [M+H]⁺ 444.4.

Example 40

2-((2R,5R)-2-(((2-(2-Hydroxyethoxy)ethyl)(methyl)amino)methyl)-5-methylpiperazin-1-yl)-1-(4-(6-methoxy-1-methyl-1H-indole-2-carbonyl)piperazin-1-yl)ethan-1-one Hydrochloride

A) (9H-Fluoren-9-yl)methyl (2-(2-hydroxyethoxy)ethyl)(methyl)carbamate

To a mixture of (9H-fluoren-9-yl)methyl (2-(2-hydroxyethoxy)ethyl)carbamate (4.72 g), TFA (40 mL) and deuterated chloroform (40 mL) was added 37% aqueous formaldehyde solution (8 mL) under ice-cooling. After the reaction mixture was stirred at the same temperature for 30 min, triethylsilane (24 mL) was added and the reaction mixture was stirred at the same temperature for 30 min. The reaction mixture was concentrated under reduced pressure, and the residue was diluted with methanol and saturated aqueous sodium bicarbonate and stirred for 1 h. The reaction mixture was acidified with ethyl acetate and 1 N hydrochloric acid and the aqueous layer was extracted with ethyl acetate. The organic layer was dried over anhydrous magnesium sulfate and the solvent was removed under reduced pressure. The residue was purified by silica gel column chromatography (ethyl acetate/hexane) to give the title compound (4.13 g).

¹H NMR (300 MHz, DMSO-$d_6$) δ 2.81 (3H, d, J=6.42 Hz), 3.08-3.30 (3H, m), 3.32-3.55 (5H, m), 4.20-4.47 (3H, m), 4.50-4.62 (1H, m), 7.24-7.48 (4H, m), 7.64 (2H, d, J=7.18 Hz), 7.89 (2H, d, J=7.55 Hz).

B) (2R,5R)-tert-Butyl 5-(chloromethyl)-4-(2-(4-(6-methoxy-1-methyl-1H-indole-2-carbonyl)piperazin-1-yl)-2-oxoethyl)-2-methylpiperazine-1-carboxylate To a mixture of (2R,5R)-tert-butyl 5-(hydroxymethyl)-4-(2-(4-(6-methoxy-1-methyl-1H-indole-2-carbonyl)piperazin-1-yl)-2-oxoethyl)-2-methylpiperazine-1-carboxylate (124.1 mg), TEA (95 µL) and THF (1.4 mL) was added methanesulfonyl chloride (21 µL) at room temperature. The reaction mixture was stirred at the same temperature overnight, and then concentrated under reduced pressure. The residue was purified by silica gel column chromatography (C18, acetonitrile/5 mM ammonium acetate) to give the title compound (61.5 mg).

MS: [M+H]⁺ 562.4.

C) (2R,5S)-tert-Butyl 5-(((2-(2-hydroxyethoxy)ethyl)(methyl)amino)methyl)-4-(2-(4-(6-methoxy-1-methyl-1H-indole-2-carbonyl)piperazin-1-yl)-2-oxoethyl)-2-methylpiperazine-1-carboxylate A mixture of (9H-fluoren-9-yl)methyl (2-(2-hydroxyethoxy)ethyl)(methyl)carbamate (21.4 mg), potassium carbonate (28.9 mg), potassium iodide (8.3 mg) and acetonitrile (418 µL) was stirred at 80° C. for 2 h. To the reaction mixture was added (2R,5R)-tert-butyl 5-(chloromethyl)-4-(2-(4-(6-methoxy-1-methyl-1H-indole-2-carbonyl)piperazin-1-yl)-2-oxoethyl)-2-methylpiperazine-1-carboxylate (23.5 mg) and the resultant mixture was stirred at the same temperature for 1 h. The reaction mixture was purified by silica gel column chromatography (C18, acetonitrile/5 mM ammonium acetate) to give the title compound (16.6 mg).

MS: [M+H]⁺ 645.5.

D) 2-((2R,5R)-2-(((2-(2-Hydroxyethoxy)ethyl)(methyl)amino)methyl)-5-methylpiperazin-1-yl)-1-(4-(6-methoxy-1-methyl-1H-indole-2-carbonyl)piperazin-1-yl)ethan-1-one Hydrochloride To a mixture of (2R,5S)-tert-butyl 5-(((2-(2-hydroxyethoxy)ethyl)(methyl)amino)methyl)-4-(2-(4-(6-methoxy-1-methyl-1H-indole-2-carbonyl)piperazin-1-yl)-2-oxoethyl)-2-methylpiperazine-1-carboxylate (2.2 mg) and ethyl acetate (0.2 mL) was added 4 N hydrogen chloride ethyl acetate solution (0.2 mL) at room temperature and the reaction mixture was stirred at the same temperature for 1 h. The reaction mixture was concentrated under reduced pressure to give the title compound (1.8 mg).

MS: [M+H]⁺ 545.4.

Example 41

(S)—N—((S)-1-Cyclohexyl-2-(4-(5,6-difluoro-1-methyl-1H-indole-2-carbonyl)piperazin-1-yl)-2-oxoethyl)-2-(methylamino)propanamide

A) tert-Butyl ((S)-1-(((S)-1-cyclohexyl-2-(4-(5,6-difluoro-1-methyl-1H-indole-2-carbonyl)piperazin-1-yl)-2-oxoethyl)amino)-1-oxopropan-2-yl)(methyl)carbamate To a mixture of 5,6-difluoro-1H-indole-2-carboxylic acid (27.0 mg), tert-butyl ((S)-1-(((S)-1-cyclohexyl-2-oxo-2-(piperazin-1-yl)ethyl)amino)-1-oxopropan-2-yl)(methyl)carbamate (46.8 mg), DIEA (40 µL) and DMF (0.3 mL) was added HATU (65.0 mg) at room temperature. After the reaction mixture was stirred at the same temperature for 2 h, iodomethane (71 µL) and potassium carbonate (158 mg) were added and the reaction mixture was stirred at the same temperature overnight. To the reaction mixture was added water, the precipitates were collected by filtration and purified by silica gel column chromatography (C18, acetonitrile/5 mM ammonium acetate) to give the title compound (59.4 mg).

MS: [M+H]⁺ 604.4.

B) (S)—N—((S)-1-Cyclohexyl-2-(4-(5,6-difluoro-1-methyl-1H-indole-2-carbonyl)piperazin-1-yl)-2-oxoethyl)-2-(methylamino)propanamide To a mixture of tert-butyl ((S)-1-(((S)-1-cyclohexyl-2-(4-(5,6-difluoro-1-methyl-1H-indole-2-carbonyl)piperazin-1- yl)-2-oxoethyl)amino)-1-oxopropan-2-yl)(methyl)carbamate (59.3 mg) and ethyl acetate (1 mL) was added 4 N hydrogen chloride ethyl acetate solution (1 mL) at room temperature and the reaction mixture was stirred at the same temperature for 1 h. The reaction mixture was concentrated under reduced pressure, and the residue was purified by silica gel column chromatography (C18, acetonitrile/5 mM ammonium acetate). The product was desalted by Amberlyst A21 in methanol to give the title compound (33.4 mg).

$^1$H NMR (300 MHz, DMSO-$d_6$) δ 0.87-1.28 (9H, m), 1.50-1.75 (6H, m), 2.17 (3H, s), 2.96 (1H, q, J=6.8 Hz), 3.49-3.70 (8H, m), 3.74 (3H, s), 4.65 (1H, t, J=7.7 Hz), 6.72 (1H, s), 7.51-7.76 (2H, m), 7.94 (1H, d, J=9.1 Hz).

Example 42

(S)—N—((S)-1-(4,4-Difluorocyclohexyl)-2-(4-(6-methoxy-1-methyl-1H-indole-2-carbonyl)piperazin-1-yl)-2-oxoethyl)-2-(methylamino)propanamide Hydrochloride A) (S)-tert-Butyl (1-(4,4-difluorocyclohexyl)-2-(4-(6-methoxy-1-methyl-1H-indole-2-carbonyl)piperazin-1-yl) 2-oxoethyl)carbamate To a mixture of (S)-2-((tert-butoxycarbonyl)amino)-2-(4,4-difluorocyclohexyl)acetic acid (381 mg), (6-methoxy-1-methyl-1H-indol-2-yl)(piperazin-1-yl)methanone hydrochloride (402.5 mg), DIEA (454 μL) and DMF (5 mL) was added and HATU (593 mg) at room temperature. The reaction mixture was stirred at the same temperature for 1 h. The reaction mixture was diluted with water and the aqueous layer was extracted with ethyl acetate. The organic layer was washed with saturated aqueous sodium bicarbonate and brine and then dried over anhydrous magnesium sulfate, and the solvent was removed under reduced pressure to give the title compound (711 mg). This compound was used for the next step without further purification.

MS: [M+Na]$^+$ 571.3.

B) (S)-2-Amino-2-(4,4-difluorocyclohexyl)-1-(4-(6-methoxy-1-methyl-1H-indole-2-carbonyl)piperazin-1-yl)ethanone Hydrochloride To a mixture of (S)-tert-butyl (1-(4,4-difluorocyclohexyl)-2-(4-(6-methoxy-1-methyl-1H-indole-2-carbonyl)piperazin-1-yl)-2-oxoethyl)carbamate (710.3 mg) and 4 N hydrogen chloride ethyl acetate solution (6.4 mL) was added methanol (1 mL) at room temperature and the reaction mixture was stirred at the same temperature for 1 h. The reaction mixture was concentrated under reduced pressure and the crude product was purified by recrystallization from methanol/ethyl acetate/diisopropyl ether to give the title compound (527 mg).

MS: [M+H]$^+$ 449.2.

C) tert-Butyl ((S)-1-(((S)-1-(4,4-difluorocyclohexyl)-2-(4-(6-methoxy-1-methyl-1H-indole-2-carbonyl)piperazin-1-yl)-2-oxoethyl)amino)-1-oxopropan-2-yl)(methyl)carbamate To a mixture of (S)-2-((tert-butoxycarbonyl)(methyl)amino)propanoic acid (12.4 mg), (S)-2-amino-2-(4,4-difluorocyclohexyl)-1-(4-(6-methoxy-1-methyl-1H-indole-2-carbonyl)piperazin-1-yl)ethanone hydrochloride (29.5 mg), DIEA (21.3 μL) and DMF (304 μL) was added HATU (27.8 mg) at room temperature. The reaction mixture was stirred at the same temperature for 1 h. The reaction mixture was concentrated under reduced pressure and the crude product was purified by recrystallization from methanol/ethyl acetate/diisopropyl ether to give the title compound (16.5 mg).

MS: [M+H]$^+$ 634.4.

D) (S)—N—((S)-1-(4,4-Difluorocyclohexyl)-2-(4-(6-methoxy-1-methyl-1H-indole-2-carbonyl)piperazin-1-yl)-2-oxoethyl)-2-(methylamino)propanamide Hydrochloride To a mixture of tert-butyl ((S)-1-(((S)-1-(4,4-difluorocyclohexyl)-2-(4-(6-methoxy-1-methyl-1H-indole-2-carbonyl)piperazin-1-yl)-2-oxoethyl)amino)-1-oxopropan-2-yl)(methyl)carbamate (16.1 mg) and ethyl acetate (0.5 mL) was added 4 N hydrogen chloride ethyl acetate solution (0.5 mL) at room temperature and the reaction mixture was stirred at the same temperature for 30 min. The reaction mixture was concentrated under reduced pressure to give the title compound (14.0 mg).

$^1$H NMR (300 MHz, DMSO-$d_6$) δ 1.21-1.44 (8H, m), 1.72 (3H, brs), 1.88 (2H, d, J=17.8 Hz), 1.96-2.12 (2H, m), 3.52-3.73 (8H, m), 3.74 (3H, s), 3.83 (3H, s), 4.63-4.89 (1H, m), 6.65 (1H, s), 6.75 (1H, dd, J=8.7, 2.3 Hz), 7.03 (1H, d, J=2.3 Hz), 7.48 (1H, d, J=9.1 Hz), 8.82 (3H, d, J=8.7 Hz).

Example 43

Methyl (E)-3-(2-(4-((S)-2-cyclohexyl-2-((S)-2-(methylamino)propanamido)acetyl)piperazine-1-carbonyl)-5-fluoro-1-methyl-1H-indol-3-yl)acrylate Hydrochloride A) (E)-Methyl 3-(2-(4-((S)-2-((S)-2-((tert-butoxycarbonyl)(methyl)amino)propanamido)-2-cyclohexylacetyl)piperazine-1-carbonyl)-5-fluoro-1-methyl-1H-indol-3-yl)acrylate To a mixture of tert-butyl ((S)-1-(((S)-1-cyclohexyl-2-(4-(5-fluoro-3-formyl-1-methyl-1H-indole-2-carbonyl)piperazin-1-yl)-2-oxoethyl)amino)-1-oxopropan-2-yl)(methyl)carbamate (127.5 mg) and toluene (1.04 mL) was added methyl (triphenylphosphoranylidene)acetate (104 mg) at room temperature. The reaction mixture was stirred at 80° C. for 3 h and concentrated under reduced pressure. The residue was purified by silica gel column chromatography (C18, acetonitrile/5 mM ammonium acetate) to give the title compound (65.6 mg).

MS: [M+H]$^+$ 670.5.

B) Methyl (E)-3-(2-(4-((S)-2-cyclohexyl-2-((S)-2-(methylamino)propanamido)acetyl)piperazine-1-carbonyl)-5-fluoro-1-methyl-1H-indol-3-yl)acrylate Hydrochloride A mixture of (E)-methyl 3-(2-(4-((S)-2-((S)-2-((tert-butoxycarbonyl)(methyl)amino)propanamido)-2-cyclohexylacetyl)piperazine-1-carbonyl)-5-fluoro-1-methyl-1H-indol-3-yl)acrylate (10.0 mg) and 4 N hydrogen chloride ethyl acetate solution (0.1 mL) was stirred at room temperature for 2 h. The reaction mixture was concentrated under reduced pressure to give the title compound (5.6 mg). MS: [M+H]$^+$ 570.5.

Example 44

(S)—N—((S)-2-(4-(1-(2-(2-(Benzyloxy)ethoxy)ethyl)-5,6-difluoro-1H-indole-2-carbonyl)piperazin-1-yl)-1-cyclohexyl-2-oxoethyl)-2-(methylamino)propanamide

A) tert-Butyl 4-((5,6-difluoro-1H-indol-2-yl)carbonyl)piperazine-1-carboxylate To a mixture of 5,6-difluoroindole-2-carboxylic acid (10 g) and DCM (300 mL) was added t-butyl piperazine-1-carboxylate (11.3 g), DIEA (17.7 mL) and TBTU (19.6 g) under ice-cooling. The reaction mixture was stirred at room temperature for 7 h. The reaction mixture was diluted with DCM, washed with saturated aqueous sodium bicarbonate and water, and then dried over anhydrous sodium sulfate, and the solvent was removed under reduced pressure. The residue was purified by silica gel column chromatography (ethyl acetate/hexane) to the title compound (15 g).

MS: [M+H]$^+$ 366.4.

B) 2-(2-(Benzyloxy)ethoxy)ethyl 4-methylbenzene-1-sulfonate

To a mixture of 2-(2-(benzyloxy)ethoxy)ethan-1-ol (10 g) and DCM (200 mL) was added TEA (10.6 mL), DMAP (3.11 g) and p-toluenesulfonyl chloride (11.7 g) under ice-cooling and the reaction mixture was stirred at room temperature for 2 h. The reaction mixture was diluted with DCM, washed with water and brine, and then dried over anhydrous sodium sulfate, and the solvent was removed under reduced pressure. The residue was purified by silica gel column chromatography (ethyl acetate/hexane) to give the title compound (9.6 g).

MS: [M+H]$^+$ 350.8

C) tert-Butyl 4-[(1-{2-[2-(benzyloxy)ethoxy]ethyl}-5,6-difluoro-1H-indol-2-yl)carbonyl]piperazine-1-carboxylate To a mixture of tert-butyl 4-((5,6-difluoro-1H-indol-2-yl)carbonyl)piperazine-1-carboxylate (3 g) and DMF (25 mL) was added cesium carbonate (6.69 g) and a solution of 2-[2-(benzyloxy)ethoxy]ethyl 4-methylbenzene-1-sulfonate (5.18 g) in DMF (5 mL) at room temperature. The reaction mixture was stirred at the same temperature for 16 h. The reaction mixture was diluted with water and the aqueous layer was extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (3.3 g).

MS: [M+H]$^+$ 543.8.

D) 1-(2-(2-(Benzyloxy)ethoxy)ethyl)-5,6-difluoro-2-((piperazin-1-yl)carbonyl)-1H-indole Hydrochloride To a mixture of tert-butyl 4-((1-(2-(2-(benzyloxy)ethoxy)ethyl)-5,6-difluoro-1H-indol-2-yl)carbonyl)piperazine-1-carboxylate (300 mg) and DCM (2 mL) was added 4 M hydrogen chloride dioxane solution (3 mL) under ice-cooling. The reaction mixture was stirred at room temperature for 3 h. The reaction mixture was concentrated under reduced pressure and the residue was washed with ether to give the title compound (200 mg).

MS: [M+H]$^+$ 444.2.

E) Methyl (2S)-2-[(2S)-2-{[(tert-butoxy)carbonyl](methyl)amino}propanamido]-2-cyclohexylacetate To a mixture of (2S)-2-{[(tert-butoxy)carbonyl](methyl)amino}propanoic acid (5 g), methyl (2S)-2-amino-2-cyclohexylacetate (5.11 g), 2-chloro-4,6-dimethoxy-1,3,5-triazine (4.751 g) and ethyl acetate (200 mL) was added N-methylmorpholine (6.76 mL) under ice-cooling. The reaction mixture was stirred at room temperature for 1.5 h. Insoluble materials were filtered off and the filtrate was washed with saturated aqueous sodium bicarbonate, 10% aqueous potassium hydrogen sulfate and brine and then dried over anhydrous sodium sulfate, and the solvent was removed under reduced pressure to give the title compound (7.9 g).

MS: [M+H]$^+$ 357.1.

F) (2S)-2-[(2S)-2-{[(tert-Butoxy)carbonyl](methyl)amino}propanamido]-2-cyclohexylacetic Acid To a mixture of methyl (2S)-2-[(2S)-2-{[(tert-butoxy)carbonyl](methyl)amino}propanamido]-2-cyclohexylacetate (7.9 g) and THF (150 mL) was added water (50 mL) and lithium hydroxide monohydrate (1.12 g) at room temperature. The reaction mixture was stirred at the same temperature for 4 h. The reaction mixture was concentrated under reduced pressure and the residue was diluted with water and washed with ether. The aqueous layer was acidified with 10% aqueous potassium hydrogen sulfate and extracted with ethyl acetate. The organic layer was washed with water and brine and then dried over anhydrous sodium sulfate, and the solvent was removed under reduced pressure to give the title compound (7.2 g).

MS: [M+H]$^+$ 343.2.

G) tert-Butyl N-[(1S)-1-{[(1S)-2-{4-[(1-{2-[2-(benzyloxy)ethoxy]ethyl}-5,6-difluoro-1H-indol-2-yl)carbonyl]-piperazin-1-yl}-1-cyclohexyl-2-oxoethyl]carbamoyl}ethyl]-N-methylcarbamate To a mixture of 1-{2-[2-(benzyloxy)ethoxy]ethyl}-5,6-difluoro-2-[(piperazin-1-yl)carbonyl]-1H-indole hydrochloride (100 mg) and DMF (2 mL) was added DIEA (0.127 mL), (2S)-2-[(2S)-2-{[(tert-butoxy)carbonyl](methyl)amino}propanamido]-2-cyclohexylacetic acid (78.5 mg) and HATU (102.9 mg) under ice-cooling and the reaction mixture was stirred at room temperature for 2 h. The reaction mixture was diluted with ice-cold water and the aqueous layer was extracted with ethyl acetate. The organic layer was washed with saturated aqueous sodium bicarbonate, water and brine and then dried over anhydrous sodium sulfate, and the solvent was removed under reduced pressure. The residue was purified by silica gel column chromatography (ethyl acetate/hexane) and preparative HPLC (Chiralpak IA (21× 250 mm), mobile phase: ethanol/hexane (containing 0.1% isopropylamine)) to give the title compound (55 mg, longer retention time).

MS: [M+H]$^+$ 768.0.

H) (S)—N—((S)-2-(4-(1-(2-(2-(Benzyloxy)ethoxy)ethyl)-5,6-difluoro-1H-indole-2-carbonyl)piperazin-1-yl)-1-cyclohexyl-2-oxoethyl)-2-(methylamino)propanamide To a mixture of tert-butyl N-[(1S)-1-{[(1S)-2-{4-[(1-{2-[2-(benzyloxy)ethoxy]ethyl}-5,6-difluoro-1H-indol-2-yl)

carbonyl]piperazin-1-yl}-1-cyclohexyl-2-oxoethyl] carbamoyl}ethyl]-N-methylcarbamate (50 mg) and DCM (2 mL) was added 4 M hydrogen chloride dioxane solution (0.5 mL) under ice-cooling. The reaction mixture was stirred at room temperature for 2 h, concentrated under reduced pressure and the residue was purified by preparative HPLC (C18, mobile phase: acetonitrile/water (containing 20 mM ammonium bicarbonate)) to give the title compound (23 mg).

$^1$H NMR (400 MHz, DMSO-d$_6$) δ 0.95-0.98 (2H, m), 1.08-1.23 (6H, m), 1.64 (6H, m), 2.16 (3H, s), 2.93-2.95 (2H, m), 3.39-3.40 (2H, m), 3.43-3.45 (2H, m), 3.50-3.63 (8H, m), 4.32 (2H, s), 4.45 (2H, t, J=4.9 Hz), 4.64 (2H, m), 6.72 (1H, s), 7.16-7.18 (2H, m), 7.25-7.31 (3H, m), 7.61 (1H, dd, J=8.4 Hz, 10.8 Hz), 7.74 (1H, dd, J=6.9 Hz, 11.4 Hz), 7.95 (1H, d, J=8.9 Hz).

Example 45

(S)—N—((S)-1-Cyclohexyl-2-(4-(5,6-difluoro-1-(2-(2-hydroxyethoxy)ethyl)-1H-indole-2-carbonyl)piperazin-1-yl)-2-oxoethyl)-2-(methylamino)propanamide A) tert-Butyl 4-({5,6-difluoro-1-[2-(2-hydroxyethoxy)ethyl]-1H-indol-2-yl}carbonyl)piperazine-1-carboxylate A mixture of tert-butyl 4-[(1-{2-[2-(benzyloxy)ethoxy]ethyl}-5,6-difluoro-1H-indol-2-yl)carbonyl]piperazine-1-carboxylate (3 g), 10% palladium on carbon (50% water content) (600 mg) and ethanol (100 mL) was stirred under the normal pressure hydrogen atmosphere at room temperature for 16 h. The catalysts were filtered off with Celite® and the filtrate was concentrated under reduced pressure to give the title compound (2.3 g).

MS: [M+H]$^+$ 454.2.

B) 2-(2-{5,6-Difluoro-2-[(piperazin-1-yl)carbonyl]-1H-indol-1-yl}ethoxy)ethan-1-ol Hydrochloride To a mixture of tert-butyl 4-({5,6-difluoro-1-[2-(2-hydroxyethoxy)ethyl]-1H-indol-2-yl}carbonyl)piperazine-1-carboxylate (2.3 g) and DCM (10 mL) was added 4 M hydrogen chloride dioxane solution (12 mL) under ice-cooling. The reaction mixture was stirred at room temperature for 3 h. The reaction mixture was concentrated under reduced pressure and the residue was washed with ether to give the title compound (1.8 g).

MS: [M+H]$^+$ 354.4.

C) tert-Butyl N-[(1S)-1-cyclohexyl-2-[4-({5,6-difluoro-1-[2-(2-hydroxyethoxy)ethyl]-1H-indol-2-yl}carbonyl)-piperazin-1-yl]-2-oxoethyl]carbamate To a mixture of 2-(2-{5,6-difluoro-2-[(piperazin-1-yl)carbonyl]-1H-indol-1-yl}ethoxy)ethan-1-ol hydrochloride (300 mg), (S)-2-((tert-butoxycarbonyl)amino)-2-cyclohexylacetic acid (198 mg) and 1-hydroxy-1H-benzotriazole monohydrate (141 mg) and DMF (3 mL) was added DIEA (0.27 mL) and 1-ethyl-3-(3-dimethylaminopropyl)carbodiimide hydrochloride (177 mg) at room temperature. The reaction mixture was stirred at the same temperature for 2 h. The reaction mixture was diluted with ice-cold water and the aqueous layer was extracted with ethyl acetate. The organic layer was washed with water, saturated aqueous sodium bicarbonate and brine and then dried over anhydrous sodium sulfate, and the solvent was removed under reduced pressure to give the title compound (400 mg).

MS: [M+H]$^+$ 593.0.

D) (2S)-2-Amino-2-cyclohexyl-1-[4-({5,6-difluoro-1-[2-(2-hydroxyethoxy)ethyl]-1H-indol-2-yl}carbonyl)-piperazin-1-yl]ethan-1-one Hydrochloride To a mixture of tert-butyl N-[(1S)-1-cyclohexyl-2-[4-({5,6-difluoro-1-[2-(2-hydroxyethoxy)ethyl]-1H-indol-2-yl}carbonyl)piperazin-1-yl]-2-oxoethyl]carbamate (300 mg) and DCM (2 mL) was added 4 M hydrogen chloride dioxane solution (2 mL) under ice-cooling. The reaction mixture was stirred at room temperature for 3 h. The reaction mixture was concentrated under reduced pressure and the residue was washed with ether to give the title compound (200 mg).

MS: [M+H]$^+$ 493.2.

E) tert-Butyl N-[(1S)-1-{[(1S)-1-cyclohexyl-2-[4-({5,6-difluoro-1-[2-(2-hydroxyethoxy)ethyl]-1H-indol-2-yl}carbonyl)piperazin-1-yl]-2-oxoethyl]carbamoyl}ethyl]-N-methylcarbamate To a mixture of (2S)-2-amino-2-cyclohexyl-1-[4-({5,6-difluoro-1-[2-(2-hydroxyethoxy)ethyl]-1H-indol-2-yl}carbonyl)-piperazin-1-yl]ethan-1-one hydrochloride (300 mg) and DMF (3 mL) was added (2S)-2-{[(tert-butoxy)carbonyl](methyl)amino}propanoic acid (146 mg), DIEA (0.35 mL) and HATU (259 mg) at room temperature. The reaction mixture was stirred at the same temperature 2 h. To the reaction mixture was added ice and the aqueous layer was extracted with ethyl acetate. The organic layer was washed with water and brine, and then dried over anhydrous sodium sulfate, and the solvent was removed under reduced pressure. The residue was purified by silica gel column chromatography (NH, ethyl acetate/hexane) to give the title compound (170 mg).

MS: [M+H]$^+$ 678.3.

F) (S)—N—((S)-1-Cyclohexyl-2-(4-(5,6-difluoro-1-(2-(2-hydroxyethoxy)ethyl)-1H-indole-2-carbonyl)piperazin-1-yl)-2-oxoethyl)-2-(methylamino)propanamide To a mixture of tert-butyl N-[(1S)-1-{[(1S)-1-cyclohexyl-2-[4-({5,6-difluoro-1-[2-(2-hydroxyethoxy)ethyl]-1H-indol-2-yl}carbonyl)piperazin-1-yl]-2-oxoethyl]carbamoyl}ethyl]-N-methylcarbamate (40 mg) and DCM (1 mL) was added 4 M hydrogen chloride dioxane solution (0.5 mL) under ice-cooling. The reaction mixture was stirred at room temperature for 3 h. The reaction mixture was concentrated under reduced pressure and the residue was purified by preparative HPLC (C18, mobile phase: acetonitrile/water (containing 20 mM ammonium bicarbonate)) to give the title compound (17 mg).

$^1$H NMR (400 MHz, DMSO-d$_6$) δ 0.95-1.23 (9H, m), 1.61-1.65 (5H, m), 2.17 (3H, s), 2.90-2.97 (2H, m), 3.23-3.41 (7H, m), 3.54-3.68 (8H, m), 4.43 (2H, t, J=5.0 Hz), 4.51 (1H, m), 4.65 (1H, m), 6.72 (1H, s), 7.60 (1H, dd, J=7.92 Hz, 10.76 Hz), 7.74 (1H, dd, J=7.08 Hz, 11.68 Hz), 7.97 (1H, d, J=8.0 Hz).

Example 46

(S)—N—((R)-2-(4-(1-(2-(2-(Benzyloxy)ethoxy)
ethyl)-5,6-difluoro-1H-indole-2-carbonyl)piperazin-
1-yl)-1-cyclohexyl-2-oxoethyl)-2-(methylamino)
propanamide Hydrochloride A) tert-Butyl N-[(1S)-1-{[(1R)-2-{4-[(1-{2-[2-(benzyloxy)ethoxy]ethyl}-5,6-difluoro-1H-indol-2-yl)carbonyl]-piperazin-1-yl}-1-cyclohexyl-2-oxoethyl]carbamoyl}ethyl]-N-methylcarbamate To a mixture of 1-{2-[2-(benzyloxy)ethoxy]ethyl}-5,6-difluoro-2-[(piperazin-1-yl)carbonyl]-1H-indole hydrochloride (100 mg) and DMF (2 mL) was added DIEA (0.127 mL), (2S)-2-[(2S)-2-{[(tert-butoxy)carbonyl](methyl)amino}-propanamido]-2-cyclohexylacetic acid (78.5 mg) and HATU (102.9 mg) under ice-cooling and the resultant mixture was stirred at room temperature for 2 h. The reaction mixture was diluted with ice-cold water and extracted with ethyl acetate. The organic layer was washed with saturated aqueous sodium bicarbonate, water and brine and then dried over anhydrous sodium sulfate, and the solvent was removed under reduced pressure. The residue was purified by silica gel column chromatography (ethyl acetate/hexane) and preparative HPLC (Chiralpak IA (21×250 mm), mobile phase: ethanol/hexane (containing 0.1% isopropylamine)) to give the title compound (15 mg, shorter retention time).
MS: [M+H]$^+$ 767.9.

B) (S)—N—(((R)-2-(4-(1-(2-(2-(Benzyloxy)ethoxy)ethyl)-5,6-difluoro-1H-indol-2-yl)carbonyl)piperazin-1-yl)-1-cyclohexyl-2-oxoethyl)-2-(methylamino)propanamide Hydrochloride To a mixture of tert-butyl N-[(1S)-1-{[(1R)-2-{4-[(1-{2-[2-(benzyloxy)ethoxy]ethyl}-5,6-difluoro-1H-indol-2-yl)carbonyl]-piperazin-1-yl}-1-cyclohexyl-2-oxoethyl]carbamoyl}ethyl]-N-methylcarbamate (10 mg) and DCM (1 mL) was added 4 M hydrogen chloride dioxane solution (0.2 mL) under ice-cooling. The reaction mixture was stirred at room temperature for 3 h. The reaction mixture was concentrated under reduced pressure and washed with ether to give the title compound (4 mg).
MS: [M+H]$^+$ 668.3.

Example 47

(S)—N—((S)-1-Cyclohexyl-2-(4-(5,6-difluoro-1-(2-(2-(2-hydroxyethoxy)ethoxy)ethyl)-1H-indole-2-carbonyl)piperazin-1-yl)-2-oxoethyl)-2-(methylamino)propanamide A) 2-{2-[2-(Benzyloxy)ethoxy]ethoxy}ethyl 4-methylbenzene-1-sulfonate To a mixture of 2-{2-[2-(benzyloxy)ethoxy]ethoxy}ethan-1-ol (5 g) and DCM (100 mL) was added TEA (4.4 mL), DMAP (1.27 g) and p-toluenesulfonyl chloride (4.8 g) under ice-cooling. The reaction mixture was stirred at room temperature for 2 h. The reaction mixture was diluted with DCM and washed with water and brine and then dried over anhydrous sodium sulfate, and the solvent was removed under reduced pressure. The residue was purified by silica gel column chromatography (ethyl acetate/hexane) to give the title compound (5.2 g).
MS: [M+H]$^+$ 395.0.

B) tert-Butyl 4-{[1-(2-{2-[2-(benzyloxy)ethoxy]ethoxy}ethyl)-5,6-difluoro-1H-indol-2-yl]carbonyl}piperazine-1-carboxylate To a mixture of tert-butyl 4-[(5,6-difluoro-1H-indol-2-yl)carbonyl]piperazine-1-carboxylate (1.7 g) and DMF (10 mL) was added cesium carbonate (3.03 g) and a mixture of 2-{2-[2-(benzyloxy)ethoxy]ethoxy}ethyl 4-methylbenzene-1-sulfonate (3.3 g) and DMF (2 mL) at room temperature. The reaction mixture was stirred at the same temperature for 16 h. The reaction mixture was diluted with ice-cold water and the aqueous layer was extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (1.6 g).
MS: [M+H]$^+$ 588.2.

C) tert-Butyl 4-[(5,6-difluoro-1-{2-[2-(2-hydroxyethoxy)ethoxy]ethyl}-1H-indol-2-yl)carbonyl]piperazine-1-carboxylate A mixture of tert-butyl 4-{[1-(2-{2-[2-(benzyloxy)ethoxy]ethoxy}ethyl)-5,6-difluoro-1H-indol-2-yl]carbonyl}piperazine-1-carboxylate (1.6 g), 10% palladium on carbon (50% water content) (320 mg) and ethanol (100 mL) was stirred under the normal pressure hydrogen atmosphere at room temperature for 16 h. The catalysts were filtered off with Celite® and the filtrate was concentrated under reduced pressure. The residue was purified by silica gel column chromatography (ethyl acetate/hexane) to give the title compound (1.2 g).
MS: [M+H]$^+$ 497.7.

D) 2-[2-(2-{5,6-Difluoro-2-[(piperazin-1-yl)carbonyl]-1H-indol-1-yl}ethoxy)ethoxy]ethan-1-ol Hydrochloride To a mixture of tert-butyl 4-[(5,6-difluoro-1-{2-[2-(2-hydroxyethoxy)ethoxy]ethyl}-1H-indol-2-yl)carbonyl]piperazine-1-carboxylate (1.2 g) and DCM (5 mL) was added 4 M hydrogen chloride dioxane solution (6 mL) under ice-cooling. The reaction mixture was stirred at room temperature for 3 h. The reaction mixture was concentrated under reduced pressure and the residue was washed with ether to give the title compound (1.03 g).
MS: [M+H]$^+$ 398.4.

E) tert-Butyl N-[(1S)-1-cyclohexyl-2-{4-[(5,6-difluoro-1-{2-[2-(2-hydroxyethoxy)ethoxy]ethyl}-1H-indol-2-yl)carbonyl]piperazin-1-yl}-2-oxoethyl]carbamate To a mixture of 2-[2-(2-{5,6-difluoro-2-[(piperazin-1-yl)carbonyl]-1H-indol-1-yl}ethoxy)ethoxy]ethan-1-ol hydrochloride (400 mg), (S)-2-((tert-butoxycarbonyl)amino)-2-cyclohexylacetic acid (237 mg), 1-hydroxybenzotriazole monohydrate (169 mg) and DMF (6 mL) was added DIEA (0.32 mL) and 1-ethyl-3-(3-dimethylaminopropyl)carbodiimide hydrochloride (212 mg) at room temperature. The reaction mixture was stirred at the same temperature for 2 h. The reaction mixture was diluted with ice-cold water and the aqueous layer was extracted with ethyl acetate. The organic layer was washed with water, saturated aqueous sodium bicarbonate and brine and then dried over anhydrous sodium sulfate, and the solvent was removed under reduced pressure to give the title compound (520 mg).
MS: [M+H]$^+$ 637.1.

F) (2S)-2-Amino-2-cyclohexyl-1-{4-[(5,6-difluoro-1-{2-[2-(2-hydroxyethoxy)ethoxy]ethyl}-1H-indol-2-yl)carbonyl]piperazin-1-yl}ethan-1-one Hydrochloride To a mixture of tert-butyl N-[(1S)-1-cyclohexyl-2-{4-[(5,6-difluoro-1-{2-[2-(2-hydroxyethoxy)ethoxy]ethyl}-1H-indol-2-yl)carbonyl]piperazin-1-yl}-2-oxoethyl]carbamate (500 mg) and DCM (5 mL) was added 4 M hydrogen chloride dioxane solution (2 mL) under ice-cooling. The reaction mixture was stirred at room temperature for 3 h. The reaction mixture was concentrated under reduced pressure and the residue was washed with ether to give the title compound (400 mg).
MS: [M+H]$^+$ 536.7.

G) tert-Butyl N-[(1S)-1-{[(1S)-1-cyclohexyl-2-{4-[(5,6-difluoro-1-{2-[2-(2-hydroxyethoxy)ethoxy]ethyl}-1H-indol-2-yl)carbonyl]piperazin-1-yl}-2-oxoethyl]carbamoyl}ethyl]-N-methylcarbamate To a mixture of (2S)-2-amino-2-cyclohexyl-1-{4-[(5,6-difluoro-1-{2-[2-(2-hydroxyethoxy)ethoxy]ethyl}-1H-indol-2-yl)carbonyl]piperazin-1-yl}ethan-1-one hydrochloride (437 mg) and DMF (5 mL) was added (2S)-2-{[(tert-butoxy)carbonyl](methyl)amino}propanoic acid (196 mg), DIEA (0.67 mL) and HATU (435 mg) at room temperature. The reaction mixture was stirred at the same temperature for 2 h. The reaction mixture was diluted with ice-cold water and the aqueous layer was extracted with ethyl acetate. The organic layer was washed with water and brine and then dried over anhydrous sodium sulfate, and the solvent was removed under reduced pressure. The residue was purified by column chromatography (NH, ethyl acetate/hexane) to give the title compound (210 mg).
MS: [M+H]$^+$ 722.4.

H) (S)—N—((S)-1-Cyclohexyl-2-(4-(5,6-difluoro-1-(2-(2-(2-hydroxyethoxy)ethoxy)ethyl)-1H-indole-2-carbonyl)piperazin-1-yl)-2-oxoethyl)-2-(methylamino)propanamide To a mixture of tert-butyl N-[(1S)-1-{[(1S)-1-cyclohexyl-2-{4-[(5,6-difluoro-1-{2-[2-(2-hydroxyethoxy)ethoxy]ethyl}-1H-indol-2-yl)carbonyl]piperazin-1-yl}-2-oxoethyl]carbamoyl}ethyl]-N-methylcarbamate (40 mg) and DCM (1 mL) was added 4 M hydrogen chloride dioxane solution (0.5 mL) under ice-cooling. The reaction mixture was stirred at room temperature for 3 h. The reaction mixture was concentrated under reduced pressure and the residue was purified by preparative HPLC (C18, mobile phase: acetonitrile/water (containing 20 mM ammonium bicarbonate) to give the title compound (15 mg).
MS: [M+H]$^+$ 622.3.
$^1$H NMR (400 MHz, DMSO-d$_6$) δ 0.92-1.04 (3H, m), 1.09 (3H, d, J=6.84 Hz), 1.15-1.23 (2H, m), 1.61-1.65 (6H, m), 2.17 (3H, s), 2.94-2.96 (1H, m), 3.26 (2H, t, J=5.2 Hz), 3.38-3.39 (6H, m), 3.53-3.69 (9H, m), 4.43 (2H, t, J=4.96 Hz), 4.52 (1H, m), 4.65 (1H, m), 6.72 (1H, s), 7.60 (1H, dd, J=8.2 Hz, 10.92 Hz), 7.73 (1H, dd, J=7.12 Hz, 11.8 Hz), 7.95 (1H, d, J=8.8 Hz).

Example 48

(S)—N—((S)-1-Cyclohexyl-2-(4-(5,6-difluoro-1-(2-(2-(2-(2-hydroxyethoxy)ethoxy)ethoxy)ethyl)-1H-indole-2-carbonyl)piperazin-1-yl)-2-oxoethyl)-2-(methylamino)propanamide A) 1-Phenyl-2,5,8,11-tetraoxatridecan-13-yl 4-methylbenzenesulfonate To a mixture of 2-{2-[2-(2-benzyloxy-ethoxy)-ethoxy]ethoxy}ethanol (15 g) and DCM (250 mL) was added TEA (11.0 mL), DMAP (3.22 g) and p-toluenesulfonyl chloride (12.1 g) under ice-cooling. The reaction mixture was stirred at room temperature for 2 h. The reaction mixture was diluted with DCM, washed with water and brine and then dried over anhydrous sodium sulfate, and the solvent was removed under reduced pressure. The residue was purified by silica gel column chromatography (ethyl acetate/hexane) to give the title compound (14 g).
MS: [M+H]$^+$ 439.2.

B) tert-Butyl 4-[1-(2-{2-[2-(2-benzyloxy-ethoxy)-ethoxy]-ethoxy}-ethyl)-5,6-difluoro-1H-indole-2-carbonyl]-piperazine-1-carboxylate To a mixture of tert-butyl 4-[(5,6-difluoro-1H-indol-2-yl)carbonyl]piperazine-1-carboxylate (3 g) and DMF (15 mL) was added cesium carbonate (5.35 g) and a mixture of 1-phenyl-2,5,8,11-tetraoxatridecan-13-yl 4-methylbenzenesulfonate (6.11 g) and DMF (5 mL) at room temperature. The reaction mixture was stirred at the same temperature for 16 h. To the reaction mixture was added water and the resultant mixture was extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (4 g).
MS: [M+H]$^+$ 632.2.

C) tert-Butyl 4-{[5,6-difluoro-1-(2-{2-[2-(2-hydroxyethoxy)ethoxy]ethoxy}ethyl)-1H-indol-2-yl]carbonyl}-piperazine-1-carboxylate A mixture of tert-butyl 4-[1-(2-{2-[2-(2-benzyloxy-ethoxy)-ethoxy]-ethoxy}-ethyl)-5,6-difluoro-1H-indole-2-carbonyl]-piperazine-1-carboxylate (4 g), 10% palladium on carbon (50% water content) (800 mg) and ethanol (100 mL) was stirred under the normal pressure hydrogen atmosphere at room temperature for 16 h. The catalysts were filtered off with Celite® and the filtrate was concentrated under reduced pressure. The residue was purified by silica gel column chromatography (ethyl acetate/hexane) to give the title compound (2.8 g).
MS: [M+H]$^+$ 542.2.

D) 2-{2-[2-(2-{5,6-Difluoro-2-[(piperazin-1-yl)carbonyl]-1H-indol-1-yl}ethoxy)ethoxy]ethoxy}ethan-1-ol hydrochloride To a mixture of tert-butyl 4-{[5,6-difluoro-1-(2-{2-[2-(2-hydroxyethoxy)ethoxy]ethoxy}ethyl)-1H-indol-2-yl]carbonyl}piperazine-1-carboxylate (2.8 g) and DCM (10 mL) was added 4 M hydrogen chloride dioxane solution (15 mL) under ice-cooling. The reaction mixture was stirred at room temperature for 3 h. The reaction mixture was concentrated under reduced pressure and the residue was washed with ether to give the title compound (2.2 g).

MS: [M+H]+ 442.4.

E) tert-Butyl N-[(1S)-1-cyclohexyl-2-(4-{[5,6-difluoro-1-(2-{2-[2-(2-hydroxyethoxy)ethoxy]ethoxy}ethyl)-1H-indol-2-yl]carbonyl}piperazin-1-yl)-2-oxoethyl]carbamate To a mixture of 2-{2-[2-(2-{5,6-difluoro-2-[(piperazin-1-yl)carbonyl]-1H-indol-1-yl}ethoxy)ethoxy]ethoxy}ethan-1-ol hydrochloride (400 mg), (S)-2-((tert-butoxycarbonyl)amino)-2-cyclohexyl-acetic acid (215 mg) and 1-hydroxybenzotriazole monohydrate (154 mg) and DMF (4 mL) was added DIEA (0.29 mL) and 1-ethyl-3-(3-dimethylaminopropyl)carbodiimide hydrochloride (193 mg) at room temperature. The reaction mixture was stirred at the same temperature for 2 h. The reaction mixture was diluted with ice-cold water and the aqueous layer was extracted with ethyl acetate. The organic layer was washed with water, saturated aqueous sodium bicarbonate and brine and then dried over anhydrous sodium sulfate, and the solvent was removed under reduced pressure to give the title compound (520 mg).

MS: [M+H]+ 681.3.

F) (2S)-2-Amino-2-cyclohexyl-1-(4-{[5,6-difluoro-1-(2-{2-[2-(2-hydroxyethoxy)ethoxy]ethoxy}ethyl)-1H-indol-2-yl]carbonyl}piperazin-1-yl)ethan-1-one Hydrochloride To a mixture of tert-butyl N-[(1S)-1-cyclohexyl-2-(4-{[5,6-difluoro-1-(2-{2-[2-(2-hydroxyethoxy)ethoxy]ethoxy}ethyl)-1H-indol-2-yl]carbonyl}piperazin-1-yl)-2-oxoethyl]carbamate (500 mg) and DCM (5 mL) was added 4 M hydrogen chloride dioxane solution (2.5 mL) under ice-cooling. The reaction mixture was stirred at room temperature for 3 h. The reaction mixture was concentrated under reduced pressure and the residue was washed with ether to give the title compound (450 mg).

MS: [M+H]+ 581.4.

G) tert-Butyl N-[(1S)-1-{[(1S)-1-cyclohexyl-2-(4-{[5,6-difluoro-1-(2-{2-[2-(2-hydroxyethoxy)ethoxy]ethoxy}ethyl)-1H-indol-2-yl]carbonyl}piperazin-1-yl)-2-oxoethyl]carbamoyl}ethyl]-N-methylcarbamate To a mixture of (2S)-2-amino-2-cyclohexyl-1-(4-{[5,6-difluoro-1-(2-{2-[2-(2-hydroxyethoxy)ethoxy]ethoxy}ethyl)-1H-indol-2-yl]carbonyl}piperazin-1-yl)ethan-1-one hydrochloride (450 mg) and DMF (5 mL) was added (2S)-2-{[(tert-butoxy)carbonyl](methyl)amino}propanoic acid (188 mg), 1-hydroxybenzotriazole monohydrate (134 mg), DIEA (0.64 mL) and 1-ethyl-3-(3-dimethylaminopropyl)carbodiimide hydrochloride (210 mg) at room temperature. The reaction mixture was stirred at the same temperature for 2 h. The reaction mixture was diluted with ice-cold water and the aqueous layer was extracted with ethyl acetate. The organic layer was washed with water, saturated aqueous sodium bicarbonate and brine and then dried over anhydrous sodium sulfate, and the solvent was removed under reduced pressure to give the title compound (190 mg).

MS: [M+H]+ 766.1.

H) (S)—N—((S)-1-Cyclohexyl-2-(4-(5,6-difluoro-1-(2-(2-(2-(2-hydroxyethoxy)ethoxy)ethoxy)ethyl)-1H-indole-2-carbonyl)piperazin-1-yl)-2-oxoethyl)-2-(methylamino)propanamide To a mixture of tert-butyl N-[(1S)-1-{[(1S)-1-cyclohexyl-2-(4-{[5,6-difluoro-1-(2-{2-[2-(2-hydroxyethoxy)ethoxy]ethoxy}ethyl)-1H-indol-2-yl]carbonyl}piperazin-1-yl)-2-oxoethyl]carbamoyl}ethyl]-N-methylcarbamate (40 mg) and DCM (2 mL) was added 4 M hydrogen chloride dioxane solution (0.2 mL) under ice-cooling. The reaction mixture was stirred at room temperature for 3 h. The reaction mixture was concentrated under reduced pressure and the residue was purified by preparative HPLC (C18, mobile phase: acetonitrile/water (containing 20 mM ammonium bicarbonate)) to give the title compound (12 mg).

$^1$H NMR (400 MHz, DMSO-d$_6$) δ 0.92-1.18 (8H, m), 1.61-1.64 (6H, m), 2.17 (3H, s), 2.95 (1H, q, J=6.44 Hz, 13.28 Hz), 3.35-3.45 (11H, m), 3.53-3.62 (9H, m), 4.43 (2H, m), 4.55 (1H, m), 4.65 (1H, m), 6.72 (1H, s), 7.60 (1H, dd, J=8.24 Hz, 10.68 Hz), 7.73 (1H, dd, J=6.96 Hz, 11.6 Hz), 7.95 (1H, d, J=8.8 Hz).

Example 49

(S)—N—((S)-2-(4-(3-(2-(2-(Benzyloxy)ethoxy)ethoxy)-5,6-difluoro-1-methyl-1H-indole-2-carbonyl)piperazin-1-yl)-1-cyclohexyl-2-oxoethyl)-2-(methylamino)propanamide A) Methyl 5,6-difluoro-1-methyl-1H-indole-2-carboxylate To a mixture of 5,6-difluoro-1H-indole-2-carboxylic acid (20 g) and DMF (200 mL) was added potassium carbonate (42.03 g) and iodomethane (18.9 mL) at room temperature. The reaction mixture was stirred at the same temperature for 18 h, and then stirred at 40° C. for 6 h. To the reaction mixture was added water, and the precipitates were collected by filtration and washed with hexane to give the title compound (20 g).

$^1$H NMR (400 MHz, DMSO-d$_6$) δ 3.85 (3H, s), 3.99 (3H, s), 7.26 (1H, s), 7.70 (1H, dd, J=8.24 Hz, 10.84 Hz), 7.78 (1H, dd, J=6.96 Hz, 11.68 Hz).

B) Methyl 5,6-difluoro-3-formyl-1-methyl-1H-indole-2-carboxylate

To a mixture of methyl 5,6-difluoro-1-methyl-1H-indole-2-carboxylate (2 g) and DCM (20 mL) was added 1 M titanium tetrachloride DCM solution (17.8 mL) and a mixture of dichloromethyl methyl ether (1.7 mL) and DCM (2 mL) at −78° C. The reaction mixture was stirred at the same temperature for 2 h. The reaction mixture was diluted with water, neutralized with saturated aqueous sodium bicarbonate. The precipitates were filtered off with Celite® and the filtrate was extracted with DCM. The organic layer was dried over anhydrous sodium sulfate, and the solvent was removed under reduced pressure to give the title compound (1.9 g).

$^1$H NMR (400 MHz, DMSO-d$_6$) δ 3.99 (3H, s), 4.02 (3H, s), 8.0 (1H, dd, J=6.92 Hz, 11.4 Hz), 8.12 (1H, dd, J=8.24 Hz, 10.76 Hz), 10.34 (1H, s).

C) Methyl 5,6-difluoro-3-hydroxy-1-methyl-1H-indole-2-carboxylate

To a mixture of methyl 5,6-difluoro-3-formyl-1-methyl-1H-indole-2-carboxylate (3.5 g) and chloroform (50 mL)

was added 3-chloroperoxybenzoic acid (77%, 5.88 g) and p-toluenesulfonic acid (3.15 g) at 5 to 10° C. The reaction mixture was stirred at the same temperature for 2 h. To the reaction mixture was added 2 M ammonia methanol solution (30 mL) and the reaction mixture was stirred at room temperature for 30 min. The solvent was removed under reduced pressure and the residue was diluted with saturated aqueous sodium bicarbonate, and extracted with DCM. The organic layer was washed with 10% aqueous sodium thiosulfate, dried over anhydrous sodium sulfate, and the solvent was removed under reduced pressure to give the title compound (3 g).

$^1$H NMR (400 MHz, DMSO-$d_6$) δ 3.81 (3H, s), 3.82 (3H, s), 7.56-7.69 (2H, m), 9.36 (1H, s).

D) tert-Butyl 4-[(5,6-difluoro-3-hydroxy-1-methyl-1H-indol-2-yl)carbonyl]piperazine-1-carboxylate To a mixture of methyl 5,6-difluoro-3-hydroxy-1-methyl-1H-indole-2-carboxylate (4.4 g), tert-butyl piperazine-1-carboxylate (5.1 g) and toluene (45 mL) was added and 2 M trimethylaluminium toluene solution (18.2 mL) under argon atmosphere at room temperature. The reaction mixture was stirred at 100° C. for 3 h. To the reaction mixture was added water, the precipitates were filtered off, and the filtrate was extracted with ethyl acetate. The organic layer was dried over anhydrous sodium sulfate, and the solvent was removed under reduced pressure. The residue was purified by silica gel column chromatography (ethyl acetate/hexane) to give the title compound (3 g).

MS: [M+H]$^+$ 393.8.

E) tert-Butyl 4-{3-[2-(2-benzyloxy-ethoxy)-ethoxy]-5,6-difluoro-1-methyl-1H-indole-2-carbonyl}piperazine-1-carboxylate To a mixture of tert-butyl 4-[(5,6-difluoro-3-hydroxy-1-methyl-1H-indol-2-yl)carbonyl]piperazine-1-carboxylate (1.5 g) and DMF (15 mL) was added potassium carbonate (786 mg) and 2-[2-(benzyloxy)ethoxy]ethyl 4-methylbenzene-1-sulfonate (1.99 g) at room temperature. The reaction mixture was stirred at the same temperature for 16 h. The reaction mixture was diluted with water and the aqueous layer was extracted with ethyl acetate. The organic layer was dried over anhydrous sodium sulfate and the solvent was removed under reduced pressure. The residue was purified by silica gel column chromatography (ethyl acetate/hexane) to give the title compound (1.4 g).

$^1$H NMR (400 MHz, DMSO-$d_6$) δ 1.40 (9H, s), 3.10 (3H, s), 3.42 (5H, m), 3.56-3.63 (9H, m), 4.13 (2H, brs), 4.45-4.47 (2H, m), 7.26-7.32 (5H, m), 7.42-7.46 (1H, m), 7.64-7.69 (1H, m).

F) 4-(3-(2-(2-(Benzyloxy)ethoxy)ethoxy)-5,6-difluoro-1-methyl-1H-indol-2-yl)(piperazin-1-yl)methanone Trifluoroacetate To a mixture of tert-butyl 4-{3-[2-(2-benzyloxy-ethoxy)-ethoxy]-5,6-difluoro-1-methyl-1H-indole-2-carbonyl}-piperazine-1-carboxylate (400 mg) and DCM (5 mL) was added TFA (0.267 mL) under ice-cooling. The reaction mixture was stirred at room temperature for 3 h. The reaction mixture was concentrated under reduced pressure, and the residue was washed with ether and pentane to give the title compound (410 mg).

MS: [M+H]$^+$ 474.4.

G) tert-Butyl [(S)-2-(4-{3-[2-(2-benzyloxyethoxy)ethoxy]-5,6-difluoro-1-methyl-1H-indole-2-carbonyl}piperazin-1-yl)-1-cyclohexyl-2-oxoethyl]carbamate To a mixture of 4-(3-(2-(2-(Benzyloxy)ethoxy)ethoxy)-5,6-difluoro-1-methyl-1H-indol-2-yl)(piperazin-1-yl)methanone trifluoroacetate (410 mg) and DMF (7 mL) was added DIEA (0.243 mL), (S)-2-((tert-butoxycarbonyl)amino)-2-cyclohexylacetic acid (179 mg), 1-hydroxybenzotriazole monohydrate (128 mg) and 1-ethyl-3-(3-dimethylaminopropyl)carbodiimide hydrochloride (161 mg) at room temperature. The reaction mixture was stirred at the same temperature for 2 h. To the reaction mixture was added ice-cold water, and the precipitates were collected by filtration and washed with water to give the title compound (300 mg).

MS: [M+H]$^+$ 713.0.

H) (S)-2-Amino-1-(4-(3-(2-(2-(benzyloxy)ethoxy)-5,6-difluoro-1-methyl-1H-indole-2-carbonyl)piperazin-1-yl)-2-cyclohexylethane-1-one Hydrochloride To a mixture of tert-Butyl [(S)-2-(4-{3-[2-(2-benzyloxyethoxy)-ethoxy]-5,6-difluoro-1-methyl-1H-indole-2-carbonyl}piperazin-1-yl)-1-cyclohexyl-2-oxo-ethyl]carbamate (300 mg) and DCM (6 mL) was added 4 M hydrogen chloride dioxane solution (1 mL) under ice-cooling. The reaction mixture was stirred at room temperature for 3 h. The reaction mixture was concentrated under reduced pressure, and the residue was washed with ether and pentane to give the title compound (270 mg).

MS: [M+H]$^+$ 613.3.

I) tert-Butyl ((S)-1-((S)-2-(4-(3-(2-(2-benzyloxyethoxy)ethoxy)-5,6-difluoro-1-methyl-1H-indole-2-carbonyl)-piperazin-1-yl)-1-cyclohexyl-2-oxo-ethyl-carbamoyl)ethyl)methylcarbamate To a mixture of (S)-2-amino-1-(4-(3-(2-(2-(benzyloxy)ethoxy)ethoxy)-5,6-difluoro-1-methyl-1H-indole-2-carbonyl)piperazin-1-yl)-2-cyclohexylethane-1-one hydrochloride (270 mg) and DMF (6 mL) was added DIEA (0.217 mL), (S)-2-(((tert-butoxy)carbonyl)(methyl)amino)propionic acid (84.5 mg) and HATU (237 mg) at room temperature. The reaction mixture was stirred at the same temperature for 16 h. The reaction mixture was poured into ice-cold water and extracted with ethyl acetate. The organic layer was dried over anhydrous sodium sulfate, and the solvent was removed under reduced pressure. The residue was purified by silica gel column chromatography (ethyl acetate/hexane) to give the title compound (120 mg).

MS: [M+H]$^+$ 798.1.

J) (S)—N—[(S)-2-(4-{3-[2-(2-(Benzyloxy)ethoxy)ethoxy]-5,6-difluoro-1-methyl-1H-indole-2-carbonyl}-piperazin-1-yl)-1-cyclohexyl-2-oxoethyl]-2-(methylamino)propanamide To a mixture of tert-Butyl ((S)-1-((S)-2-(4-(3-(2-(2-benzyloxyethoxy)ethoxy)-5,6-difluoro-1-methyl-1H-indole-2-carbonyl)piperazin-1-yl)-1-cyclohexyl-2-oxo-ethylcarbamoyl)ethyl)methylcarbamate (30 mg) and DCM (1 mL) was added 4 M hydrogen chloride dioxane solution (0.2 mL) under ice-cooling. The reaction mixture was stirred at room temperature for 3 h. The reaction mixture was concentrated under reduced pressure, and the residue was purified by preparative HPLC (C18, mobile phase: acetonitrile/water (containing 20 mM ammonium bicarbonate)) to give the title compound (10 mg).

¹H NMR (400 MHz, DMSO-$d_6$) δ 0.85 (2H, m), 0.94 (3H, m), 1.09-1.23 (8H, m), 1.65 (6H, m), 2.15 (3H, s), 2.92 (2H, m), 3.54-3.57 (4H, m), 3.64 (6H, s), 4.14 (2H, m), 4.46 (2H, s), 4.63-4.68 (2H, m), 7.26-7.32 (4H, m), 7.65-7.69 (2H, m), 7.93-7.95 (1H, m)

Example 50

(S)—N—((S)-1-Cyclohexyl-2-(4-(5,6-difluoro-3-(2-(2-hydroxyethoxy)ethoxy)-1-methyl-1H-indole-2-carbonyl)piperazin-1-yl)-2-oxoethyl)-2-(methylamino)propanamide A) tert-Butyl ((S)-1-((S)-1-cyclohexyl-2-(4-(5,6-difluoro-3-(2-(2-hydroxyethoxy)ethoxy)-1-methyl-1H-indole-2-carbonyl)piperazin-1-yl)-2-oxoethylcarbamoyl)ethyl)methylcarbamate A mixture of tert-butyl ((S)-1-((S)-2-(4-(3-(2-(2-benzyloxyethoxy)ethoxy)-5,6-difluoro-1-methyl-1H-indole-2-carbonyl)piperazin-1-yl)-1-cyclohexyl-2-oxoethylcabamoyl)ethyl)methylcarbamate (90 mg), 10% palladium on carbon (50% water content) (30 mg) and ethanol (3 mL) was stirred under the normal pressure hydrogen atmosphere at room temperature for 3 h. The catalysts were filtered off with Celite® and the filtrate was concentrated under reduced pressure to give the title compound (73 mg). MS: [M+H]⁺ 708.4.

B) (S)—N—[(S)-1-Cyclohexyl-2-(4-{5,6-difluoro-3-[2-(2-hydroxyethoxy)ethoxy]-1-methyl-1H-indole-2-carbonyl}piperazin-1-yl)-2-oxoethyl]-2-methylaminopropanamide To a mixture of {(S)-1-[(S)-1-cyclohexyl-2-(4-{5,6-difluoro-3-[2-(2-hydroxy-ethoxy)-ethoxy]-1-methyl-1H-indole-2-carbonyl}-piperazin-1-yl)-2-oxo-ethylcarbamoyl]-ethyl}-methyl-carbamic acid tert-butyl ester (30 mg) and DCM (1 mL) was added 4 M hydrogen chloride dioxane solution (0.2 mL) under ice-cooling. The reaction mixture was stirred at room temperature for 2 h. The reaction mixture was concentrated under reduced pressure and the residue was purified by preparative HPLC (C18, mobile phase: acetonitrile/water (containing 20 mM ammonium bicarbonate)) to give the title compound (8 mg).

¹H NMR (400 MHz, DMSO-$d_6$) δ 1.10-1.23 (9H, m), 1.61-1.65 (6H, m), 1.90 (2H, s), 2.17 (3H, s), 2.96 (1H, m), 3.43-3.56 (7H, m), 3.64 (8H, m), 4.13-4.14 (2H, d, J=3.88 Hz), 7.64-7.69 (2H, m), 7.95 (1H, d, J=7.92 Hz).

Example 51

(S)—N—((S)-1-Cyclohexyl-2-(4-(1-(2-methoxyethyl)-3-methyl-1H-indol-2-carbonyl)piperazin-1-yl)-2-oxoethyl)-2-(methylamino)propanamide A) Ethyl 1-(2-methoxyethyl)-3-methyl-1H-indole-2-carboxylate To a mixture of ethyl 3-methyl-1H-indole-2-carboxylate (200 mg) and DMF (2 mL) was added potassium carbonate (272 mg) and 2-bromo-1-methoxyethane (0.19 mL) at room temperature. The reaction mixture was stirred at 60° C. for 10 h. To the reaction mixture was added water and the aqueous layer was extracted with ethyl acetate. The reaction mixture was washed with water and brine, and then dried over anhydrous sodium sulfate and the solvent was removed under reduced pressure. The residue was purified by silica gel column chromatography (ethyl acetate/hexane) to give the title compound (127 mg).

MS: [M+H]⁺ 262.0.

B) 1-(2-Methoxyethyl)-3-methyl-1H-indole-2-carboxylic Acid

To a mixture of ethyl 1-(2-methoxyethyl)-3-methyl-1H-indole-2-carboxylate (120 mg) and THF/methanol/water (3:1:1, 10 mL) was added lithium hydroxide monohydrate (39 mg) at room temperature. The reaction mixture was stirred at the same temperature for 16 h and the solvent was removed under reduced pressure. The residue was diluted with water, the pH was adjusted to 4 with 2 M hydrochloric acid and the aqueous layer was extracted with DCM. The organic layer was washed with water and brine and then dried over anhydrous sodium sulfate, and the solvent was removed under reduced pressure to give the title compound (90 mg).

¹H NMR (400 MHz, CDCl₃) δ 2.66 (3H, s), 3.30 (3H, s), 3.75 (2H, t, J=5.8 Hz), 4.70 (2H, t, J=5.76 Hz), 7.15 (1H, m), 7.37 (1H, m), 7.45 (1H, d, J=8.4 Hz), 7.68 (1H, d, J=8.04 Hz).

C) tert-Butyl N-[(1S)-1-{[(1S)-1-cyclohexyl-2-(4-{[1-(2-methoxyethyl)-3-methyl-1H-indol-2-yl]carbonyl}-piperazin-1-yl)-2-oxoethyl]carbamoyl}ethyl]-N-methylcarbamate To a mixture of N-[(1S)-1-{[(1S)-1-cyclohexyl-2-oxo-2-(piperazin-1-yl)ethyl]carbamoyl}ethyl]-N-methylcarbamate (50 mg) and DMF (2 mL) was added 1-(2-methoxyethyl)-3-methyl-1H-indole-2-carboxylic acid (34.1 mg), DIEA (0.06 mL) and TBTU (46.9 mg) at room temperature. To the reaction mixture was added ice-cold water and the aqueous layer was extracted with ethyl acetate. The organic layer was washed with water, saturated aqueous sodium bicarbonate and brine and then dried over anhydrous sodium sulfate, and the solvent was removed under reduced pressure. The residue was purified by silica gel column chromatography (ethyl acetate/hexane) to give the title compound (20 mg).

MS: [M+H]⁺ 625.9.

D) (S)—N—((S)-1-Cyclohexyl-2-(4-(1-(2-methoxyethyl)-3-methyl-1H-indol-2-carbonyl)piperazin-1-yl)-2-oxoethyl)-2-(methylamino)propanamide To a mixture of tert-butyl N-[(1S)-1-{[(1S)-1-cyclohexyl-2-(4-{[1-(2-methoxyethyl)-3-methyl-1H-indol-2-yl]carbonyl}piperazin-1-yl)-2-oxoethyl]carbamoyl}ethyl]-N-methylcarbamate (15 mg) and DCM (1 mL) was added 4 M hydrogen chloride dioxane solution (0.5 mL) under ice-cooling. The reaction mixture was stirred at room temperature for 2 h. The reaction mixture was concentrated under reduced pressure and the residue was purified by preparative HPLC (C18, mobile phase: acetonitrile/water (containing 20 mM ammonium bicarbonate)) to give the title compound (5 mg).

¹H NMR (400 MHz, DMSO-$d_6$) δ 0.97-1.23 (8H, m), 1.66 (6H, m), 2.17-2.25 (6H, m), 2.99 (1H, m), 3.12 (3H, d, J=10.04 Hz), 3.39-3.69 (10H, m), 4.31-4.38 (2H, m), 4.63-

4.68 (1H, m), 7.08 (1H, m), 7.22 (1H, m), 7.49 (1H, d, J=8.4 Hz), 7.56 (1H, d, J=7.96 Hz), 7.97 (1H, m).

Example 52

(S)—N—((S)-1-Cyclohexyl-2-(4-(5-fluoro-1-(2-methoxyethyl)-1H-indole-2-carbonyl)piperazin-1-yl)-2-oxoethyl)-2-(methylamino)propanamide A) Ethyl 5-fluoro-1-(2-methoxyethyl)-1H-indole-2-carboxylate To a mixture of ethyl 5-fluoro-1H-indole-2-carboxylate (200 mg) and DMF (2 mL) was added potassium carbonate (267 mg) and 2-bromo-1-methoxyethane (0.18 mL) at room temperature. The reaction mixture was stirred at 60° C. for 10 h. To the reaction mixture was added water and the aqueous layer was extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (165 mg).

MS: $[M+H]^+$ 266.1.

B) 5-Fluoro-1-(2-methoxyethyl)-1H-indole-2-carboxylic Acid

To a mixture of ethyl 5-fluoro-1-(2-methoxyethyl)-1H-indole-2-carboxylate (165 mg) and THF/methanol/water (3:1:1, 10 mL) was added lithium hydroxide monohydrate (52 mg) at room temperature. The reaction mixture was stirred at the same temperature for 16 h and the solvent was removed under reduced pressure. The residue was diluted with water, the pH was adjusted to 4 with 2 M hydrochloric acid and the aqueous layer was extracted with DCM. The organic layer was washed with water and brine and then dried over anhydrous sodium sulfate, and the solvent was removed under reduced pressure to give the title compound (140 mg).

MS: $[M–H]^+$ 236.0.

C) tert-Butyl N-[(1S)-1-{[(1S)-1-cyclohexyl-2-(4-{[5-fluoro-1-(2-methoxyethyl)-1H-indol-2-yl]carbonyl}-piperazin-1-yl)-2-oxoethyl]carbamoyl}ethyl]-N-methylcarbamate To a mixture of N-[(1S)-1-{[(1S)-1-cyclohexyl-2-oxo-2-(piperazin-1-yl)ethyl]-carbamoyl}ethyl]-N-methylcarbamate (50 mg) and DMF (2 mL) was added 5-fluoro-1-(2-methoxyethyl)-1H-indole-2-carboxylic acid (36.7 mg), DIEA (0.06 mL) and TBTU (46.9 mg) at room temperature. To the reaction mixture was added ice-cold water and the aqueous layer was extracted with ethyl acetate. The organic layer was washed with water, saturated aqueous sodium bicarbonate and brine and then dried over anhydrous sodium sulfate, and the solvent was removed under reduced pressure. The residue was purified by silica gel column chromatography (ethyl acetate/hexane) to give the title compound (55 mg).

MS: $[M+H]^+$ 630.4.

D) (S)—N—((S)-1-Cyclohexyl-2-(4-(5-fluoro-1-(2-methoxyethyl)-1H-indole-2-carbonyl)piperazin-1-yl)-2-oxoethyl)-2-(methylamino)propanamide To a mixture of tert-butyl N-[(1S)-1-{[(1S)-1-cyclohexyl-2-(4-{[5-fluoro-1-(2-methoxyethyl)-1H-indol-2-yl]carbonyl}piperazin-1-yl)-2-oxoethyl]carbamoyl}ethyl]-N-methylcarbamate (50 mg) and DCM (1 mL) was added 4 M hydrogen chloride dioxane solution (0.5 mL) under ice-cooling. The reaction mixture was stirred at room temperature for 2 h. The reaction mixture was concentrated under reduced pressure and the residue was purified by preparative HPLC (C18, mobile phase: acetonitrile/water (containing 10 mM ammonium acetate)) to give the title compound (17 mg).

$^1$H NMR (400 MHz, DMSO-$d_6$) δ 0.90-1.20 (8H, m), 1.59-1.72 (6H, m), 2.14 (3H, s), 2.91-2.95 (1H, m), 3.09 (3H, s), 3.48-3.53 (4H, m), 3.60-3.63 (6H, m), 4.43 (2H, m), 4.62 (1H, m), 6.66 (1H, s), 7.04-7.08 (1H, m), 7.32-7.35 (1H, m), 7.55-7.58 (1H, m), 7.91 (1H, d, J=9.0 Hz).

Example 53

(S)—N—((S)-1-cyclohexyl-2-(4-(6-fluoro-1-(2-methoxyethyl)-1H-indole-2-carbonyl)piperazin-1-yl)-2-oxoethyl)-2-(methylamino)propanamide A) Ethyl 6-fluoro-1-(2-methoxyethyl)-1H-indole-2-carboxylate To a mixture of ethyl 6-fluoro-1H-indole-2-carboxylate (200 mg) and DMF (2 mL) was added potassium carbonate (267 mg) and 2-bromo-1-methoxyethane (0.18 mL) at room temperature. The reaction mixture was stirred at 60° C. for 10 h. To the reaction mixture was added water and the aqueous layer was extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (180 mg) MS: $[M+H]^+$ 266.2.

B) 6-Fluoro-1-(2-methoxyethyl)-1H-indole-2-carboxylic Acid

To a mixture of ethyl 6-fluoro-1-(2-methoxyethyl)-1H-indole-2-carboxylate (180 mg) and THF/methanol/water (3:1:1, 10 mL) was added lithium hydroxide monohydrate (57 mg) at room temperature. The reaction mixture was stirred at the same temperature for 12 h, and the solvent was removed under reduced pressure. The residue was diluted with water, the pH was adjusted to 4 with 2 M hydrochloric acid and the aqueous layer was extracted with DCM. The organic layer was washed with water and brine and then the organic layer was dried over anhydrous sodium sulfate, and the solvent was removed under reduced pressure to give the title compound (146 mg).

MS: $[M–H]^+$ 236.1.

C) tert-Butyl N-[(1S)-1-{[(1S)-1-cyclohexyl-2-(4-{[6-fluoro-1-(2-methoxyethyl)-1H-indol-2-yl]carbonyl}-piperazin-1-yl)-2-oxoethyl]carbamoyl}ethyl]-N-methylcarbamate To a mixture of N-[(1S)-1-{[(1S)-1-cyclohexyl-2-oxo-2-(piperazin-1-yl)ethyl]carbamoyl}ethyl]-N-methylcarbamate (50 mg) and DMF (2 mL) was added 6-fluoro-1-(2-methoxy-ethyl)-1H-indole-2-carboxylic acid (36.7 mg), DIEA (0.06 mL) and TBTU (46.9 mg) at room temperature. To the reaction mixture was added ice-cold water and the aqueous layer was extracted with ethyl acetate. The organic layer was washed with water, saturated aqueous sodium bicarbonate and brine and then dried over anhydrous sodium sulfate and the solvent was removed under reduced pressure. The residue was purified by silica gel column chromatography (ethyl acetate/hexane) to give the title compound (52 mg).

MS: [M+H]$^+$ 630.2.

D) (S)—N—((S)-1-cyclohexyl-2-(4-(6-fluoro-1-(2-methoxyethyl)-1H-indol-2-carbonyl)piperazin-1-yl)-2-oxoethyl)-2-(methylamino)propanamide To a mixture of tert-butyl N-[(1S)-1-{[(1S)-1-cyclohexyl-2-(4-{[6-fluoro-1-(2-methoxyethyl)-1H-indol-2-yl]carbonyl}piperazin-1-yl)-2-oxoethyl]carbamoyl}ethyl]-N-methylcarbamate (50 mg) and DCM (1 mL) was added 4 M hydrogen chloride dioxane solution (0.5 mL) under icecooling. The reaction mixture was stirred at room temperature for 3 h. The reaction mixture was concentrated under reduced pressure. The residue was purified by preparative HPLC (C18, mobile phase: acetonitrile/water (containing 20 mM ammonium bicarbonate)) to give the title compound (8 mg).

$^1$H NMR (400 MHz, DMSO-d$_6$) δ 0.93-1.23 (8H, m), 1.61-1.66 (6H, m), 2.18 (3H, s), 2.97-2.98 (1H, m), 3.12 (3H, s), 3.49-3.68 (10H, m), 4.44 (2H, t, J=4.76 Hz), 4.65 (1H, m), 6.73 (1H, s), 6.96 (1H, m), 7.45 (1H, d, J=10.52 Hz), 7.59-7.62 (1H, m), 7.96 (1H, d, J=8.64 Hz).

Example 54

(S)—N—((S)-1-Cyclohexyl-2-(4-(5,6-difluoro-1-(2-methoxyethyl)-1H-indol-2-carbonyl)piperazin-1-yl)-2-oxoethyl)-2-(methylamino)propanamide A) Ethyl 5,6-difluoro-1-(2-methoxyethyl)-1H-indole-2-carboxylate To a mixture of ethyl 5,6-difluoro-1H-indole-2-carboxylate (150 mg) and DMF (2 mL) was added potassium carbonate (230 mg) and 2-bromo-1-methoxy ethane (0.13 mL) at room temperature. The reaction mixture was stirred at the same temperature for 24 h. To the reaction mixture was added water and the aqueous layer was extracted with ethyl acetate. The organic layer was washed with water and brine and then dried over anhydrous sodium sulfate and the solvent was removed under reduced pressure. The residue was purified by silica gel column chromatography (ethyl acetate/hexane) to give the title compound (104 mg).

$^1$H NMR (400 MHz, CDCl$_3$) δ 1.39 (3H, t, J=7.16 Hz), 3.26 (3H, s), 3.70 (2H, t, J=5.4 Hz), 4.35 (2H, q, J=7.12 Hz, 14.24 Hz), 4.63 (2H, t, J=5.4 Hz), 7.24-7.29 (2H, m), 7.33-7.37 (1H, m).

B) 5,6-Difluoro-1-(2-methoxy-ethyl)-1H-indole-2-carboxylic Acid

To a mixture of ethyl 5,6-difluoro-1-(2-methoxyethyl)-1H-indole-2-carboxylate (104 mg) and THF/methanol/water (3:1:1, 5 mL) was added lithium hydroxide monohydrate (23 mg) at room temperature. The reaction mixture was stirred at the same temperature for 3 h and the solvent was removed under reduced pressure. The residue was diluted with water, the pH was adjusted to 4 with 2 M hydrochloric acid, and the aqueous layer was extracted with DCM. The organic layer was washed with water and brine and then dried over anhydrous sodium sulfate, and the solvent was removed under reduced pressure to give the title compound (90 mg).

MS: [M−H]$^+$ 253.8.

C) tert-Butyl N-[(1S)-1-{[(1S)-1-cyclohexyl-2-(4-{[5,6-difluoro-1-(2-methoxyethyl)-1H-indol-2-yl]carbonyl}piperazin-1-yl)-2-oxoethyl]carbamoyl}ethyl]-N-methylcarbamate To a mixture of N-[(1S)-1-{[(1S)-1-cyclohexyl-2-oxo-2-(piperazin-1-yl)ethyl]carbamoyl}ethyl]-N-methylcarbamate (50 mg) and DMF (2 mL) was added 5,6-difluoro-1-(2-methoxyethyl)-1H-indole-2-carboxylic acid (39.3 mg), DIEA (0.06 mL) and TBTU (46.9 mg) at room temperature. To the reaction mixture was added ice-cold water and the aqueous layer was extracted with ethyl acetate. The organic layer was washed with water, saturated aqueous sodium bicarbonate and brine and then dried over anhydrous sodium sulfate, and the solvent was removed under reduced pressure. The residue was purified by silica gel column chromatography (ethyl acetate/hexane) to give the title compound (51 mg).

MS: [M+H]$^+$ 648.4.

D) (S)—N—((S)-1-Cyclohexyl-2-(4-(5,6-difluoro-1-(2-methoxyethyl)-1H-indol-2-carbonyl)piperazin-1-yl)-2-oxoethyl)-2-(methylamino)propanamide To a mixture of tert-butyl N-[(1S)-1-{[(1S)-1-cyclohexyl-2-(4-{[5,6-difluoro-1-(2-methoxyethyl)-1H-indol-2-yl]carbonyl}piperazin-1-yl)-2-oxoethyl]carbamoyl}ethyl]-N-methylcarbamate (50 mg) and DCM (1 mL) was added 4 M hydrogen chloride dioxane solution (0.5 mL) under ice-cooling. The reaction mixture was stirred at room temperature for 2 h. The reaction mixture was concentrated under reduced pressure and the residue was purified by preparative HPLC (C18, mobile phase: acetonitrile/water (containing 20 mM ammonium bicarbonate)) to give the title compound (12 mg).

$^1$H NMR (400 MHz, DMSO-d$_6$) δ 0.96-1.18 (8H, m), 1.61-1.66 (6H, m), 2.18 (3H, s), 2.97-2.99 (1H, m), 3.12 (3H, s), 3.49-3.65 (10H, m), 4.45 (2H, t, J=4.84 Hz), 4.65 (1H, m), 6.71 (1H, s), 7.58-7.63 (1H, m), 7.71-7.75 (1H, m), 7.96 (1H, d, J=8.84 Hz).

Example 55

2-(4-((S)-2-Cyclohexyl-2-((S)-2-(methylamino)propanamido)acetyl)piperazine-1-carbonyl)-N-(2-(2-(2-(4-(4-((3-(3,4-dimethoxyphenyl)-3H-[1,2,3]triazolo[4,5-d]pyrimidin-5-yl)amino)phenyl)piperazin-1-yl)-2-oxoethoxy)ethoxy)ethyl)-6-methoxy-1-methyl-1H-indole-3-carboxamide A) 2-Chloro-N-(3,4-dimethoxyphenyl)-5-nitropyrimidin-4-amine To a mixture of 2,4-dichloro-5-nitropyrimidine (5.0 g) and THF (215 mL) was added a mixture of 3,4-dimethoxyaniline (3.99 g) and THF (43 mL) under ice-cooling, and the reaction mixture was stirred at room temperature overnight. The insoluble materials were filtered off and the filtrate was concentrated under reduced pressure. The residue was washed with ethyl acetate/hexane to give the title compound (5.51 g).

MS: [M+H]$^+$ 311.1.

B) 2-Chloro-N4-(3,4-dimethoxyphenyl)pyrimidine-4,5-diamine

A mixture of 2-chloro-N-(3,4-dimethoxyphenyl)-5-nitropyrimidin-4-amine (5.51 g), reduced iron (2.97 g), ammonium chloride (2.85 g), ethanol (90 mL) and water (22.5 mL) was stirred at 80° C. for 1.5 h. The insoluble materials were filtered off and the filtrate was concentrated under reduced pressure to give the title compound (4.95 g).

MS: [M+H]$^+$ 281.0.

C) 5-Chloro-3-(3,4-dimethoxyphenyl)-3H-[1,2,3]triazolo[4,5-d]pyrimidine

To a mixture of 2-chloro-N4-(3,4-dimethoxyphenyl)pyrimidine-4,5-diamine (1.0 g) and 37% hydrochloric acid (7 mL) was slowly added sodium nitrite (270 mg) under ice-cooling. The reaction mixture was stirred at room temperature overnight. To the reaction mixture was added water and the precipitates were collected by filtration and dissolved in ethyl acetate, and then washed with water and brine. The solvent was removed under reduced pressure following drying with anhydrous magnesium sulfate, to give the title compound. (740 mg).

$^1$H NMR (400 MHz, DMSO-d$_6$) δ 3.87 (6H, d, J=7.3 Hz), 7.28 (1H, d, J=8.3 Hz), 7.51-7.62 (2H, m), 9.84 (1H, s).

D) tert-Butyl 4-(4-((3-(3,4-dimethoxyphenyl)-3H-[1,2,3]triazolo[4,5-d]pyrimidin-5-yl)amino)phenyl)piperazine-1-carboxylate A mixture of 5-chloro-3-(3,4-dimethoxyphenyl)-3H-[1,2,3]triazolo[4,5-d]pyrimidine (740 mg), tert-butyl 4-(4-aminophenyl)piperazine-1-carboxylate (844 mg), DIEA (1.33 mL) and DMSO (12 mL) was stirred at 90° C. for 1.5 h. To the reaction mixture was added water and the aqueous layer was extracted with ethyl acetate. The organic layer was washed with water and brine and then dried over anhydrous magnesium sulfate, and the solvent was removed under reduced pressure. The residue was purified by silica gel column chromatography (ethyl acetate/hexane) to give the title compound (720 mg).

MS: [M+H]$^+$ 533.2.

E) 3-(3,4-Dimethoxyphenyl)-N-(4-(piperazin-1-yl)phenyl)-3H-[1,2,3]triazolo[4,5-d]pyrimidin-5-amine Hydrochloride To a mixture of tert-butyl 4-(4-((3-(3,4-dimethoxyphenyl)-3H-[1,2,3]triazolo[4,5-d]pyrimidin-5-yl)amino)phenyl)piperazine-1-carboxylate (720 mg) and THF (6.8 mL) was added 4 N hydrochloride THF solution (13.7 mL) at room temperature and the reaction mixture was stirred at the same temperature for 3 days. The reaction mixture was concentrated under reduced pressure and the residue was washed with ethyl acetate to give the title compound (648 mg).

MS: [M+H]$^+$ 433.1.

F) 2-(4-((S)-2-Cyclohexyl-2-((S)-2-(methylamino)propanamido)acetyl)piperazine-1-carbonyl)-N-(2-(2-(2-(4-(4-((3-(3,4-dimethoxyphenyl)-3H-[1,2,3]triazolo[4,5-d]pyrimidin-5-yl)amino)phenyl)piperazin-1-yl)-2-oxoethoxy)ethoxy)ethyl)-6-methoxy-1-methyl-1H-indole-3-carboxamide To a mixture of 3-(3,4-dimethoxyphenyl)-N-(4-(piperazin-1-yl)phenyl)-3H-[1,2,3]triazolo[4,5-d]pyrimidin-5-amine hydrochloride (251 mg), 1-(9H-fluoren-9-yl)-3-oxo-2,7,10-trioxa-4-azadodecan-12-oic acid (217 mg), DIEA (374 μL) and DMF (2.7 mL) was added 1.7 M 2,4,6-tripropyl-1,3,5,2,4,6-trioxatriphosphinane 2,4,6-trioxide DMF solution (630 μL) at room temperature. The reaction mixture was stirred at the same temperature for 1 h. The reaction mixture was diluted with ethyl acetate and water, and the aqueous layer was extracted with ethyl acetate. The organic layer was dried over anhydrous magnesium sulfate and the solvent was removed under reduced pressure, and the residue was purified by silica gel column chromatography (methanol/ethyl acetate). To a mixture of ((9H-fluoren-9-yl)methyl(2-(2-(2-(4-(4-((3-(3,4-dimethoxyphenyl)-3H-[1,2,3]triazolo[4,5-d]pyrimidin-5-yl)amino)phenyl)piperazin-1-yl)-2-oxoethoxy)ethoxy)ethyl)carbamate thus obtained and DMF (2.7 mL) was added piperidine (266 μL) at room temperature and the reaction mixture was stirred at room temperature for 10 min. The reaction mixture was diluted with ethyl acetate and water, and the aqueous layer was extracted with ethyl acetate. The organic layer was dried over anhydrous magnesium sulfate and the solvent was removed under reduced pressure. After the concentration under reduced pressure, the residue was purified by column chromatography (C18, acetonitrile/5 mM ammonium acetate).

To a mixture of obtained 2-(2-(2-aminoethoxy)ethoxy)-1-(4-(4-((3-(3,4-dimethoxyphenyl)-3H-[1,2,3]triazolo[4,5-d]pyrimidin-5-yl)amino)phenyl)piperazin-1-yl)ethenone thus obtained, 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (117 mg), DIEA (95 μL) and DMF (0.9 mL) was added HATU (138 mg) at room temperature and the reaction mixture was stirred at room temperature for 1 h. The reaction mixture was diluted with ethyl acetate and water, and the aqueous layer was extracted with ethyl acetate. The organic layer was dried over anhydrous magnesium sulfate and the solvent was removed under reduced pressure. The residue was purified by silica gel column chromatography (C18, acetonitrile/5 mM ammonium acetate) and the product was desalted by Amberlyst A21 in methanol.

To a mixture of tert-butyl ((S)-1-(((S)-1-cyclohexyl-2-(4-(3-((2-(2-(2-(4-(4-((3-(3,4-dimethoxyphenyl)-3H-[1,2,3]triazolo[4,5-d]pyrimidin-5-yl)amino)phenyl)piperazin-1-yl)-2-oxoethoxy)ethoxy)ethyl)carbamoyl)-6-methoxy-1-methyl-1H-indole2-carbonyl)piperazin-1-yl)-2-oxoethyl)amino)-1-oxopropan-2-yl)(methyl)carbamate thus obtained and ethyl acetate (0.9 mL) was added 4 N hydrogen chloride ethyl acetate solution (0.9 mL) at room temperature and the reaction mixture was stirred at the same temperature for 1 h. The reaction mixture was concentrated under reduced pressure and the residue was purified by silica gel column chromatography (C18, acetonitrile/5 mM ammonium acetate). The product was desalted by Amberlyst A21 in methanol to give the title compound (22.5 mg).

$^1$H NMR (400 MHz, CD$_3$OD) δ 0.78-1.38 (8H, m), 1.53-1.84 (6H, m), 2.31 (3H, brs), 2.94-3.08 (4H, m), 3.10-4.07 (33H, m), 4.29 (2H, s), 4.53-4.82 (1H, m), 6.84-7.01 (4H, m), 7.18 (1H, d, J=8.8 Hz), 7.64 (2H, d, J=9.0 Hz), 7.72 (1H, dd, J=8.6, 2.4 Hz), 7.80 (1H, d, J=8.6 Hz), 7.85 (1H, d, J=2.4 Hz), 9.19 (1H, s).

Example 56

(S)—N—((S)-1-Cyclohexyl-2-((R)-4-(5,6-difluoro-1-methyl-1H-indole-2-carbonyl)-2-methylpiperazin-1-yl)-2-oxoethyl)-2-(methylamino)propanamide Trifluoroacetate

A) 5,6-Difluoro-1-methyl-1H-indole-2-carboxylic Acid

To a mixture of methyl 5,6-difluoro-1-methyl-1H-indole-2-carboxylate (2 g), THF (14 mL), methanol (7 mL) and water (7 mL) was added lithium hydroxide monohydrate (1.1 g) and the reaction mixture was stirred at room temperature for 4 h. The reaction mixture was concentrated under reduced pressure, and the residue was dissolved in water, acidified by adding aqueous potassium sulfate, and extracted with ethyl acetate. The organic layer was washed with brine, dried over anhydrous sodium sulfate, and the solvent was removed under reduced pressure to give the title compound (1.8 g).

MS: [M−H]$^+$ 210.0.

B) Benzyl (3R)-4-[(2S)-2-{[(tert-butoxy)carbonyl]amino}-2-cyclohexylacetyl]-3-methylpiperazine-1-carboxylate To a mixture of (S)-2-((tert-butoxycarbonyl)amino)-2-cyclohexylacetic acid (5 g), benzyl (3R)-3-methylpiperazine-1-carboxylate (4.6 g), 1-hydroxybenzotriazole (3.2 g) and DMF (50 mL) was added DIEA (8.6 mL) and 1-ethyl-3-(3-dimethylaminopropyl)carbodiimide hydrochloride (4.4 g). The reaction mixture was stirred at room temperature for 6 h, then ice-cold water was added thereto and extracted with ethyl acetate. The organic layer was washed with saturated aqueous sodium bicarbonate and brine and then dried over anhydrous sodium sulfate, and the solvent was removed under reduced pressure to give the title compound (7.7 g).

MS: [M+H]$^+$ 474.1.

C) Benzyl (3R)-4-[(2S)-2-amino-2-cyclohexylacetyl]-3-methylpiperazine-1-carboxylate Hydrochloride To a mixture of benzyl (3R)-4-[(2S)-2-{[(tert-butoxy)carbonyl]amino}-2-cyclohexylacetyl]-3-methylpiperazine-1-carboxylate (7.7 g) and DCM (15 mL) was added 4 M hydrogen chloride dioxane solution (15 mL) under ice-cooling, the reaction mixture was stirred at room temperature for 2 h, and the solvent was removed under reduced pressure to give the title compound (6 g).

MS: [M+H]$^+$ 374.2.

D) Benzyl (3R)-4-[(2S)-2-[(2S)-2-{[(tert-butoxy)carbonyl](methyl)amino}propanamido]-2-cyclohexylacetyl]-3-methylpiperazine-1-carboxylate To a mixture of benzyl (3R)-4-[(2S)-2-amino-2-cyclohexylacetyl]-3-methylpiperazine-1-carboxylate hydrochloride (6.5 g) and DMF (50 mL) was added (2S)-2-{[(tert-butoxy)carbonyl](methyl)amino}propanoic acid (3.2 g), DIEA (9.7 mL) and HATU (9.0 g), the reaction mixture was stirred at room temperature for 16 h, then ice-cold water was added thereto and extracted with ethyl acetate. The organic layer was washed with water, saturated aqueous sodium bicarbonate and brine, dried over anhydrous sodium sulfate, and the solvent was removed under reduced pressure. The residue was purified by silica gel column chromatography (ethyl acetate/hexane) to give the title compound (7.5 g).

MS: [M+H]$^+$ 559.4.

E) tert-Butyl N-[(1S)-1-{[(1S)-1-cyclohexyl-2-[(2R)-2-methylpiperazin-1-yl]-2-oxoethyl]carbamoyl}ethyl]-N-methylcarbamate To a mixture of benzyl (3R)-4-[(2S)-2-[(2S)-2-{[(tert-butoxy)carbonyl](methyl)amino}-propanamido]-2-cyclohexylacetyl]-3-methylpiperazine-1-carboxylate (7.5 g,) and ethanol (150 mL) was added 10% palladium on carbon (50% water content) (1.5 g) and the reaction mixture was stirred under the normal pressure hydrogen atmosphere at room temperature for 16 h. The reaction mixture was filtered with Celite® and the filtrate was concentrated under reduced pressure to give the title compound (5 g).

MS: [M+H]$^+$ 425.2

F) tert-Butyl N-[(1S)-1-{[(1S)-1-cyclohexyl-2-[(2R)-4-[(5,6-difluoro-1-methyl-1H-indol-2-yl)carbonyl]-2-methylpiperazin-1-yl]-2-oxoethyl]carbamoyl}ethyl]-N-methylcarbamate To a mixture of tert-butyl N-[(1S)-1-{[(1S)-1-cyclohexyl-2-[(2R)-2-methylpiperazin-1-yl]-2-oxoethyl]carbamoyl}ethyl]-N-methylcarbamate (92 mg) and DMF (5 mL) was added 5,6-difluoro-1-methyl-1H-indole-2-carboxylic acid (50 mg), DIEA (0.13 mL) and HATU (99 mg). The reaction mixture was stirred at room temperature for 4 h, ice-cold water was added thereto and extracted with ethyl acetate. The organic layer was washed with water and brine, and then dried over anhydrous sodium sulfate, and the solvent was removed under reduced pressure. The residue was purified by silica gel column chromatography (ethyl acetate/hexane) to give the title compound (105 mg).

MS: [M+H]$^+$ 618.3.

G) (S)—N—((S)-1-Cyclohexyl-2-((R)-4-(5,6-difluoro-1-methyl-1H-indole-2-carbonyl)-2-methylpiperazin-1-yl)-2-oxoethyl)-2-(methylamino)propanamide Trifluoroacetate To a mixture of tert-butyl N-[(1S)-1-{[(1S)-1-cyclohexyl-2-[(2R)-4-[(5,6-difluoro-1-methyl-1H-indol-2-yl)carbonyl]-2-methylpiperazin-1-yl]-2-oxoethyl]carbamoyl}ethyl]-N-methylcarbamate (48 mg) and DCM (4 mL) was added TFA (0.018 mL) under ice-cooling. The reaction mixture was stirred at room temperature for 16 h, the solvent was removed under reduced pressure, and the resultant was washed with diethyl ether to give the title compound (35 mg).

$^1$H NMR (400 MHz, 100° C., DMSO-d$_6$,) δ 1.05-1.19 (8H, m), 1.36-1.38 (3H, m), 1.63-1.72 (6H, m), 2.53 (3H, s), 3.02-3.31 (3H, m), 3.76 (3H, s), 3.88-4.18 (4H, m), 4.55-4.68 (2H, m), 6.69 (1H, s), 7.53-7.60 (2H, m), 8.34-8.37 (2H, m).

Example 57

(S)—N—[(S)-1-Cyclohexyl-2-[(R)-4-[(5-fluoro-6-methoxy-1-methyl-1H-indole-2carbonyl]-2-methylpiperazin-1-yl]-2-oxoethyl]-2-(methylamino)propanamide Trifluoroacetate

A) Methyl 5-fluoro-6-methoxy-1-methyl-1H-indole-2-carboxylate

To a mixture of methyl 5-fluoro-6-methoxy-1H-indole-2-carboxylate (200 mg) and DMF (2 mL) was added potassium carbonate (371 mg) and iodomethane (0.167 mL), the reaction mixture was stirred at the same temperature for 2 h, ice-cold water was added thereto, and extracted with ethyl acetate. The organic layer was washed with water and brine and then dried over anhydrous sodium sulfate, and the solvent was removed under reduced pressure to give the title compound (208 mg).

MS: [M+H]$^+$ 238.2.

B) 5-Fluoro-6-methoxy-1-methyl-1H-indole-2-carboxylic Acid

To a mixture of methyl 5-fluoro-6-methoxy-1-methyl-1H-indole-2-carboxylate (216 mg), THF and methanol was added a mixture of lithium hydroxide monohydrate (51.3 mg) and water (2 mL) and the reaction mixture was stirred at room temperature for 2 h. The solvent was removed under reduced pressure, the residue was acidified by adding potassium hydrogen sulfate, and the precipitates were collected by filtration to give the title compound (171 mg).

$^1$H NMR (400 MHz, DMSO-d$_6$) δ 3.92 (3H, s), 4.00 (3H, s), 7.13 (1H, s), 7.25 (1H, d, J=7.2 Hz), 7.44 (1H, d, J=11.2 Hz), 12.74 (1H, s).

C) tert-Butyl N-[(1S)-1-{[(1S)-1-cyclohexyl-2-[(2R)-4-[(5-fluoro-6-methoxy-1-methyl-1H-indol-2-yl)carbonyl]-2-methylpiperazin-1-yl]-2-oxoethyl]carbamoyl}ethyl]-N-methylcarbamate To a mixture of 5-fluoro-6-methoxy-1-methyl-1H-indole-2-carboxylic acid (50 mg) and DMF (5 mL) was added tert-butyl N-[(1S)-1-{[(1S)-1-cyclohexyl-2-[(2R)-2-methylpiperazin-1-yl]-2-oxoethyl]carbamoyl}ethyl]-N-methylcarbamate (90 mg), DIEA (0.14 mL) and HATU (102 mg). The reaction mixture was stirred at room temperature for 4 h, and ice-cold water was added thereto and extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (120 mg).

MS: [M+H]$^+$ 630.3.

D) (S)—N—((S)-1-Cyclohexyl-2-((R)-4-(5-fluoro-6-methoxy-1-methyl-1H-indole-2-carbonyl)-2-methylpiperazin-1-yl)-2-oxoethyl)-2-(methylamino)propanamide Trifluoroacetate To a mixture of tert-butyl N-[(1S)-1-{[(1S)-1-cyclohexyl-2-[(2R)-4-[(5-fluoro-6-methoxy-1-methyl-1H-indol-2-yl)carbonyl]-2-methylpiperazin-1-yl]-2-oxoethyl]carbamoyl}ethyl]-N-methylcarbamate (50 mg) and DCM (4 mL) was added TFA (0.024 mL) under ice-cooling. The reaction mixture was stirred at room temperature for 2 h and the solvent was removed under reduced pressure. The residue was washed with ether to give the title compound (42 mg).

$^1$H NMR (400 MHz, DMSO-d$_6$) δ 1.06-1.31 (9H, m), 1.37 (3H, d, J=6.9 Hz), 1.64-1.74 (5H, m), 2.54 (3H, s), 3.13-3.29 (2H, m), 3.76 (3H, s), 3.88-3.93 (4H, m), 4.06-4.21 (3H, m), 4.66-4.70 (2H, m), 6.60 (1H, s), 7.20 (1H, d, J=7.2 Hz), 7.35 (1H, d, J=11.5 Hz), 8.36-8.38 (1H, m), 8.73-8.80 (2H, m).

Example 58

(S)—N—((S)-1-Cyclohexyl-2-((R)-4-(5-fluoro-1-methyl-1H-indole-2-carbonyl)-2-methylpiperazin-1-yl)-2-oxoethyl)-2-(methylamino)propanamide Trifluoroacetate

A) tert-Butyl N-[(1S)-1-{[(1S)-1-cyclohexyl-2-[(2R)-4-[(5-fluoro-1-methyl-1H-indol-2-yl)carbonyl]-2-methyl piperazin-1-yl]-2-oxoethyl]carbamoyl}ethyl]-N-methylcarbamate To a mixture of tert-butyl N-[(1S)-1-{[(1S)-1-cyclohexyl-2-[(2R)-2-methylpiperazin-1-yl]-2-oxoethyl]carbamoyl}ethyl]-N-methylcarbamate (100 mg) and DMF (5 mL) was added 5-fluoro-1-methyl-1H-indole-2-carboxylic acid (50 mg), DIEA (0.14 mL) and HATU (108 mg). The reaction mixture was stirred at room temperature for 2 h, and ice-cold water was added thereto and extracted with ethyl acetate. The organic layer was washed with water and brine and then dried over anhydrous sodium sulfate, and the solvent was removed under reduced pressure. The residue was washed with ether/pentane (1:1) to give the title compound (103 mg).

MS: [M+H]$^+$ 600.1.

B) (S)—N—((S)-1-Cyclohexyl-2-((R)-4-(5-fluoro-1-methyl-1H-indole-2-carbonyl)-2-methylpiperazin-1-yl)-2-oxoethyl)-2-(methylamino)propanamide Trifluoroacetate To a mixture of tert-butyl N-((1S)-1-(((1S)-1-cyclohexyl-2-((2R)-4-((5-fluoro-1-methyl-1H-indol-2-yl)carbonyl)-2-methyl piperazin-1-yl)-2-oxoethyl)carbamoyl)ethyl)-N-methylcarbamate (48 mg) and DCM (4 mL) was added TFA (0.018 mL) under ice-cooling. The reaction mixture was stirred at room temperature for 2 h and the solvent was removed under reduced pressure. The residue was washed with ether to give the title compound (43 mg).

MS: [M+H]$^+$ 500.5.

Example 61

N-(2-(2-(2-Azidoethoxy)ethoxy)ethyl)-2-(4-((S)-2-cyclohexyl-2-((S)-2-(methylamino)propanamido)acetyl)piperazine-1-carbonyl)-6-methoxy-1-methyl-1H-indole-3-carboxamide To a mixture of 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (50.6 mg), 2-(2-(2-azidoethoxy)ethoxy)ethan-1-amine (20.6 mg), DIEA (0.042 mL) and DMF (0.5 mL) was added HATU (60.0 mg). The reaction mixture was stirred at room temperature for 1 h and water was added thereto and extracted with ethyl acetate. The organic layer was dried over anhydrous magnesium sulfate and the solvent was removed under reduced pressure. The residue was purified by silica gel column chromatography (C18, acetonitrile/5 mM ammonium acetate). The obtained fraction was concentrated under reduced pressure, dissolved again in ethyl acetate, washed with saturated aqueous sodium bicarbonate, and then dried over anhydrous magnesium sulfate, and the solvent was removed under reduced pressure. To a mixture of the residue and ethyl acetate (0.3 mL) was added 4 M hydrochloride dioxane solution (0.6 mL). The reaction mixture was stirred at room temperature for 1 h, the solvent was removed under reduced pressure. The residue was dissolved in ethanol and desalted by Amberlyst A21 to give the title compound (32.8 mg).
MS: [M+H]+ 698.5.

Example 62

(S)—N—((S)-1-Cyclohexyl-2-(4-(5,6-difluoro-3-(2-(2-(2-hydroxyethoxy)ethoxy)ethoxy)-1-methyl-1H-indole-2-carbonyl)piperazin-1-yl)-2-oxoethyl)-2-(methylamino)propanamide A) tert-Butyl 4-(3-{2-[2-(2-benzyloxyethoxy)ethoxy]ethoxy}-5,6-difluoro-1-methyl-1H-indole-2-carbonyl)piperazine-1-carbamate To a mixture of tert-butyl 4-((5,6-difluoro-3-hydroxy-1-methyl-1H-indol-2-yl)carbonyl)piperazine-1-carbamate (1 g) and DMF (10 mL) was added cesium carbonate (2.06 g) and 2-(2-(benzyloxyethoxy)ethoxy)ethyl 4-methylbenzene-1-sulfonate (1.49 g). The reaction mixture was stirred at room temperature for 6 h, and water was added thereto and the extracted with ethyl acetate. The organic layer was washed with brine and then dried over anhydrous sodium sulfate, and the solvent was removed under reduced pressure. The residue was purified by silica gel column chromatography (ethyl acetate/hexane) to give the title compound (1.26 g).
MS: [M+H]+ 618.

B) (3-{2-[2-(2-Benzyloxyethoxy)ethoxy]ethoxy}-5,6-difluoro-1-methyl-1H-indol-2-yl)piperazin-1-yl-methanone Hydrochloride To a mixture of tert-butyl 4-(3-(2-(2-(2-benzyloxycarbonyloxyethoxy)ethoxy)ethoxy)-5,6-difluoro-1-methyl-1H-indole-2-carbonyl)piperazine-1-carbamate (1.2 g) and DCM (12 mL) was added 4 M hydrogen chloride dioxane solution (2 mL) under ice-cooling. The reaction mixture was stirred at room temperature for 4 h and the solvent was removed under reduced pressure. The residue was washed with diethyl ether to give the title compound (1 g).
MS: [M+H]+ 517.9.

C) tert-Butyl N-[(1S)-1-{[(1S)-2-(4-{[3-(2-{2-[2-(benzyloxy)ethoxy]ethoxy}ethoxy)-5,6-difluoro-1-methyl-1H-indol-2-yl]carbonyl}piperazin-1-yl)-1-cyclohexyl-2-oxoethyl]carbamoyl}ethyl]-N-methylcarbamate To a mixture of (3-(2-(2-(2-benzyloxyethoxy)ethoxy)ethoxy)-5,6-difluoro-1-methyl-1H-indol-2-yl)piperazin-1-yl-methanone hydrochloride (1.1 g) and DMF (10 mL) was added DIEA (0.83 mL), the reaction mixture was stirred for 15 min, (S)-2-((tert-butoxycarbonyl)amino)-2-cyclohexylacetic acid (512 mg), 1-hydroxybenzotriazole (366 mg) and 1-ethyl-3-(3-dimethylaminopropyl)carbodiimide hydrochloride (458 mg) were added thereto. The reaction mixture was stirred at room temperature for 2 h, poured into ice-cold water and extracted with ethyl acetate. The organic layer was dried over anhydrous sodium sulfate and the solvent was removed under reduced pressure. To a mixture of tert-butyl 4-(3-(2-(2-(2-benzyloxyethoxy)ethoxy)ethoxy)-5,6-difluoro-1-methyl-1H-indole-2-carbonyl)-piperazine-1-carbamate (1.1 g) thus obtained and DCM (10 mL) was added 4 M hydrogen chloride dioxane solution (10 mL) under ice-cooling. The reaction mixture was stirred at room temperature for 3 h. The solvent was removed under reduced pressure. To a mixture of (S)-2-amino-1-(4-(3-(2-(2-(2-(benzyloxyethoxy)ethoxy)ethoxy)-5,6-difluoro-1-methyl-1H-indol-2-carbonyl)piperazin-1-yl)-2-cyclohexylethane-1-one hydrochloride (1.1 g) thus obtained and DMF (10 mL) was added DIEA (0.83 mL). The reaction mixture was stirred for 15 min, (S)-2-((tert-butoxycarbonyl)(methyl)amino) propionic acid (323 mg) and HATU (905 mg) were added thereto, the reaction mixture was additionally stirred at room temperature for 16 h, ice-cold water was added thereto, and extracted with ethyl acetate. The organic layer was washed with brine, dried over anhydrous sodium sulfate, and the solvent was removed under reduced pressure. The residue was purified by silica gel column chromatography (ethyl acetate/hexane) to give the title compound (850 mg).
MS: [M+H]+ 842.1.

D) tert-Butyl N-[(1S)-1-{[(1S)-1-cyclohexyl-2-{4-[(5,6-difluoro-3-{2-[2-(2-hydroxyethoxy)ethoxy]ethoxy}-1-methyl-1H-indol-2-yl)carbonyl]piperazin-1-yl}-2-oxoethyl]carbamoyl}ethyl]-N-methylcarbamate A mixture of tert-butyl N-[(1S)-1-{[(1S)-2-(4-{[3-(2-{2-[2-(benzyloxy)ethoxy]ethoxy}ethoxy)-5,6-difluoro-1-methyl-1H-indol-2-yl]carbonyl}piperazin-1-yl)-1-cyclohexyl-2-oxoethyl]carbamoyl}ethyl]-N-methylcarbamate (850 mg), 10% palladium on carbon (50% water content) (200 mg) and ethanol (10 mL) was stirred under the normal pressure hydrogen atmosphere at room temperature for 3 h. The reaction mixture was filtered with Celite® and the filtrate was concentrated under reduced pressure to give the title compound (740 mg).
MS: [M+H]+ 752.6.

E) (S)—N—((S)-1-Cyclohexyl-2-(4-(5,6-difluoro-3-(2-(2-(2-hydroxyethoxy)ethoxy)ethoxy)-1-methyl-1H-indole-2-carbonyl)piperazine-1-yl)-2-oxoethyl)-2-(methylamino)propanamide To a mixture of tert-butyl N-[(1S)-1-{[(1S)-1-cyclohexyl-2-{4-[(5,6-difluoro-3-{2-[2-(2-hydroxyethoxy)ethoxy]ethoxy}-1-methyl-1H-indol-2-yl)carbonyl]piperazin-1-yl}-2-oxoethyl]carbamoyl}ethyl]-N-methylcarbamate (50 mg) and DCM (1 mL) was added 4 M hydrogen chloride dioxane solution (0.5 mL) under ice-cooling. The reaction mixture was stirred at room temperature for 3 h and the solvent was removed under reduced pressure. The residue was purified by preparative HPLC (C18, mobile phase: acetonitrile/water (containing 20 mM ammonium bicarbonate)) to give the title compound (15 mg).
$^1$H NMR (400 MHz, DMSO-$d_6$) δ 0.94-1.23 (9H, m), 1.61-1.66 (6H, m), 2.17 (3H, s), 2.95 (1H, m), 3.39 (2H, t, J=5.12 Hz), 3.47-3.52 (8H, m), 3.64 (9H, m), 4.13 (2H, brs), 4.55 (1H, m), 4.63-4.68 (1H, m), 7.64-7.69 (2H, m), 7.95 (1H, d, J=8.2 Hz).

Example 63

(S)—N—((S)-1-Cyclohexyl-2-(4-(5,6-difluoro-3-(2-(2-(2-hydroxyethoxy)ethoxy)ethoxy)-1-methyl-1H-indole-2-carbonyl)piperazin-1-yl)-2-oxoethyl)-2-(methylamino)propanamide A) tert-Butyl 4-(3-(2-(2-(2-(2-benzyloxyethoxy)ethoxy)ethoxy)ethoxy)-5,6-difluoro-1-methyl-1H-indole-2-carbonyl)piperazine-1-carbamate To a mixture of tert-butyl 4-((5,6-difluoro-3-hydroxy-1-methyl-1H-indol-2-yl)carbonyl)piperazine-1-carbamate (900 mg) and DMF (15 mL) was added cesium carbonate (1.85 g) and 2-(2-(2-(benzyloxyethoxyl)ethoxy)ethoxy) ethyl 4-methylbenzene-1-sulfonate (1.49 g). The reaction mixture was stirred at room temperature for 16 h, and water was added thereto and extracted with ethyl acetate. The organic layer was washed with brine and then dried over anhydrous sodium sulfate, and the solvent was removed under reduced pressure. The residue was purified by silica gel column chromatography (ethyl acetate/hexane) to give the title compound (780 mg).

MS: [M+H]$^+$ 662.1.

B) tert-Butyl 4-[5,6-Difluoro-3-(2-{2-[2-(2-hydroxyethoxy)ethoxy]ethoxy}ethoxy)-1-methyl-1H-indole-2-carbonyl]piperazine-1-carbamate A mixture of tert-butyl 4-[3-(2-{2-[2-(2-benzyloxyethoxy)ethoxy]ethoxy}ethoxy)-5,6-difluoro-1-methyl-1H-indole-2-carbonyl]piperazine-1-carbamate (860 mg), 10% palladium on carbon (50% water content) (138 mg) and ethanol (12 mL) was stirred under the normal pressure hydrogen atmosphere at room temperature for 2 h. The reaction mixture was filtered with Celite® and the filtrate was concentrated under reduced pressure to give the title compound (700 mg).

MS: [M+H]$^+$ 571.9.

C) [5,6-Difluoro-3-(2-{2-[2-(2-hydroxyethoxy)ethoxy]ethoxy}ethoxy)-1-methyl-1H-indol-2-yl]piperazin-1-yl-methanone Hydrochloride To a mixture of tert-butyl 4-[5,6-difluoro-3-(2-{2-[2-(2-hydroxyethoxy)ethoxy]ethoxy}ethoxy)-1-methyl-1H-indole-2-carbonyl]piperazine-1-carbamate (700 mg) and DCM (10 mL) was added 4 M hydrogen chloride dioxane solution (1 mL) under ice-cooling. The reaction mixture was stirred at room temperature for 4 h and the solvent was removed under reduced pressure. The residue was washed with diethyl ether to give the title compound (540 mg).

MS: [M+H]$^+$ 472.2.

D) tert-Butyl-N-[(1S)-1-{[(1S)-1-cyclohexyl-2-(4-{[5,6-difluoro-3-(2-{2-[2-(2-hydroxyethoxy)ethoxy]ethoxy}ethoxy)-1-methyl-1H-indol-2-yl]carbonyl}piperazin-1-yl)-2-oxoethyl]carbamoyl}ethyl]-N-methylcarbamate To a mixture of (5,6-difluoro-3-(2-(2-(2-(2-hydroxyethoxy)ethoxy)ethoxy)ethoxy)-1-methyl-1H-indol-2-yl)piperazin-1-yl-methanone hydrochloride (494.0 mg) and DMF (7 mL) was added DIEA (0.339 mL), (S)-2-((tert-butoxycarbonyl)amino)-2-cyclohexylacetic acid (250.4 mg), 1-hydroxy benzotriazole (179 mg) and 1-ethyl-3-(3-dimethylaminopropyl)carbodiimide hydrochloride (224 mg). The reaction mixture was stirred at room temperature for 2 h, poured into ice-cold water and extracted with ethyl acetate. The organic layer was dried over anhydrous sodium sulfate and the solvent was removed under reduced pressure. To a mixture of tert-butyl-N-[(1S)-1-cyclohexyl-2-(4-{[5,6-difluoro-3-(2-{2-[2-(2-hydroxyethoxy)ethoxy]ethoxy}ethoxy)-1-methyl-1H-indol-2-yl]carbonyl}piperazin-1-yl)-2-oxoethyl]carbamate (512 mg) thus obtained and DCM (8 mL) was added 4 M hydrogen chloride dioxane solution (5 mL) under ice-cooling. The reaction mixture was stirred at room temperature for 3 h and the solvent was removed under reduced pressure.

To a mixture of (1S)-1-cyclohexyl-2-(4-{[5,6-difluoro-3-(2-{2-[2-(2-hydroxyethoxy)ethoxy]ethoxy}ethoxy)-1-methyl-1H-indol-2-yl]carbonyl}piperazin-1-yl)-2-oxoethan-1-amine hydrochloride (466 mg) thus obtained and DMF (6 mL) was added DIEA (0.376 mL), (S)-2-((tert-butoxycarbonyl)(methyl)amino)propionic acid (146.4 mg) and HATU (410.8 mg). The reaction mixture was stirred at room temperature for 16 h, poured into ice-cold water and extracted with ethyl acetate. The organic layer was washed with brine, dried over anhydrous sodium sulfate, and the solvent was removed under reduced pressure. The residue was purified by silica gel column chromatography (methanol/DCM) to give the title compound (300 mg).

MS: [M+H]$^+$ 796.3.

E) (S)—N—((S)-1-Cyclohexyl-2-(4-(5,6-difluoro-3-(2-(2-(2-hydroxyethoxy)ethoxy)ethoxy)-1-methyl-1H-indole-2-carbonyl)piperazin-1-yl)-2-oxoethyl)-2-(methylamino)propanamide To a mixture of tert-butyl N-((1S)-1-(((1S)-1-cyclohexyl-2-(4-((5,6-difluoro-3-(2-(2-(2-hydroxyethoxy)ethoxy)ethoxy)-1-methyl-1H-indol-2-yl)carbonyl)piperazin-1-yl)-2-oxoethyl)carbamoyl)ethyl)-N-methylcarbamate (50 mg) and DCM (1 mL) was added 4 M hydrogen chloride dioxane solution (0.5 mL) under ice-cooling. The reaction mixture was stirred at room temperature for 3 h and the solvent was removed under reduced pressure. The residue was purified by preparative HPLC (C18, mobile phase: acetonitrile/water (containing 20 mM ammonium bicarbonate)) to give the title compound (14 mg).

$^1$H NMR (400 MHz, DMSO-d$_6$) δ0.95-1.14 (9H, m), 1.61-1.66 (6H, m), 2.17 (3H, s), 2.95-2.96 (1H, m), 3.38-3.52 (14H, m), 3.64-3.68 (9H, m), 4.13 (2H, brs), 4.56 (1H, m), 4.63-4.69 (1H, m), 7.64-7.69 (2H, m), 7.94 (1H, d, J=8.92 Hz).

Example 64

1-((R)-4-(5,6-Difluoro-1-methyl-1H-indole-2-carbonyl)-2-methylpiperazin-1-yl)-2-((2R,5R)-2-(2-(2-(2-hydroxyethoxy)ethoxy)ethoxymethyl)-5-methylpiperazin-1-yl)ethan-1-one

A) 5,6-Difluoro-1-methyl-2-{[(3R)-3-methylpiperazin-1-yl]carbonyl}-1H-indole To a mixture of 5,6-difluoro-1-methyl-1H-indole-2-carboxylic acid (1.8 g) and DMF (45 mL) was added DIEA (4.4 mL), (R)-2-methyl-piperazine (1.02 g) and HATU (4.8 g). The reaction mixture was stirred at room temperature for 3 h, poured into ice-cold water and extracted with ethyl acetate. The organic layer was washed with brine and then dried with anhydrous sodium sulfate, and the solvent was removed under reduced pressure. The residue was purified by silica gel column chromatography (methanol/DCM) to give the title compound (1.9 g).

MS: [M+H]$^+$ 294.3.

B) 2-Chloro-1-[(2R)-4-[(5,6-difluoro-1-methyl-1H-indol-2-yl)carbonyl]-2-methylpiperazin-1-yl]ethan-1-one To a mixture of 5,6-difluoro-1-methyl-2-{[(3R)-3-methylpiperazin-1-yl]carbonyl}-1H-indole (1.9 g) and DCM (25 mL) was added TEA (1.35 mL) and chloroacetyl chloride (0.6 mL) under ice-cooling. The reaction mixture was stirred at room temperature for 3 h, diluted with DCM, and washed with water and brine. The organic layer was dried over anhydrous sodium sulfate and the solvent was removed under reduced pressure. The residue was purified by silica gel column chromatography (ethyl acetate/hexane) to give the title compound (1.8 g).

MS: [M+H]$^+$ 370.2.

C) 2-{2-[2-(Benzyloxy)ethoxy]ethoxy}ethyl Methanesulfonate

To a mixture of 2-[2-(2-benzyloxyethoxy)ethoxy]ethanol (2 g) and DCM (15 mL) was added TEA (1.7 mL) and methanesulfonyl chloride (0.77 mL) under ice-cooling. The reaction mixture was stirred at room temperature for 12 h, diluted with DCM, washed with water and brine and then dried over anhydrous sodium sulfate, and the solvent was removed under reduced pressure to give the title compound (2.5 g).

$^1$H NMR (400 MHz, CDCl$_3$) δ 3.02-3.05 (3H, m), 3.61-3.65 (8H, m), 3.74-3.76 (2H, m), 4.34-4.36 (2H, m), 4.54 (2H, s), 7.27-7.33 (5H, m).

D) tert-Butyl (2R,5R)-4-benzyl-2-methyl-5-(12-phenyl-2,5,8,11-tetraoxadodecan-1-yl)piperazine-1-carboxylate To a mixture of tert-butyl (2R,5R)-4-benzyl-5-hydroxymethyl-2-methyl-piperazine-1-carboxylate (700 mg) and DMF (10 mL) was added sodium hydride (60%, dispersion in paraffin liquid, 105 mg). The reaction mixture was stirred at room temperature for 1 h, 2-(2-(2-(benzyloxy)ethoxy)ethoxy)ethyl methanesulfonate (695 mg) was added thereto and additionally stirred at 60° C. for 4 h. The reaction mixture was cooled to room temperature and 2-(2-(2-(benzyloxy)ethoxy)ethoxy)ethyl methanesulfonate (556 mg) was added thereto and additionally stirred at 60° C. for 5 h. The reaction mixture was diluted with water and the aqueous layer was extracted with ethyl acetate. The organic layer was washed with brine and then dried over anhydrous sodium sulfate, and the solvent was removed under reduced pressure. The residue was purified by silica gel column chromatography (ethyl acetate/hexane) to give the title compound (900 mg).

MS: [M+H]$^+$ 543.2.

E) tert-Butyl (2R,5R)-5-({2-[2-(2-hydroxyethoxy)ethoxy]ethoxy}methyl)-2-methylpiperazine-1-carboxylate To a mixture of tert-butyl (2R,5R)-4-benzyl-2-methyl-5-(12-phenyl-2,5,8,11-tetraoxadodecan-1-yl)piperazine-1-carboxylate (900 mg), acetic acid (0.1 mL) and ethanol (10 mL) and was added 10% palladium on carbon (200 mg). The reaction mixture was stirred under the normal pressure hydrogen atmosphere at room temperature for 16 h and filtered Celite® and the filtrate was concentrated under reduced pressure. The residue was diluted with 10% methanol/DCM, washed with saturated aqueous sodium bicarbonate, the organic layer was dried over anhydrous sodium sulfate and the solvent was removed under reduced pressure to give the title compound (600 mg).

$^1$H NMR (400 MHz, DMSO-d$_6$) δ 1.12 (3H, d, J=6.72 Hz), 1.39 (9H, s), 2.41 (1H, dd, J=2.74, 12.5 Hz), 2.88-2.94 (2H, m), 3.07 (1H, dd, J=4.16, 13.5 Hz), 3.31-3.52 (15H, m), 3.60-3.62 (1H, m), 3.98 (1H, bs).

F) tert-Butyl (2R,5R)-4-{2-[(2R)-4-[(5,6-difluoro-1-methyl-1H-indol-2-yl)carbonyl]-2-methylpiperazin-1-yl]-2-oxoethyl}-5-({2-[2-(2-hydroxyethoxy)ethoxy]ethoxy}methyl)-2-methylpiperazine-1-carboxylate To a mixture of tert-butyl (2R,5R)-5-({2-[2-(2-hydroxyethoxy)ethoxy]ethoxy}methyl)-2-methylpiperazine-1-carboxylate (592 mg) and THF (15 mL) were added TEA (0.3 mL), 2-chloro-1-[(2R)-4-[(5,6-difluoro-1-methyl-1H-indol-2-yl)carbonyl]-2-methylpiperazin-1-yl]ethan-1-one (550 mg) and tetrabutylammonium iodide (549 mg) and the resultant mixture was stirred at 60° C. for 24 h. The reaction mixture was diluted with ethyl acetate, washed with water and brine and then dried over anhydrous sodium sulfate, and the solvent was removed under reduced pressure. The residue was purified by silica gel column chromatography (methanol/ethyl acetate) to give the title compound (740 mg).

MS: [M+H]$^+$ 696.5.

G) 1-((R)-4-(5,6-Difluoro-1-methyl-1H-indole-2-carbonyl)-2-methylpiperazin-1-yl)-2-((2R,5R)-2-((2-(2-(2-hydroxyethoxy)ethoxy)ethoxy)methyl)-5-methylpiperazin-1-yl)ethan-1-one To a mixture of tert-butyl (2R,5R)-4-{2-[(2R)-4-[(5,6-difluoro-1-methyl-1H-indol-2-yl)carbonyl]-2-methylpiperazin-1-yl]-2-oxoethyl}-5-({2-[2-(2-hydroxyethoxy)ethoxy]ethoxy}methyl)-2-methylpiperazine-1-carboxylate (20 mg) and DCM (1 mL) was added TFA (0.011 mL) under ice-cooling. The reaction mixture was stirred at room temperature for 1 h and the solvent was removed under reduced pressure. The residue was purified by preparative HPLC (C18, mobile phase: acetonitrile/water (containing 20 mM ammonium bicarbonate)) to give the title compound (4 mg).

MS: [M+H]$^+$ 596.6.

Example 65

1-((R)-4-(5,6-Difluoro-1-methyl-1H-indole-2-carbonyl)-2-methylpiperazin-1-yl)-2-((2R,5R)-2-(13-hydroxy-2,5,8,11-tetraoxatridecyl)-5-methylpiperazin-1-yl)ethan-1-one A) 2-(2-(2-(2-(benzyloxy)ethoxy)ethoxy)ethyl Methansulfonate To a mixture of 2-(2-(2-(2-benzyloxyethoxy)ethoxy)ethanol (1.5 g) and DCM (15 mL) was added TEA (1.1 mL) and methanesulfonyl chloride (0.45 mL) under ice-cooling. The reaction mixture was stirred at room temperature for 3 h, diluted with DCM, washed with water and brine and then dried over anhydrous sodium sulfate, and the solvent was removed under reduced pressure to give the title compound (1.87 g).

MS: [M+H]$^+$ 362.9.

B) tert-Butyl (2R,5R)-4-benzyl-2-methyl-5-(15-phenyl-2,5,8,11,14-pentaoxapentadecan-1-yl)piperazine-1-carboxylate To a mixture of tert-butyl (2R,5R)-4-benzyl-5-(hydroxymethyl)-2-methylpiperazine-1-carboxylate (700 mg) and DMF (10 mL) was added sodium hydride (60%, dispersion in paraffin liquid, 105 mg). The reaction mixture was stirred for 1 h, 2-(2-(2-(2-(2-(benzyloxy)ethoxy)ethoxy)

ethoxy)ethoxy)ethyl methansulfonate (791 mg) was added thereto, the reaction mixture was additionally stirred at 60° C. for 4 h. The reaction mixture was cooled to room temperature, 2-(2-(2-(2-(2-(benzyloxy)ethoxy)ethoxy)ethoxy)ethoxy)ethyl methansulfonate (633 mg) was added thereto and the resultant mixture was additionally stirred at 60° C. for 5 h. To the reaction mixture was added water and extracted with ethyl acetate. The organic layer was washed with brine, dried over anhydrous sodium sulfate and the solvent was removed under reduced pressure. The residue was purified by silica gel column chromatography (ethyl acetate/hexane) to give the title compound (910 mg).
MS: [M+H]$^+$ 587.0.

C) tert-Butyl (2R,5R)-5-((2-(2-(2-(2-hydroxyethoxy)ethoxy)ethoxy)ethoxy)methyl)-2-methylpiperazine-1-carboxylate To a mixture of tert-butyl (2R,5R)-4-benzyl-2-methyl-5-(15-phenyl-2,5,8,11,14-pentaoxapentadecan-1-yl)piperazine-1-carboxylate (910 mg), acetic acid (0.1 mL) and ethanol (10 mL) was added 10% palladium on carbon (50% water content) (200 mg). The reaction mixture was stirred under the normal pressure hydrogen atmosphere at room temperature for 16 h, filtered with Celite® and the filtrate was concentrated under reduced pressure. 10% methanol/DCM was added to the residue, the resultant mixture was washed with saturated aqueous sodium bicarbonate and then the organic layer was dried over anhydrous sodium sulfate, and the solvent was removed under reduced pressure to give the title compound (500 mg).
$^1$H NMR (400 MHz, DMSO-d$_6$) δ 1.12 (3H, d, J=6.64 Hz), 1.38 (9H, s), 2.36-2.39 (1H, m), 2.87 (2H, m), 3.05 (1H, dd, J=3.92, 12.12 Hz), 3.35-3.61 (20H, m), 3.95 (1H, brs), 4.57 (1H, brs).

D) tert-Butyl (2R,5R)-4-{2-[(2R)-4-[(5,6-difluoro-1-methyl-1H-indol-2-yl)carbonyl]-2-methylpiperazin-1-yl]-2-oxoethyl}-5-((2-(2-(2-(2-hydroxyethoxy)ethoxy)ethoxy)ethoxy)methyl)-2-methylpiperazine-1-carboxylate To a mixture of tert-butyl (2R,5R)-5-((2-(2-(2-(2-hydroxyethoxy)ethoxy)ethoxy)ethoxy)methyl)-2-methylpiperazine-1-carboxylate (338.5 mg) and THF (10 mL) was added TEA (0.2 mL), 2-chloro-1-[(2R)-4-[(5,6-difluoro-1-methyl-1H-indol-2-yl)carbonyl]-2-methylpiperazin-1-yl] ethan-1-one (280 mg) and tetrabutylammonium iodide (279.6 mg). The reaction mixture was stirred at room temperature for 10 h, and then at 60° C. for 14 h. The reaction mixture was diluted with ethyl acetate, washed with water and brine and then the organic layer was dried over anhydrous sodium sulfate, and the solvent was removed under reduced pressure. The residue was purified by silica gel column chromatography (methanol/ethyl acetate) to give the title compound (310 mg).
MS: [M+H]$^+$ 740.5.

E) 1-((R)-4-(5,6-difluoro-1-methyl-1H-indole-2-carbonyl)-2-methylpiperazin-1-yl)-2-((2R,5R)-2-(13-hydroxy-2,5,8,11-tetraoxatridecyl)-5-methylpiperazin-1-yl)ethan-1-one To a mixture of tert-butyl (2R,5R)-4-{2-[(2R)-4-[(5,6-difluoro-1-methyl-1H-indol-2-yl)carbonyl]-2-methylpiperazin-1-yl]-2-oxoethyl}-5-((2-(2-(2-(2-hydroxyethoxy)ethoxy)ethoxy)ethoxy)methyl)-2-methylpiperazine-1-carboxylate (20 mg) and DCM (1 mL) was added TFA (0.01 mL) under ice-cooling. The reaction mixture was stirred at room temperature for 1 h and the solvent was removed under reduced pressure. The residue was purified by preparative HPLC (C18, mobile phase: acetonitrile/water (containing 20 mM ammonium bicarbonate)) to give the title compound (7.9 mg).
$^1$H NMR (400 MHz, DMSO-d6) δ 0.88 (3H, s), 1.07-1.20 (4H, m), 1.75-1.80 (1H, m), 1.90 (3H, s), 2.19-2.25 (2H, m), 2.60 (1H, d, J=8.9 Hz), 2.78-2.85 (2H, m), 3.46-3.47 (16H, m), 3.74 (3H, s), 3.82-3.97 (2H, m), 4.27-4.46 (4H, m), 6.70 (2H, bs), 7.60-7.64 (1H, m), 7.68-7.72 (1H, m).

Example 66

(S)—N—((S)-2-(4-(4-(2-(2-(2-(Benzyloxy)ethoxy)ethoxy)ethoxy)-5,6-difluoro-1-methyl-1H-indole-2-carbonyl)piperazin-1-yl)-1-cyclohexyl-2-oxoethyl)-2-(methylamino)propanamide A) 2-(Benzyloxy)-3, 4-difluorobenzaldehyde To a mixture of 3,4-difluoro-2-hydroxy-benzaldehyde (5 g) and acetonitrile (50 mL) was added potassium carbonate (6.6 g), benzyl bromide (4.5 mL) and sodium iodide (2.4 g), and the reaction mixture was stirred at 60° C. for 6 h. The reaction mixture was filtered with Celite® and the filtrate was concentrated under reduced pressure. The residue was purified by silica gel column chromatography (ethyl acetate/hexane) to give the title compound (7.0 g).
MS: [M+H]$^+$ 247.2.

B) Methyl (2Z)-2-azido-3-[2-(benzyloxy)-3, 4-difluorophenyl] prop-2-enoate

To a mixture of methyl azidoacetate (3.1 mL), 2-(benzyloxy)-3,4-difluorobenzaldehyde (2.0 g) and methanol (10 mL) was added dropwise a mixture of sodium methoxide (1.7 g) and methanol (10 mL) at −10° C. under argon atmosphere. The reaction mixture was stirred at the same temperature for 4 h and was additionally stirred at 4° C. for 16 h, and ice-cold water was added thereto. The precipitates were collected by filtration to give the title compound (2.1 g).
$^1$H NMR (400 MHz, DMSO-d$_6$): δ 3.83 (3H, s), 5.14 (2H, s), 6.94 (1H, s), 7.26 (1H, m), 7.38-7.40 (5H, m), 7.97 (1H, t, J=6.9 Hz).

C) Methyl 4-(benzyloxy)-5, 6-difluoro-1H-indole-2-carboxylate

A mixture of methyl (2Z)-2-azido-3-[2-(benzyloxy)-3, 4-difluorophenyl] prop-2-enoate (2.0 g) and xylene (30 mL) was stirred at 140° C. for 2 h. The reaction mixture was cooled, the precipitates were collected by filtration and dried to give the title compound (700 mg).
MS: [M+H]$^+$ 316.0.

D) Methyl 4-(benzyloxy)-5, 6-difluoro-1-methyl-1H-indole-2-carboxylate

To a mixture of methyl 4-(benzyloxy)-5, 6-difluoro-1H-indole-2-carboxylate (1.7 g) and DMF (20 mL) was added potassium carbonate (1.1 g) and iodomethane (0.4 mL). The reaction mixture was stirred at room temperature for 2 h, and ice-cold water was added thereto and extracted with ethyl acetate. The organic layer was washed with water and brine, dried over anhydrous sodium sulfate, and the solvent was removed under reduced pressure to give the title compound (1.5 g).
MS: [M+H]$^+$ 332.1.

E) 4-(Benzyloxy)-5, 6-difluoro-1-methyl-1H-indole-2-carboxylic Acid

To a mixture of methyl 4-(benzyloxy)-5,6-difluoro-1-methyl-1H-indole-2-carboxylate (1.5 g) and THF (30 mL) was added water (6.0 mL) and lithium hydroxide monohydrate (0.29 g). The reaction mixture was stirred at room temperature for 6 h and the solvent was removed under reduced pressure. The residue was acidified with 1 M hydrochloric acid and extracted with ethyl acetate. The organic layer was washed with water and brine and then dried over anhydrous sodium sulfate, and the solvent was removed under reduced pressure to give the title compound (1.4 g).
MS: [M+H]$^+$ 318.1.

F) tert-Butyl N-[(1S)-1-{[(1S)-2-(4-{[4-(benzyloxy)-5,6-difluoro-1-methyl-1H-indol-2-yl]carbonyl}piperazin-1-yl)-1-cyclohexyl-2-oxoethyl]carbamoyl}ethyl]-N-methylcarbamate To a mixture of 4-(benzyloxy)-5,6-difluoro-1-methyl-1H-indole-2-carboxylic acid (1.4 g) and DMF (20 mL) was added tert-butyl((S)-1-(((S)-1-cyclohexyl-2-oxo-2-(piperazin-1-yl)ethyl)amino)-1-oxopropan-2-yl)(methyl)carbamate (1.8 g), HATU (2.5 g) and DIEA (1.9 mL). The reaction mixture was stirred at room temperature for 2 h, ice-cold water was added thereto and extracted with ethyl acetate. The organic layer was washed with saturated aqueous sodium bicarbonate, water and brine and then dried over anhydrous sodium sulfate, and the solvent was removed under reduced pressure. The residue was purified by silica gel column chromatography (ethyl acetate/hexane) to give the title compound (2.1 g).

G) tert-Butyl N-[(1S)-1-{[(1S)-1-cyclohexyl-2-{4-[(5,6-difluoro-4-hydroxy-1-methyl-1H-indol-2-yl)carbonyl]piperazin-1-yl}-2-oxoethyl]carbamoyl}ethyl]-N-methylcarbamate To a mixture of tert-butyl N-[(1S)-1-{[(1S)-2-(4-{[4-(benzyloxy)-5,6-difluoro-1-methyl-1H-indol-2-yl]carbonyl}piperazin-1-yl)-1-cyclohexyl-2-oxoethyl]carbamoyl}ethyl]-N-methylcarbamate (2.1 g) and ethanol (50 mL) was added palladium on carbon (0.4 g). The reaction mixture was stirred under the normal pressure hydrogen atmosphere at room temperature for 2 h, filtered with Celite® and the filtrate was concentrated under reduced pressure to give the title compound (1.7 g).
MS: [M+H]$^+$ 620.4.

H) (S)—N—((S)-2-(4-(4-(2-(2-(2-(Benzyloxy)ethoxy)ethoxy)ethoxy)-5,6-difluoro-1-methyl-1H-indol-2-carbonyl)piperazin-1-yl)-1-cyclohexyl-2-oxoethyl)-2-(methylamino)propanamide To a mixture of tert-butyl N-[(1S)-1-{[(1S)-1-cyclohexyl-2-{4-[(5,6-difluoro-4-hydroxy-1-methyl-1H-indol-2-yl) carbonyl]piperazin-1-yl}-2-oxoethyl]carbamoyl}ethyl]-N-methylcarbamate (450 mg) and DMF (5 mL) was added cesium carbonate (591 mg) and 2-{2-[2-(benzyloxy)ethoxy]ethoxy}ethyl 4-methylbenzene-1-sulfonate (516 mg). The reaction mixture was stirred at room temperature for 16 h, and ice-cold water was added thereto and extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (500 mg).
MS: [M+H]$^+$ 842.0.

I) (S)—N—((S)-2-(4-(4-(2-(2-(2-(Benzyloxy)ethoxy)ethoxy)ethoxy)-5,6-difluoro-1-methyl-1H-indole-2-carbonyl)piperazin-1-yl)-1-cyclohexyl-2-oxoethyl)-2-(methylamino)propanamide To a mixture of (S)—N—((S)-2-(4-(4-(2-(2-(2-(benzyloxy)ethoxy)ethoxy)ethoxy)-5,6-difluoro-1-methyl-1H-indole-2-carbonyl)piperazin-1-yl)-1-cyclohexyl-2-oxoethyl)-2-(methylamino)propanamide (40 mg) and DCM (4 mL) was added 4 M hydrogen chloride dioxane solution (0.048 mL) under ice-cooling. The reaction mixture was stirred at room temperature for 2 h and the solvent was removed under reduced pressure. The residue was purified by preparative HPLC (C18, mobile phase: acetonitrile/water (containing 20 mM ammonium acetate)) to give the title compound (11 mg).
$^1$H NMR (400 MHz, DMSO-d$_6$) δ 0.96-1.23 (10H, m), 1.61-1.65 (8H, m), 1.90 (2H, s), 2.17 (3H, s), 2.95-2.97 (1H, m), 3.53-3.76 (16H, m), 4.40-4.51 (5H, m), 6.81 (1H, s), 7.25-7.31 (6H, m), 7.92-7.94 (1H, m).

Example 67

(S)—N—((S)-1-Cyclohexyl-2-(4-(5,6-difluoro-4-(2-(2-(2-hydroxyethoxy)ethoxy)ethoxy)-1-methyl-1H-indole-2-carbonyl)piperazin-1-yl)-2-oxoethyl)-2-(methylamino)propanamide A) tert-Butyl N-[(1S)-1-{[(1S)-1-cyclohexyl-2-{4-[(5,6-difluoro-4-{2-[2-(2-hydroxyethoxy)ethoxy]ethoxy}-1-methyl-1H-indol-2-yl)carbonyl]piperazin-1-yl}-2-oxoethyl]carbamoyl}ethyl]-N-methylcarbamate To a mixture of tert-butyl N-[(1S)-1-{[(1S)-2-(4-{[4-(2-{2-[2-(benzyloxy)ethoxy]ethoxy}ethoxy)-5,6-difluoro-1-methyl-1H-indol-2-yl]carbonyl}piperazin-1-yl)-1-cyclohexyl-2-oxoethyl]carbamoyl}ethyl]-N-methylcarbamate (500 mg) and ethanol (20 mL) was added palladium on carbon (100 mg). The reaction mixture was stirred under the normal pressure hydrogen atmosphere for 8 h, filtered with Celite® and the filtrate was concentrated under reduced pressure to give the title compound (380 mg).
MS: [M+H]$^+$ 752.5.

B) (S)—N—((S)-1-Cyclohexyl-2-(4-(5,6-difluoro-4-(2-(2-(2-hydroxyethoxy)ethoxy)ethoxy)-1-methyl-1H-indole-2-carbonyl)piperazin-1-yl)-2-oxoethyl)-2-(methylamino)propanamide To a mixture of tert-butyl N-[(1S)-1-{[(1S)-1-cyclohexyl-2-{4-[(5,6-difluoro-4-{2-[2-(2-hydroxyethoxy)ethoxy]ethoxy}-1-methyl-1H-indol-2-yl)carbonyl]piperazin-1-yl}-2-oxoethyl]carbamoyl}ethyl]-N-methylcarbamate (30 mg) and DCM (4 mL) was added 4 M hydrogen chloride dioxane solution (0.6 mL) under ice-cooling. The reaction mixture was stirred at room temperature for 2 h and the reaction mixture was concentrated under reduced pressure. The residue was purified by preparative HPLC (C18, mobile phase: acetonitrile/water (containing 10 mM ammonium acetate)) to give the title compound (5 mg).
MS: [M+H]⁺ 652.6.

Example 68

(S)—N—((S)-1-Cyclohexyl-2-(4-(5,6-difluoro-4-(2-(2-(2-(2-hydroxyethoxy)ethoxy)ethoxy)ethoxy)-1-methyl-1H-indole-2-carbonyl)piperazin-1-yl)-2-oxoethyl)-2-(methylamino)propanamide A) tert-Butyl N-[(1S)-1-{[(1S)-1-cyclohexyl-2-[4-({5,6-difluoro-1-methyl-4-[(1-phenyl-2,5,8,11-tetraoxatridecan-13-yl)oxy]-1H-indol-2-yl}carbonyl)piperazin-1-yl]-2-oxoethyl]carbamoyl}ethyl]-N-methylcarbamate To a mixture of tert-butyl N-[(1S)-1-{[(1S)-1-cyclohexyl-2-{4-[(5,6-difluoro-4-hydroxy-1-methyl-1H-indol-2-yl)carbonyl]piperazin-1-yl}-2-oxoethyl]carbamoyl}ethyl]-N-methylcarbamate (450 mg) and DMF (5 mL) was added cesium carbonate (591 mg) and 1-phenyl-2,5,8,11-tetraoxatridecan-13-yl 4-methylbenzene-1-sulfonate (573 mg). The reaction mixture was stirred at room temperature for 16 h and ice-cold water was added thereto and extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (490 mg).
MS: [M+H]⁺ 886.4.

B) tert-Butyl N-[(1S)-1-{[(1S)-1-cyclohexyl-2-(4-{[5,6-difluoro-4-(2-{2-[2-(2-hydroxyethoxy)ethoxy]ethoxy-}ethoxy)-1-methyl-1H-indol-2-yl]carbonyl}piperazin-1-yl)-2-oxoethyl]carbamoyl}ethyl]-N-methyl-carbamate To a mixture of tert-butyl N-[(1S)-1-{[(1S)-1-cyclohexyl-2-[4-({5,6-difluoro-1-methyl-4-[(1-phenyl-2,5,8,11-tetraoxatridecan-13-yl)oxy]-1H-indol-2-yl}carbonyl)piperazin-1-yl]-2-oxoethyl]carbamoyl}ethyl]-N-methylcarbamate (490 mg) and ethanol (15 mL) was added palladium on carbon (100 mg). The reaction mixture was stirred under the normal pressure hydrogen atmosphere at room temperature for 16 h, filtered with Celite® and the filtrate was concentrated under reduced pressure to give the title compound (360 mg).
MS: [M+H]⁺ 796.2.

C) (S)—N—((S)-1-Cyclohexyl-2-(4-(5,6-difluoro-4-(2-(2-(2-(2-hydroxyethoxy)ethoxy)ethoxy)ethoxy)-1-methyl-1H-indole-2-carbonyl)piperazin-1-yl)-2-oxoethyl)-2-(methylamino)propanamide To a mixture of tert-butyl N-[(1S)-1-{[(1S)-1-cyclohexyl-2-(4-{5,6-difluoro-4-(2-{2-[2-(2-hydroxyethoxy)ethoxy]ethoxy}ethoxy)-1-methyl-1H-indol-2-yl]carbonyl}piperazin-1-yl)-2-oxoethyl]carbamoyl}ethyl]-N-methylcarbamate (30 mg) and DCM (4 mL) was added 4 M hydrogen chloride dioxane solution (0.6 mL) under ice-cooling. The reaction mixture was stirred at room temperature for 2 h and the solvent was removed under reduced pressure. The residue was purified by preparative HPLC (C18, mobile phase: acetonitrile/water (containing 10 mM ammonium acetate)) to give the title compound (12 mg).

¹H NMR (400 MHz, DMSO-d₆) δ 0.96-1.18 (10H, m), 1.61-1.65 (8H, m), 2.17 (3H, s), 2.94-2.96 (1H, m), 3.37-3.74 (22H, m), 4.41 (2H, bs), 4.50-4.51 (2H, m), 6.82 (1H, s), 7.38-7.39 (1H, m), 7.94-7.96 (1H, m).

Example 69

(S)—N—((S)-1-Cyclohexyl-2-(4-(1-(2-(2-(2-hydroxyethoxy)ethoxy)ethyl)-2-methyl-1H-indole-5-carbonyl)piperazine-1-yl)-2-oxoethyl)-2-(methylamino)propanamide A) tert-Butyl N-((1S)-1-(((1S)-1-cyclohexyl-2-(4-((2-methyl-1H-indol-5-yl)carbonyl)piperazin-1-yl)-2-oxoethyl)carbamoyl)ethyl)-N-methylcarbamate To a mixture of tert-butyl ((S)-1-(((S)-1-cyclohexyl-2-oxo-2-(piperazin-1-yl)ethyl)amino)-1-oxopropan-2-yl) (methyl)carbamate (4.0 g) and DMF (70 mL) was added 2-methyl-1H-indole-5-carboxylic acid (1.9 g), DIEA (6.8 mL) and HATU (4.5 g). The reaction mixture was stirred at room temperature for 16 h, and water was added thereto and extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (4 g).
MS: [M+H]⁺ 568.3.

B) t-Butyl N-[(1S)-1-{[(1S)-2-(4-{[1-(2-{2-[2-(benzyloxy)ethoxy]ethoxy}ethyl)-2-methyl-1H-indol-5-yl]carbonyl}piperazin-1-yl)-1-cyclohexyl-2-oxoethyl]carbamoyl}ethyl]-N-methylcarbamate To a mixture of tert-butyl N-((1S)-1-(((1S)-1-cyclohexyl-2-(4-((2-methyl-1H-indol-5-yl)carbonyl)piperazin-1-yl)-2-oxoethyl)carbamoyl)ethyl)-N-methylcarbamate (2.0 g) and DMF (50 mL) was added cesium carbonate (2.9 g). The reaction mixture was stirred at room temperature for 5 min, 2-(2-(2-(benzyloxy)ethoxy)ethoxy)ethyl 4-methylbenzene-1-sulfonate (2.4 g) was added thereto and stirred at 80° C. for 16 h, and water was added and extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (1.5 g).
MS: [M+H]⁺ 790.3.

C) tert-Butyl N-[(1S)-1-{[(1S)-1-cyclohexyl-2-{4-[(1-{2-[2-(2-hydroxyethoxy)ethoxy]ethyl}-2-methyl-1H-indol-5-yl)carbonyl]piperazin-1-yl}-2-oxoethyl]carbamoyl}ethyl]-N-methylcarbamate To a mixture of tert-butyl N-[(1S)-1-{[(1S)-2-(4-{[1-(2-{2-[2-(benzyloxy)ethoxy]ethoxy}ethyl)-2-methyl-1H-indol-5-yl]carbonyl}piperazin-1-yl)-1-cyclohexyl-2-oxoethyl]carbamoyl}ethyl]-N-methylcarbamate (1.5 g) and ethanol (50 mL) was added 10% palladium on carbon (250 mg). The reaction mixture was stirred under the normal pressure hydrogen atmosphere at room temperature for 16 h, filtered with Celite® and the filtrate was concentrated under reduced pressure to give the title compound (1.3 g).
MS: [M+H]⁺ 700.4.

D) (S)—N—((S)-1-Cyclohexyl-2-(4-(1-(2-(2-(2-hydroxyethoxy)ethoxy)ethyl)-2-methyl-1H-indole-5-carbonyl)piperazin-1-yl)-2-oxoethyl)-2-(methylamino)propanamide To a mixture of tert-butyl N-[(1S)-1-{[(1S)-1-cyclohexyl-2-{4-[(1-{2-[2-(2-hydroxyethoxy)ethoxy]ethyl}-2-methyl-1H-indol-5-yl)carbonyl]piperazin-1-yl}-2-oxoethyl]carbamoyl}-ethyl]-N-methylcarbamate (16 mg) and DCM (2 mL) was added trifluoroacetic acid (0.02 mL) under ice-cooling. The reaction mixture was stirred for 10 h and the solvent was removed under reduced pressure. The residue was purified by preparative HPLC (C18, acetonitrile/water (containing 10 mM ammonium acetate)) to give the title compound (7 mg).
MS: [M+H]$^+$ 600.6.

Example 70

(S)—N—((S)-1-Cyclohexyl-2-(4-(1-(2-(2-(2-(2-hydroxyethoxy)ethoxy)ethoxy)ethyl)-2-methyl-1H-indole-5-carbonyl)piperazin-1-yl)-2-oxoethyl)-2-(methylamino)propanamide

A) tert-Butyl N-[(1S)-1-{[(1S)-1-cyclohexyl-2-(4-{[2-methyl-1-(1-phenyl-2,5,8,11-tetraoxatridecan-13-yl)-1H-indol-5-yl]carbonyl}piperazin-1-yl)-2-oxoethyl]carbamoyl}ethyl]-N-methylcarbamate To a mixture of tert-butyl N-[(1S)-1-{[(1S)-1-cyclohexyl-2-{4-[(2-methyl-1H-indol-5-yl)carbonyl]piperazin-1-yl}-2-oxoethyl]carbamoyl}ethyl]-N-methylcarbamate (2 g) and DMF (30 mL) was added cesium carbonate (2.87 g), the resultant mixture was stirred at room temperature for 5 min, 1-phenyl-2,5,8,11-tetraoxatridecan-13-yl 4-methylbenzene-1-sulfonate (2.78 g) was added thereto, and stirred at 80° C. for 16 h. Water was added to the reaction mixture and extracted with ethyl acetate. The organic layer was washed with water and brine and then dried over anhydrous sodium sulfate, and the solvent was removed under reduced pressure. The residue was purified by silica gel column chromatography (NH, ethyl acetate/hexane) to give the title compound (1.3 g).
MS: [M+H]$^+$ 834.4.

B) tert-Butyl N-[(1S)-1-{[(1S)-1-cyclohexyl-2-(4-{[1-(2-{2-[2-(2-hydroxyethoxy)ethoxy]ethoxy}ethyl)-2-methyl-1H-indol-5-yl]carbonyl}piperazin-1-yl)-2-oxoethyl]carbamoyl}ethyl]-N-methylcarbamate To a mixture of tert-butyl N-[(1S)-1-{[(1S)-1-cyclohexyl-2-(4-{[2-methyl-1-(1-phenyl-2,5,8,11-tetraoxatridecan-13-yl)-1H-indol-5-yl]carbonyl}piperazin-1-yl)-2-oxoethyl]carbamoyl}ethyl]-N-methylcarbamate (1.3 g) and ethanol (50 mL) was added 10% palladium on carbon (250 mg). The reaction mixture was stirred under the normal pressure hydrogen atmosphere at room temperature for 16 h, filtered with Celite® and the filtrate was concentrated under reduced pressure to give the title compound (1.1 g).
MS: [M+H]$^+$ 744.3.

C) (S)—N—((S)-1-Cyclohexyl-2-(4-(1-(2-(2-(2-(2-hydroxyethoxy)ethoxy)ethoxy)ethyl)-2-methyl-1H-indole-5-carbonyl)piperazin-1-yl)-2-oxoethyl)-2-(methylamino)propanamide To a mixture of tert-butyl N-[(1S)-1-{[(1S)-1-cyclohexyl-2-(4-{[1-(2-{2-[2-(2-hydroxyethoxy)ethoxy]ethoxy}ethyl)-2-methyl-1H-indol-5-yl]carbonyl}piperazin-1-yl)-2-oxoethyl]carbamoyl}ethyl]-N-methylcarbamate (30 mg) and DCM (3 mL) was added trifluoroacetic acid (0.009 mL) under ice-cooling. The reaction mixture was stirred at room temperature for 6 h and the solvent was removed under reduced pressure. The residue was purified by preparative HPLC (C18, acetonitrile/water (containing 10 mM ammonium acetate)) to give the title compound (4 mg).
MS: [M+H]$^+$ 644.6.

Example 71

(S)—N—((S)-1-Cyclohexyl-2-(4-(3-fluoro-1-(2-(2-(2-hydroxyethoxy)ethoxy)ethyl)-2-methyl-1H-indole-5-carbonyl)piperazin-1-yl)-2-oxoethyl)-2-(methylamino)propanamide

A) Methyl 2-methyl-1H-indole-5-carboxylate

To a mixture of 2-methyl-1H-indole-5-carboxylic acid (500 mg) and methanol (6 mL) was added concentrated hydrochloric acid (1.2 mL). The reaction mixture was refluxed for 8 h, saturated aqueous sodium bicarbonate was added thereto and the solvent was removed under reduced pressure. Ethyl acetate was added to the residue, washed with water and brine, respectively and then dried over anhydrous sodium sulfate, and purified by silica gel column chromatography (ethyl acetate/hexane) to give the title compound (448 mg). MS: [M+H]$^+$ 190.1.

B) Methyl 1-(2-{2-[2-(benzyloxy)ethoxy]ethoxy}ethyl)-2-methyl-1H-indole-5-carboxylate To a mixture of methyl 2-methyl-1H-indole-5-carboxylate (350 mg) and DMF (10 mL) was added cesium carbonate (1.2 g) and 2-{2-[2-(benzyloxy)ethoxy]ethoxy}ethyl 4-methylbenzene-1-sulfonate (1.09 g). The reaction mixture was stirred at room temperature for 16 h, and then diluted with ethyl acetate. The organic layer was washed with ice-cold water and brine and then dried over anhydrous sodium sulfate, and the solvent was removed under reduced pressure. The residue was purified by silica gel column chromatography (ethyl acetate/hexane) to give the title compound (600 mg).
MS: [M+H]$^+$ 412.0.

C) Methyl 1-(2-{2-[2-(benzyloxy)ethoxy]ethoxy}ethyl)-3-fluoro-2-methyl-1H-indole-5-carboxylate To a mixture of methyl 1-(2-{2-[2-(benzyloxy)ethoxy]ethoxy}ethyl)-2-methyl-1H-indole-5-carboxylate (400 mg) and acetonitrile (7 mL) was added Selectfluor (344 mg) under ice-cooling. The reaction mixture was stirred for 30 min, saturated aqueous sodium bicarbonate was added thereto and extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (160 mg).
MS: [M+H]$^+$ 429.8.

D) 1-(2-{2-[2-(Benzyloxy)ethoxy]ethoxy}ethyl)-3-fluoro-2-methyl-1H-indole-5-carboxylic Acid To a mixture of methyl 1-(2-{2-[2-(benzyloxy)ethoxy]ethoxy}ethyl)-3-fluoro-2-methyl-1H-indole-5-carboxylate and THF:methanol:water (3:1:1) (5 mL) was added lithium hydroxide monohydrate (31 mg). The reaction mixture was stirred at 15° C. for 16 h, the solvent was removed under reduced pressure, the residue was dissolved in water and washed with ether. The aqueous layer was acidified with 2 M hydrochloric acid and extracted with DCM. The organic layer was dried over anhydrous sodium sulfate, and the solvent was removed under reduced pressure to give the title compound (50 mg).

MS: [M+H]$^+$ 416.2.

E) tert-Butyl N-[(1S)-1-{[(1S)-2-(4-{[1-(2-{2-[2-(benzyloxy)ethoxy]ethoxy}ethyl)-3-fluoro-2-methyl-1H-indol-5-yl]carbonyl}piperazin-1-yl)-1-cyclohexyl-2-oxoethyl]carbamoyl}ethyl]-N-methylcarbamate To a mixture of 1-(2-{2-[2-(benzyloxy)ethoxy]ethoxy}ethyl)-3-fluoro-2-methyl-1H-indole-5-carboxylic acid (42 mg) and DMF (2 mL) was added tert-butyl N-[(1S)-1-{[(1S)-1-cyclohexyl-2-oxo-2-(piperazin-1-yl)ethyl]carbamoyl}ethyl]-N-methylcarbamate (41.5 mg), DIEA (0.07 mL), and HATU (46 mg). The reaction mixture was stirred at room temperature for 16 h, and ice-cold water was added thereto and extracted with ethyl acetate. The organic layer was washed with water and brine and then dried over anhydrous sodium sulfate, and the solvent was removed under reduced pressure. The residue was purified by silica gel column chromatography (ethyl acetate/hexane) to give the title compound (60 mg).

MS: [M+H]$^+$ 808.4.

F) tert-Butyl N-[(1S)-1-{[(1S)-1-cyclohexyl-2-{4-[(3-fluoro-1-{2-[2-(2-hydroxyethoxy)ethoxy]ethyl}-2-methyl-1H-indol-5-yl)carbonyl]piperazin-1-yl}-2-oxoethyl]carbamoyl}ethyl]-N-methylcarbamate To a mixture of tert-butyl N-[(1S)-1-{[(1S)-2-(4-{[1-(2-{2-[2-(benzyloxy)ethoxy]ethoxy}ethyl)-3-fluoro-2-methyl-1H-indol-5-yl]carbonyl}piperazin-1-yl)-1-cyclohexyl-2-oxoethyl]carbamoyl}ethyl]-N-methylcarbamate (60 mg) and ethanol (5 mL) was added palladium on carbon (50% water content) (15 mg). The reaction mixture was stirred under the normal pressure hydrogen atmosphere at room temperature for 3 h and then filtered with Celite®, and the filtrate was concentrated under reduced pressure to give the title compound (40 mg).

MS: [M+H]$^+$ 718.7.

G) (2S)—N-[(1S)-1-Cyclohexyl-2-{4-[(3-fluoro-1-{2-[2-(2-hydroxyethoxy)ethoxy]ethyl}-2-methyl-1H-indol-5-yl)carbonyl]piperazin-1-yl}-2-oxoethyl]-2-(methylamino)propanamide To a mixture of tert-butyl N-[(1S)-1-{[(1S)-1-cyclohexyl-2-{4-[(3-fluoro-1-{2-[2-(2-hydroxyethoxy)ethoxy]ethyl}-2-methyl-1H-indol-5-yl)carbonyl]piperazin-1-yl}-2-oxoethyl]carbamoyl}ethyl]-N-methylcarbamate (40 mg) and DCM (2 mL) was added trifluoroacetic acid (0.02 mL) under ice-cooling. The reaction mixture was stirred at room temperature for 10 h and the solvent was removed under reduced pressure. The residue was purified by preparative HPLC (C18, acetonitrile/water (containing 10 mM ammonium acetate)) to give the title compound (2 mg).

MS: [M+H]$^+$ 618.3

Example 72

N-(2-(2-(2-(2-((S)-4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-(4-((S)-2-cyclohexyl-2-((S)-2-(methylamino)propanamido)acetyl)piperazine-1-carbonyl)-6-methoxy-1-methyl-1H-indole-3-carboxamide hydrochloride A) tert-Butyl (S)-(2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)carbamate To a mixture of (S)-2-(4-(4-chlorophenyl)-2,3,9-trimethyl-6H-thieno[3,2-f][1,2,4]triazolo[4,3-a][1,4]diazepin-6-yl)acetic acid (27.5 mg), tert-butyl (2-(2-(2-aminoethoxy)ethoxy)ethyl)carbamate (80 mg), DIEA (0.2 mL) and DMF (0.3 mL) was added HATU (52.2 mg). The reaction mixture was stirred at room temperature for 1 h, and water was added to the reaction mixture and extracted with ethyl acetate. The organic layer was washed with water, 0.1 M hydrochloric acid, saturated aqueous sodium bicarbonate and brine, respectively and then dried over anhydrous magnesium sulfate, and the solvent was removed under reduced pressure to give the title compound (29.5 mg).

MS: [M+H]$^+$ 631.4.

B) (S)—N-(2-(2-(2-Aminoethoxy)ethoxy)ethyl)-2-(4-(4-chlorophenyl)-2,3,9-trimethyl-6H-thieno[3,2-f][1,2,4]triazolo[4,3-a][1,4]diazepin-6-yl)acetamide Hydrochloride To a mixture of tert-butyl (S)-(2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)carbamate (29.5 mg) and ethyl acetate (0.3 mL) was added 4 M hydrogen chloride dioxane solution (0.4 mL). The reaction mixture was stirred at room temperature for 30 min and the solvent was removed under reduced pressure to give the title compound (26.3 mg).

MS: [M+H]$^+$ 531.3.

C) tert-Butyl ((S)-1-(((S)-2-(4-(3-((2-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)carbamoyl)-6-methoxy-1-methyl-1H-indole-2-carbonyl)piperazin-1-yl)-1-cyclohexyl-2-oxoethyl)amino)-1-oxopropan-2-yl)(methyl)carbamate To a mixture of (S)—N-(2-(2-(2-aminoethoxy)ethoxy)ethyl)-2-(4-(4-chlorophenyl)-2,3,9-trimethyl-6H-thieno[3,2-f][1,2,4]triazolo[4,3-a][1,4]diazepin-6-yl)acetamide hydrochloride (26.3 mg), 2-(4-((S)-2-((S)-2-((tert-butoxycarbonyl)(methyl)amino)propanamido)-2-cyclohexylacetyl)piperazine-1-carbonyl)-6-methoxy-1-methyl-1H-indole-3-carboxylic acid (33.2 mg), DIEA (0.0242 mL) and DMF (0.3 mL) was added HATU (35.2 mg). The reaction mixture was stirred at room temperature for 1 h, and water was added thereto and extracted with ethyl acetate. The organic layer was washed with 0.1 M hydrochloric acid, saturated aqueous sodium bicarbonate and brine, respectively and then dried over anhydrous magnesium sulfate, and the solvent was removed under reduced pressure. The residue was purified by silica gel column chromatography (C18, acetonitrile/5 mM ammonium acetate) and concentrated under reduced pressure. To the residual aqueous layer was added sodium bicarbonate, which was subjected to ethyl acetate extraction. The organic layer was washed with brine and then dried over anhydrous magnesium sulfate, and the solvent was removed under reduced pressure to give the title compound (12.8 mg).
MS: [M+H]$^+$ 1154.6.

D) N-(2-(2-(2-(2-((S)-4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-(4-((S)-2-cyclohexyl-2-((S)-2-(methylamino)propanamido)acetyl)piperazine-1-carbonyl)-6-methoxy-1-methyl-1H-indole-3-carboxamide Hydrochloride To a mixture of tert-butyl ((S)-1-(((S)-2-(4-(3-((2-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)carbamoyl)-6-methoxy-1-methyl-1H-indole-2-carbonyl)piperazin-1-yl)-1-cyclohexyl-2-oxoethyl)amino)-1-oxopropan-2-yl)(methyl)carbamate (12.8 mg), ethyl acetate (0.4 mL) and methanol (0.1 mL) was added 4 M hydrochloride ethyl acetate solution (0.5 mL). The reaction mixture was stirred at room temperature for 1 h and the solvent was removed under reduced pressure to give the title compound (12.0 mg).
MS: [M+H]$^+$ 1054.7.

Example 78

N-(2-(2-(2-(4-(2-((S)-4-(4-Chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethyl)-2-(4-((S)-2-cyclohexyl-2-((S)-2-(methylamino)propanamido)acetyl)piperazine-1-carbonyl)-5,6-difluoro-1-methyl-1H-indole-3-carboxamide hydrochloride A) tert-Butyl N-[(1S)-1-{[(1S)-1-cyclohexyl-2-[4-({5,6-difluoro-1-methyl-3-[(2-{2-[2-(4-nitrophenoxy)ethoxy]ethoxy}ethyl)carbamoyl]-1H-indol-2-yl}carbonyl)piperazin-1-yl]-2-oxoethyl]carbamoyl}ethyl]-N-methyl carbamate To a mixture of tert-butyl N-[(1S)-1-{[(1S)-1-cyclohexyl-2-(4-{[5,6-difluoro-3-({2-[2-(2-hydroxyethoxy)ethoxy]ethyl}carbamoyl)-1-methyl-1H-indol-2-yl]carbonyl}piperazin-1-yl)-2-oxoethyl]carbamoyl}ethyl]-N-methylcarbamate (45 mg), 4-nitrophenol (12 mg) and toluene (6 mL) was added triphenylphosphine (75.7 mg) and di-tert-butyl azodicarboxylate (53.2 mg). The reaction mixture was stirred at room temperature for 16 h and the solvent was removed under reduced pressure. The residue was purified by preparative thin layer chromatography (ethyl acetate) to give the title compound (45 mg).
MS: [M+H]$^+$ 899.9.

B) tert-Butyl N-[(1S)-1-{[(1S)-2-[4-({3-[(2-{2-[2-(4-aminophenoxy)ethoxy]ethoxy}ethyl)carbamoyl]-5,6-difluoro-1-methyl-1H-indol-2-yl}carbonyl)piperazin-1-yl]-1-cyclohexyl-2-oxoethyl]carbamoyl}ethyl]-N-methylcarbamate To a mixture of tert-butyl N-[(1S)-1-{[(1S)-1-cyclohexyl-2-[4-({5,6-difluoro-1-methyl-3-[(2-{2-[2-(4-nitrophenoxy)ethoxy]ethoxy}ethyl)carbamoyl]-1H-indol-2-yl}carbonyl)piperazin-1-yl]-2-oxoethyl]carbamoyl}ethyl]-N-methylcarbamate (35 mg), ethanol (5 mL) and water (1 mL) was added iron powder (21.7 mg) and ammonium chloride (10.5 mg). The reaction mixture was stirred at 80° C. for 1 h, cooled to room temperature and filtered with Celite®, the filtrate was washed with water and brine and then dried over anhydrous sodium sulfate, and the solvent was removed under reduced pressure to give the title compound (30 mg). MS: [M+H]$^+$ 869.9.

C) tert-Butyl N-[(1S)-1-{[(1S)-2-[4-({3-[(2-{2-[2-(4-{2-[(9S)-7-(4-chlorophenyl)-4,5,13-trimethyl-3-thia-1,8,11,12-tetraazatricyclo[8.3.0.0^{2,6}]trideca-2(6),4,7,10,12-pentaen-9-yl]acetamido}phenoxy)ethoxy]ethoxy}ethyl)carbamoyl]-5,6-difluoro-1-methyl-1H-indol-2-yl}carbonyl)piperazin-1-yl]-1-cyclohexyl-2-oxoethyl]carbamoyl}ethyl]-N-methylcarbamate To a mixture of tert-butyl N-[(1S)-1-{[(1S)-2-[4-({3-[(2-{2-[2-(4-aminophenoxy)ethoxy]ethoxy}ethyl)carbamoyl]-5,6-difluoro-1-methyl-1H-indol-2-yl}carbonyl)piperazin-1-yl]-1-cyclohexyl-2-oxoethyl]carbamoyl}ethyl]-N-methylcarbamate (30 mg) and (S)-2-(4-(4-chlorophenyl)-2,3,9-trimethyl-6H-thieno[3,2-f][1,2,4]triazolo[4,3-a][1,4]diazepin-6-yl)acetic acid (14 mg) and DMF (1 mL) was added 1-[bis(dimethylamino)methylene]-1H-benzotriazolium 3-oxide hexafluorophosphate (16 mg) and DIEA (0.03 mL). The reaction mixture was stirred at room temperature for 2 h, and ice-cold water was added thereto and extracted with ethyl acetate. The organic layer was washed with saturated aqueous sodium bicarbonate, water and brine, respectively and then dried over anhydrous sodium sulfate, and the solvent was removed under reduced pressure. The residue was purified by preparative thin layer chromatography to give the title compound (25 mg).
MS: [M+H]$^+$ 1252.0.

D) N-(2-(2-(2-(4-(2-((S)-4-(4-Chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethyl)-2-(4-((S)-2-cyclohexyl-2-((S)-2-(methylamino)propanamido)acetyl)piperazine-1-carbonyl)-5,6-difluoro-1-methyl-1H-indole-3-carboxamide Hydrochloride To a mixture of tert-butyl N-[(1S)-1-{[(1S)-2-[4-({3-[(2-{2-[2-(4-{2-[(9S)-7-(4-chlorophenyl)-4,5,13-trimethyl-3-thia-1,8,11,12-tetraazatricyclo[8.3.0.0^{2,6}]trideca-2(6),4,7,10,12-pentaen-9-yl]acetamido}phenoxy)ethoxy]ethoxy}ethyl)carbamoyl]-5,6-difluoro-1-methyl-1H-indol-2-yl}carbonyl)piperazin-1-yl]-1-cyclohexyl-2-oxoethyl]carbamoyl}ethyl]-N-methylcarbamate (25 mg) and DCM (2 mL) was added 4 M hydrogen chloride dioxane solution (2 mL). The reaction mixture was stirred at room temperature for 2 h, the solvent was removed under reduced pressure. The residue was washed with n-pentane to give the title compound (21 mg).
MS: [M+H]$^+$ 1152.8.

Example 80

N-(2-Chloro-6-methylphenyl)-2-((6-(4-(2-(2-(2-(4-((S)-2-cyclohexyl-2-((S)-2-(methylamino)propanamide)acetyl)piperazine-1-carbonyl)-5,6-difluoro-1-methyl-1H-indole-3-carboxamido)ethoxy)ethyl)piperazin-1-yl)-2-methylpyrimidin-4-yl)amino)thiazole-5-carboxamide

A) 5,6-Difluoro-3-formyl-1-methyl-1H-indole-2-carboxylic Acid

To a mixture of methyl 5,6-difluoro-3-formyl-1-methyl-1H-indole-2-carboxylate (15 g), THF (225 mL), methanol (75 mL) and water (75 mL) was added lithium hydroxide monohydrate (3.73 g). The reaction mixture was stirred at room temperature for 3 h and the solvent was removed under reduced pressure. The reaction mixture was acidified with aqueous potassium sulfate and the precipitates were collected by filtration to give the title compound (13 g).

MS: [M+H]$^+$ 240.1.

B) 2-(4-((S)-2-((S)-2-((tert-Butoxycarbonyl)(methyl)amino)propanamido)-2-cyclohexylacetyl)piperazine-1-carbonyl)-5,6-difluoro-1-methyl-1H-indole-3-carboxylic Acid To a mixture of tert-butyl ((S)-1-(((S)-1-cyclohexyl-2-oxo-2-(piperazin-1-yl)ethyl)amino)-1-oxopropan-2-yl)(methyl)carbamate (4.63 g), 5,6-difluoro-3-formyl-1-methyl-1H-indole-2-carboxylic acid (2.45 g), DIEA (2.7 mL) and DMF (50 mL) was added HATU (4.67 g). After the reaction mixture was stirred at room temperature for 2 h, water was added thereto and extracted with ethyl acetate. The organic layer was washed with 0.1 M hydrochloric acid, saturated aqueous sodium bicarbonate and brine, respectively and then dried over anhydrous magnesium sulfate, and the solvent was removed under reduced pressure. The residue was purified by silica gel column chromatography (ethyl acetate/hexane).

To a mixture of the compound (6.44 g) thus obtained, sodium dihydrogen phosphate (4.90 g), 2-methylbut-2-ene (5.5 mL), tert-butanol (90 mL) and water (30 mL) was added sodium chlorite (2.24 g). The reaction mixture was stirred at room temperature overnight, aqueous sodium thiosulfate solution was added thereto and extracted with ethyl acetate. The organic layer was washed with water and brine and dried over anhydrous magnesium sulfate, and the solvent was removed under reduced pressure. The residue was purified by silica gel column chromatography (ethyl acetate/hexane and methanol/ethyl acetate) to give the title compound (5.46 g)

MS: [M+H]$^+$ 648.5.

C) tert-Butyl N-[(1S)-1-{[(1S)-1-cyclohexyl-2-{4-[(5,6-difluoro-3-{[2-(2-hydroxyethoxy)ethyl]carbamoyl}-1-methyl-1H-indol-2-yl)carbonyl]piperazin-1-yl}-2-oxoethyl]carbamoyl}ethyl]-N-methylcarbamate To a mixture of 2-(4-((S)-2-((S)-2-((tert-Butoxycarbonyl)(methyl)amino)propanamido)-2-cyclohexylacetyl)piperazine-1-carbonyl)-5,6-difluoro-1-methyl-1H-indole-3-carboxylic acid (1.5 g), 2-(2-aminoethoxy)ethan-1-ol (243 mg) and DMF (15 mL) was added DIEA (1.42 mL) and HATU (1.06 mg). The reaction mixture was stirred at room temperature for 2 h, and ice-cold water was added thereto and extracted with ethyl acetate. The organic layer was washed with water and brine and dried over anhydrous sodium sulfate, and the solvent was removed under reduced pressure. The residue was purified by silica gel column chromatography (methanol/DCM) to give the title compound (1.18 g).

MS: [M+H]$^+$ 735.4.

D) tert-Butyl N-[(1S)-1-{[(1S)-1-cyclohexyl-2-{4-[(5,6-difluoro-1-methyl-3-{[2-(2-{[(4-methylbenzene)sulfonyl]oxy}ethoxy)ethyl]carbamoyl}-1H-indol-2-yl)carbonyl]piperazin-1-yl}-2-oxoethyl]carbamoyl}ethyl]-N-methylcarbamate To a mixture of tert-butyl N-[(1S)-1-{[(1S)-1-cyclohexyl-2-{4-[(5,6-difluoro-3-{[2-(2-hydroxyethoxy)ethyl]carbamoyl}-1-methyl-1H-indol-2-yl)carbonyl]piperazin-1-yl}-2-oxoethyl]carbamoyl}ethyl]-N-methylcarbamate (100 mg) and DCM (5 mL) was added TEA (0.028 mL), N,N-dimethyl-4-aminopyridine (41.5 mg) and p-toluenesulfonyl chloride (130 mg) under ice-cooling. The reaction mixture was stirred at room temperature for 16 h and the solvent was removed under reduced pressure. The residue was purified by silica gel column chromatography (methanol/DCM) to give the title compound (90 mg).

MS: [M+H]$^+$ 889.1.

E) tert-Butyl N-[(1S)-1-{[(1S)-2-{4-[(3-{[2-(2-{4-[6-({5-[(2-chloro-6-methylphenyl)carbamoyl]-1,3-thiazol-2-yl}amino)-2-methylpyrimidin-4-yl]piperazin-1-yl}ethoxy)ethyl]carbamoyl}-5,6-difluoro-1-methyl-1H-indol-2-yl)carbonyl]piperazin-1-yl}-1-cyclohexyl-2-oxoethyl]carbamoyl}ethyl]-N-methylcarbamate To a mixture of N-(2-chloro-6-methylphenyl)-2-{[2-methyl-6-(piperazin-1-yl)pyrimidin-4-yl]amino}-1,3-thiazole-5-carboxamide hydrochloride (30 mg) and DMF (2 mL) was added DIEA (0.033 mL), a mixture of tert-butyl N-[(1S)-1-{[(1S)-1-cyclohexyl-2-{4-[(5,6-difluoro-1-methyl-3-{[2-(2-{[(4-methylbenzene)sulfonyl]oxy}ethoxy)ethyl]carbamoyl}-1H-indol-2-yl) carbonyl]piperazin-1-yl}-2-oxoethyl]carbamoyl}ethyl]-N-methylcarbamate (66.7 mg) and DMF (0.5 mL). The reaction mixture was stirred at 80° C. for 16 h, and ice-cold water was added thereto and extracted with ethyl acetate. The organic layer was washed with water and brine and then dried over anhydrous sodium sulfate, and the solvent was removed under reduced pressure. The residue was purified by preparative thin layer chromatography (methanol/DCM) to give the title compound (10 mg).

MS: [M+H]$^+$ 1160.8.

F) N-(2-Chloro-6-methylphenyl)-2-((6-(4-(2-(2-(2-(4-((S)-2-cyclohexyl-2-((S)-2-(methylamino)propanamido)acetyl)piperazine-1-carbonyl)-5,6-difluoro-1-methyl-1H-indole-3-carboxamido)ethoxy)ethyl)piperazin-1-yl)-2-methylpyrimidin-4-yl)amino)thiazole-5-carboxamide trifluoroacetate To a mixture of tert-butyl N-[(1S)-1-{[(1S)-2-{4-[(3-{[2-(2-{4-[6-({5-[(2-chloro-6-methylphenyl)carbamoyl]-1,3-thiazol-2-yl}amino)-2-methylpyrimidin-4-yl]piperazin-1-yl}ethoxy)ethyl]carbamoyl}-5,6-difluoro-1-methyl-1H-indol-2-yl)carbonyl]piperazin-1-yl}-1-cyclohexyl-2-oxoethyl]carbamoyl}ethyl]-N-methylcarbamate (10 mg) and DCM (2 mL) was added trifluoroacetic acid (0.005 mL)

under ice-cooling. The reaction mixture was stirred at room temperature for 6 h and the solvent was removed under reduced pressure. The residue was washed with ether to give the title compound (9 mg).

MS: [M+H]+ 1060.8.

Example 81

N-(2-Chloro-6-methylphenyl)-2-((6-(4-(2-(2-(2-(2-(4-((S)-2-cyclohexyl-2-((S)-2-(methylamino)propanamido)acetyl)piperazine-1-carbonyl)-5,6-difluoro-1-methyl-1H-indole-3-carboxamido)ethoxy)ethoxy)ethyl)piperazin-1-yl)-2-methylpyrimidin-4-yl)amino)thiazole-5-carboxamide Trifluoroacetate A) tert-Butyl N-[(1S)-1-{[(1S)-1-cyclohexyl-2-(4-{[5,6-difluoro-3-({2-[2-(2-hydroxyethoxy)ethoxy]ethyl}-carbamoyl)-1-methyl-1H-indol-2-yl]carbonyl}piperazin-1-yl)-2-oxoethyl]carbamoyl}ethyl]-N-methyl-carbamate To a mixture of 2-(4-((S)-2-((S)-2-((tert-butoxycarbonyl)(methyl)amino)propanamido)-2-cyclohexylacetyl)piperazine-1-carbonyl)-5,6-difluoro-1-methyl-1H-indole-3-carboxylic acid (1.5 g), 2-[2-(2-aminoethoxy)ethoxy]ethan-1-ol (346 mg) and DMF (15 mL) was added DIEA (1.42 mL) and HATU (1.06 mg). The reaction mixture was stirred at room temperature for 2 h, and ice-cold water was added and extracted with ethyl acetate. The organic layer was washed with water, saturated aqueous sodium bicarbonate and brine and dried over anhydrous sodium sulfate, and the solvent was removed under reduced pressure. The residue was purified by silica gel column chromatography (methanol/DCM) to give the title compound (1.16 g).

MS: [M+H]+ 735.4.

B) tert-Butyl N-[(1S)-1-{[(1S)-1-cyclohexyl-2-(4-{[5,6-difluoro-1-methyl-3-({2-[2-(2-{[(4-methylbenzene)sulfonyl]oxy}ethoxy)ethoxy]ethyl}carbamoyl)-1H-indol-2-yl]carbonyl}piperazin-1-yl)-2-oxoethyl]carbamoyl}ethyl]-N-methylcarbamate To a mixture of tert-butyl N-[(1S)-1-{[(1S)-1-cyclohexyl-2-(4-{[5,6-difluoro-3-({2-[2-(2-hydroxyethoxy)ethoxy]ethyl}carbamoyl)-1-methyl-1H-indol-2-yl]carbonyl}piperazin-1-yl)-2-oxoethyl]carbamoyl}ethyl]-N-methylcarbamate (100 mg) and DCM (10 mL) was added TEA (0.026 mL), N,N-dimethyl-4-aminopyridine (7.8 mg) and p-toluenesulfonyl chloride (122.5 mg) under ice-cooling. The reaction mixture was stirred at room temperature for 16 h and the solvent was removed under reduced pressure. The residue was purified by silica gel column chromatography (methanol/DCM) to give the title compound (95 mg).

MS: [M+H]+ 932.9.

C) tert-Butyl N-[(1S)-1-{[(1S)-2-(4-{[3-({2-[2-(2-{4-[6-({5-[(2-chloro-6-methylphenyl)carbamoyl]-1,3-thiazol-2-yl}amino)-2-methylpyrimidin-4-yl]piperazin-1-yl}ethoxy)ethoxy]ethyl}carbamoyl)-5,6-difluoro-1-methyl-1H-indol-2-yl]carbonyl}piperazin-1-yl)-1-cyclohexyl-2-oxoethyl]carbamoyl}ethyl]-N-methyl Carbamate To a mixture of N-(2-chloro-6-methylphenyl)-2-{[2-methyl-6-(piperazin-1-yl)pyrimidin-4-yl]amino}-1,3-thiazole-5-carboxamide hydrochloride (30 mg) and DMF (2 mL) was added DIEA (0.033 mL) and a mixture of tert-butyl N-[(1S)-1-{[(1S)-1-cyclohexyl-2-(4-{[5,6-difluoro-1-methyl-3-({2-[2-(2-{[(4-methylbenzene)sulfonyl]oxy}ethoxy)ethoxy]ethyl}carbamoyl)-1H-indol-2-yl]carbonyl}piperazin-1-yl)-2-oxoethyl]carbamoyl}ethyl]-N-methylcarbamate (70 mg) and DMF (0.5 mL). The reaction mixture was stirred at 80° C. for 16 h, ice-cold water was added thereto and extracted with ethyl acetate. The organic layer was washed with water and brine and then dried over anhydrous sodium sulfate, and the solvent was removed under reduced pressure. The residue was purified by preparative thin layer chromatography (methanol/DCM) to give the title compound (12 mg).

MS: [M+H]+ 1204.9.

D) N-(2-Chloro-6-methylphenyl)-2-((6-(4-(2-(2-(2-(2-(4-((S)-2-cyclohexyl-2-((S)-2-(methylamino)propanamido)acetyl)piperazine-1-carbonyl)-5,6-difluoro-1-methyl-1H-indole-3-carboxamido)ethoxy)ethoxy)ethyl)piperazin-1-yl)-2-methylpyrimidin-4-yl)amino)thiazole-5-carboxamide Trifluoroacetate To a mixture of tert-butyl N-[(1S)-1-{[(1S)-2-(4-{[3-({2-[2-(2-{4-[6-({5-[(2-chloro-6-methylphenyl)carbamoyl]-1,3-thiazol-2-yl}amino)-2-methylpyrimidin-4-yl]piperazin-1-yl}ethoxy)ethoxy]ethyl}carbamoyl)-5,6-difluoro-1-methyl-1H-indol-2-yl]carbonyl}piperazin-1-yl)-1-cyclohexyl-2-oxoethyl]carbamoyl}ethyl]-N-methylcarbamate (12 mg) and DCM (2 mL) was added trifluoroacetic acid (0.006 mL) under ice-cooling. The reaction mixture was stirred at room temperature for 6 h and the solvent was removed under reduced pressure. The residue was washed with ether to give the title compound (11 mg).

MS: [M+H]+ 1105.0.

Example 82

N-(2-Chloro-6-methylphenyl)-2-((6-(4-(1-(2-(4-((S)-2-cyclohexyl-2-((S)-2-(methylamino)propanamido)acetyl)piperazine-1-carbonyl)-5,6-difluoro-1-methyl-1H-indol-3-yl)-1-oxo-5,8,11-trioxa-2-azatridecan-13-yl)piperazin-1-yl)-2-methylpyrimidin-4-yl)amino)thiazole-5-carboxamide Trifluoroacetate A) tert-Butyl N-[(1S)-1-{[(1S)-1-cyclohexyl-2-[4-({5,6-difluoro-3-[(2-{2-[2-(2-hydroxyethoxy)ethoxy]ethoxy}ethyl)carbamoyl]-1-methyl-1H-indol-2-yl}carbonyl)piperazin-1-yl]-2-oxoethyl]carbamoyl}ethyl]-N-methylcarbamate To a mixture of 2-(4-((S)-2-((S)-2-((tert-butoxycarbonyl)(methyl)amino)propanamido)-2-cyclohexylacetyl)piperazine-1-carbonyl)-5,6-difluoro-1-methyl-1H-indole-3-carboxylic acid (1.5 g), 2-{2-[2-(2-aminoethoxy)ethoxy]ethoxy}ethan-1-ol (448 mg) and DMF (15 mL) was added DIEA (1.41 mL) and HATU (1.06 g). The reaction mixture was stirred at room temperature for 2 h, ice-cold water was added thereto and extracted with ethyl acetate. The organic layer was washed with water, saturated aqueous sodium bicarbonate and brine and then dried over anhydrous sodium sulfate and the solvent was removed under reduced pressure. The residue was purified by silica gel column chromatography (methanol/DCM) to give the title compound (1.21 g).

MS: [M+H]+ 821.5.

B) tert-Butyl N-[(1S)-1-{[(1S)-1-cyclohexyl-2-[4-({5,6-difluoro-1-methyl-3-[(2-{2-[2-(2-{[(4-methyl-benzene) sulfonyl]oxy}ethoxy)ethoxy]ethoxy}ethyl) carbamoyl]-1H-indol-2-yl}carbonyl)piperazin-1-yl]-2-oxoethyl]carbamoyl}ethyl]-N-methylcarbamate To a mixture of tert-butyl N-[(1S)-1-{[(1S)-1-cyclohexyl-2-[4-({5,6-difluoro-3-[(2-{2-[2-(2-hydroxyethoxy)ethoxy]ethoxy}ethyl)carbamoyl]-1-methyl-1H-indol-2-yl}carbonyl)piperazin-1-yl]-2-oxoethyl]carbamoyl}ethyl]-N-methylcarbamate (100 mg) and DCM (5 mL) was added TEA (0.042 mL), N,N-dimethyl-4-aminopyridine (7.4 mg) and p-toluenesulfonyl chloride (115.8 mg) under ice-cooling. The reaction mixture was stirred at room temperature for 16 h and the solvent was removed under reduced pressure. The residue was purified by silica gel column chromatography (methanol/DCM) to give the title compound (85 mg).

MS: [M+H]$^+$ 977.1.

C) tert-Butyl N-[(1S)-1-{[(1S)-2-[4-({3-[(2-{2-[2-(2-{4-[6-({5-[(2-chloro-6-methylphenyl)carbamoyl]-1,3-thiazol-2-yl}amino)-2-methylpyrimidin-4-yl]piperazin-1-yl}ethoxy)ethoxy]ethoxy}ethyl) carbamoyl]-5,6-difluoro-1-methyl-1H-indol-2-yl}carbonyl)piperazin-1-yl]-1-cyclohexyl-2-oxoethyl]carbamoyl}ethyl]-N-methylcarbamate To a mixture of N-(2-chloro-6-methylphenyl)-2-{[2-methyl-6-(piperazin-1-yl)pyrimidin-4-yl]amino}-1,3-thiazole-5-carboxamide hydrochloride (30 mg) and DMF (2 mL) was added DIEA (0.033 mL) and a mixture of tert-butyl N-[(1S)-1-{[(1S)-1-cyclohexyl-2-[4-({5,6-difluoro-1-methyl-3-[(2-{2-[2-(2-{[(4-methylbenzene)sulfonyl] oxy}ethoxy)ethoxy]ethoxy}ethyl) carbamoyl]-1H-indol-2-yl}carbonyl)piperazin-1-yl]-2-oxoethyl]carbamoyl}ethyl]-N-methylcarbamate (73.2 mg) and DMF (0.5 mL). The reaction mixture was stirred at 80° C. for 16 h, and ice-cold water was added thereto and extracted with ethyl acetate. The organic layer was washed with water and brine and then dried over anhydrous sodium sulfate, and the solvent was removed under reduced pressure. The residue was purified by preparative thin layer chromatography (methanol/DCM) to give the title compound (19 mg).

MS: [M+H]$^+$ 1248.8

D) N-(2-Chloro-6-methylphenyl)-2-((6-(4-(1-(2-(4-((S)-2-cyclohexyl-2-((S)-2-(methylamino)propana-mido)acetyl)piperazine-1-carbonyl)-5,6-difluoro-1-methyl-1H-indol-3-yl)-1-oxo-5,8,11-trioxa-2-azatridecan-13-yl)piperazin-1-yl)-2-methylpyrimidin-4-yl)amino)thiazole-5-carboxamide Trifluoroacetate To a mixture of tert-butyl N-[(1S)-1-{[(1S)-2-[4-({3-[(2-{2-[2-(2-{4-[6-({5-[(2-chloro-6-methylphenyl)carbamoyl]-1,3-thiazol-2-yl}amino)-2-methylpyrimidin-4-yl]piperazin-1-yl}ethoxy)ethoxy]ethoxy}ethyl)carbamoyl]-5,6-difluoro-1-methyl-1H-indol-2-yl}carbonyl)piperazin-1-yl]-1-cyclohexyl-2-oxoethyl]carbamoyl}ethyl]-N-methylcarbamate (20 mg) and DCM (2 mL) was added trifluoroacetic acid (0.01 mL) under ice-cooling. The reaction mixture was stirred at room temperature for 16 h and the solvent was removed under reduced pressure. The residue was washed with ether to give the title compound (14 mg).

MS: [M+H]$^+$ 1149.0

Example 86

N,N'-((Ethan-1,2-diylbis(oxy))bis(ethan-2,1-diyl))bis(2-(4-((S)-2-cyclohexyl-2-((S)-2-(methylamino)pro-panamido)acetyl)piperazine-1-carbonyl)-5-fluoro-1-methyl-1H-indole-3-carboxamide) bistrifluoroacetate A) 2-({4-[(2S)-2-[(2S)-2-{[(tert-Butoxy)carbonyl](methyl)amino}propanamido]-2-cyclohexylacetyl] piperazin-1-yl}carbonyl)-5-fluoro-1-methyl-1H-indole-3-carboxylic Acid To a mixture of tert-butyl ((S)-1-(((S)-1-cyclohexyl-2-(4-(5-fluoro-3-formyl-1-methyl-1H-indole-2-carbonyl)piper-azin-1-yl)-2-oxoethyl)amino)-1-oxopropan-2-yl)(methyl) carbamate (4.8 g), sodium dihydrogen phosphate (3.75 g), 2-methylbut-2-ene (4.14 mL), tert-butylalcohol (90 mL) and water (50 mL) was added sodium chlorite (1.41 g) at room temperature.

The reaction mixture was stirred at the same temperature for 24 h. To the reaction mixture was added sodium sulfite and the aqueous layer was extracted with ethyl acetate. The organic layer was washed with water and brine and then dried over anhydrous sodium sulfate, and the solvent was removed under reduced pressure. The residue was triturated with ether/pentane (1:1) to give the title compound (4.0 g)

MS: [M+H]$^+$ 630.2

B) tert-Butyl N-[(1S)-1-{[(1S)-2-(4-{[3-({2-[2-(2-{[2-({4-[(2S)-2-[(2S)-2-{[(tert-butoxy)carbonyl](methyl) amino}propanamido]-2-cyclohexylacetyl] piperazin-1-yl}carbonyl)-5-fluoro-1-methyl-1H-indol-3-yl]formamido}ethoxy)ethoxy] ethyl}carbamoyl)-5-fluoro-1-methyl-1H-indol-2-yl] carbonyl}piperazin-1-yl)-1-cyclohexyl-2-oxoethyl] carbamoyl}ethyl]-N-methylcarbamate To a mixture of 2-({4-[(2S)-2-[(2S)-2-{[(tert-butoxy)car-bonyl](methyl)amino}propanamido]-2-cyclohexylacetyl] piperazin-1-yl}carbonyl)-5-fluoro-1-methyl-1H-indole-3-carboxylic acid (50 mg) and DCM (1 mL) was added 2-[2-(2-aminoethoxy)ethoxy]ethan-1-amine (11.8 mg), 1-ethyl-3-(3-dimethylaminopropyl)carbodiimide hydro-chloride (18 mg), DIEA (0.048 mL) and 1-hydroxybenzo-triazole (12.8 mg). The reaction mixture was stirred at room temperature for 2 h, and ice-cold water was added thereto and extracted with DCM. The organic layer was washed with water, saturated aqueous sodium bicarbonate and brine and then dried over anhydrous sodium sulfate, and the solvent was removed under reduced pressure. The residue was purified by preparative HPLC (C18, mobile phase: acetonitrile/water (containing 10 mM ammonium acetate)) to give the title compound (12 mg).

MS: [M+H]$^+$ 1372.6.

C) N,N'-((Ethan-1,2-diylbis(oxy))bis(ethan-2,1-diyl))bis(2-(4-((S)-2-cyclohexyl-2-((S)-2-(methyl-amino)propanamido)acetyl)piperazine-1-carbonyl)-5-fluoro-1-methyl-1H-indole-3-carboxamide) bistrifluoroacetate To a mixture of tert-butyl N-[(1S)-1-{[(1S)-2-(4-{[3-({2-[2-(2-{[2-({4-[(2S)-2-[(2S)-2-{[(tert-butoxy)carbonyl](methyl)amino}propanamido]-2-cyclohexylacetyl]piperazin-1-yl}carbonyl)-5-fluoro-1-methyl-1H-indol-3-yl]formamido}ethoxy]ethoxy]ethyl}carbamoyl)-5-fluoro-1-methyl-1H-indol-2-yl]carbonyl}piperazin-1-yl)-1-cyclohexyl-2-oxoethyl]carbamoyl}ethyl]-N-methylcarbamate (10.3 mg) and DCM (3 mL) was added TFA (3 mL) under ice-cooling. The reaction mixture was stirred at room temperature for 4 h and the solvent was removed under reduced pressure to give the title compound (12 mg).

$^1$H NMR (400 MHz, DMSO-$d_6$) δ 0.97-1.35 (m, 16H), 1.38 (d, J=6.9 Hz, 6H), 1.55-1.80 (m, 14H), 2.54 (s, 6H), 3.46 (q, J=5.9 Hz, 4H), 3.55-3.68 (m, 16H), 3.71 (s, 6H), 3.90 (q, J=6.9 Hz, 2H), 4.65 (t, J=7.9 Hz, 2H), 7.07-7.22 (m, 4H), 7.57 (dd, J=4.5, 9.0 Hz, 2H), 7.67 (dd, J=2.5, 10.1 Hz, 2H), 8.36 (d, J=8.1 Hz, 2H), 8.43-9.15 (m, 2H).

Example 87

(S)—N—((S)-1-Cyclohexyl-2-(4-(1-(2-((2-(2-(2-(2-(4-((R)-2-cyclohexyl-2-((R)-2-(methylamino)propanamide)acetyl)piperazine-1-carbonyl)-5-fluoro-1H-indol-1-yl)acetamide)ethoxy)ethyl)amino)-2-oxoethyl)-5-fluoro-1H-indole-2-carbonyl)piperazin-1-yl)-2-oxoethyl)-2-(methylamino)propanamide Bistrifluoroacetate A) tert-Butyl ((S)-1-(((S)-1-cyclohexyl-2-(4-(5,6-difluoro-1H-indole-2-carbonyl)piperazin-1-yl)-2-oxoethyl)amino)-1-oxopropan-2-yl)(methyl)carbamate To a mixture of tert-butyl N-[(1S)-1-{[(1S)-1-cyclohexyl-2-oxo-2-(piperazin-1-yl)ethyl]carbamoyl}ethyl]-N-methylcarbamate (7 g) and DMF (60 mL) was added 5-fluoro-1H-indole-2-carboxylic acid (3.00 g), DIEA (68.2 mL) and 1-ethyl-3-(3-dimethylaminopropyl)carbodiimide hydrochloride (118.3 mg). The reaction mixture was stirred at room temperature for 16 h, water was added thereto and extracted with ethyl acetate. The organic layer was washed with water, saturated ammonium chloride solution, saturated aqueous sodium bicarbonate and brine, respectively, and dried over anhydrous sodium sulfate. The solvent was removed under reduced pressure to give the title compound (9.5 g).
MS: [M+H]$^+$ 572.0.

B) Methyl 2-[2-({4-[(2S)-2-[(2S)-2-{[(tert-butoxy)carbonyl](methyl)amino}propanamido]-2-cyclohexylacetyl] piperazin-1-yl}carbonyl)-5-fluoro-1H-indol-1-yl]acetate To a mixture of tert-butyl ((S)-1-(((S)-1-cyclohexyl-2-(4-(5,6-difluoro-1H-indole-2-carbonyl)piperazin-1-yl)-2-oxoethyl)amino)-1-oxopropane-2-yl)(methyl)carbamate (9.5 g) and DMF (50 mL) was added potassium carbonate (6.89 g), methyl bromoacetate (4.59 mL) under ice-cooling. The reaction mixture was stirred at room temperature for 16 h, and water was added thereto and extracted with ethyl acetate. The organic layer was washed with water and brine, respectively and then dried over anhydrous sodium sulfate, and the solvent was removed under reduced pressure. The residue was purified by silica gel column chromatography (ethyl acetate/hexane) to give the title compound (8.6 g).
MS: [M+H]$^+$ 644.1.

C) 2-[2-({4-[(2S)-2-[(2S)-2-{[(tert-Butoxy)carbonyl](methyl)amino}propanamido]-2-cyclohexylacetyl] piperazin-1-yl}carbonyl)-5-fluoro-1H-indol-1-yl] acetic Acid To a mixture of methyl 2-[2-({4-[(2S)-2-[(2S)-2-{[(tert-butoxy)carbonyl](methyl)amino}propanamido]-2-cyclohexylacetyl]piperazin-1-yl}carbonyl)-5-fluoro-1H-indol-1-yl]acetate (8.6 g) and methanol (25 mL) was added aqueous 2 M sodium hydroxide solution (13.4 mL) and the reaction mixture was stirred at room temperature for 20 min. The reaction mixture was diluted with water and ethyl acetate, and the organic layer was extracted with aqueous 0.01 M sodium hydroxide. The aqueous layer was acidified with 6 M hydrochloric acid and extracted with ethyl acetate. The organic layer was dried over anhydrous sodium sulfate and the solvent was removed under reduced pressure to give the title compound (8.1 g).
MS: [M+H]$^+$ 630.2.

D) tert-Butyl N-[(1S)-1-{[(1S)-2-(4-{[1-({[2-(2-{2-[2-({4-[(2S)-2-[(2S)-2-{[(tert-butoxy)carbonyl](methyl) amino}propanamido]-2-cyclohexylacetyl]piperazin-1-yl}carbonyl)-5-fluoro-1H-indol-1-yl] acetamido}ethoxy)ethyl]carbamoyl}methyl)-5-fluoro-1H-indol-2-yl]carbonyl}piperazin-1-yl)-1-cyclohexyl-2-oxoethyl]carbamoyl}ethyl]-N-methylcarbamate To a mixture of 2-[2-({4-[(2S)-2-[(2S)-2-{[(tert-butoxy)carbonyl](methyl)amino}propanamido]-2-cyclohexylacetyl]piperazin-1-yl}carbonyl)-5-fluoro-1H-indol-1-yl] acetic acid (20 mg) and DCM (20 mL) was added 2-(2-aminoethoxy)ethan-1-amine (84.6 mg), DIEA (0.1 mL) and HATU (87.6 mg). The reaction mixture was stirred at room temperature for 2 h, and ice-cold water was added thereto and extracted with ethyl acetate. The organic layer was washed with water and then dried over anhydrous sodium sulfate, and the solvent was removed under reduced pressure. The residue was purified by preparative HPLC (C18, mobile phase: acetonitrile/water (containing 20 mM ammonium bicarbonate)) to give the title compound (8 mg). MS: [M+H]$^+$ 1327.6.

E) (S)—N—((S)-1-Cyclohexyl-2-(4-(1-(2-((2-(2-(2-(2-(4-((R)-2-cyclohexyl-2-((R)-2-(methylamino) propanamide)acetyl)piperazine-1-carbonyl)-5-fluoro-1H-indol-1-yl)acetamide)ethoxy)ethyl) amino)-2-oxoethyl)-5-fluoro-1H-indole-2-carbonyl) piperazin-1-yl)-2-oxoethyl)-2-(methylamino) propanamide Bistrifluoroacetate To a mixture of tert-butyl N-[(1S)-1-{[(1S)-2-(4-{[1-({[2-(2-{2-[2-({4-[(2S)-2-[(2S)-2-{[(tert-butoxy)carbonyl](methyl)amino}propanamido]-2-cyclohexylacetyl]piperazin-1-yl}carbonyl)-5-fluoro-1H-indol-1-yl] acetamido}ethoxy)ethyl]carbamoyl}methyl)-5-fluoro-1H-indol-2-yl]carbonyl}piperazin-1-yl)-1-cyclohexyl-2-oxoethyl]carbamoyl}ethyl]-N-methylcarbamate (8 mg) and DCM (3 mL) was added TFA (0.003 mL) under ice-cooling. The reaction mixture was stirred at room temperature for 4 h, the solvent was removed under reduced pressure, and the residue was washed with DCM to give the title compound (7.5 mg).
MS: [M+H]$^+$ 1128.6.

Example compound produced according to the above-mentioned production methods or Examples or a method analogous thereto are shown in the following Tables 4-1 to 4-21. MS in the tables means actual measured value.

TABLE 4-1

| Example No. | Compound Name | Structure | Salt | MS |
|---|---|---|---|---|
| 1 | (S)-N-((S)-1-cyclohexyl-2-(4-(6-methoxy-1-methyl-1H-indole-2-carbonyl)-piperazin-1-yl)-2-oxoethyl)-2-(methylamino)propanamide | 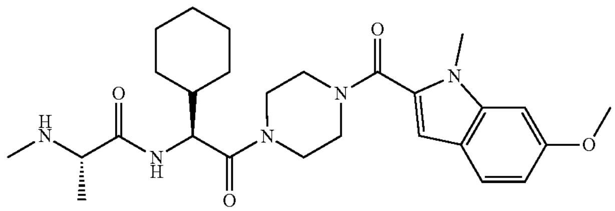 | HCl | 498.4 |
| 2 | (S)-N-((S)-1-cyclohexyl-2-oxo-2-(4-(pyrazolo[1,5-a]pyridine-5-carbonyl)piperazin-1-yl)ethyl)-2-(methylamino)propanamide | 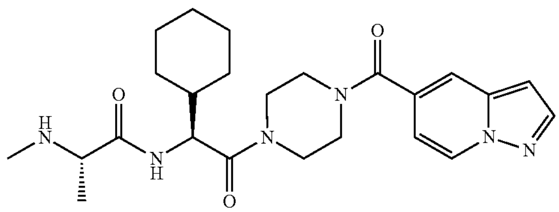 [SMILES: CN[C@@H](C)C(=O)N[C@H](C(=O)N1CCN(C(=O)c2ccn3nccc3c2)CC1)C1CCCCC1] | 2HCl | 455.3 |
| 3 | (S)-N-((S)-1-cyclohexyl-2-(4-(6-methylpyrazolo[1,5-a]pyridine-5-carbonyl)piperazin-1-yl)-2-oxoethyl)-2-(methylamino)propanamide | 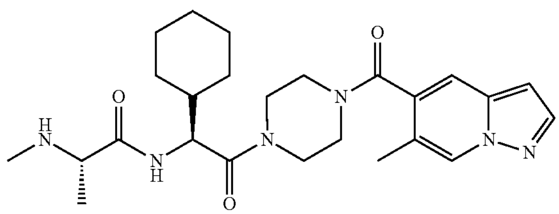 [SMILES: CN[C@@H](C)C(=O)N[C@H](C(=O)N1CCN(C(=O)c2cc3ccnn3cc2C)CC1)C1CCCCC1] | 2HCl | 469.3 |
| 4 | (S)-N-((S)-1-cyclohexyl-2-(4-(4-methylpyrazolo[1,5-a]pyridine-5-carbonyl)piperazin-1-yl)-2-oxoethyl)-2-(methylamino)propanamide | 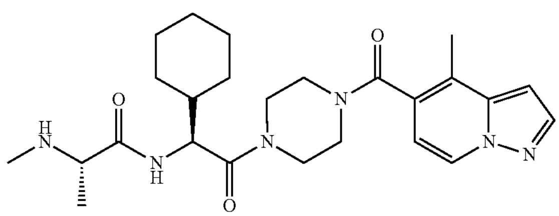 [SMILES: CN[C@@H](C)C(=O)N[C@H](C(=O)N1CCN(C(=O)c2ccn3nccc3c2C)CC1)C1CCCCC1] | 2HCl | 469.4 |
| 5 | (S)-N-((S)-1-cyclohexyl-2-(4-(4-fluoropyrazolo[1,5-a]pyridine-5-carbonyl)piperazin-1-yl)-2-oxoethyl)-2-(methylamino)propanamide | 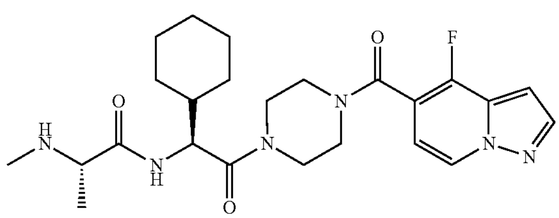 [SMILES: CN[C@@H](C)C(=O)N[C@H](C(=O)N1CCN(C(=O)c2ccn3nccc3c2F)CC1)C1CCCCC1] | 2HCl | 473.3 |

TABLE 4-2

| Example No. | Compound Name | Structure | Salt | MS |
|---|---|---|---|---|
| 6 | (S)-N-((S)-1-cyclohexyl-2-(4-(6-fluoropyrazolo[1,5-a]-pyridine-5-carbonyl)-piperazin-1-yl)-2-oxoethyl)-2-(methylamino)propanamide | 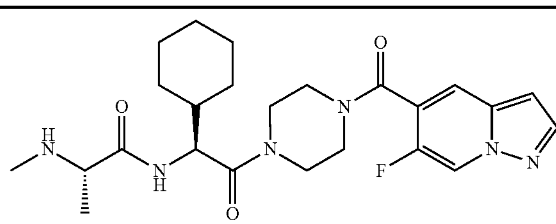 | 2HCl | 473.3 |

TABLE 4-2-continued

| Example No. | Compound Name | Structure | Salt | MS |
|---|---|---|---|---|
| 7 | (S)-N-((S)-1-cyclohexyl-2-(4-(indolizine-2-carbonyl)-piperazin-1-yl)-2-oxoethyl)-2-(methylamino)propanamide | 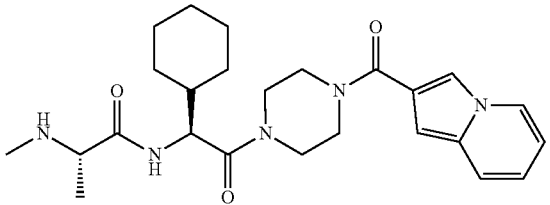 [SMILES: CN[C@@H](C)C(=O)N[C@H](C(=O)N1CCN(C(=O)c2cc3ccccn3c2)CC1)C1CCCCC1] | HCl | 454.3 |
| 8 | (S)-N-((S)-1-cyclohexyl-2-(4-(3-(2-methoxyethoxy)-1-methyl-1H-pyrazole5-carbonyl)piperazin-1-yl)-2-oxoethyl)-2-(methylamino)-propanamide | 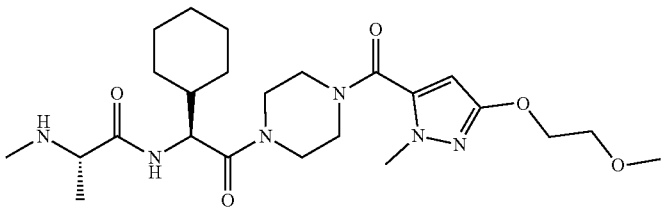 | 2HCl | 493.4 |
| 9 | (S)-N-((S)-1-cyclohexyl-2-(4-(3-cyclopropyl-1-methyl-1H-pyrazole-5-carbonyl)piperazin-1-yl)-2-oxoethyl)-2-(methylamino)propanamide | 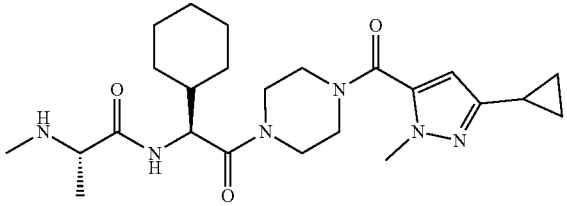 [SMILES: CN[C@@H](C)C(=O)N[C@H](C(=O)N1CCN(C(=O)c2cc(C3CC3)nn2C)CC1)C1CCCCC1] | 2HCl | 459.4 |
| 10 | (S)-N-((S)-1-cyclohexyl-2-(4-(1-methyl-3-propyl-1H-pyrazole-5-carbonyl)-piperazin-1-yl)-2-oxoethyl)-2-(methylamino)propanamide | 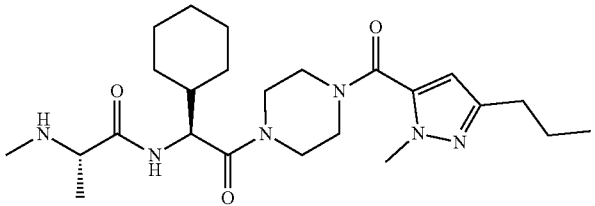 [SMILES: CCCc1cc(C(=O)N2CCN(C(=O)[C@@H](NC(=O)[C@H](C)NC)C3CCCCC3)CC2)n(C)n1] | 2HCl | 461.4 |

TABLE 4-3

| Example No. | Compound Name | Structure | Salt | MS |
|---|---|---|---|---|
| 11 | (S)-N-((S)-1-cyclohexyl-2-(4-(1-methyl-3-(trifluoromethyl)-1H-pyrazole-5-carbonyl)piperazin-1-yl)-2-oxoethyl)-2-(methylamino)-propanamide | 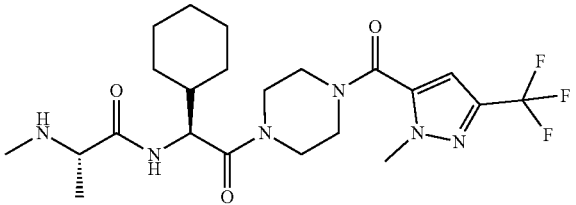 [SMILES: CN[C@@H](C)C(=O)N[C@H](C(=O)N1CCN(C(=O)c2cc(C(F)(F)F)nn2C)CC1)C1CCCCC1] | 2HCl | 487.3 |
| 12 | (S)-N-((S)-1-cyclohexyl-2-(4-(3-ethoxy-1-methyl-1H-pyrazole-5-carbonyl)-piperazin-1-yl)-2-oxoethyl)-2-(methylamino)propanamide | 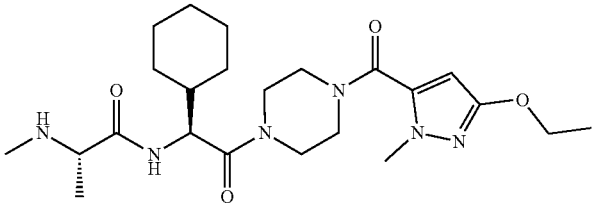 [SMILES: CCOc1cc(C(=O)N2CCN(C(=O)[C@@H](NC(=O)[C@H](C)NC)C3CCCCC3)CC2)n(C)n1] | 2HCl | 463.4 |

TABLE 4-3-continued

| Example No. | Compound Name | Structure | Salt | MS |
|---|---|---|---|---|
| 13 | (S)-N-((S)-1-cyclohexyl-2-(4-(1-methyl-1H-pyrrolo[2,3-b]pyridine-2-carbonyl)piperazin-1-yl)-2-oxoethyl)-2-(methylamino)propanamide | 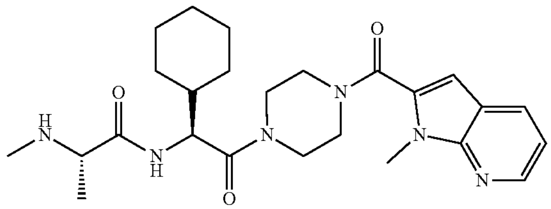 [SMILES: CN[C@@H](C)C(=O)N[C@H](C(=O)N1CCN(C(=O)c2cc3cccnc3n2C)CC1)C1CCCCC1] | 2HCl | 469.4 |
| 14 | (S)-N-((S)-1-cyclohexyl-2-(4-(6-fluoro-1-methyl-1H-indole-2-carbonyl)piperazin-1-yl)-2-oxoethyl)-2-(methylamino)propanamide | 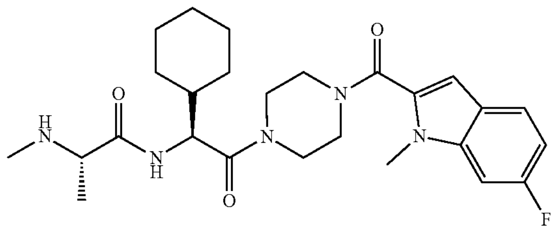 [SMILES: CN[C@@H](C)C(=O)N[C@H](C(=O)N1CCN(C(=O)c2cc3ccc(F)cc3n2C)CC1)C1CCCCC1] | HCl | 486.3 |
| 15 | (S)-N-((S)-1-cyclohexyl-2-(4-(5-fluoro-1-methyl-1H-indole-2-carbonyl)piperazin-1-yl)-2-oxoethyl)-2-(methylamino)propanamide | 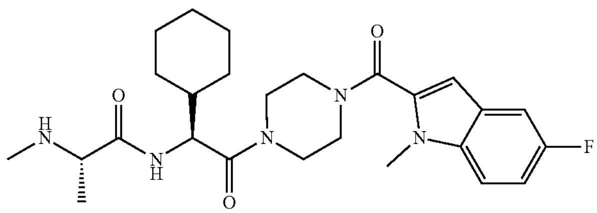 [SMILES: CN[C@@H](C)C(=O)N[C@H](C(=O)N1CCN(C(=O)c2cc3cc(F)ccc3n2C)CC1)C1CCCCC1] | HCl | 486.4 |

TABLE 4-4

| Example No. | Compound Name | Structure | Salt | MS |
|---|---|---|---|---|
| 16 | (S)-N-((S)-1-cyclohexyl-2-(4-(1,7-dimethyl-1H-indole-2-carbonyl)piperazin-1-yl)-2-oxoethyl)-2-(methylamino)propanamide | 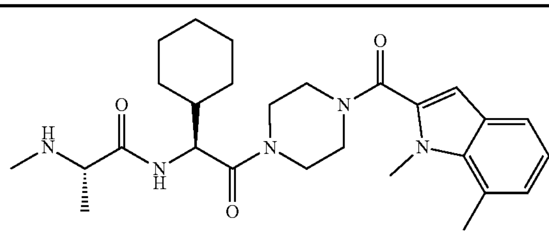 | HCl | 482.4 |
| 17 | (S)-N-((S)-1-cyclohexyl-2-(4-(1-methyl-1H-indazole-6-carbonyl)piperazin-1-yl)-2-oxoethyl)-2-(methylamino)propanamide | 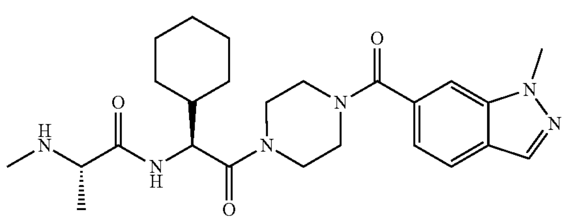 [SMILES: CN[C@@H](C)C(=O)N[C@H](C(=O)N1CCN(C(=O)c2ccc3cnn(C)c3c2)CC1)C1CCCCC1] | 2HCl | 469.3 |
| 18 | (S)-N-((S)-1-cyclohexyl-2-(4-(1,2-dimethyl-1H-benzo[d]imidazole-6-carbonyl)piperazin-1-yl)-2-oxoethyl)-2-(methylamino)propanamide | 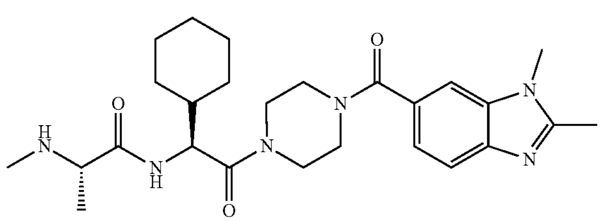 | 2HCl | 483.4 |

TABLE 4-4-continued

| Example No. | Compound Name | Structure | Salt | MS |
|---|---|---|---|---|
| 19 | (S)-N-((S)-1-cyclohexyl-2-(4-(2-methyl-[1,2,4]triazolo[1,5-a]pyridine-6-carbonyl)piperazin-1-yl)-2-oxoethyl)-2-(methylamino)propanamide | 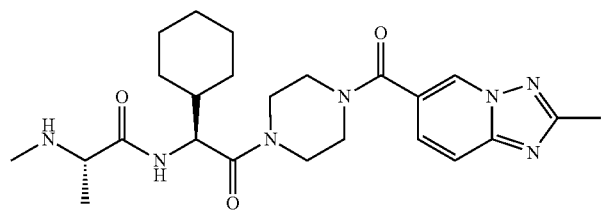 | 2HCl | 470.3 |
| 20 | (S)-N-((S)-1-cyclohexyl-2-(4-(2-methyl-indolizine-6-carbonyl)piperazin-1-yl)-2-oxoethyl)-2-(methylamino)propanamide | 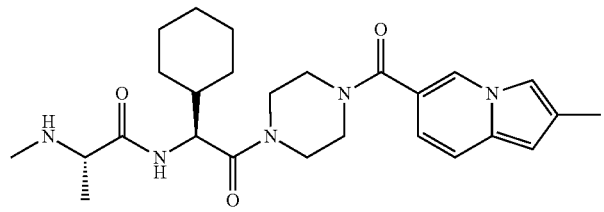 | HCl | 468.4 |

TABLE 4-5

| Example No. | Compound Name | Structure | Salt | MS |
|---|---|---|---|---|
| 21 | (S)-N-((S)-1-cyclohexyl-2-(4-(2-methyl-imidazo[1,2-a]pyridine-7-carbonyl)piperazin-1-yl)-2-oxoethyl)-2-(methylamino)propanamide | 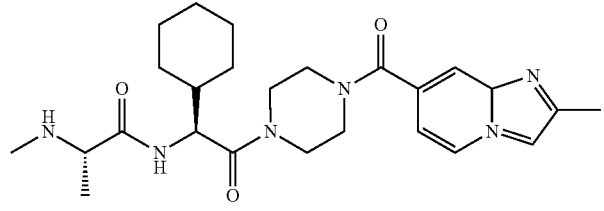 | 2HCl | 469.3 |
| 22 | (S)-N-((S)-1-cyclohexyl-2-(4-(2-methyl-2H-indazole-5-carbonyl)piperazin-1-yl)-2-oxoethyl)-2-(methylamino)propanamide | 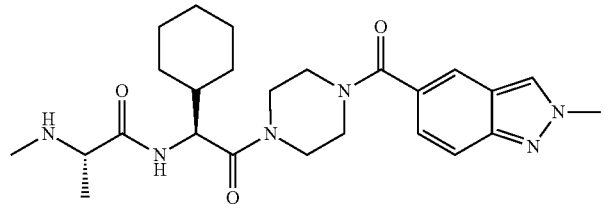 | 2HCl | 469.3 |
| 23 | (S)-N-((S)-1-cyclohexyl-2-(4-(2,3-dimethyl-2H-indazole-6-carbonyl)piperazin-1-yl)-2-oxoethyl)-2-(methylamino)propanamide | 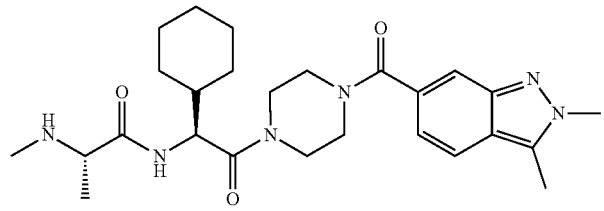 | 2HCl | 483.4 |
| 24 | (S)-N-((S)-1-cyclohexyl-2-((R)-4-(6-methoxy-1-methyl-1H-indole-2-carbonyl)-2-methylpiperazin-1-yl)-2-oxoethyl)-2-(methylamino)propanamide | 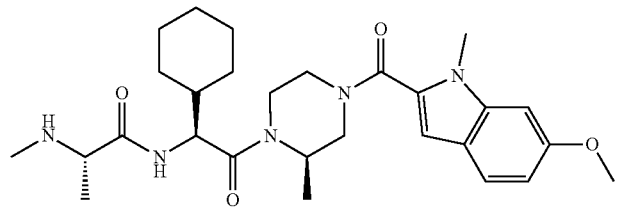 | HCl | 512.2 |

TABLE 4-5-continued

| Example No. | Compound Name | Structure | Salt | MS |
|---|---|---|---|---|
| 25 | 2-(4-((S)-2-cyclohexyl-2-((S)-2-(methylamino)propanamido)acetyl)piperazin-1-carbonyl)-6-methoxy-N-(2-methoxyethyl)-1-methyl-1H-indole-3-carboxamide | 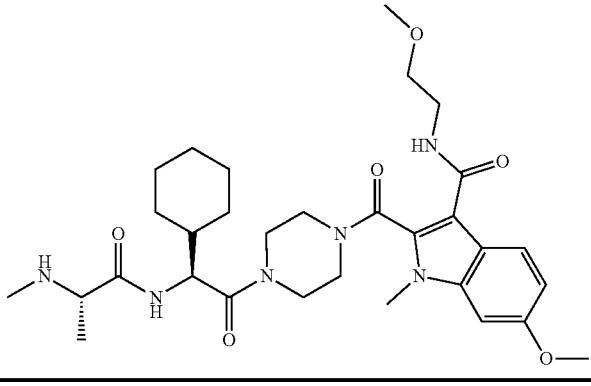 | HCl | 599.4 |

TABLE 4-6

| Example No. | Compound Name | Structure | Salt | MS |
|---|---|---|---|---|
| 26 | 2-(4-((S)-2-cyclohexyl-2-((S)-2-(methylamino)propanamido)acetyl)piperazin-1-carbonyl)-6-methoxy-N-(2-methoxyethyl)-N,1-dimethyl-1H-indole-3-carboxamide | 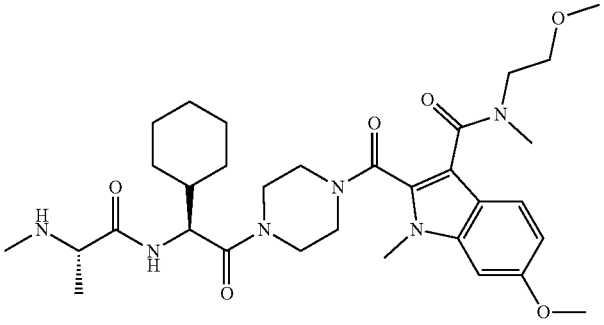 | HCl | 613.5 |
| 27 | methyl (2-(4-((S)-2-cyclohexyl-2-((S)-2-(methylamino)propanamido)acetyl)piperazine-1-carbonyl)-6-methoxy-1-methyl-1H-indole-3-carbonyl)glycinate | 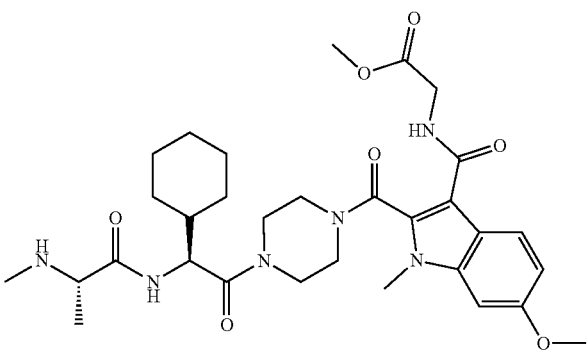 | HCl | 613.4 |

TABLE 4-6-continued

| Example No. | Compound Name | Structure | Salt | MS |
|---|---|---|---|---|
| 28 | methyl N-(2-(4-((S)-2-cyclohexyl-2-((S)-2-(methylamino)propanamido)acetyl)-piperazine-1-carbonyl)-6-methoxy-1-methyl-1H-indole-3-carbonyl)-N-methylglycinate | 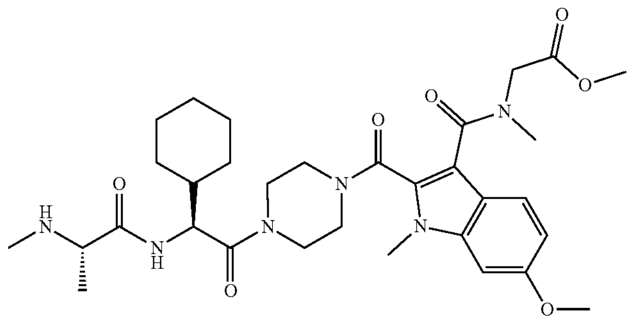 | HCl | 627.4 |
| 29 | (S)-N-((S)-1-cyclohexyl-2-(4-(6-methoxy-3-((S)-2-(methoxymethyl)pyrrolidine-1-carbonyl)-1-methyl-1H-indole-2-carbonyl)piperazin-1-yl)-2-oxoethyl)-2-(methylamino)propanamide | 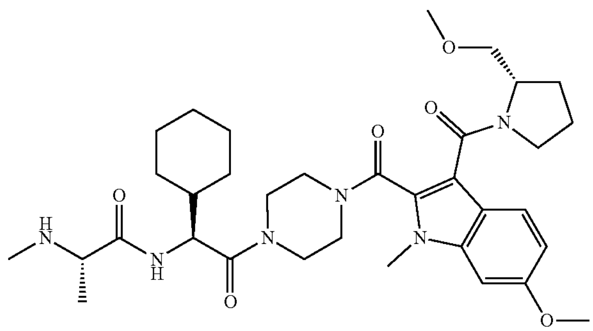 | HCl | 639.5 |

TABLE 4-7

| Example No. | Compound Name | Structure | Salt | MS |
|---|---|---|---|---|
| 30 | (S)-N-((S)-1-cyclohexyl-2-(4-(6-methoxy-3-((R)-2-(methoxymethyl)pyrrolidine-1-carbonyl)-1-methyl-1H-indole-2-carbonyl)piperazin-1-yl)-2-oxoethyl)-2-(methylamino)-propanamide | 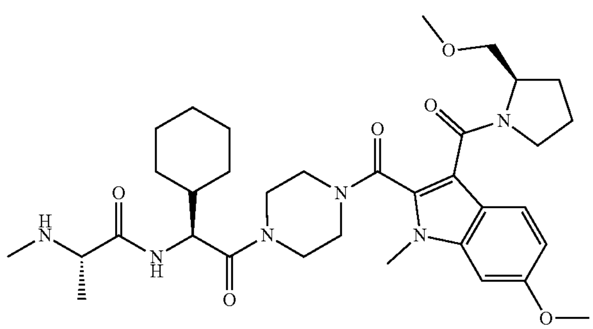 | HCl | 639.5 |
| 31 | (S)-N-((S)-1-cyclohexyl-2-(4-(6-methoxy-3-(3-methoxyazetidine-1-carbonyl)-1-methyl-1H-indole-2-carbonyl)-piperazin-1-yl)-2-oxoethyl)-2-(methylamino)propanamide | 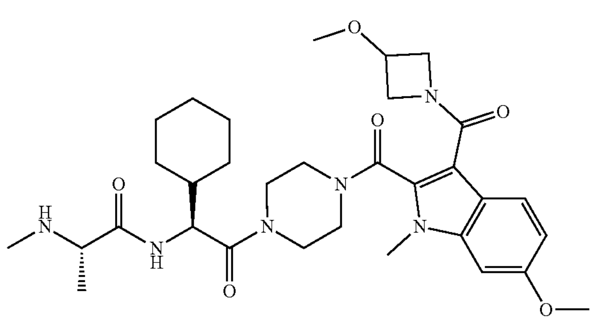 | HCl | 611.4 |

TABLE 4-7-continued

| Example No. | Compound Name | Structure | Salt | MS |
|---|---|---|---|---|
| 32 | (S)-N-((S)-1-cyclohexyl-2-((S)-4-(6-methoxy-1-methyl-1H-indole-2-carbonyl)-2-methylpiperazin-1-yl)-2-oxoethyl)-2-(methylamino)propanamide | 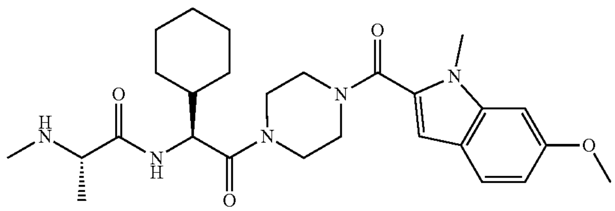 | HCl | 512.4 |
| 33 | (S)-N-((S)-1-cyclohexyl-2-((S)-4-(6-methoxy-1-methyl-1H-indole-2-carbonyl)-3-methylpiperazin-1-yl)-2-oxoethyl)-2-(methylamino)propanamide | 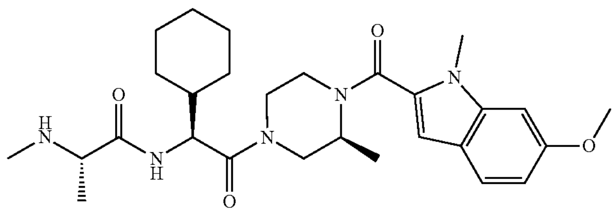 | HCl | 512.4 |

TABLE 4-8

| Example No. | Compound Name | Structure | Salt | MS |
|---|---|---|---|---|
| 34 | (S)-N-((S)-1-cyclohexyl-2-((R)-4-(6-methoxy-1-methyl-1H-indole-2-carbonyl)-3-methylpiperazin-1-yl)-2-oxoethyl)-2-(methylamino)propanamide | 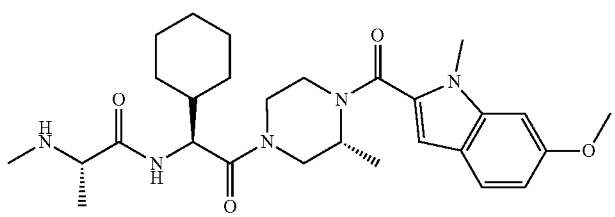 | HCl | 512.4 |
| 35 | (S)-N-((S)-1-cyclohexyl-2-(4-(5-fluoro-3-formyl-1-methyl-1H-indole-2-carbonyl)piperazin-1-yl)-2-oxoethyl)-2-(methylamino)propanamide | 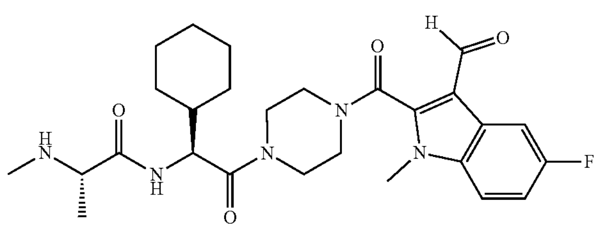 [SMILES: CN[C@@H](C)C(=O)N[C@H](C(=O)N1CCN(C(=O)c2c(C=O)c3cc(F)ccc3n2C)CC1)C1CCCCC1] | HCl | 514.4 |
| 36 | 1-(4-(6-methoxy-1-methyl-1H-indole-2-carbonyl)-piperazin-1-yl)-2-((2R,5R)-5-methyl-2-(((R)-3-methylmorpholino)methyl)piperazin-1-yl)ethan-1-one | 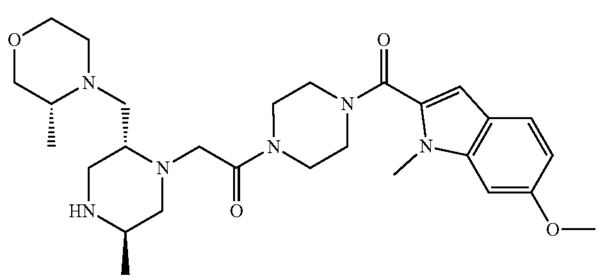 [SMILES: COc1ccc2cc(C(=O)N3CCN(C(=O)CN4C[C@@H](C)NC[C@@H]4CN4CCOC[C@H]4C)CC3)n(C)c2c1] | | |

1H NMR (300 MHz, CD$_3$OD) δ 0.74-1.29 (7H, m), 1.34-1.45 (3H, m), 1.48-1.79 (6H, m), 2.57 (3H, brs), 3.45-3.68 (14H, m), 3.79 (7H, s), 3.95-4.05 (3H, m), 6.84 (1H, dd, J =8.7, 1.5 Hz), 6.92 (1H, d, J = 1.5 Hz), 7.69 (1H, d, J = 9.1 Hz).

TABLE 4-8-continued

| Example No. | Compound Name | Structure | Salt | MS |
|---|---|---|---|---|
| 37 | 2-(2-(2-(2-(4-((S)-2-cyclohexyl-2-((S)-2-(methylamino)propanamido)acetyl)piperazine-1-carbonyl)-6-methoxy-1-methyl-1H-indole-3-carboxamido)ethoxy)ethoxy)-acetic acid | 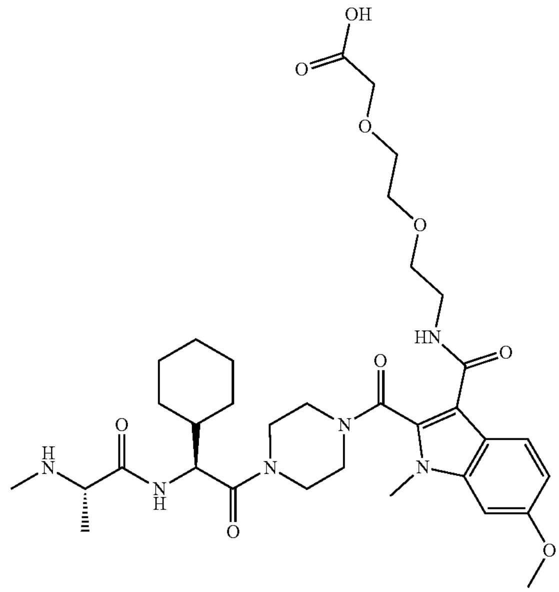 [SMILES: CN[C@@H](C)C(=O)N[C@H](C(=O)N1CCN(C(=O)c2c(C(=O)NCCOCCOCC(=O)O)c3ccc(OC)cc3n2C)CC1)C1CCCCC1] | HCl | 687.2 |

TABLE 4-9

| No. | Name | Structure | Salt | MS |
|---|---|---|---|---|
| 38 | (9H-fluoren-9-yl)methyl (2-(2-(2-(2-(4-((S)-2-cyclohexyl-2-((S)-2-(methylamino)propanamido)acetyl)piperazine-1-carbonyl)-6-methoxy-1-methyl-1H-indole-3-carboxamido)ethoxy)ethoxy)ethyl)carbamate | 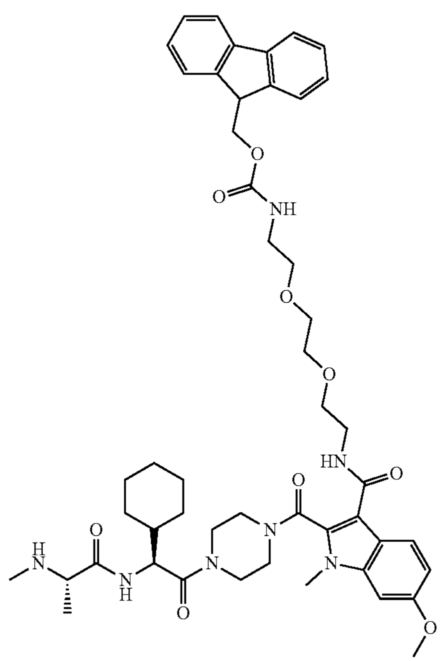 [SMILES: CN[C@@H](C)C(=O)N[C@H](C(=O)N1CCN(C(=O)c2c(C(=O)NCCOCCOCCNC(=O)OCC3c4ccccc4-c4ccccc43)c3ccc(OC)cc3n2C)CC1)C1CCCCC1] | HCl | 894.6 |

TABLE 4-9-continued

| No. | Name | Structure | Salt | MS |
|---|---|---|---|---|
| 39 | 2-((2R,5R)-2-(hydroxymethyl)-5-methylpiperazin-1-yl)-1-(4-(6-methoxy-1-methyl-1H-indole-2-carbonyl)piperazin-1-yl)ethan-1-one | 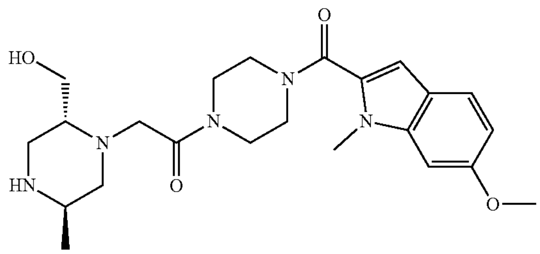 [SMILES: COc1ccc2cc(C(=O)N3CCN(C(=O)CN4C[C@@H](C)NC[C@@H]4CO)CC3)n(C)c2c1] | HCl | 444.4 |
| 40 | 2-((2R,5R)-2-(((2-(2-hydroxyethoxy)ethyl)(methyl)amino)methyl)-5-methylpiperazin-1-yl)-1-(4-(6-methoxy-1-methyl-1H-indole-2-carbonyl)piperazin-1-yl)ethan-1-one | 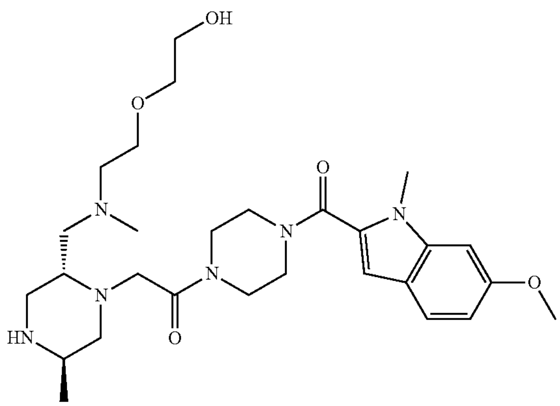 [SMILES: COc1ccc2cc(C(=O)N3CCN(C(=O)CN4C[C@@H](C)NC[C@@H]4CN(C)CCOCCO)CC3)n(C)c2c1] | HCl | 545.4 |
| 41 | (S)-N-((S)-1-cyclohexyl-2-(4-(5,6-difluoro-1-methyl-1H-indole-2-carbonyl)piperazin-1-yl)-2-oxoethyl)-2-(methylamino)propanamide | 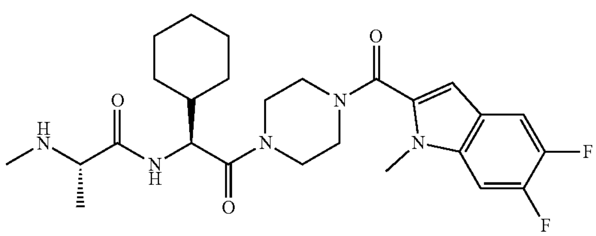 [SMILES: CN[C@@H](C)C(=O)N[C@H](C(=O)N1CCN(C(=O)c2cc3cc(F)c(F)cc3n2C)CC1)C1CCCCC1] | | 504.3 |

TABLE 4-10

| Example No. | Compound Name | Structure | Salt | MS |
|---|---|---|---|---|
| 42 | (S)-N-((S)-1-(4,4-difluorocyclohexyl)-2-(4-(6-methoxy-1-methyl-1H-indole-2-carbonyl)piperazin-1-yl)-2-oxoethyl)-2-(methylamino)propanamide | 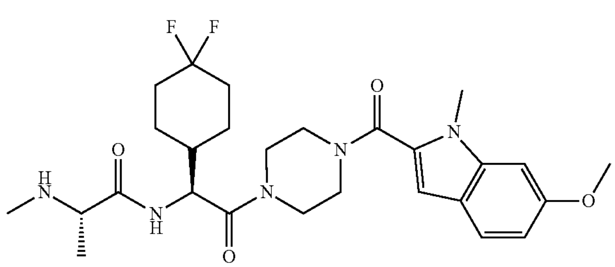 | HCl | 534.3 |

TABLE 4-10-continued

| Example No. | Compound Name | Structure | Salt | MS |
|---|---|---|---|---|
| 43 | methyl (E)-3-(2-(4-((S)-2-cyclohexyl-2-((S)-2-(methylamino)propanamido)acetyl)piperazine-1-carbonyl)-5-fluoro-1-methyl-1H-indol-3-yl)acrylate | 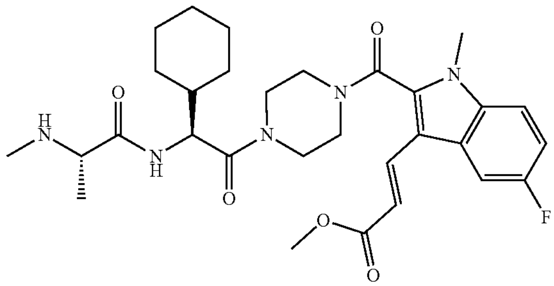 [SMILES: CN[C@@H](C)C(=O)N[C@H](C(=O)N1CCN(C(=O)c2c(/C=C/C(=O)OC)c3cc(F)ccc3n2C)CC1)C1CCCCC1] | HCl | 570.5 |
| 44 | (S)-N-((S)-2-(4-(1-(2-(2-(benzyloxy)ethoxy)ethyl)-5,6-difluoro-1H-indole-2-carbonyl)piperazin-1-yl)-1-cyclohexyl-2-oxoethyl)-2-(methylamino)propanamide | 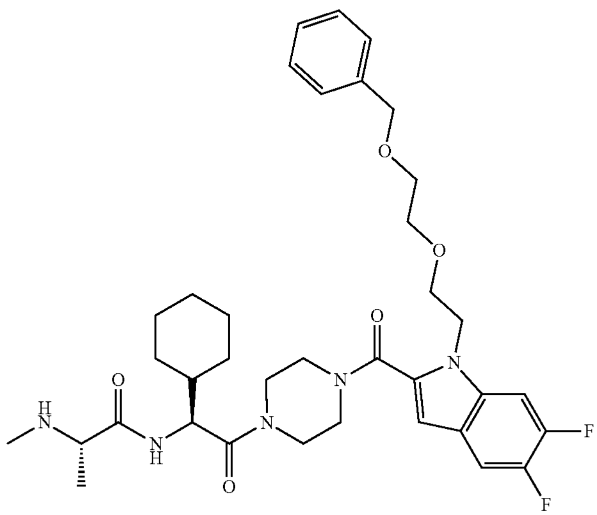 [SMILES: CN[C@@H](C)C(=O)N[C@H](C(=O)N1CCN(C(=O)c2cc3cc(F)c(F)cc3n2CCOCCOCc2ccccc2)CC1)C1CCCCC1] | | 668.4 |
| 45 | (S)-N-((S)-1-cyclohexyl-2-(4-(5,6-difluoro-1-(2-(2-hydroxyethoxy)ethyl)-1H-indole-2-carbonyl)-piperazin-1-yl)-2-oxoethyl)-2-(methylamino)propanamide | 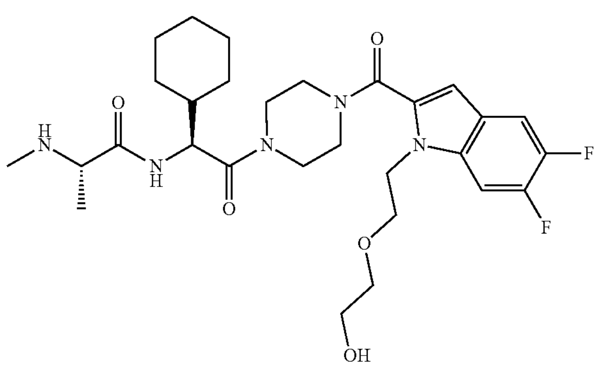 [SMILES: CN[C@@H](C)C(=O)N[C@H](C(=O)N1CCN(C(=O)c2cc3cc(F)c(F)cc3n2CCOCCO)CC1)C1CCCCC1] | | 578.3 |

TABLE 4-11

| Example No. | Compound Name | Structure | Salt | MS |
|---|---|---|---|---|
| 46 | (S)-N-((R)-2-(4-(1-(2-(2-(benzyloxy)ethoxy)ethyl)-5,6-difluoro-1H-indole-2-carbonyl)piperazin-1-yl)-1-cyclohexyl-2-oxoethyl)-2-(methylamino)propanamide | 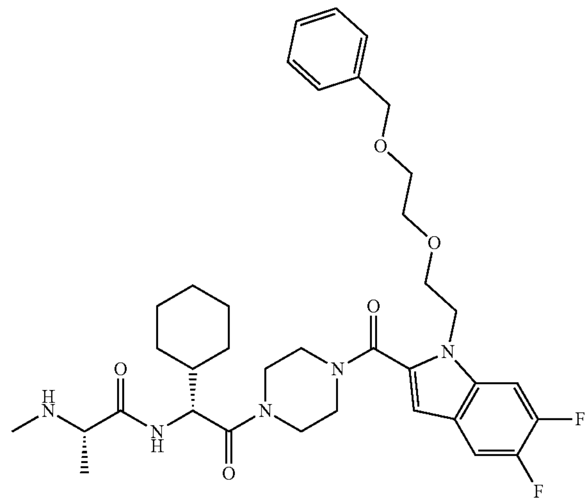 [SMILES: CN[C@@H](C)C(=O)N[C@@H](C(=O)N1CCN(C(=O)c2cc3cc(F)c(F)cc3n2CCOCCOCc2ccccc2)CC1)C1CCCCC1] | HCl | 668.3 |
| 47 | (S)-N-((S)-1-cyclohexyl-2-(4-(5,6-difluoro-1-(2-(2-(2-hydroxyethoxy)ethoxy)ethyl)-1H-indole-2-carbonyl)piperazin-1-yl)-2-oxoethyl)-2-(methylamino)propanamide | 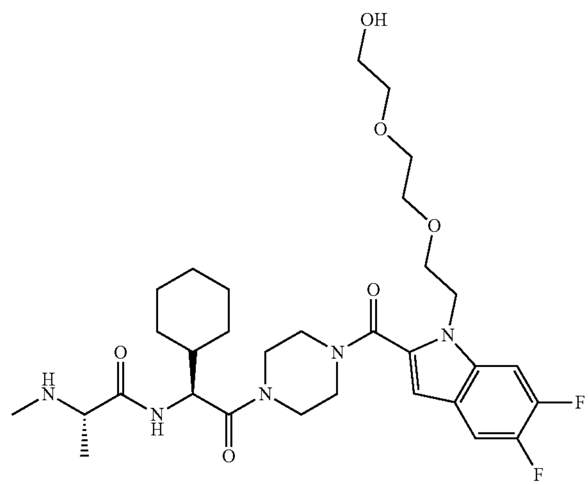 [SMILES: CN[C@@H](C)C(=O)N[C@H](C(=O)N1CCN(C(=O)c2cc3cc(F)c(F)cc3n2CCOCCOCCO)CC1)C1CCCCC1] | | 622.3 |
| 48 | (S)-N-((S)-1-cyclohexyl-2-(4-(5,6-difluoro-1-(2-(2-(2-(2-hydroxyethoxy)ethoxy)ethoxy)ethyl)-1H-indole-2-carbonyl)piperazin-1-yl)-2-oxoethyl)-2-(methylamino)propanamide | 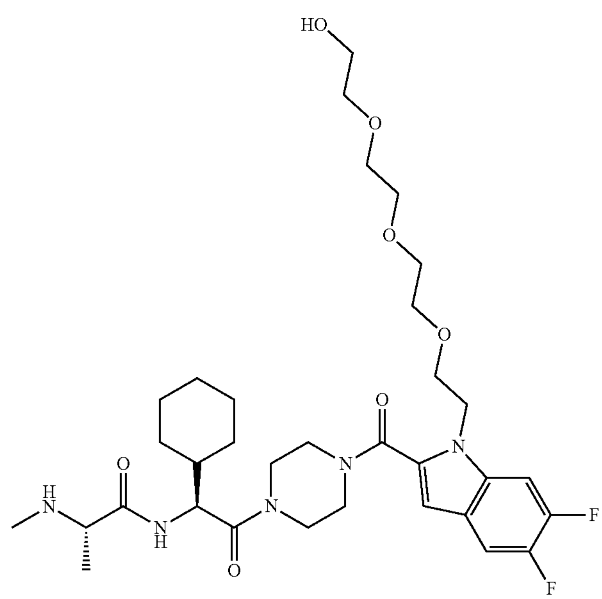 [SMILES: CN[C@@H](C)C(=O)N[C@H](C(=O)N1CCN(C(=O)c2cc3cc(F)c(F)cc3n2CCOCCOCCOCCO)CC1)C1CCCCC1] | | 666.3 |

TABLE 4-11-continued

| Example No. | Compound Name | Structure | Salt | MS |
|---|---|---|---|---|
| 49 | (S)-N-((S)-2-(4-(3-(2-(2-(benzyloxy)ethoxy)ethoxy)-5,6-difluoro-1-methyl-1H-indole-2-carbonyl)piperazin-1-yl)-1-cyclohexyl-2-oxoethyl)-2-(methylamino)propanamide | 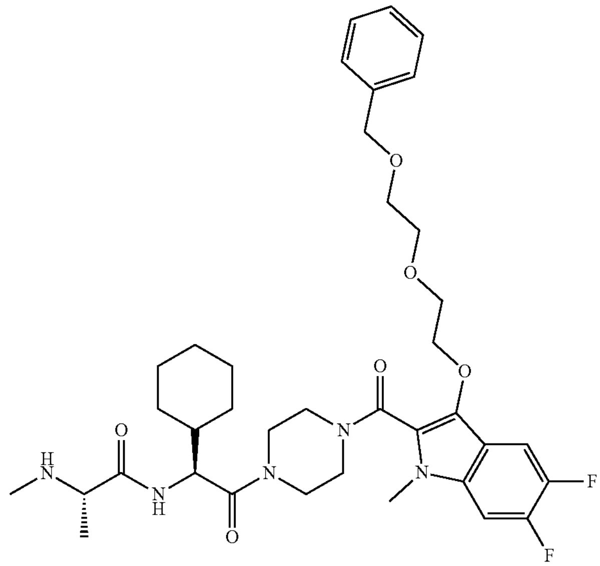 [SMILES: CN[C@@H](C)C(=O)N[C@H](C(=O)N1CCN(C(=O)c2c(OCCOCCOCc3ccccc3)c3cc(F)c(F)cc3n2C)CC1)C1CCCCC1] | | 698.9 |

TABLE 4-12

| Example No. | Compound Name | Structure | Salt | MS |
|---|---|---|---|---|
| 50 | (S)-N-((S)-1-cyclohexyl-2-(4-(5,6-difluoro-3-(2-(2-hydroxyethoxy)ethoxy)-1-methyl-1H-indole-2-carbonyl)piperazin-1-yl)-2-oxoethyl)-2-(methylamino)propanamide | 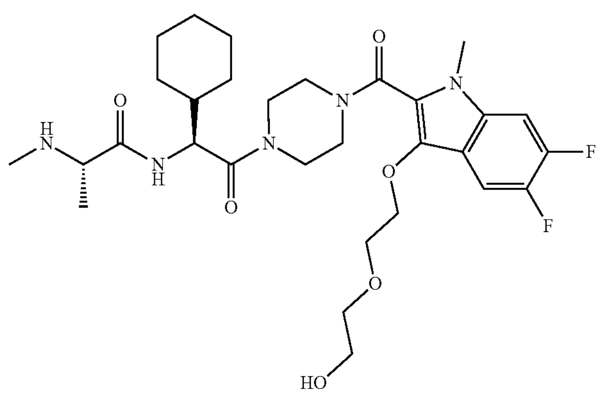 [SMILES: CN[C@@H](C)C(=O)N[C@H](C(=O)N1CCN(C(=O)c2c(OCCOCCO)c3cc(F)c(F)cc3n2C)CC1)C1CCCCC1] | | 608.4 |
| 51 | (S)-N-((S)-1-cyclohexyl-2-(4-(1-(2-methoxyethyl)-3-methyl-1H-indole-2-carbonyl)piperazin-1-yl)-2-oxoethyl)-2-(methylamino)propanamide | 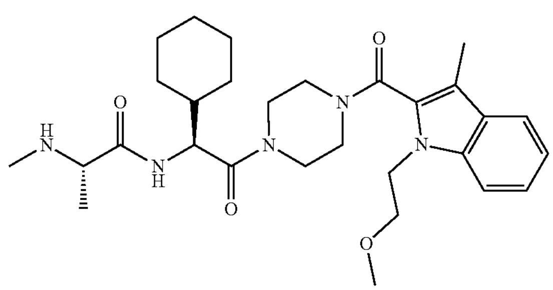 [SMILES: CN[C@@H](C)C(=O)N[C@H](C(=O)N1CCN(C(=O)c2c(C)c3ccccc3n2CCOC)CC1)C1CCCCC1] | | 526.1 |

TABLE 4-12-continued

| Example No. | Compound Name | Structure | Salt | MS |
|---|---|---|---|---|
| 52 | (S)-N-((S)-1-cyclohexyl-2-(4-(5-fluoro-1-(2-methoxyethyl)-1H-indole-2-carbonyl)piperazin-1-yl)-2-oxoethyl)-2-(methylamino)propanamide | 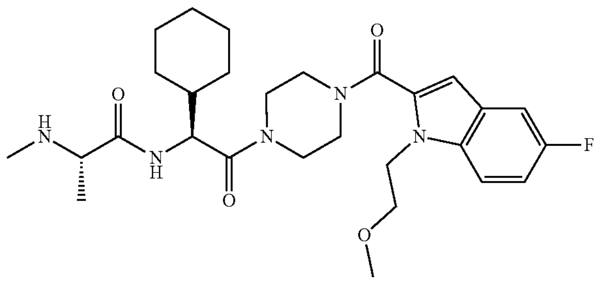 [SMILES: CN[C@@H](C)C(=O)N[C@H](C(=O)N1CCN(C(=O)c2cc3cc(F)ccc3n2CCOC)CC1)C1CCCCC1] | | 530.3 |
| 53 | (S)-N-((S)-1-cyclohexyl-2-(4-(6-fluoro-1-(2-methoxyethyl)-1H-indole-2-carbonyl)piperazin-1-yl)-2-oxoethyl)-2-(methylamino)propanamide | 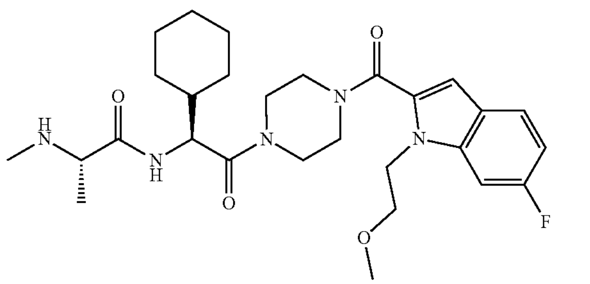 [SMILES: CN[C@@H](C)C(=O)N[C@H](C(=O)N1CCN(C(=O)c2cc3ccc(F)cc3n2CCOC)CC1)C1CCCCC1] | | 530.4 |

TABLE 4-13

| Example No. | Compound Name | Structure | Salt | MS |
|---|---|---|---|---|
| 54 | (S)-N-((S)-1-cyclohexyl-2-(4-(5,6-difluoro-1-(2-methoxyethyl)-1H-indole-2-carbonyl)piperazin-1-yl)-2-oxoethyl)-2-(methylamino)propanamide | 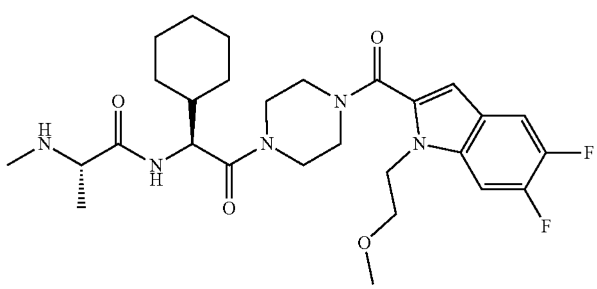 [SMILES: CN[C@@H](C)C(=O)N[C@H](C(=O)N1CCN(C(=O)c2cc3cc(F)c(F)cc3n2CCOC)CC1)C1CCCCC1] | | 548.3 |
| 55 | 2-(4-((S)-2-cyclohexyl-2-((S)-2-(methylamino)propanamide)acetyl)piperazine-1-carbonyl)-N-(2-(2-(2-(4-(4-((3-(3,4-dimethoxyphenyl)-3H-[1,2,3]triazolo[4,5-d]pyrimidin-5-yl)amino)phenyl)piperazin-1-yl)-2-oxoethoxy)ethoxy)ethyl)-6-methoxy-1-methyl-1H-indole-3-carboxamide | 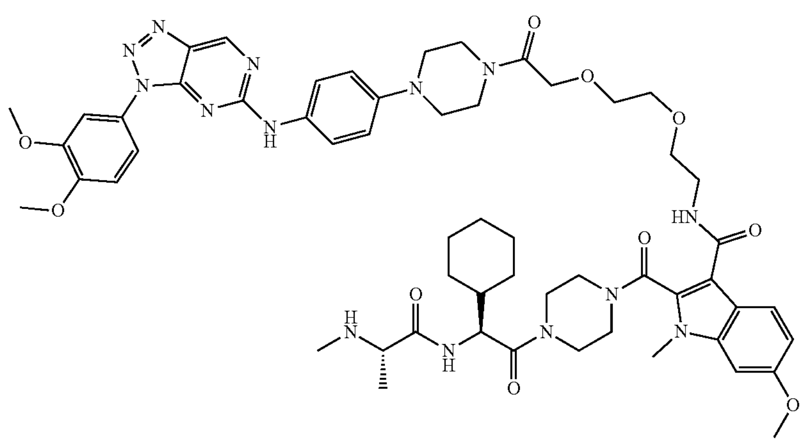 [SMILES: CN[C@@H](C)C(=O)N[C@H](C(=O)N1CCN(C(=O)c2c(C(=O)NCCOCCOCC(=O)N3CCN(c4ccc(Nc5ncc6nnn(-c7ccc(OC)c(OC)c7)c6n5)cc4)CC3)c3ccc(OC)cc3n2C)CC1)C1CCCCC1] | | 1101.5 |

TABLE 4-13-continued

| Example No. | Compound Name | Structure | Salt | MS |
|---|---|---|---|---|
| 56 | (S)-N-((S)-1-cyclohexyl-2-((R)-4-(5,6-difluoro-1-methyl-1H-indole-2-carbonyl)-2-methylpiperazin-1-yl)-2-oxoethyl)-2-(methylamino)propanamide | 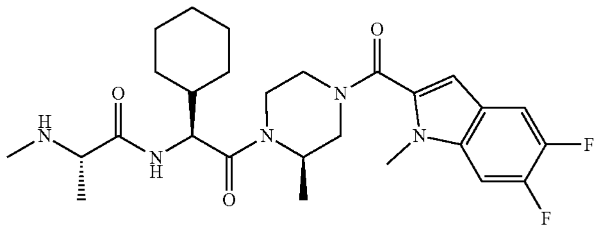 [SMILES: CN[C@@H](C)C(=O)N[C@H](C(=O)N1CCN(C(=O)c2cc3cc(F)c(F)cc3n2C)C[C@H]1C)C1CCCCC1] | TEA | 518.6 |
| 57 | (S)-N-((S)-1-cyclohexyl-2-((R)-4-(5-fluoro-6-methoxy-1-methyl-1H-indole-2-carbonyl)-2-methylpiperazin-1-yl)-2-oxoethyl)-2-(methylamino)propanamide | 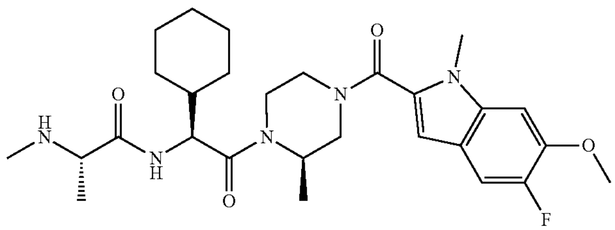 | TEA | 530.5 |
| 58 | (S)-N-((S)-1-cyclohexyl-2-((R)-4-(5-fluoro-1-methyl-1H-indole-2-carbonyl)-2-methylpiperazin-1-yl)-2-oxoethyl)-2-(methylamino)propanamide | 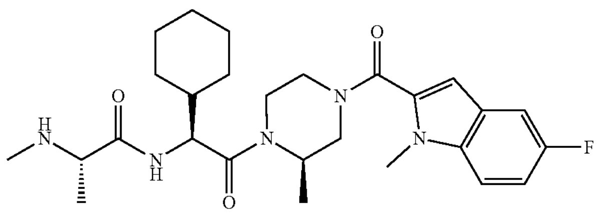 [SMILES: CN[C@@H](C)C(=O)N[C@H](C(=O)N1CCN(C(=O)c2cc3cc(F)ccc3n2C)C[C@H]1C)C1CCCCC1] | TEA | 500.5 |

TABLE 4-14

| Example No. | Compound Name | Structure | Salt | MS |
|---|---|---|---|---|
| 59 | (2S)-N-((1S)-1-cyclohexyl-2-(5-((5,6-difluoro-1-methyl-1H-indol-2-yl)carbonyl)-2,5-diazabicyclo[2.2.2]octan-2-yl)-2-oxoethyl)-2-(methylamino)propanamide (stereoisomer) | 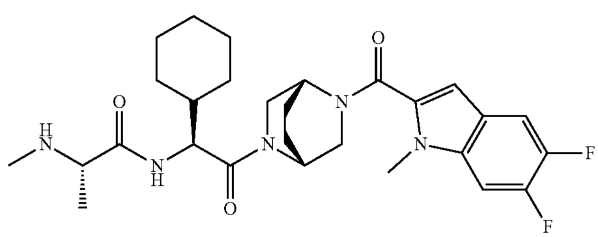 [SMILES: CN[C@@H](C)C(=O)N[C@H](C(=O)N1C[C@H]2CC[C@@H]1CN2C(=O)c1cc2cc(F)c(F)cc2n1C)C1CCCCC1] | | 530.4 |
| 60 | (2 S)-N-((1S)-1-cyclohexyl-2-(3-((5,6-difluoro-1-methyl-1H-indol-2-yl)carbonyl)-3,6-diazabicyclo[3.1.1]heptan-6-yl)-2-oxoethyl)-2-(methylamino)propanamide | 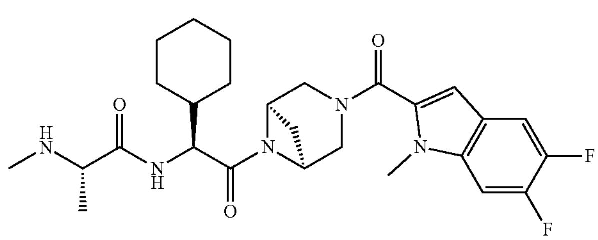 | | 517.4 |

TABLE 4-14-continued
| Example No. | Compound Name | Structure | Salt | MS |
|---|---|---|---|---|
| 61 | N-(2-(2-(2-azidoethoxy)ethoxy)ethyl)-2-(4-((S)-2-cyclohexyl-2-((S)-2-(methylamino)propanamido)acetyl)piperazine-1-carbonyl)-6-methoxy-1-methyl-1H-indole-3-carboxamide | 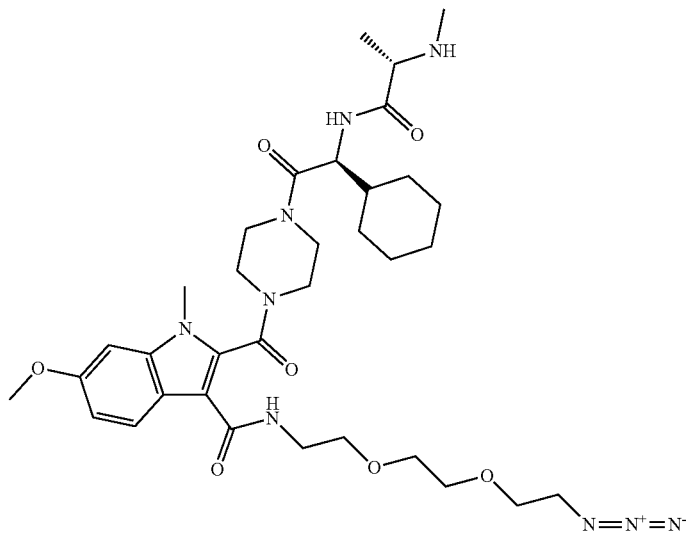 [SMILES: CN[C@@H](C)C(=O)N[C@H](C(=O)N1CCN(C(=O)c2c(C(=O)NCCOCCOCCN=[N+]=[N-])c3ccc(OC)cc3n2C)CC1)C1CCCCC1] | | 698.5 |
| 62 | (S)-N-((S)-1-cyclohexyl-2-(4-(5,6-difluoro-3-(2-(2-(2-hydroxyethoxy)ethoxy)ethoxy)-1-methyl-1H-indole-2-carbonyl)piperazin-1-yl)-2-oxoethyl)-2-(methylamino)propanamide | 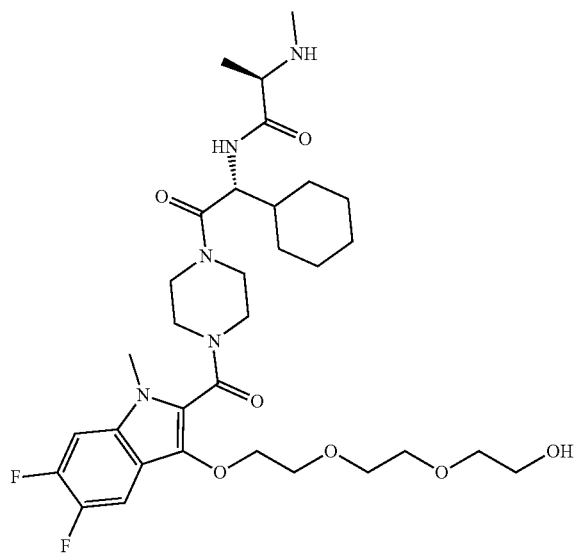 [SMILES: CN[C@H](C)C(=O)N[C@@H](C(=O)N1CCN(C(=O)c2c(OCCOCCOCCO)c3cc(F)c(F)cc3n2C)CC1)C1CCCCC1] | | 651.8 |

TABLE 4-14-continued

| Example No. | Compound Name | Structure | Salt | MS |
|---|---|---|---|---|
| 63 | (S)-N-((S)-1-cyclohexyl-2-(4-(5,6-difluoro-3-(2-(2-(2-(2-hydroxyethoxy)ethoxy)ethoxy)ethoxy)-1-methyl-1H-indole-2-carbonyl)piperazin-1-yl)-2-oxoethyl)-2-(methylamino)propanamide | 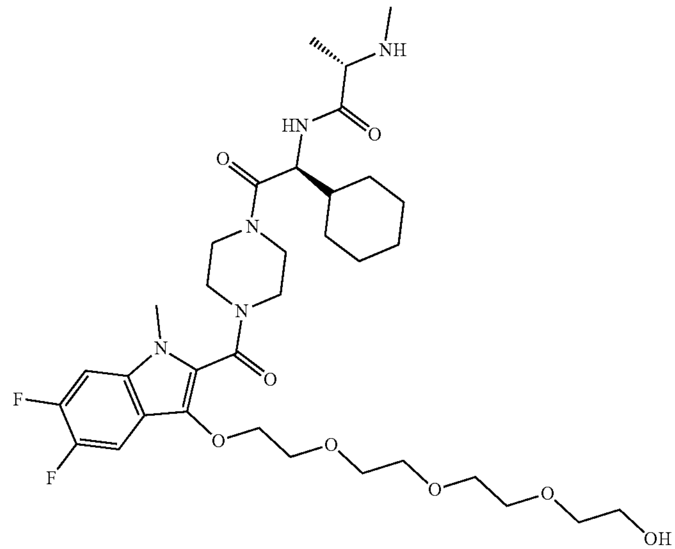 [SMILES: CN[C@@H](C)C(=O)N[C@H](C(=O)N1CCN(C(=O)c2c(OCCOCCOCCOCCO)c3cc(F)c(F)cc3n2C)CC1)C1CCCCC1] | | 695.9 |

TABLE 4-15

| Example No. | Compound Name | Structure | Salt | MS |
|---|---|---|---|---|
| 64 | 1-((R)-4-(5,6-difluoro-1-methyl-1H-indole-2-carbonyl)-2-methylpiperazin-1-yl)-2-((2R, 5R)-2-((2-)-2-(2-hydroxyethoxy)ethoxy)methyl)-5-methylpiperazin-1-yl)ethan-1-one | 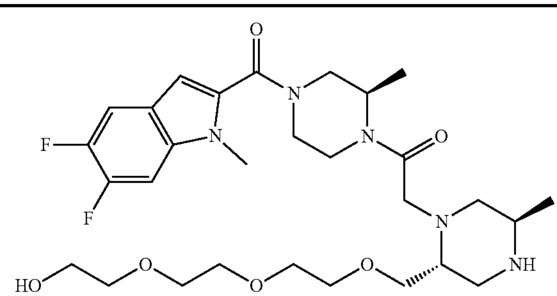 | | 596.6 |
| 65 | 1-((R)-4-(5,6-difluoro-1-methyl-1H-indole-2-carbonyl)-2-methylpiperazin-1-yl)-2-((2R, 5R)-2-(13-hydroxy-2,5,8,11-tetraoxatridecyl)-5-methylpiperazin-1-yl)-ethan-1-one | 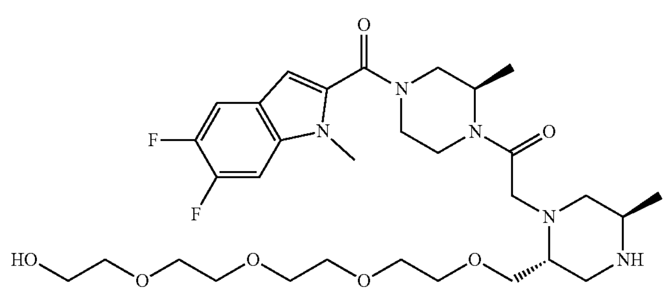 [SMILES: C[C@@H]1CN(CC(=O)N2CCN(C(=O)c3cc4cc(F)c(F)cc4n3C)C[C@H]2C)[C@@H](COCCOCCOCCOCCO)CN1] | | 640.6 |
| 66 | (S)-N-((S)-2-(4-(4-)-2-(2-(2-(benzyloxy)ethoxy)ethoxy)ethoxy)-5,6-difluoro-1-methyl-1H-indole-2-carbonyl)piperazin-1-yl)-1-cyclohexyl-2-oxoethyl)-2-(methylamino)propanamide | 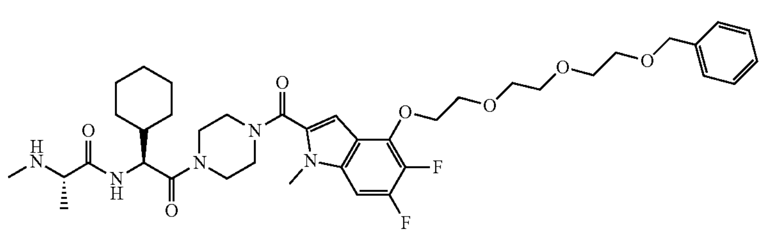 [SMILES: CN[C@@H](C)C(=O)N[C@H](C(=O)N1CCN(C(=O)c2cc3c(OCCOCCOCCOCc4ccccc4)c(F)c(F)cc3n2C)CC1)C1CCCCC1] | | 742.7 |

TABLE 4-15-continued

| Example No. | Compound Name | Structure | Salt | MS |
|---|---|---|---|---|
| 67 | (S)-N-((S)-1-cyclohexyl-2-(4-(5,6-difluoro-4-(2-(2-(2-hydroxyethoxy)ethoxy)-ethoxy)-1-methyl-1H-indole-2-carbonyl)-piperazin-1-yl)-2-oxoethyl)-2-(methylamino)propanamide | 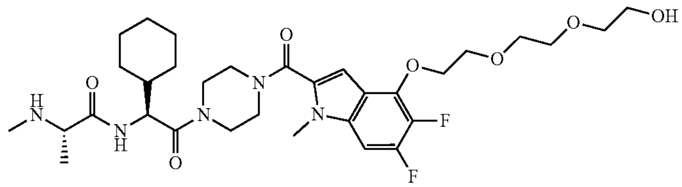 [SMILES: CN[C@@H](C)C(=O)N[C@H](C(=O)N1CCN(C(=O)c2cc3c(OCCOCCOCCO)c(F)c(F)cc3n2C)CC1)C1CCCCC1] | | 652.6 |
| 68 | (S)-N-((S)-1-cyclohexyl-2-(4-(5,6-difluoro-4-(2-(2-(2-hydroxyethoxy)ethoxy)ethoxy)-1-methyl-1H-indole-2-carbonyl)piperazin-1-yl)-2-oxoethyl)-2-(methylamino)propanamide | 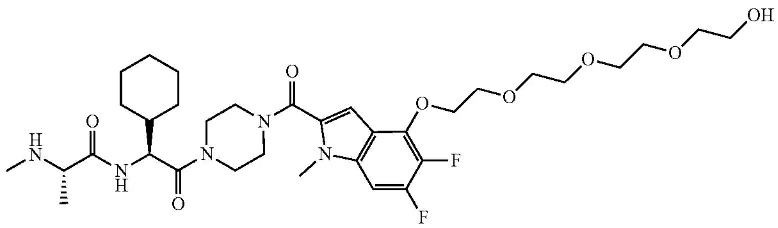 [SMILES: CN[C@@H](C)C(=O)N[C@H](C(=O)N1CCN(C(=O)c2cc3c(OCCOCCOCCOCCO)c(F)c(F)cc3n2C)CC1)C1CCCCC1] | | 696.6 |

TABLE 4-16

| Example No. | Compound Name | Structure | Salt | MS |
|---|---|---|---|---|
| 69 | (S)-N-((S)-1-cyclohexyl-2-(4-(1-(2-(2-)-2-hydroxyethoxy)ethoxy)ethyl)-2-methyl-1H-indole-5-carbonyl)piperazin-1-yl)-2-oxoethyl)-2-(methylamino)propanamide | 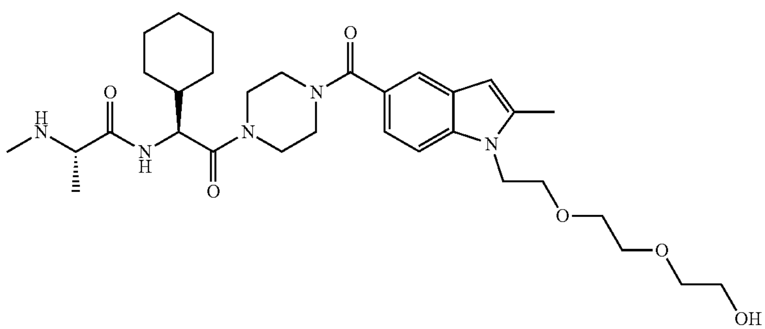 [SMILES: CN[C@@H](C)C(=O)N[C@H](C(=O)N1CCN(C(=O)c2ccc3c(c2)cc(C)n3CCOCCOCCO)CC1)C1CCCCC1] | | 600.6 |
| 70 | (S)-N-((S)-1-cyclohexyl-2-(4-(1-(2-(2-)-2-(2-hydroxyethoxy)ethoxy)ethoxy)ethyl)-2-methyl-1H-indole-5-carbonyl)piperazin-1-yl)-2-oxoethyl)-2-(methylamino)propanamide | 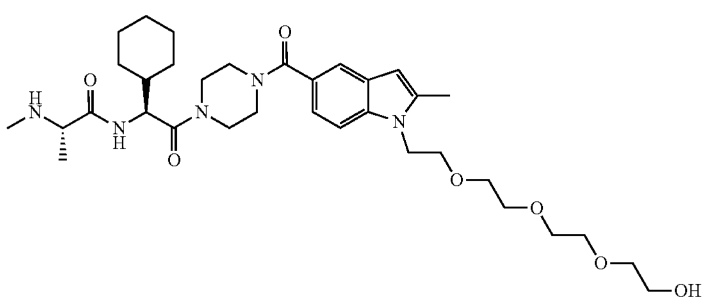 [SMILES: CN[C@@H](C)C(=O)N[C@H](C(=O)N1CCN(C(=O)c2ccc3c(c2)cc(C)n3CCOCCOCCOCCO)CC1)C1CCCCC1] | | 644.6 |
| 71 | (S)-N-((S)-1-cyclohexyl-2-(4-(3-fluoro-1-(2-(2-(2-hydroxyethoxy)ethoxy)ethyl)-2-methyl-1H-indole-5-carbonyl)piperazin-1-yl)-2-oxoethyl)-2-(methylamino)propanamide | 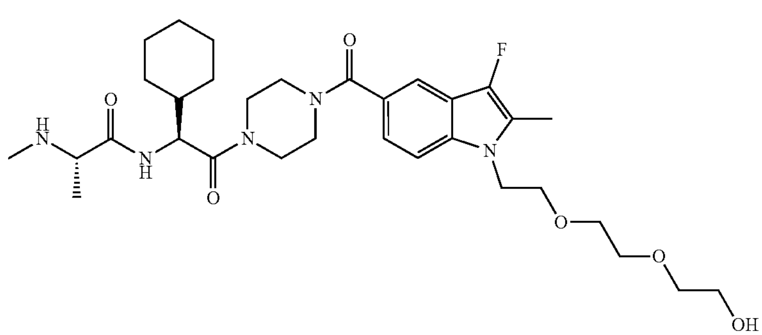 [SMILES: CN[C@@H](C)C(=O)N[C@H](C(=O)N1CCN(C(=O)c2ccc3c(c2)c(F)c(C)n3CCOCCOCCO)CC1)C1CCCCC1] | | 618.4 |

TABLE 4-16-continued

| Example No. | Compound Name | Structure | Salt | MS |
|---|---|---|---|---|
| 72 | N-(2-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-(4-((S)-2-cyclohexyl-2-((S)-2-(methylamino)propanamido)acetyl)piperazine-1-carbonyl)-6-methoxy-1-methyl-1H-indole-3-carboxamide | 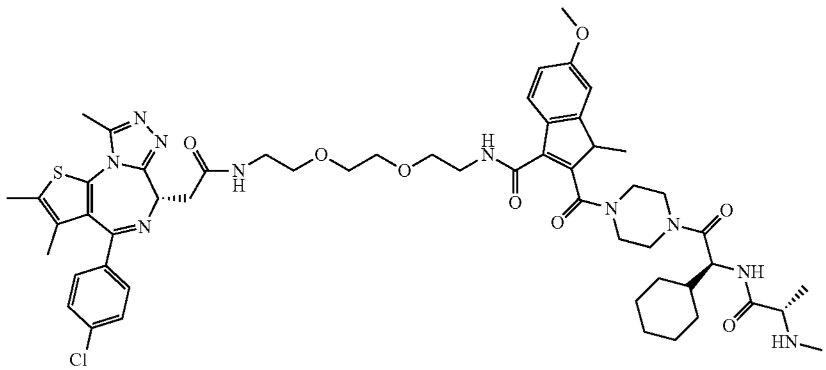 | HCl | 1054.7 |

TABLE 4-17

| Example No. | Name | Structure | Salt | MS |
|---|---|---|---|---|
| 73 | N-(1-((S)-4-(4-chlorophenyl)-2,3,9-trimethyl-6H-thieno[3,2-f][1,2,4]triazolo[4,3-a][1,4]diazepin-6-yl)-2-oxo-6,9,12-trioxa-3-azatetradecan-14-yl)-2-(4-((S)-2-cyclohexyl-2-((S)-2-(methylamino)propanamido)acetyl)piperazine-1-carbonyl)-6-methoxy-1-methyl-1H-indole-3-carboxamide | 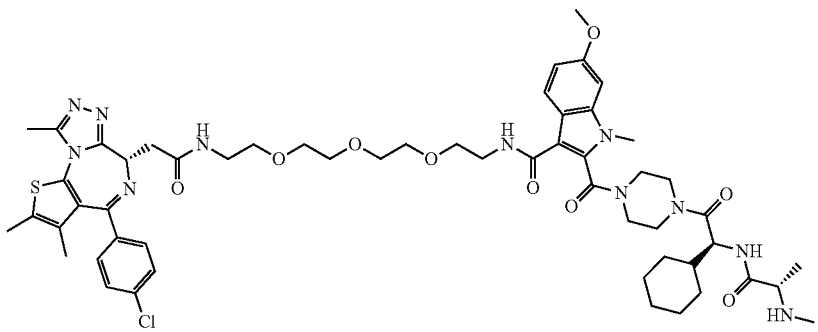 | HCl | 1098.5 |
| 74 | N-(1-((S)-4-(4-chlorophenyl)-2,3,9-trimethyl-6H-thieno[3,2-f][1,2,4]triazolo[4,3-a][1,4]diazepin-6-yl)-2-oxo-6,9,12-trioxa-3-azatetradecan-14-yl)-2-(4-((S)-2-cyclohexyl-2-((S)-2-(methylamino)propanamido)acetyl)piperazine-1-carbonyl)-5,6-difluoro-1-methyl-1H-indole-3-carboxamide | 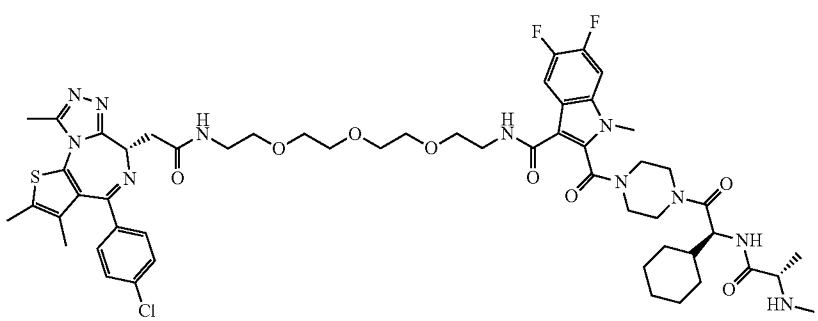 | TFA | 1105.1 |
| 75 | (S)-N-((S)-2-(4-(1-(2-((2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethyl)amino)-2-oxoethyl)-5-fluoro-1H-indole-2-carbonyl)piperazin-1-yl)-1-cyclohexyl-2-oxoethyl)-2-(methylamino)propanamide | 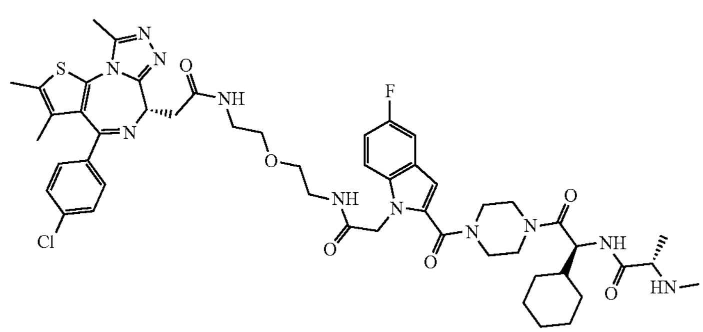 | | 998.8 |

TABLE 4-18

| Example No. | Compound Name | Structure | Salt | MS |
|---|---|---|---|---|
| 76 | (S)-N-((S)-2-(4-(1-)-14-((S)-4-(4-chlorophenyl)-2,3,9-trimethyl-6H-thieno[3,2-f] [1,2,4]triazolo [4,3-a] [1,4]diazepin-6-yl)-2,13-dioxo-6,9-dioxa-3,12-diazatetradecyl)-5-fluoro-1H-indole-2-carbonyl)piperazin-1-yl)-1-cyclohexyl-2-oxoethyl)-2-(methylamino)propanamide | 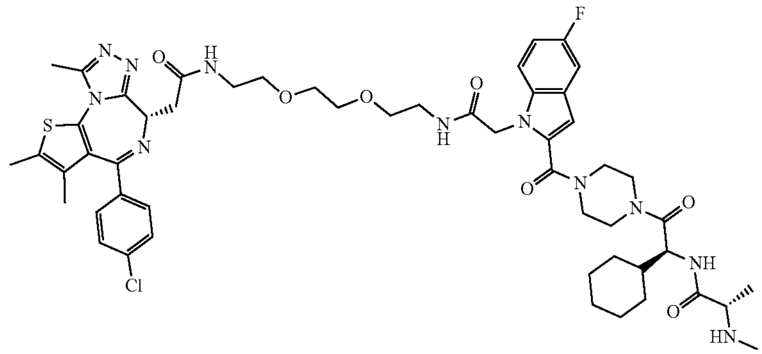 | | 1042.4 |
| 77 | (S)-N-((S)-2-(4-(1-17-((S)-4-(4-chlorophenyl)-2,3,9-trimethyl-6H-thieno[3,2-f] [1,2,4]triazolo [4,3-a] [1,4]diazepin-6-yl)-2,16-dioxo-6,9,12-trioxa-3,15-diazaheptadecyl)-5-fluoro-1H-indole-2-carbonyl)piperazin-1-yl)-1-cyclohexyl-2-oxoethyl)-2-(methylamino)propanamide | 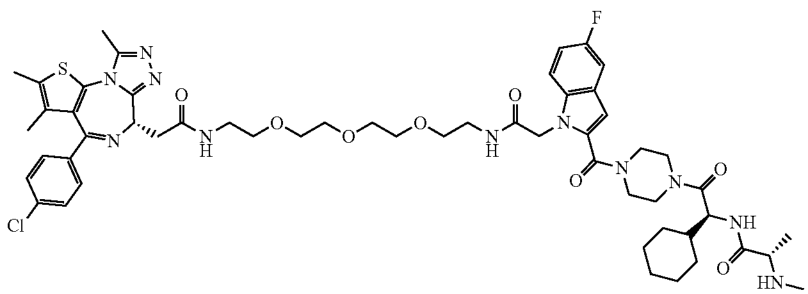 | | 1086.3 |
| 78 | N-(2-(2-(2-(4-(2-((S)-4-(4-chlorophenyl)-2,3,9-trimethyl-6H-thieno[3,2-f][1,2,4]triazolo[4,3-a][1,4]diazepin-6-yl)acetamido)phenoxy)thoxy)ethoxy)ethyl)-2-(4-((S)-2-cyclohexyl-2-((S)-2-(methylamino)propanamido)-acetyl) piperazine-1-carbonyl)-5,6-difluoro-1-methyl-1H-indole-3-carboxamide | 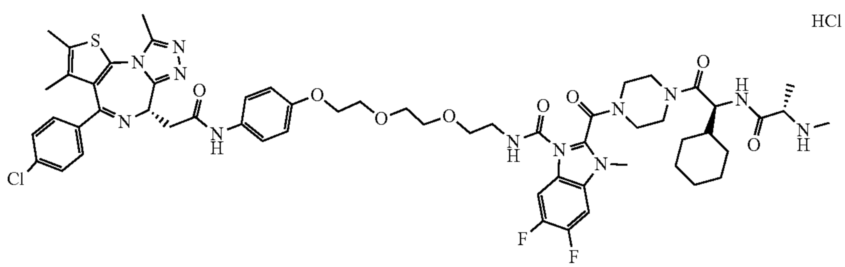 | HCl | 1152.8 |

TABLE 4-19

| Example No. | Name | Structure | Salt | MS |
|---|---|---|---|---|
| 79 | N-(2-(2-(2-(2-(4-(2-((S)-4-(4-chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethoxy)ethyl)-2-(4-((S)-2-cyclohexyl-2-((S)-2-(methylamino)-propanamido)acetyl)-piperazine-1-carbonyl)-5,6-difluoro-1-methyl-1H-indole-3-carboxamide | 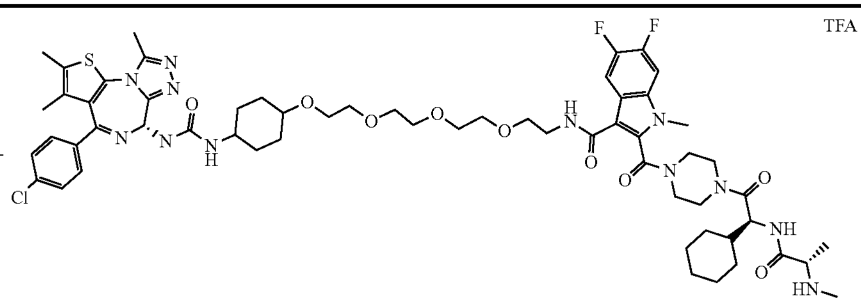 | TFA | 1197.1 |

TABLE 4-19-continued

| Example No. | Name | Structure | Salt | MS |
|---|---|---|---|---|
| 80 | N-(2-chloro-6-methyl-phenyl)-2-((6-(4-(2-(2-(2-(4-((S)-2-cyclohexyl-2-((S)-2-)-methylamino)propan-amido)acetyl)piper-azine-1-carbonyl)-5,6-difluoro-1-methyl-1H-indole-3-carbox-amido)ethoxy)ethyl)piperazin-1-yl)-2-methylpyrimidin-4-yl)-amino)thiazole-5-carboxamide | 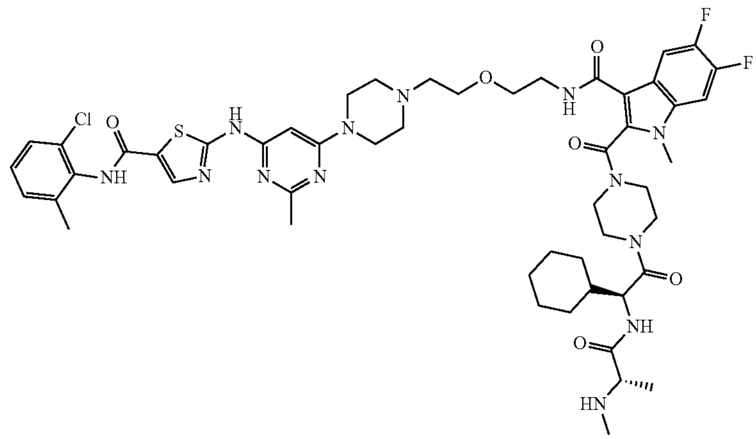 [SMILES: CN[C@@H](C)C(=O)N[C@H](C(=O)N1CCN(C(=O)c2c(C(=O)NCCOCCN3CCN(c4cc(Nc5ncc(C(=O)Nc6c(C)cccc6Cl)s5)nc(C)n4)CC3)c3cc(F)c(F)cc3n2C)CC1)C1CCCCC1] | TFA | 1060.8 |
| 81 | N-(2-chloro-6-methyl-phenyl)-2-((6-(4-(2-(2-(2-(2-(4-((S)-2-cyclohexyl-2-((S)-2-(methylamino)pro-panamido)acetyl)piper-azine-1-carbonyl)-5,6-difluoro-1-me-thyl-1H-indole-3-car-boxamido)eth-oxy)ethyl)piperazin-1-yl)-2-methylpy-rimidin-4-yl)amino)-thiazole-5-carboxamide | 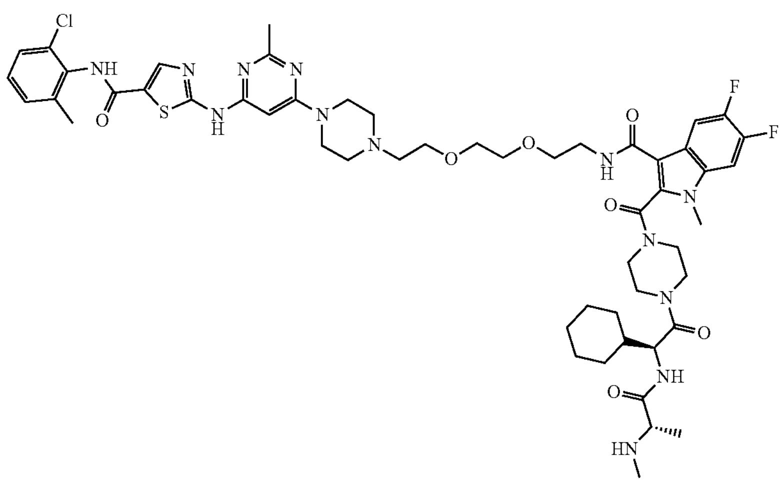 [SMILES: CN[C@@H](C)C(=O)N[C@H](C(=O)N1CCN(C(=O)c2c(C(=O)NCCOCCOCCN3CCN(c4cc(Nc5ncc(C(=O)Nc6c(C)cccc6Cl)s5)nc(C)n4)CC3)c3cc(F)c(F)cc3n2C)CC1)C1CCCCC1] | TFA | 1150.0 |

TABLE 4-20

| Example No. | Name | Structure | Salt | MS |
|---|---|---|---|---|
| 82 | N-(2-chloro-6-methyl-phenyl)-2-((6-(4-(1-(2-(4-((S)-2-cyclo-hexyl-2-((S)-2-(meth-ylamino)propana-mido)acetyl)piper-azine-1-carbonyl)-5,6-difluoro-1-methyl-1H-indol-3-yl)-1-oxo-5,8,11-trioxa-2-aza-tridecan-13-yl)piper-azin-1-yl)-2-methyl-pyrimidin-4-yl)-amino)thiazole-5-carbox-amide | 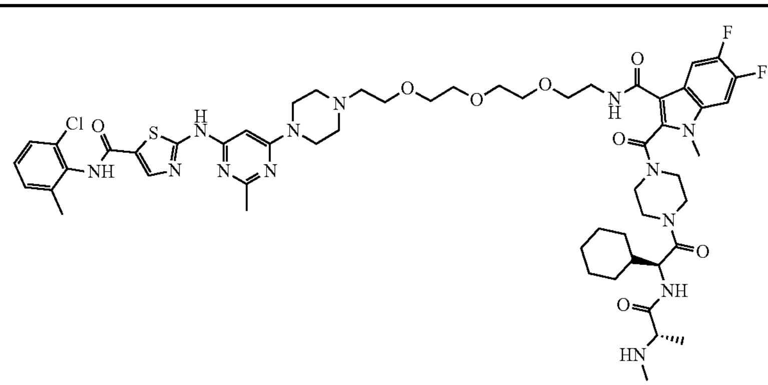 | TFA | 1149.0 |

TABLE 4-20-continued

| Example No. | Name | Structure | Salt | MS |
|---|---|---|---|---|
| 83 | N-(2-chloro-6-methylphenyl)-2-((6-(4-(2-(2-(2-(((2R, 5R)-1-(2-((R)-4-(5,6-difluoro-1-methyl-1H-indole-2-carbonyl)-2-methylpiperazin-1-yl)-2-oxoethyl)-5-methylpiperazin-2-yl)methoxy)ethoxy)ethoxy)ethyl)piperazin-1-yl)-2-methylpyrimidin-4-yl)amino)-thiazole-5-carboxamide | 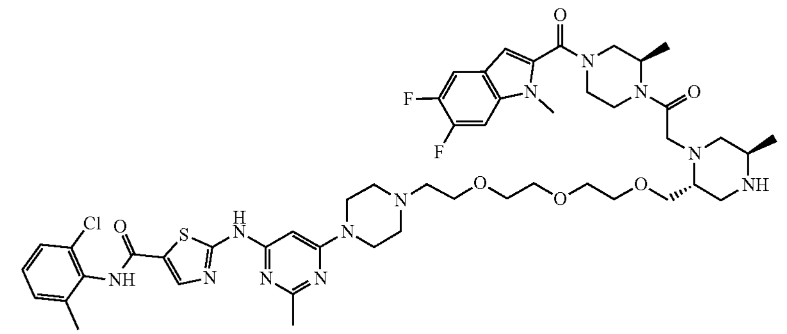 [SMILES: Cc1nc(Nc2ncc(C(=O)Nc3c(C)cccc3Cl)s2)cc(N2CCN(CCOCCOCCOC[C@H]3CN[C@H](C)CN3CC(=O)N3CCN(C(=O)c4cc5cc(F)c(F)cc5n4C)C[C@H]3C)CC2)n1] | TFA | 1021.5 |
| 84 | N-(2-chloro-6-methylphenyl)-2-((6-(4-(1-(2-(4-((S)-2-cyclohexyl-2-((S)-2-(methylamino) propanamido)acetyl)piperazine-1-carbonyl)-5-fluoro-1-methyl-1H-indol-3-yl)-1-oxo-5,8,11-trioxa-2-azatridecan-13-oyl)piperazin-1-yl)-2-methylpyrimidin-4-yl)amino)thiazole-5-carboxamide | 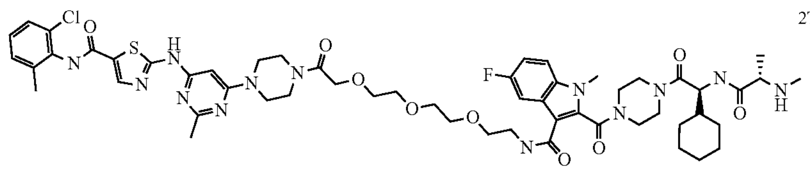 | 2TFA | 1144.9 |

TABLE 4-21

| Example No. | Compound Name | Structure | Salt | MS |
|---|---|---|---|---|
| 85 | N-(2-chloro-6-methylphenyl)-2-((6-(4-(2-(2-(2-(2-(4-((S)-2-cyclohexyl-2-((S)-2-(methylamino)propanamido)acetyl)piperazine-1-carbonyl)-5-fluoro-1-methyl-1H-indole-3-carboxamido)ethoxy)ethoxy)acetyl)piperazin-1-yl)-2-methylpyrimidin-4-yl)amino)thiazole-5-carboxamide | 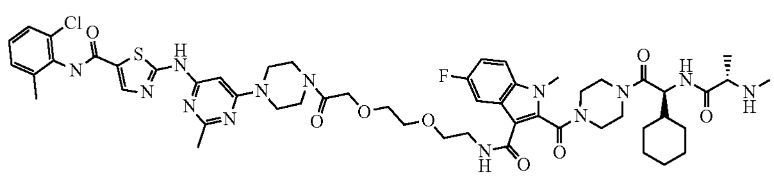 [SMILES: CN[C@@H](C)C(=O)N[C@H](C(=O)N1CCN(C(=O)c2c(C(=O)NCCOCCOCC(=O)N3CCN(c4cc(Nc5ncc(C(=O)Nc6c(C)cccc6Cl)s5)nc(C)n4)CC3)c3cc(F)ccc3n2C)CC1)C1CCCCC1] | 2TFA | 1099.5 |
| 86 | N,N'-((ethane-1,2-diylbis(oxy))bis-(ethane-2,1-diyl))bis(2-(4-((S)-2-cyclohexyl-2-((S)-2-(methylamino)propanamido)acetyl)piperazine-1-carbonyl)-5-fluoro-1-methyl-1H-indole-3-carboxamide) | 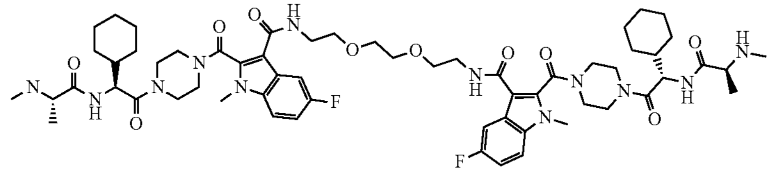 | 2TFA | 1172.1 |

TABLE 4-21-continued

| Example No. | Compound Name | Structure | Salt | MS |
|---|---|---|---|---|
| 87 | (S)-N-((S)-1-cyclohexyl-2-(4-(1-(2-((2-(2-(2-(2-(4-((R)-2-cyclohexyl-2-((R)-2-(methylamino)-propanamido)acetyl)-piperazine-1-carbonyl)-5-fluoro-1H-indol-1-yl)acetamido)ethoxy)ethyl)-amino)-2-oxoethyl)-5-fluoro-1H-indole-2-carbonyl)piperazin-1-yl)-2-oxoethyl)-2-(methylamino)-propanamide | 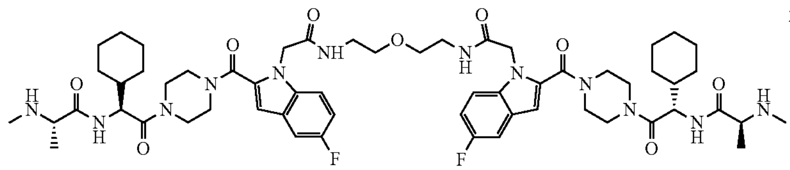 | 2TFA | 1128.6 |

Experimental Example 1: Measurement of XIAP Binding Inhibitory Activity

Human XIAP binding inhibitory activity were measured by the Homogeneous Time Resolved Fluorescence (HTRF) method with using commercially available human XIAP_BIR3 domain purified protein (R & D) and as a ligand a Smac N-terminal peptide (AVPIAQK (SEQ ID NO: 1)) (hereinafter referred to as "b-Smac"; Peptide Research Laboratories, Inc.) biotinylated at the C-terminus according to a conventional method.

The HTRF method will be described in detail below.

A test compound diluted with a reaction buffer was added to a 384-well white shallow bottom plate (Greiner 784076) at 1 μL/well and flash centrifuged for 30 seconds.

Subsequently, human XIAP_BIR3 domain purified protein was diluted with the reaction buffer (25 mM HEPES Buffer containing 100 mM NaCl, 0.1% BSA, and 0.1% triton X-100, pH 7.5) to obtain a 90 nM sample diluent, and the resultant sample diluent was added to the above-mentioned white superficial plate at 4.5 μL/well and flash centrifuged for 30 seconds. Subsequently, b-Smac diluted to 90 nM with the reaction buffer was added to the above-mentioned white superficial plat at 4.5 μL/well and flash centrifuged for 30 seconds. A mixed solution of Anti-6 HIS-Cryptate (Eu3+ Cryptate-conjugated mouse monoclonal antibody anti-6 Histidine; cisbio) and Streptavidin-XL$^{ent!}$ (Highgrade XL665-conjugated streptavidin; cisbio) both diluted 100-fold with HTRF detection buffer (cisbio) at a volume ratio of 1:1 was added to the above white superficial plate at 10 μL/well. After flash centrifuging the white shallow bottom plate for 30 seconds, the white shallow bottom plate was left at room temperature for 4 hours or more in the dark. The white superficial plate after being left was subjected to fluorescence intensity measurement (excitation wavelength: 320 nm, fluorescence wavelength: 665 nm and 615 nm) by EnVision (Perkin Elmer).

The binding inhibition rate (%) was calculated based on the HTRF ratio in the presence of the test compound to the HTRF ratio in the absence of the test compound (fluorescence intensity at 665 nm/fluorescence intensity at 615 nm).

As to the XIAP binding inhibition rate (%) of test compounds, XIAP binding inhibition ratio described as A≥75%, 75%>B≥50%, 50%>C≥25%, D>25% when the concentration of the test compound is 3 μM, or 50% inhibitory concentration (IC50 value) described as A<0.3 μM, 0.3 μM≤B<3 μM, 3 μM≤C<30 μM, are shown in the table below.

TABLE 5

| Compound | *Binding inhibition rate |
|---|---|
| Example 1 | A/— |
| Example 2 | C/— |
| Example 3 | C/— |
| Example 4 | B/— |
| Example 5 | C/— |
| Example 6 | D/— |
| Example 7 | A/— |
| Example 8 | D/— |
| Example 9 | D/— |
| Example 10 | D/— |
| Example 11 | D/— |
| Example 12 | D/— |
| Example 13 | D/— |
| Example 14 | B/— |
| Example 15 | A/— |
| Example 16 | B/— |
| Example 17 | D/— |
| Example 18 | D/— |
| Example 19 | D/— |
| Example 20 | A/— |
| Example 21 | D/— |
| Example 22 | C/— |
| Example 23 | D/— |
| Example 24 | A/— |
| Example 25 | A/— |
| Example 26 | B/— |
| Example 27 | A/— |
| Example 28 | B/— |
| Example 29 | B/— |
| Example 30 | B/— |
| Example 31 | B/— |
| Example 32 | B/— |
| Example 33 | A/— |
| Example 34 | A/— |
| Example 35 | A/— |
| Example 36 | A/— |
| Example 37 | B/— |
| Example 38 | A/— |
| Example 39 | B/— |
| Example 40 | A/— |
| Example 41 | A/— |
| Example 42 | A/— |
| Example 43 | A/— |
| Example 44 | —/C |
| Example 45 | —/C |
| Example 46 | —/C |
| Example 47 | —/C |

TABLE 5-continued

| Compound | *Binding inhibition rate |
|---|---|
| Example 48 | —/C |
| Example 49 | —/C |
| Example 50 | —/C |
| Example 51 | —/C |
| Example 52 | —/C |
| Example 53 | —/C |
| Example 54 | —/C |
| Example 55 | A/— |
| Example 56 | —/C |
| Example 57 | —/B |
| Example 58 | —/B |
| Example 59 | —/C |
| Example 60 | —/C |
| Example 61 | A/— |
| Example 62 | C/— |
| Example 63 | C/— |
| Example 64 | —/C |
| Example 65 | —/C |
| Example 66 | —/C |
| Example 67 | —/B |
| Example 68 | —/B |
| Example 69 | —/A |
| Example 70 | —/B |
| Example 71 | A/— |
| Example 72 | —/A |
| Example 73 | —/A |
| Example 74 | C/— |
| Example 75 | D/— |
| Example 76 | D/— |
| Example 77 | D/— |
| Example 78 | —/B |
| Example 79 | —/B |
| Example 80 | —/B |
| Example 81 | —/B |
| Example 82 | —/B |
| Example 83 | —/C |
| Example 84 | B/— |
| Example 85 | B/— |
| Example 86 | A/ A |
| Example 87 | A/— |

*Binding inhibition rate: binding inhibition rate when the concentration of the test compound is 3 μM/IC50 value From the above results, it was shown that the compounds of the present invention have an excellent IAP (in particular XIAP) binding (inhibition) activities.

Experimental Example 2: Measurement of Binding Inhibitory Activity of GSK3α/β and GCN2

Each of GSK3α/β and GCN2 binding inhibitory activity was evaluated using active site-dependent competitive assay KINOMEscan provided by Discover X (Goldstein, D. M. et al. High-throughput kinase profiling as a platform for drug discovery. Nat. Rev. Drug Discovery. 7, 391-397 (2008)). the "% Ctrl" when the concentration of the test compound is 1 μM is shown in the table below. The "% Ctrl" is calculated by the following formula.

(test compound signal−positive control compound signal)/(negative control compound signal−positive control compound signal)×100

Negative control compound=DMSO (100% Ctrl)
Positive control compound=control compound (0% Ctrl)

TABLE 6

| Compound | GSK3α | GSK3β | GCN2 |
|---|---|---|---|
| Example 55 | 39% | 11% | 0.35% |

Experimental Example 3: Measurement of in vitro Degradation Activity of GSK3α/β and GCN2

In vitro degradation activities of GSK3α/β and GCN2 of the example compounds were evaluated by the following method. THP1 cells were purchased from ATCC and cultured in RPMI-1640 supplemented with 10% FBS and 1% penicillin/streptomycin. THP1 cells were seeded at a density of $1 \times 10^6$ cells/well in 24-well plate and treated with DMSO control or Example 55 (1, 3, 10 μM), and then incubated for 24 hours. The cells were collected and lysed on ice for 30 minutes in RIPA buffer (Thermo Fisher #87787) containing a protease inhibitor cocktail (Sigma-Aldrich). The lysates were sonicated for 30 sec ON/30 sec OFF for ten cycles and centrifuged for 15 minutes at 15 krpm at 4° C. Protein concentrations were determined by the BCA assay (Thermo Fisher). Proteins were separated with Nu-PAGE (Thermo Fisher) and analyzed by western blotting (standard protocol) using antibodies of anti-GSK3α/β (Cell Signaling #5676), GCN2 (Cell Signaling #3302), and β-actin (Sigma #A2066) (FIG. 1). Bands (luminescent intensities) were quantified using LAS-4000 luminescent image analyzer (Fuji). The values of GSK3α/β and GCN2 were corrected by the internal control value of β-actin and analyzed relative to DMSO control set at 100. The results are shown in the table below. The remaining protein rate (%) are described as A≤25, 25%<B≤50%, 50%<C≤75, D>75% when the concentration of the test compound is 10 μM.

TABLE 7

| Compound | GSK3α | GSK3β | GCN2 |
|---|---|---|---|
| Example 55 | B | B | A |

Figure 2:
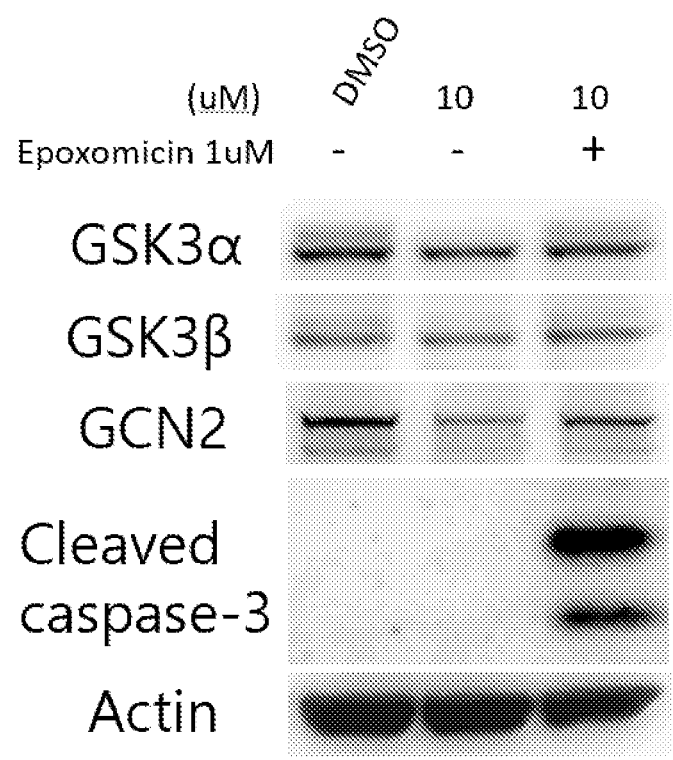
FIG. 2 shows the results of Western blotting confirming that GSK3α/β and GCN2 degradation activities of the example compounds are canceled by epoxomicin, a proteasome inhibitor.

Experimental Example 4: Molecular Mechanism: Studies of the Ubiquitin-Proteasome System Dependency THP1 cells were seeded at a density of $1 \times 10^6$ cells/well in 24-well plate and treated with DMSO control or Example 55 (10 μM) with or without 1 μM of Epoxomicin and incubated for 8 hours. The cells were collected and lysed on ice for 30 minutes in RIPA buffer (Thermo Fisher #87787) containing a protease inhibitor cocktail (Sigma-Aldrich). The lysates were sonicated for 30 sec ON/30 sec OFF for ten cycles and centrifuged for 15 minutes at 15 krpm at 4° C. Protein concentrations were determined by the BCA assay (Thermo Fisher). Proteins were separated with Nu-PAGE (Thermo Fisher) and analyzed by western blotting (standard protocol) using antibodies of anti-GSK3α/β (Cell Signaling #5676), GCN2 (Cell Signaling #3302), and β-actin (Sigma #A2066) (FIG. 2).

FIG. 1 shows the protein levels of GSK3α/β and GCN2 treated with Example 55 in THP1 human monocyte-derived cells and its degradation activity. FIG. 2 shows that the degradation activity of GSK3α/β and GCN2 treated with Example 55 were cancelled by the proteasome inhibitor Epoxomicin treatment.

Experimental Example 5: Measurement of In Vitro Degradation Activity of BCR-ABL

In vitro degradation activities of BCR-ABL of the example compounds were evaluated by the following method. K562 cells were purchased from ECACC and cultured in RPMI-1640 supplemented with 10% FBS and 1% penicillin/streptomycin. K562 cells were seeded at a density of $1\times10^6$ cells/well in 24-well plate and treated with DMSO control or Example 80 and 81 (1, 3, 10, 30 µM), and then incubated for 24 hours. The cells were collected and lysed on ice for 30 minutes in lysis buffer (0.5% Triton X-100, 0.01 M Tris-HCl (pH 8.0), 0.15 M NaCl) containing a protease inhibitor cocktail (Sigma-Aldrich). The lysates were vortexed for 2 minutes and centrifuged for 15 minutes at 15 krpm at 4° C. Protein concentrations were determined by the BCA assay (Thermo Fisher). Proteins were separated with Nu-PAGE (Thermo Fisher) and analyzed by western blotting (standard protocol) using antibodies of anti-BCR (Cell Signaling #3902), and β-actin (Sigma #A2066). Bands (luminescent intensities) were quantified using LAS-4000 luminescent image analyzer (Fuji). The values of BCR-ABL were corrected by the internal control value of β-actin and analyzed relative to DMSO control set at 100. The results are shown in the table below. The remaining protein rate (%) are described as A≤25%, 25%<B≤50%, 50%<C≤75%, D>75% when the concentration of the test compound is 30 µM.

TABLE 8

| Compound | BCR-ABL |
|---|---|
| Example 80 | C |
| Example 81 | D |

Experimental Example 6: Measurement of In Vitro Degradation Activity of XIAP

In vitro degradation activities of XIAP of the example compounds were evaluated by the following method. THP1 cells were purchased from ATCC and cultured in RPMI-1640 supplemented with 10% FBS and 1% penicillin/streptomycin. THP1 cells were seeded at a density of $1\times10^6$ cells/well in 24-well plate and treated with DMSO control or Example 86 and 87 (0.001, 0.01, 0.1, 1, 10 µM), and then incubated for 24 hours. The cells were collected and lysed on ice for 30 minutes in lysis buffer (0.5% Triton X-100, 0.01 M Tris-HCl (pH 8.0), 0.15 M NaCl) containing a protease inhibitor cocktail (Sigma-Aldrich). The lysates were sonicated for 30 sec ON/30 sec OFF for ten cycles and centrifuged for 15 minutes at 15 krpm at 4° C. Protein concentrations were determined by the BCA assay (Thermo Fisher). Proteins were separated with Nu-PAGE (Thermo Fisher) and analyzed by western blotting (standard protocol) using antibodies of anti-XIAP (Cell Signaling #14334), and β-actin (Sigma #A2066). Bands (luminescent intensities) were quantified using LAS-4000 luminescent image analyzer (Fuji). The values of XIAP were corrected by the internal control value of β-actin and analyzed relative to DMSO control set at 100. The results are shown in the table below. The remaining protein rate (%) are described as A≤25%, 25%<B≤50%, 50%<C≤75%, D>75% when the concentration of the test compound is 10 µM.

TABLE 9

| Compound | XIAP |
|---|---|
| Example 86 | C |
| Example 87 | C |

Based on the above results, it was shown that the compound of the present invention can provide biologically useful activity when binding to two target proteins including XIAP (bi-functional compound)(including a case where both target proteins are both XIAP). For example, it was shown to have superior binding activity to a IAP (particularly XIAP) and to have a targeted protein degradation-inducing activity depending on a ubiquitin-proteasome system.

Formulation Example 1

A medicament containing the compound of the present invention as an active ingredient can be produced, for example, by the following composition.

1. Capsule

| | |
|---|---|
| (1) Compound obtained in Example 1 | 40 mg |
| (2) Lactose | 70 mg |
| (3) Microcrystalline cellulose | 9 mg |
| (4) Magnesium stearate | 1 mg |
| 1 capsule | 120 mg |

After mixing (1), (2), (3) and 1/2 volume of (4), the mixture is granulated. The remaining (4) is added to this, and then the whole is encapsulated in a gelatin capsule.

2. Tablet

| | |
|---|---|
| (1) Compound obtained in Example 1 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| 1 tablet | 120 mg |

After mixing (1), (2), (3) and 2/3 volume of (4) and 1/2 volume of (5), the mixture is granulated. Then, the remaining (4) and (5) are added to the granules and pressed-molded into tablets.

Formulation Example 2

After dissolving 50 mg of the compound obtained in Example 1 in 50 mL of distilled water for injection (Japanese Pharmacopoeia grade), the distilled water for injection is added to make 100 mL. The solution is filtered under sterile conditions, then, 1 mL each of this solution is taken, filled under sterile conditions into vials for injection, lyophilized and sealed.

The foregoing merely illustrates objects and subjects of the present invention, and is not intended to be limiting the accompanying Claims. Without departing from the accompanying Claims, various modifications and alterations to the described embodiments will be apparent to those skilled in the art in view of the teachings herein.

INDUSTRIAL APPLICABILITY

The compound of the present invention has an IAP (particularly XIAP) binding (inhibiting) activity and is expected to provide a drug that can be used for XIAP-related diseases. Further, the compound of the present invention can also bind to a target protein and provide useful activity, and is expected to provide a drug effective for prophylaxis or treatment of a disease related to the target protein.

The invention claimed is:

1. A compound represented by the following formula (I):

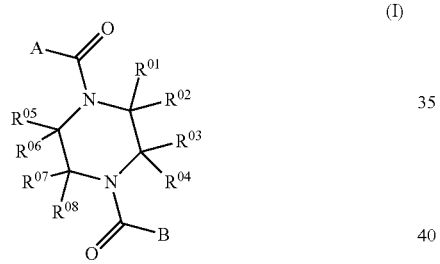

(I)

wherein $R^{01}$, $R^{02}$, $R^{03}$, $R^{04}$, $R^{05}$, $R^{06}$, $R^{07}$ and $R^{08}$ each independently represent a hydrogen atom or a C1-6 alkyl group which optionally forms a ring with each other, A represents a group represented by the formula (AI-1)

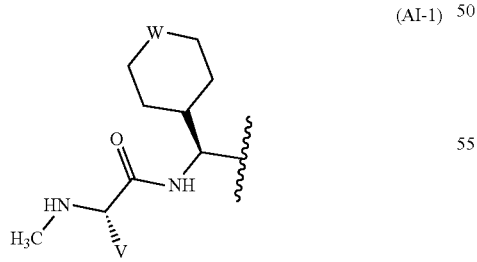

(AI-1)

wherein V represents an optionally halogenated C1-3 alkyl group; W represents a methylene group, a difluoromethylene group, O, S, SO, $SO_2$, NR wherein R represents a hydrogen atom, a C1-6 alkyl group, a C1-6 alkyl-carbonyl group, a C6-14 aryl-carbonyl group or a C1-6 alkylsulfonyl group, an imino group, or the formula (L1): $N-L^{11}-L^{12}-L^{13}-L^{14}-L^{15}-L^{16}-L^{17}-R^1$ wherein $L^{11}$, $L^{12}$, $L^{13}$, $L^{14}$, $L^{15}$, $L^{16}$ and $L^{17}$ each independently represent a bond, an oxygen atom, a sulfur atom, a C1-6 alkylene group, a C3-10 cycloalkylene group, a carbonyl group, an imino group optionally substituted with a C1-6 alkyl group, an ethynylene group, a vinylene group optionally substituted with a C1-6 alkyl group, a C3-10 cycloalkenylene group, a phenylene group, a thiazolilene group, a pyrrolidinylene group optionally substituted with a fluorine atom, an azetidinylene group optionally substituted with a fluorine atom, the formula —$SO_2$—, the formula —$CH_2CH_2O$—, the formula —$OCH_2CH_2$—, the formula —$COCH_2$—, the formula —$CH_2CO$—, the formula —$CO_2$—, the formula —OCO—, the formula —$COCHR^{101}NR^{102}$—, the formula —$OCH_2CHR^{103}NR^{104}$—, the formula —$NR^{105}CHR^{106}CO$—, the formula —$NR^{107}CO$—, the formula —$CONR^{108}$—, the formula —$SO_2NR^{109}$—, the formula —$NR^{110}SO_2$— or the formula —$NR^{111}CHR^{112}CH_2O$— wherein $R^{101}$, $R^{103}$, $R^{106}$ and $R^{112}$ each independently represent a hydrogen atom, a C1-6 alkyl group, a 3-guanidinopropyl group, a carbamoylmethyl group, a carboxymethyl group, a mercaptomethyl group, a 2-carbamoylethyl group, a 2-carboxyethyl group, an imidazole-4-ylmethyl group, a 4-aminobutyl group, a 2-methylthioethyl group, a benzyl group, a hydroxymethyl group, a 1-hydroxyethyl group, an indol-3-ylmethyl group, a 4-hydroxyphenylmethyl group or a pyridylmethyl group; and, $R^{102}$, $R^{104}$, $R^{105}$, $R^{107}$, $R^{108}$, $R^{109}$, $R^{110}$ and $R^{111}$ each independently represent a hydrogen atom or a C1-6 alkyl group; and $R^1$ represents a bond, a hydrogen atom, a methyl group, a benzyl group, a t-butoxycarbonyl group, a benzyloxycarbonyl group, a 9-fluorenylmethyloxycarbonyl group, an azide group, a group represented by the formula (II) as a ligand of GSK3α/β and GCN2

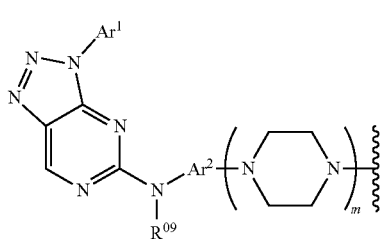

(II)

wherein Ar¹ represents an optionally substituted C6-14 aryl group or an optionally substituted aromatic heterocyclic group; Ar² represents a divalent group derived from an optionally substituted C6-14 aryl group or an optionally substituted aromatic heterocyclic group; m represents any integer of 0 to 1; $R^{09}$ represents a hydrogen atom or a C1-3 alkyl group, a group represented by the formula (III) as a ligand of BRD,

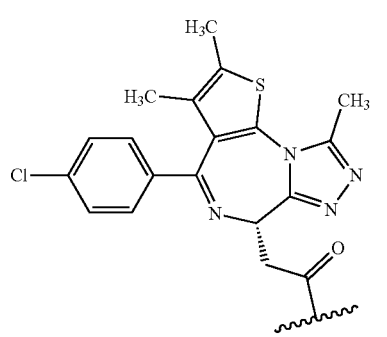

(III)

a group represented by the formula (IV) as a ligand of ABL, BCR-ABL, SRC, KIT, DDR, TEC, EPH-A2, and PDGFR,

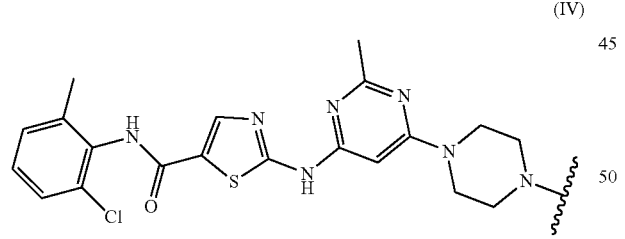

(IV)

or a compound of Smac peptide mimetics as a ligand of XIAP,

B represents a pyrazolyl group, an indolyl group, an indazolyl group, a benzoimidazoyl group, a 7-azaindolyl group, an indolidinyl group, a 1-azaindolidinyl group, a 3-azaindolidinyl group or a 1,3-diazaindolidinyl group, any of which optionally substituted with any of a halogen atom, a C3-10 cycloalkyl group, an optionally halogenated C1-6 alkyl group, a C1-6 alkoxy group, a C1-6 alkoxy group substituted with a C1-6 alkoxy group, or a vinyl group substituted with a C1-6 alkoxy-carbonyl group, or the following formula (B'):

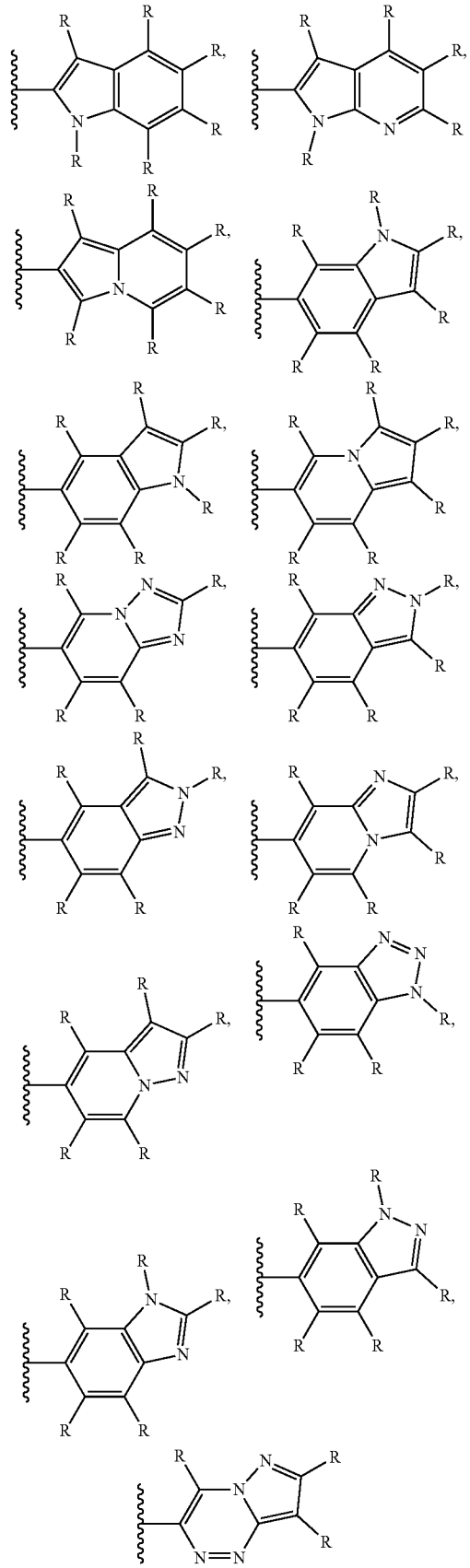

wherein R each independently represents a hydrogen atom, a halogen atom, a C1-6 alkyl group, a C1-6 alkoxy group, or the formula (L3): —Z-$L^{31}$-$L^{32}$-$L^{33}$-$L^{34}$-$L^{35}$-$L^{36}$-$L^{37}$-$R^3$ wherein Z represents an oxygen atom, a carbonyl group, a C1-6 alkylene group, a C3-10 cycloalkylene group, the formula —$NR^{31}$—, the formula —$CONR^{32}$—, the formula —$NR^{33}CO$—, the formula —$SO_2NR^{34}$— or the formula —$NR^{35}SO_2$— wherein $R^{31}$, $R^{32}$, $R^{33}$, $R^{34}$ and $R^{35}$ each independently represent a hydrogen atom or a C1-6 alkyl group; $L^{31}$, $L^{32}$, $L^{33}$, $L^{34}$, $L^{35}$, $L^{36}$ and $L^{37}$ each independently represent a bond, an oxygen atom, a sulfur atom, a C1-6 alkylene group, a C3-10 cycloalkylene group, a carbonyl group, an imino group optionally substituted with a C1-6 alkyl group, an ethynylene group, a vinylene group optionally substituted with a C1-6 alkyl group, a C3-10 cycloalkenylene group, a phenylene group, a thiazolilene group, a pyrrolidinylene group optionally substituted with a fluorine atom, an azetidinylene group optionally substituted with a fluorine atom, the formula —$SO_2$—, the formula —$CH_2CH_2O$—, the formula —$OCH_2CH_2$—, the formula —$COCH_2$—, the formula —$CH_2CO$—, the formula —$CO_2$—, the formula —$OCO$—, the formula —$COCHR^{301}NR^{302}$—, the formula —$OCH_2CHR^{303}NR^{304}$—, the formula —$NR^{305}CHR^{306}CO$—, the formula —$NR^{307}CO$—, the formula —$CONR^{308}$—, the formula —$SO_2NR^{309}$—, the formula —$NR^{310}SO_2$— or the formula —$NR^{311}CHR^{312}CH_2O$— wherein $R^{301}$, $R^{303}$, $R^{306}$ and $R^{312}$ each independently represent a hydrogen atom, a C1-6 alkyl group, a 3-guanidinopropyl group, a carbamoylmethyl group, a carboxymethyl group, a mercaptomethyl group, a 2-carbamoylethyl group, a 2-carboxyethyl group, an imidazole-4-ylmethyl group, a 4-aminobutyl group, a 2-methylthioethyl group, a benzyl group, a hydroxymethyl group, a 1-hydroxyethyl group, an indol-3-ylmethyl group, a 4-hydroxyphenylmethyl group or a pyridylmethyl group, and $R^{302}$, $R^{304}$, $R^{305}$, $R^{307}$, $R^{308}$, $R^{309}$, $R^{310}$ and $R^{311}$ each independently represent a hydrogen atom or a C1-6 alkyl group; and $R^3$ represents a bond, a hydrogen atom, a methyl group, a benzyl group, a t-butoxycarbonyl group, a benzyloxycarbonyl group, a 9-fluorenylmethyloxycarbonyl group, an azide group, a group represented by the formula (II) as a ligand of GSK3α/β and GCN2,

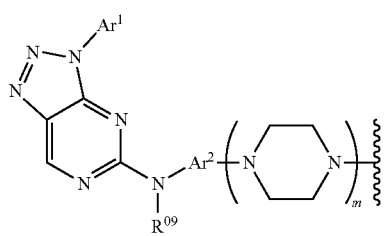

(II)

wherein $Ar^1$ represents an optionally substituted C6-14 aryl group or an optionally substituted aromatic heterocyclic group; $Ar^2$ represents a divalent group derived from an optionally substituted C6-14 aryl group or an optionally substituted aromatic heterocyclic group; m represents any integer of 0 to 1; and $R^{09}$ represents a hydrogen atom or a C1-3 alkyl group, a group represented by the formula (III) as a ligand of BRD,

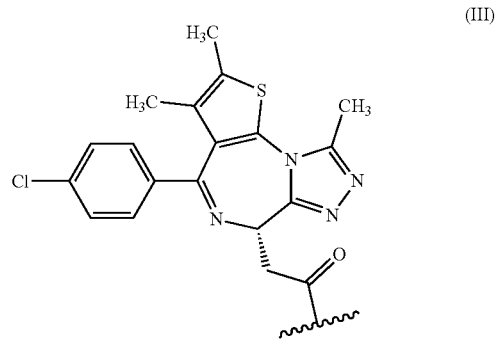 [SMILES: *C(=O)C[C@@H]1N=C(c2ccc(Cl)cc2)c2c(sc(C)c2C)-n2c(C)nnc21]

(III)

a group represented by the formula (IV) as a ligand of ABL, BCR-ABL, SRC, KIT, DDR, TEC, EPH-A2, and PDGFR,

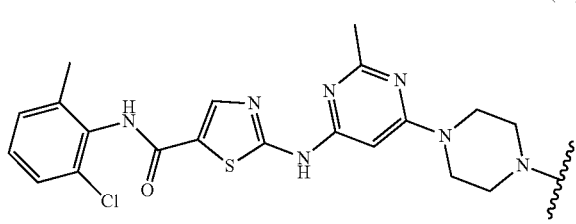

(IV)

or a compound of Smac peptide mimetics as a ligand of XIAP, wherein when R binds to N, R is not a halogen atom or a C1-6 alkoxy group, and two or more groups R are not simultaneously represented by the formula (L3), or a salt thereof.

2. The compound or salt thereof according to claim 1, wherein B in the formula (I) is represented by the formula (B-1)

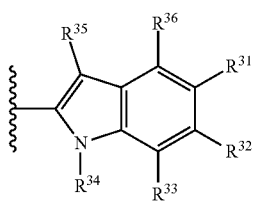

(B-1)

wherein $R^{31}$, $R^{32}$, and $R^{33}$ each independently represent a hydrogen atom, a halogen atom, a C1-6 alkyl group or a C1-6 alkoxy group; $R^{35}$ and $R^{36}$ each independently represent a hydrogen atom, a halogen atom, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above, $R^{34}$ represents a hydrogen atom, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above, wherein two or more of $R^{34}$, $R^{35}$ and $R^{36}$ are not simultaneously represented by the formula (L3).

3. The compound or salt thereof according to claim 1, wherein B in the formula (I) is represented by the formula (B-2)

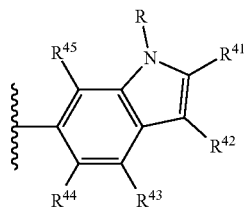
(B-2)

wherein $R^{41}$, $R^{42}$, $R^{43}$, $R^{44}$, and $R^{45}$ each independently represent a hydrogen atom, a halogen atom, a C1-6 alkyl group or a C1-6 alkoxy group; R represents a hydrogen atom or the formula (L3): —Z-$L^{31}$-$L^{32}$-$L^{33}$-$L^{34}$-$L^{35}$-$L^{36}$-$L^{37}$-$R^3$ wherein Z, L3, $L^{32}$, $L^{33}$, $L^{34}$, $L^{35}$, $L^{36}$, $L^{37}$ and $R^3$ represent the same definition as described above.

4. The compound or salt thereof according to claim 1, wherein in the formula (AI-1)

W represents a group represented by the formula (L1): N-$L^{11}$-$L^{12}$-$L^{13}$-$L^{14}$-$L^{15}$-$L^{16}$-$L^{17}$-$R^1$ wherein $L^{11}$, $L^{12}$, $L^{13}$, $L^{14}$, $L^{15}$, $L^{16}$ and $L^{17}$ have the same definition as above, and $R^1$ represents a group represented by the formula (II) as a ligand of GSK3α/β and GCN2,

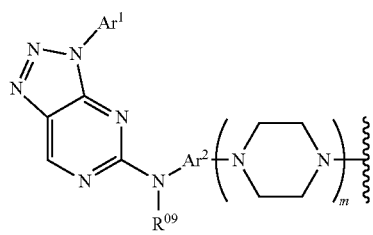
(II)

wherein the definition of $Ar^1$, $Ar^2$, and $R^{09}$ is the same as above, a group represented by the formula (III) as a ligand of BRD,

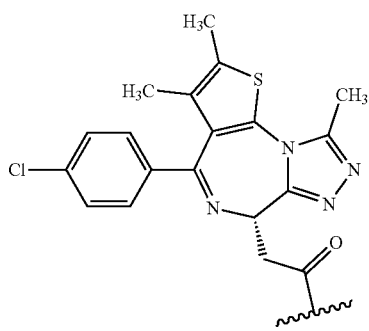
(III)

a group represented by the formula (IV) as a ligand of ABL, BCR-ABL, SRC, KIT, DDR, TEC, EPH-A2, and PDGFR,

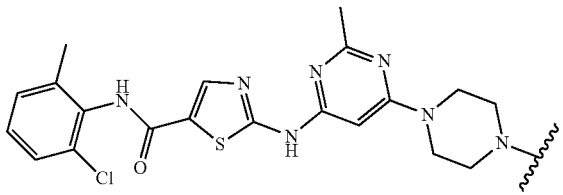
(IV)

or a compound of Smac peptide mimetics as a ligand of XIAP, and

B represents a pyrazolyl group, an indolyl group, an indazolyl group, a benzoimidazoyl group, a 7-azaindolyl group, an indolidinyl group, a 1-azaindolizinyl group, a 3-azaindolizinyl group or a 1,3-diazaindolizinyl group, any of which optionally substituted with any of a halogen atom, a C3-10 cycloalkyl group, an optionally halogenated C1-6 alkyl group, a C1-6 alkoxy group, a C1-6 alkoxy group substituted with a C1-6 alkoxy group, or a vinyl group substituted with a C1-6 alkoxy-carbonyl group, or represented by the formula (B'):

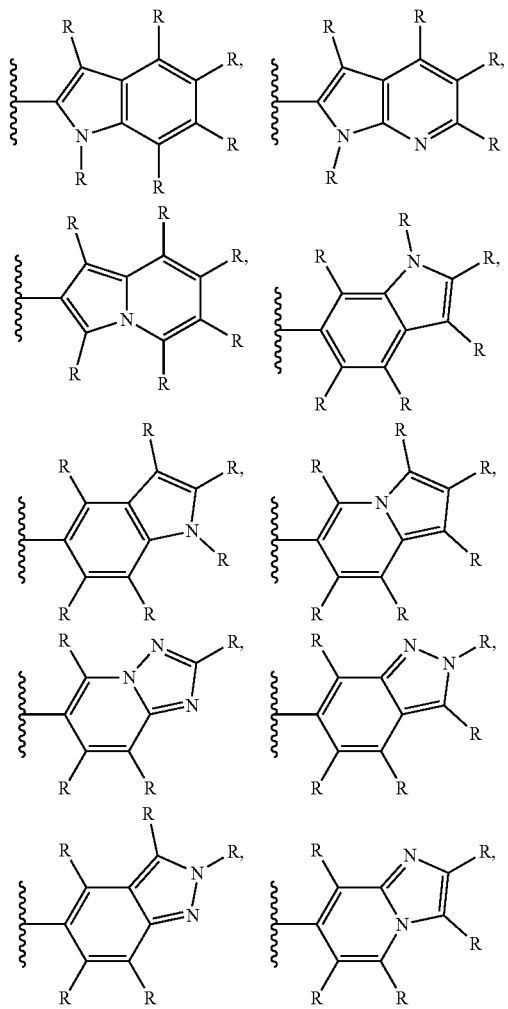

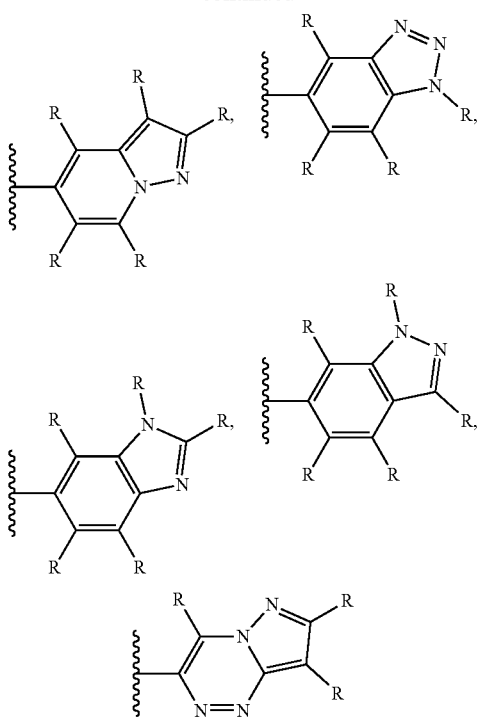

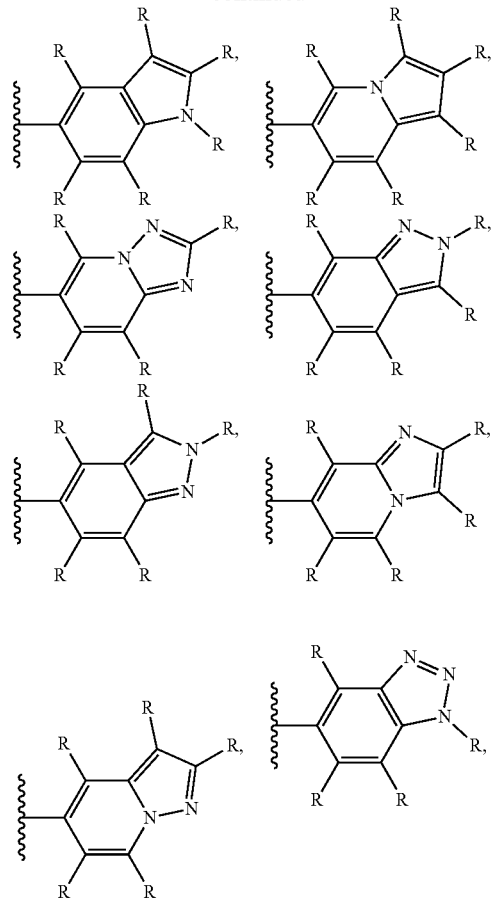

wherein groups R bonded to N each independently represent a hydrogen atom, a C1-6 alkyl group or an amide group; and other groups R each independently represent a hydrogen atom, a halogen atom, a C1-6 alkyl group, a C1-6 alkoxy group or an amide group.

5. The compound or salt thereof according to claim 1, wherein in the formula (AI-1)

W represents a methylene group, a difluoromethylene group, O, S, SO, SO$_2$, NR wherein R represents a hydrogen atom, a C1-6 alkyl group, a C1-6 alkyl-carbonyl group, a C6-14 aryl-carbonyl group or a C1-6 alkylsulfonyl group, or an imino group; and B represents a group represented by the following formula (B'):

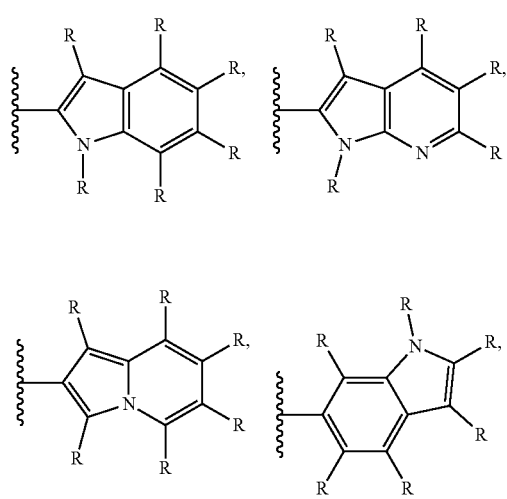

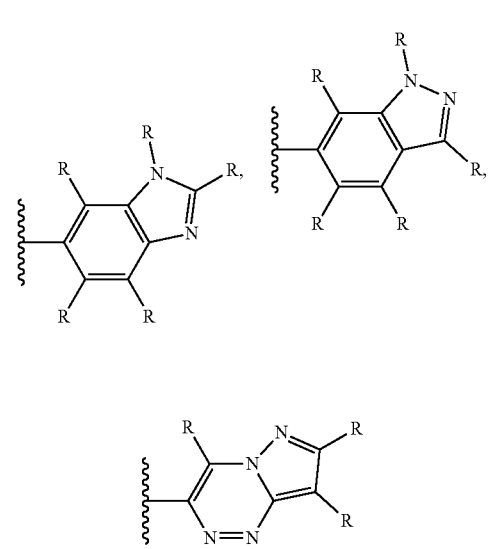

wherein one R is represented by the formula (L3): —Z-L$^{11}$-L$^{32}$-L$^{33}$-L$^{34}$-L$^{35}$-L$^{36}$-L$^{37}$-R$^3$ wherein Z, L$^3$, L$^{32}$, L$^{33}$, L$^{34}$, L$^{35}$, L$^{36}$ and L$^{37}$ have the same definition as described above; and R$^3$ represents a group represented by the formula (II) as a ligand of GSK3α/β and GCN2,

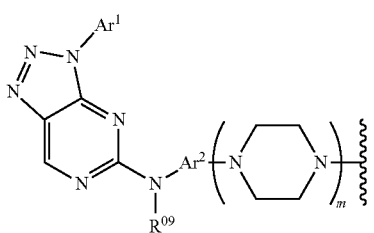

(II)

wherein the definition of Ar¹, Ar², and R⁰⁹ is the same as above, a group represented by the formula (III) as a ligand of BRD,

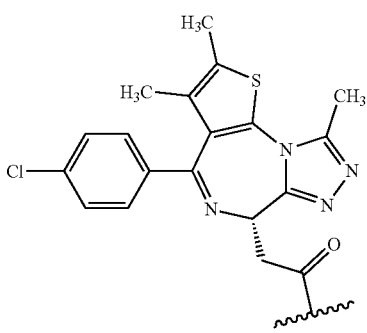

(III)

a group represented by the formula (IV) as a ligand of ABL, BCR-ABL, SRC, KIT, DDR, TEC, EPH-A2, and PDGFR,

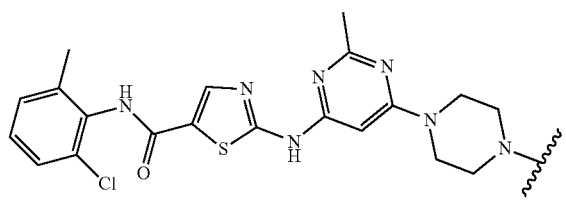

(IV)

or a compound of Smac peptide mimetics as a ligand of XIAP; and other groups R each independently represent a hydrogen atom, a halogen atom, a C1-6 alkyl group or a C1-6 alkoxy group,
wherein when R binds to N, R is not a halogen atom or a C1-6 alkoxy group.

6. The compound or salt thereof according to claim 5, wherein B in the formula (I) is the formula (B-1)

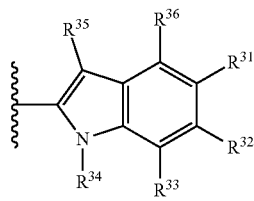

(B-1)

wherein $R^{31}$, $R^{32}$ and $R^{33}$ each independently represent a hydrogen atom, a halogen atom, a C1-6 alkyl group or a C1-6 alkoxy group; $R^{35}$ and $R^{36}$ each independently represent a hydrogen atom, a halogen atom, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above; and $R^{34}$ represents a hydrogen atom, or the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above,
wherein one of $R^{34}$, $R^{35}$ and $R^{36}$ represents the formula (L3).

7. The compound or salt thereof according to claim 5, wherein B in the formula (I) is represented by the formula (B-2)

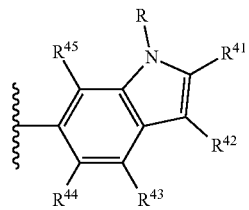

(B-2)

wherein $R^{41}$, $R^{42}$, $R^{43}$, $R^{44}$ and $R^{45}$ each independently represent a hydrogen atom, a halogen atom, a C1-6 alkyl group or a C1-6 alkoxy group; R represents the formula (L3): —Z-$L^{31}$-$L^{32}$-$L^{33}$-$L^{34}$-$L^{35}$-$L^{36}$-$L^{37}$-$R^3$ wherein Z, $L^{31}$, $L^{32}$, $L^{33}$, $L^{34}$, $L^{35}$, $L^{36}$, $L^{37}$ and $R^3$ represent the same definition as described above.

8. The compound or salt thereof according to claim 1, wherein any two compounds selected from the group consisting of the following (i) and (ii) are bonded:
(i) a compound of the formula (I) in which A is the formula (AI-1) wherein W is the formula (L1): N-$L^{11}$-$L^{12}$-$L^{13}$-$L^{14}$-$L^{15}$-$L^{16}$-$L^{17}$-$R^1$ wherein $L^{11}$, $L^{12}$, $L^{13}$, $L^{14}$, $L^{15}$ $L^{16}$ and $L^{17}$ have the same definition as described above, and $R^1$ represents a bond,
(ii) a compound of the formula (I) in which B is the formula (B'):

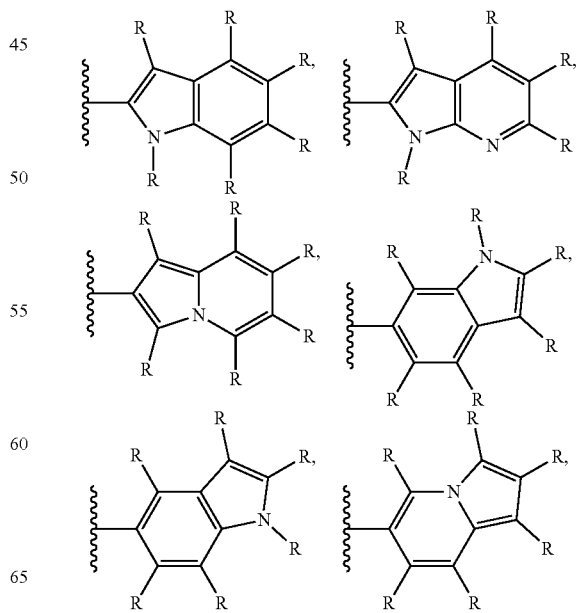

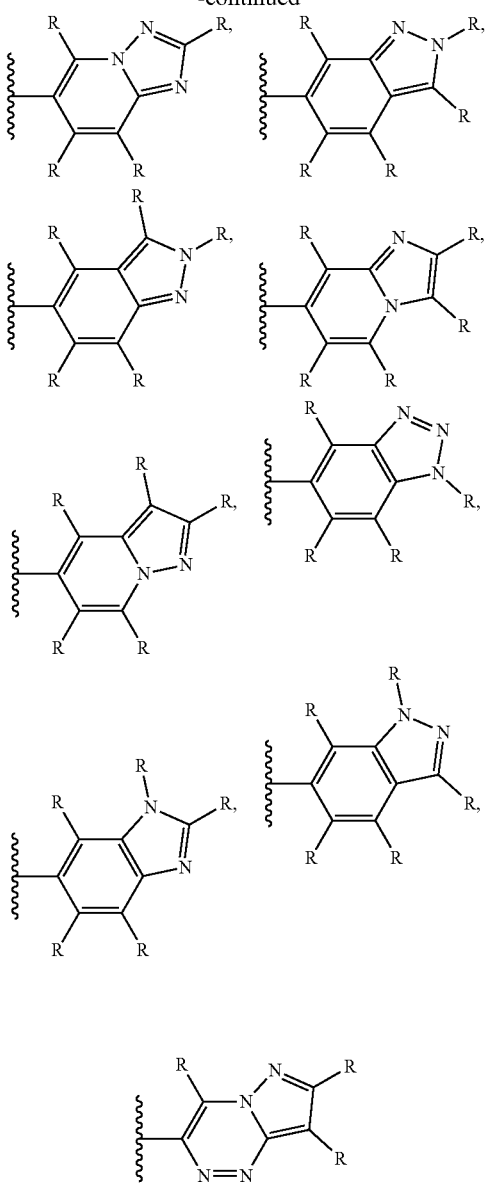

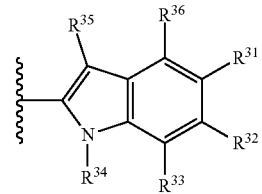

wherein $R^{31}$, $R^{32}$ and $R^{33}$ each independently represent a hydrogen atom, a halogen atom, a C1-6 alkyl group or a C1-6 alkoxy group; $R^{35}$ and $R^{36}$ each independently represent a hydrogen atom, a halogen atom, or the formula (L3): $-Z-L^{31}-L^{32}-L^{33}-L^{34}-L^{35}-L^{36}-L^{37}-R^3$ wherein Z, $L^{31}$, $L^{32}$, $L^{33}$, $L^{34}$, $L^{35}$, $L^{36}$ and $L^{37}$ have the same definition as described above, and $R^3$ represents a bond and $R^{34}$ represents a hydrogen atom or the formula (L3): $-Z-L^{31}-L^{32}-L^{33}-L^{34}-L^{35}-L^{36}-L^{37}-R^3$ wherein Z, $L^{31}$, $L^{32}$, $L^{33}$, $L^{34}$, $L^{35}$, $L^{36}$ and $L^{37}$ have the same definition as described above, and $R^3$ represents a bond, wherein any one of $R^{34}$, $R^{35}$ and $R^{36}$ represents the formula (L3), and A is the formula (AI-1) wherein W is not the formula (L1), and (b) a compound of the formula (I) in which B is the formula (B'-2)

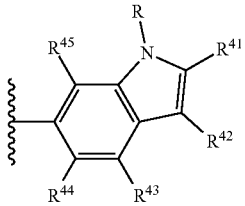

wherein $R^{41}$, $R^{42}$, $R^{43}$, $R^{44}$ and $R^{45}$ each independently represent a hydrogen atom, a halogen atom, a C1-6 alkyl group or a C1-6 alkoxy group; R represents a hydrogen atom or the formula (L3): $-Z-L^{31}-L^{32}-L^{33}-L^{34}-L^{35}-L^{36}-L^{37}-R^3$ wherein Z, $L^{31}$, $L^{32}$, $L^{33}$, $L^{34}$, $L^{35}$, $L^{36}$ and $L^{37}$ have the same definition as described above, and $R^3$ represents a bond, wherein any one of $R^{41}$, $R^{42}$, $R^{43}$, $R^{44}$ and $R^{45}$ represents the formula (L3), and A is the formula (AI-1) wherein W is not the formula (L1).

10. A medicament comprising the compound or salt thereof according to claim 1.

11. The medicament according to claim 10, which is an IAP inhibitor.

12. The medicament according to claim 10, which is a targeted protein degrader.

13. The medicament according to claim 10, which is a prophylactic or therapeutic agent for pathogenic protein-related diseases.

14. A method of inhibiting IAP(s) in mammals, the method comprising administering an effective amount of the compound or salt thereof according to claim 1 to the mammals.

15. A method of inducing targeted protein degradation in mammals, the method comprising administering an effective amount of the compound or salt thereof according to claim 1 to the mammals.

wherein groups R each independently represent a hydrogen atom, a halogen atom, a C1-6 alkyl group, a C1-6 alkoxy group, or the formula (L3): $-Z-L^{31}-L^{32}-L^{33}-L^{34}-L^{35}-L^{36}-L^{37}-R^3$ wherein Z, $L^{31}$, $L^{32}$, $L^{33}$, $L^{34}$, $L^{35}$, $L^{36}$ and $L^{37}$ have the same definition as described above, and $R^3$ represents a bond, wherein when R binds to N, R is not a halogen atom or a C1-6 alkoxy group, and any one R represents the formula (L3): $-Z-L^{31}-L^{32}-L^{33}-L^{34}-L^{35}-L^{36}-L^{37}-R^3$ wherein Z, $L^{31}$, $L^{32}$, $L^{33}$, $L^{34}$, $L^{35}$, $L^{36}$ and $L^{37}$ have the same definition as described above, and $R^3$ represents a bond, and A is the formula (AI-1) wherein W is not the formula (L1).

9. The compound or salt thereof according to claim wherein any two compounds selected from the group consisting of the following (a) and (b) are bonded:

(a) a compound of the formula (I) in which B is the formula (B'-1)

* * * * *

SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: a partial sequence of Smac peptide

<400> SEQUENCE: 1

Ala Val Pro Ile Ala Gln Lys
1               5

<210> SEQ ID NO 2
<211> LENGTH: 4
<212> TYPE: PRT
<213> ORGANISM: Artificial Sequence
<220> FEATURE:
<223> OTHER INFORMATION: a partial sequence of Smac peptide

<400> SEQUENCE: 2

Ala Val Pro Ile
1